(12) United States Patent
Suzuki et al.

(10) Patent No.: US 8,604,224 B2
(45) Date of Patent: Dec. 10, 2013

(54) BENZO[$B$]NAPHTHO[1,2-$D$]FURAN COMPOUND AS LIGHT-EMITTING ELEMENT MATERIAL

(75) Inventors: Hiroki Suzuki, Kanagawa (JP); Satoshi Seo, Kanagawa (JP); Sachiko Kawakami, Kanagawa (JP); Tsunenori Suzuki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 13/334,752

(22) Filed: Dec. 22, 2011

(65) Prior Publication Data
US 2012/0165556 A1 Jun. 28, 2012

(30) Foreign Application Priority Data
Dec. 28, 2010 (JP) ................. 2010-292638

(51) Int. Cl.
*C07D 307/77* (2006.01)
*B32B 9/00* (2006.01)

(52) U.S. Cl.
USPC ............ 549/457; 549/429; 428/690; 428/917

(58) Field of Classification Search
USPC .................. 549/429, 457; 428/690, 917
See application file for complete search history.

(56) References Cited

U.S. PATENT DOCUMENTS

| 6,525,088 B1 * | 2/2003 | Nagano et al. ............. 514/452 |
| 2008/0152950 A1 | 6/2008 | Je et al. |

(Continued)

FOREIGN PATENT DOCUMENTS

| CN | 101679337 A | 3/2010 |
| CN | 101835874 A | 9/2010 |

(Continued)

OTHER PUBLICATIONS

Kawamura et al (2010): STN International HCAPLUS database, Columbus (OH), accession No. 2010: 1493416.*

(Continued)

*Primary Examiner* — Golam M M Shameem
(74) *Attorney, Agent, or Firm* — Husch Blackwell LLP

(57) ABSTRACT

Provided is a benzo[b]naphtho[1,2-d]furan compound having a wide band gap which gives excellent color purity of blue. Further provided are a light-emitting element, a light-emitting device, and an electronic device each of which uses the benzo[b]naphtho[1,2-d]furan compound and is highly reliable. A benzo[b]naphtho[1,2-d]furan compound represented by a general formula (G1) is provided. In the general formula (G1), An represents an anthryl group represented by a general formula (An-1) or (An-2) below, $\alpha^1$ and $\alpha^2$ separately represent a substituted or unsubstituted phenylene group represented by any one of general formulae ($\alpha$-1) to ($\alpha$-3) below, and $R^1$ to $R^9$ separately represent either hydrogen or an alkyl group having 1 to 4 carbon atoms. Further, in the general formula (G1), n and m separately represent 0 or 1.

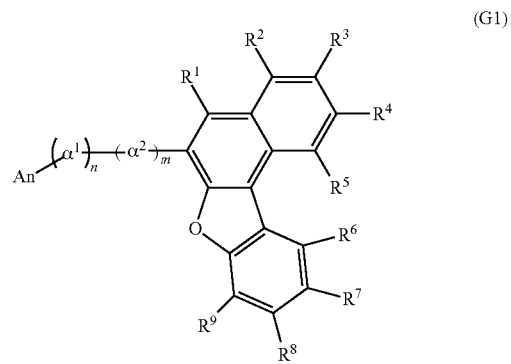

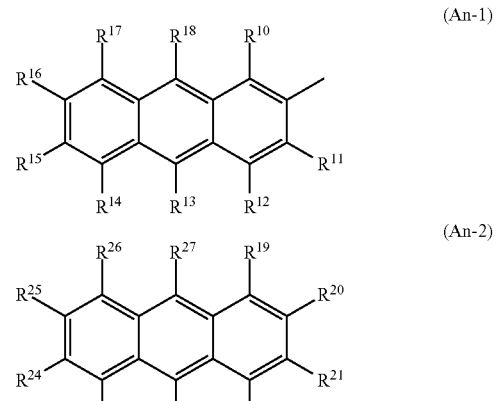

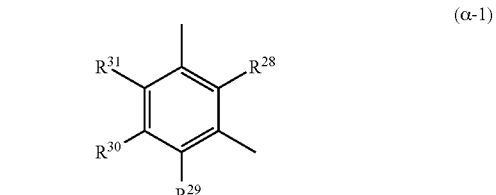

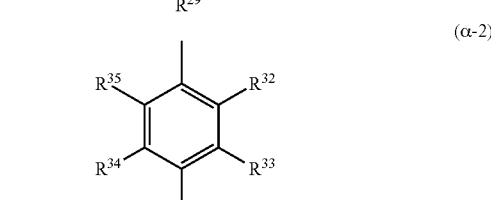

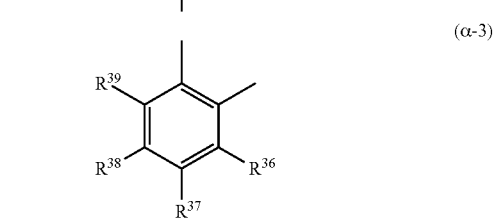

24 Claims, 53 Drawing Sheets

(56) References Cited

U.S. PATENT DOCUMENTS

| | | |
|---|---|---|
| 2008/0315754 A1 | 12/2008 | Kawamura et al. |
| 2011/0114928 A1 | 5/2011 | Suzuki et al. |
| 2011/0168992 A1 | 7/2011 | Bae et al. |
| 2012/0165550 A1 | 6/2012 | Suzuki et al. |

FOREIGN PATENT DOCUMENTS

| | | |
|---|---|---|
| CN | 102070584 A | 5/2011 |
| CN | 102224148 A | 10/2011 |
| EP | 2 163 550 A1 | 3/2010 |
| EP | 2 330 102 A1 | 6/2011 |
| EP | 2 332 931 A2 | 6/2011 |
| JP | 2008-94777 | 4/2008 |
| JP | 2008-169197 | 7/2008 |
| JP | 2011-121940 | 6/2011 |
| KR | 10-2008-0049213 | 6/2008 |
| KR | 10-2010-0017136 | 2/2010 |
| KR | 10-2010-0034719 | 4/2010 |
| KR | 10-2010-0093064 | 8/2010 |
| KR | 10-2011-0053198 | 5/2011 |
| WO | WO 2008/143229 A1 | 11/2008 |
| WO | WO 2009/069537 A1 | 6/2009 |
| WO | WO 2010/036027 A2 | 4/2010 |
| WO | WO 2010/137285 A1 | 12/2010 |

OTHER PUBLICATIONS

Baumgartner, M.T. et al, "The Reactivity of Oxygen Nucleophiles with Aryl Radicals in the $S_{RN}1$ Mechanism," Tetrahedron Letters, vol. 33, No. 17, 1992, pp. 2323-2326.

Baumgartner, M.T. et al, "Photostimulated Reactions of o-Dihalobenzenes with Nucleophiles Derived from the 2-Naphthyl System. Competition Between Electron Transfer, Fragmentation, and Ring Closure Reactions," J. Org. Chem., vol. 58, No. 9, 1993, pp. 2593-2598.

Goldfinger et al, "Directed Electrophilic Cyclizations: Efficient Methodology for the Synthesis of Fused Polycyclic Aromatics," J. Am. Chem. Soc., vol. 119, No. 20, 1997, pp. 4578-4593.

International Search Report re application No. PCT/JP2011/080137, dated Feb. 28, 2012.

Written Opinion re application No. PCT/JP2011/080137, dated Feb. 28, 2012.

* cited by examiner

BENZO[B]NAPHTHO[1,2-D]FURAN COMPOUND AS LIGHT-EMITTING ELEMENT MATERIAL

TECHNICAL FIELD

The present invention relates to a benzo[b]naphtho[1,2-d]furan compound, and a light-emitting element material and a light-emitting element each including the benzo[b]naphtho[1,2-d]furan compound. The present invention also relates to a light-emitting device, an electronic device, and a lighting device each including the light-emitting element.

BACKGROUND ART

In recent years, research and development have been extensively conducted on light-emitting elements using electroluminescence (EL). In a basic structure of light-emitting elements, a layer containing a substance having a light-emitting property is interposed between a pair of electrodes. Voltage application to this element causes the substance having a light-emitting property to emit light.

Such light-emitting elements are self-luminous elements and have advantages over liquid crystal displays in having high pixel visibility and eliminating the need for backlights, for example; thus, light-emitting elements are thought to be suitable for flat panel display elements. Such light-emitting elements are also highly advantageous in that they can be thin and lightweight. Besides, very high speed response is also one of the features of such elements.

Furthermore, since such light-emitting elements can be formed in, a film form, they make it possible to provide planar light emission easily; thus, large-area elements using planar light emission can be formed. This is a difficult feature to obtain with point light sources typified by incandescent lamps and LEDs or linear light sources typified by fluorescent, lamps. Thus, light-emitting elements also have great potential as planar light sources applicable to lighting devices and the like.

Light-emitting elements utilizing electroluminescence are broadly classified according to whether they use an organic compound or an inorganic compound as a light-emitting substance. In the case where an organic compound is used as a light-emitting substance, application of a voltage to a light-emitting element causes injection of electrons and holes from a pair of electrodes into a layer containing the light-emitting organic compound, and thus a current flows. Then, recombination of these carriers (i.e., electrons and holes) brings the organic compound having a light-emitting property into an excited state, and the return from the excited state to the ground state is accompanied by light emission. Note that an excited state formed by an organic compound can be a singlet excited state or a triplet excited state, and luminescence from the singlet excited state is referred to as fluorescence, and luminescence from the triplet excited state is referred to as phosphorescence.

In improving element characteristics of such light-emitting elements, there are a lot of problems that depend on substances, and in order to solve the problems, improvement of the element structures, development of the substances, and the like have been carried out (for example, see Patent Document 1).

The emission wavelength of a light-emitting element is determined by energy difference between a ground state and an excited state, that is, the band gap, of light-emitting molecules included in the light-emitting element. Therefore, a variety of emission colors can be obtained by devising a structure of the light-emitting molecule. With use of light-emitting elements capable of emitting red light, blue light, and green light, which are the three primary colors of light, a full-color light-emitting device can be manufactured.

REFERENCE

[Patent Document]

Patent Document 1: PCT International Publication No. 2010-036027

DISCLOSURE OF INVENTION

A problem with a full-color light-emitting device is that manufacture of a light-emitting element with excellent color purity is not always easy. This is because of the difficulty in realizing a light-emitting element with high reliability and excellent color purity, although manufacture of a light-emitting device having superior color reproducibility needs red, blue and green light-emitting elements with excellent color purity. Especially for a blue light-emitting element, the achievement level of such a task has still been low.

In view of the above problem, an object of the present invention is to provide a benzo[b]naphtho[1,2-d]furan compound having a wide band gap which gives excellent color purity of blue. Another object is to provide a light-emitting element, a light-emitting device, and an electronic device each of which uses the benzo[b]naphtho[1,2-d]furan compound and is highly reliable.

A benzo[b]naphtho[1,2-d]furan compound according to one embodiment of the present invention has no other substituent than an alkyl group having 1 to 4 carbon atoms at the 5-position and has an anthryl group having a carrier-transport property at the 6-position.

One embodiment of the present invention is a benzo[b]naphtho[1,2-d]furan compound represented by a general formula (G1).

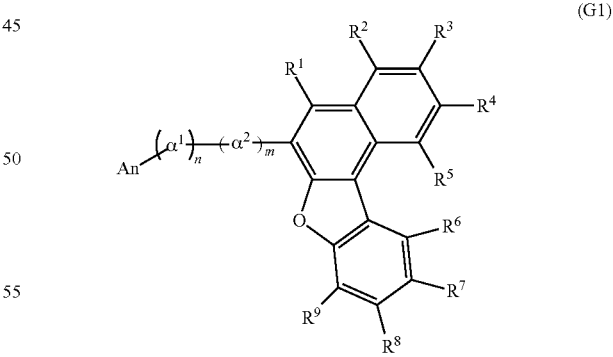

(G1)

In the general formula (G1), An represents an anthryl group represented by a general formula (An-1) or (An-2) below, $\alpha^1$ and $\alpha^2$ separately represent a substituted or unsubstituted phenylene group represented by any one of general formulae ($\alpha$-1) to ($\alpha$-3) below, and $R^1$ to $R^9$ separately represent either hydrogen or an alkyl group having 1 to 4 carbon atoms. Further, in the general formula (G1), n and m separately represent 0 or 1.

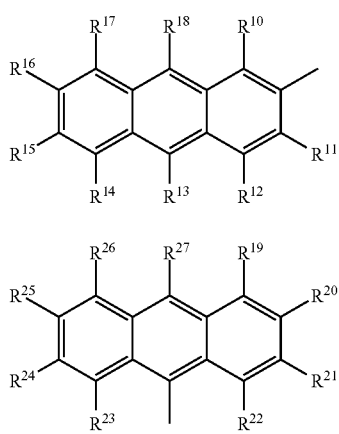
(An-1)

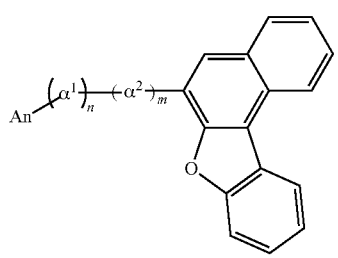
(G2)

In the general formula (G2), An represents an anthryl group represented by a general formula (An-1) or (An-2) below, and $\alpha^1$ and $\alpha^2$ separately represent a phenylene group represented by any one of general formulae ($\alpha$-4) to ($\alpha$-6) below. In addition, in the general formula (G2), n and m separately represent 0 or 1.

For the general formula (G1), $R^{10}$ to $R^{27}$ in the general formulae (An-1) and (An-2) represent any one of hydrogen, an alkyl group having 1 to 6 carbon atoms, and a substituted or unsubstituted aryl group having 6 to 13 carbon atoms. Further, when $R^{10}$ to $R^{27}$ have two or more substituents, the substituents may be bonded to each other to form a ring. In addition, when $R^{10}$ to $R^{27}$ have two or more substituents, one carbon atom may have two substituents, and in this case, the substituents may be bonded to each other to form a spiro ring.

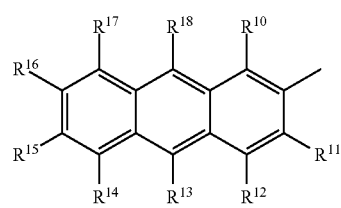
(An-1)

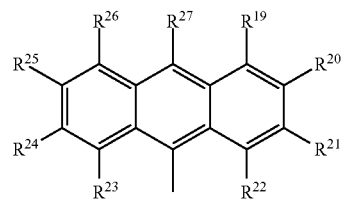
(An-2)

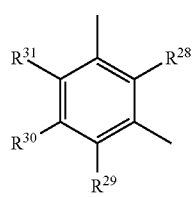
($\alpha$-1)

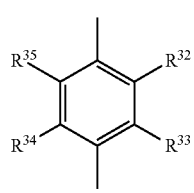
($\alpha$-2)

For the general formula (G2), $R^{10}$ to $R^{27}$ in the general formulae (An-1) and (An-2) represent any one of hydrogen, an alkyl group having 1 to 6 carbon atoms, and a substituted or unsubstituted aryl group having 6 to 13 carbon atoms. Further, when $R^{10}$ to $R^{27}$ have two or more substituents, the substituents may be bonded to each other to form a ring. In addition, when $R^{10}$ to $R^{27}$ have two or more substituents, one carbon atom may have two substituents, and in this case, the substituents may be bonded to each other to form a spiro ring.

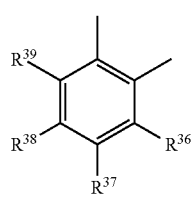
($\alpha$-3)

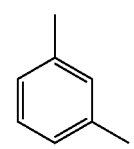
($\alpha$-4)

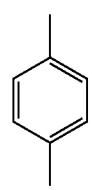
($\alpha$-5)

For the general formula (G1), $R^{28}$ to $R^{39}$ in the general formulae ($\alpha$-1) to ($\alpha$-3) separately represent either hydrogen or an alkyl group having 1 to 4 carbon atoms.

One embodiment of the present invention is a benzo[b]naphtho[1,2-d]furan compound represented by a general formula (G2).

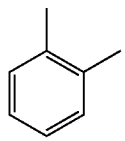
(α-6)

One embodiment of the present invention is a benzo[b]naphtho[1,2-d]furan compound represented by a general formula (G3).

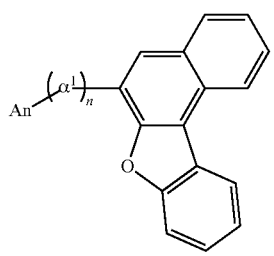
(G3)

In the general formula (G3), An represents an anthryl group represented by a general formula (An-1) or (An-2) below, and α¹ represents a phenylene group represented by a general formula (α-4) or (α-5) below. In addition, in the general formula (G3), n represents 0 or 1.

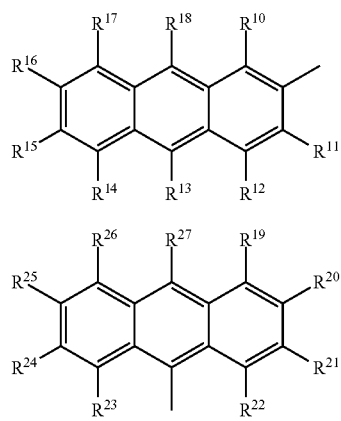
(An-1)

(An-2)

For the general formula (G3), $R^{10}$ to $R^{27}$ in the general formulae (An-1) and (An-2) represent any one of hydrogen, an alkyl group having 1 to 6 carbon atoms, and a substituted or unsubstituted aryl group having 6 to 13 carbon atoms. Further, when $R^{10}$ to $R^{27}$ have two or more substituents, the substituents may be bonded to each other to form a ring. In addition, when $R^{10}$ to $R^{27}$ have two or more substituents, one carbon atom may have two substituents, and in this case, the substituents may be bonded to each other to form a spiro ring.

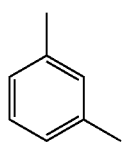
(α-4)

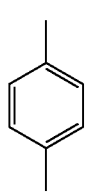
(α-5)

One embodiment of the present invention is a benzo[b]naphtho[1,2-d]furan compound represented by a general formula (G4).

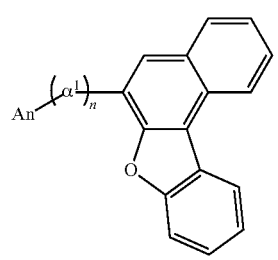
(G4)

In the general formula (G4), An represents an anthryl group represented by a general formula (An-3) or (An-4) below, and α¹ represents a phenylene group represented by a general formula (α-4) or (α-5) below. In addition, in the general formula (G4), n represents 0 or 1.

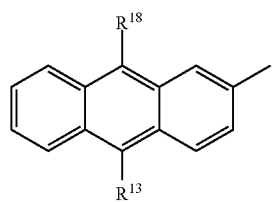
(An-3)

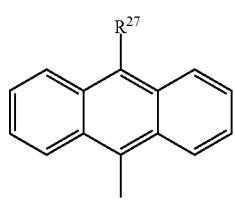
(An-4)

For the general formula (G4), $R^{13}$, $R^{18}$, and $R^{27}$ in the general formulae (An-3) and (An-4) represent any one of hydrogen, an alkyl group having 1 to 6 carbon atoms, and a substituted or unsubstituted aryl group having 6 to 13 carbon atoms. Further, when $R^{13}$, $R^{18}$, and $R^{27}$ have two or more substituents, the substituents may be bonded to each other to form a ring. In addition, when $R^{13}$, $R^{18}$, and $R^{27}$ have two or more substituents, one carbon atom may have two substituents, and in this case, the substituents may be bonded to each other to form a spiro ring.

(α-4)
(α-5)

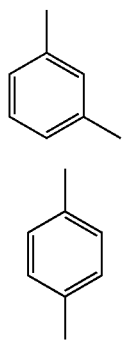

Another embodiment of the present invention is a light-emitting element material including any of the above benzo[b]naphtho[1,2-d]furan compounds.

Another embodiment of the present invention is a light-emitting element including any of the above benzo[b]naphtho[1,2-d]furan compounds. In the light-emitting element, any of the above benzo[b]naphtho[1,2-d]furan compounds can be included in a light-emitting layer. The light-emitting layer may include any of the above benzo[b]naphtho[1,2-d]furan compounds for a host material or an emission center material.

Another embodiment of the present invention is a light-emitting device including the above light-emitting element.

Another embodiment of the present invention is an electronic device or a lighting device including the above light-emitting device.

Note that the light-emitting device in this specification includes an image display device and a light source. In addition, the light-emitting device includes all the following modules: a module in which a connector, such as a flexible printed circuit (FPC), a tape automated bonding (TAB) tape, or a tape carrier package (TCP), is attached to a panel, a module in which a printed wiring board is provided at the end of a TAB tape or a TCP, and a module in which an integrated circuit (IC) is directly mounted on a light-emitting element by a chip-on-glass (COG) method.

The benzo[b]naphtho[1,2-d]furan compounds according to one embodiment of the present invention, each of which has no other substituent than an alkyl group having 1 to 4 carbon atoms at the 5-position and has an anthryl group having a carrier-transport property the 6-position, have a large band gap and accordingly enable light emission at a relatively short wavelength; thus, the benzo[b]naphtho[1,2-d]furan compounds are the ones with which blue light emission with good color purity can be highly efficiently obtained. Further, the benzo[b]naphtho[1,2-d]furan compounds according to one embodiment of the present invention have high electrochemical stability.

The benzo[b]naphtho[1,2-d]furan compounds according to one embodiment of the present invention each have no other substituent than an alkyl group having 1 to 4 carbon atoms at the 5-position and have an anthryl group having a carrier-transport property at the 6-position. Since there is no bulky substituent having a π electron, such as an aryl group or a hetero aryl group, at the 5-position, even introduction of a bulkier aryl group such as an anthryl group than a phenyl group to the 6-position does not complicate the synthesis method; accordingly, a wide variety of structures can be easily obtained. Thus, they can be manufactured at high productivity and low cost, which enables higher purification, and high-quality benzo[b]naphtho[1,2-d]furan compounds can be provided inexpensively.

Further, a layer is formed containing any of the benzo[b]naphtho[1,2-d]furan compounds according to one embodiment of the present invention, and a light-emitting material (hereinafter referred to as a dopant) having a smaller band gap than the benzo[b]naphtho[1,2-d]furan compound is added to the layer, so that light emission from the dopant can be obtained. The benzo[b]naphtho[1,2-d]furan compounds according to one embodiment of the present invention enables a dopant having an emission maximum of about 450 nm to 700 nm to efficiently emit light. Since the benzo[b]naphtho[1,2-d]furan compounds according to one embodiment of the present invention have a large band gap, not light emission from the benzo[b]naphtho[1,2-d]furan compound but light emission from the dopant can be efficiently obtained even when the dopant that is used shows light emission at a relatively short wavelength. Specifically, even when a material having an emission maximum of about 450 nm to 470 nm, which is a light-emitting material showing excellent color purity of blue, is used for a dopant, a light-emitting element capable of blue light emission with good color purity can be obtained.

Alternatively, any of the benzo[b]naphtho[1,2-d]furan compounds according to one embodiment of the present invention is added in a layer containing a material (hereinafter referred to as a host) having a larger band gap than the benzo[b]naphtho[1,2-d]furan compound to fabricate a light-emitting element, so that light emission form the benzo[b]naphtho[1,2-d]furan compound according to one embodiment of the present invention can be obtained. That is, the benzo[b]naphtho[1,2-d]furan compounds according to one embodiment of the present invention can also function as a dopant. In this case, since the benzo[b]naphtho[1,2-d]furan compounds according to one embodiment of the present invention have a large band gap and show light emission at a relatively short wavelength, blue light emission with good color purity can be highly efficiently obtained with the fabricated light-emitting element.

The benzo[b]naphtho[1,2-d]furan compounds according to one embodiment of the present invention have a wide band gap and are bipolar materials having a high electron-transport property and a high hole-transport property. Therefore, the benzo[b]naphtho[1,2-d]furan compounds according to one embodiment of the present invention can be used for a carrier-transport layer to function as a hole-transport layer, a hole-injection layer, an electron-transport layer, or an electron-injection layer. Thus, the use of any of the benzo[b]naphtho[1,2-d]furan compounds according to one embodiment of the present invention in a light-emitting element realizes the light-emitting element which has good carrier balance and low driving voltage.

Further, a light-emitting element including any of the above benzo[b]naphtho[1,2-d]furan compounds according to one embodiment of the present invention is a light-emitting element that can give excellent color purity of blue. Furthermore, a light-emitting element including any of the above benzo[b]naphtho[1,2-d]furan compounds according to one embodiment of the present invention is a light-emitting element that does not easily deteriorate and has a long lifetime and high reliability.

Further, a light-emitting device as one embodiment of the present invention which includes the above light-emitting element is a light-emitting device with high color reproducibility or a light-emitting device with high display quality. The light-emitting device according to one embodiment of the present invention which includes the above light-emitting element is a light-emitting device with high reliability. The light-emitting device according to one embodiment of the present invention which includes the above light-emitting element is a light-emitting device with low power consumption.

Further, an electronic device as one embodiment of the present invention which includes the above light-emitting element is an electronic device with high color reproducibility or an electronic device with high display quality. The electronic device according to one embodiment of the present invention which includes the above light-emitting element is an electronic device with high reliability. The electronic device according to one embodiment of the present invention which includes the above light-emitting element is an electronic device with low power consumption.

BEST MODE FOR CARRYING OUT THE INVENTION

Figure 1A:
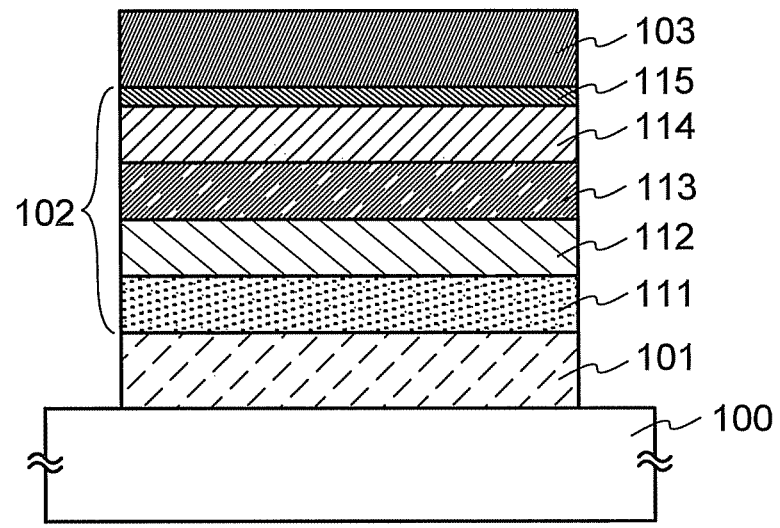
FIGS. 1A and 1B each illustrate a light-emitting element according to one embodiment of the present invention.

Hereinafter, embodiments will be described in detail with reference to the accompanying drawings. Note that the present invention is not limited to the description below because it will be easily understood by those skilled in the art that various changes and modifications can be made without departing from the spirit and scope of the present invention. Therefore, the present invention should not be interpreted as being limited to the content of the embodiments and examples below.

[Embodiment 1]

In this embodiment, benzo[b]naphtho[1,2-d]furan compounds according to one embodiment of the present invention are described.

A benzo[b]naphtho[1,2-d]furan compound according to one embodiment of the present invention is the benzo[b]naphtho[1,2-d]furan compound represented by the following general formula (G1).

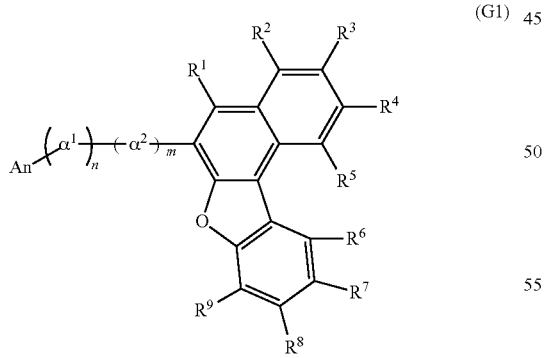

(G1)

In the general formula (G1), An represents an anthryl group represented by the general formula (An-1) or (An-2) below, $\alpha^1$ and $\alpha^2$ separately represent a substituted or unsubstituted phenylene group represented by any one of the general formulae ($\alpha$-1) to ($\alpha$-3) below, and $R^1$ to $R^9$ separately represent either hydrogen or an alkyl group having 1 to 4 carbon atoms. Further, in the general formula (G1), n and m separately represent 0 or 1.

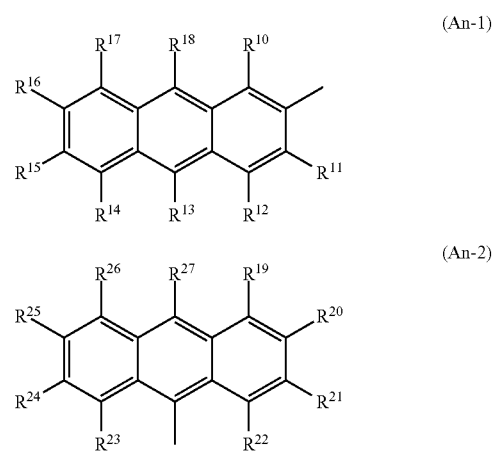

(An-1)

(An-2)

For the general formula (G1), $R^{10}$ to $R^{27}$ in the general formulae (An-1) and (An-2) represent any one of hydrogen, an alkyl group having 1 to 6 carbon atoms, and a substituted or unsubstituted aryl group having 6 to 13 carbon atoms. Further, when $R^{10}$ to $R^{27}$ have two or more substituents, the substituents may be bonded to each other to form a ring. In addition, when $R^{10}$ to $R^{27}$ have two or more substituents, one carbon atom may have two substituents, and in this case, the substituents may be bonded to each other to form a spiro ring.

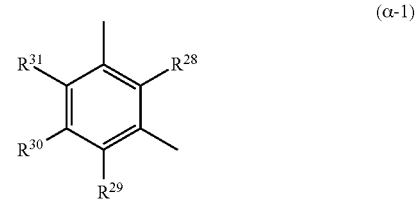

($\alpha$-1)

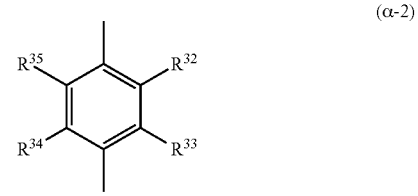

($\alpha$-2)

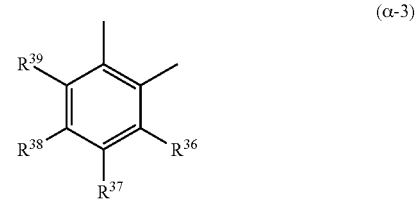

($\alpha$-3)

For the general formula (G1), $R^{28}$ to $R^{39}$ in the general formulae ($\alpha$-1) to ($\alpha$-3) separately represent either hydrogen or an alkyl group having 1 to 4 carbon atoms.

One embodiment of the present invention is the benzo[b]naphtho[1,2-d]furan compound represented by the general formula (G2).

(G2)

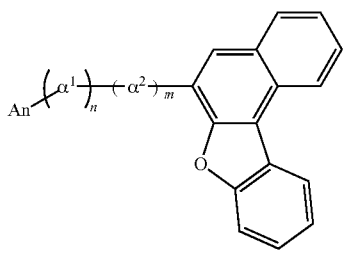

In the general formula (G2), An represents an anthryl group represented by the general formula (An-1) or (An-2) below, and $\alpha^1$ and $\alpha^2$ separately represent a phenylene group represented by any one of the general formulae ($\alpha$-4) to ($\alpha$-6) below. In addition, in the general formula (G2), n and m separately represent 0 or 1.

(An-1)

(An-2)

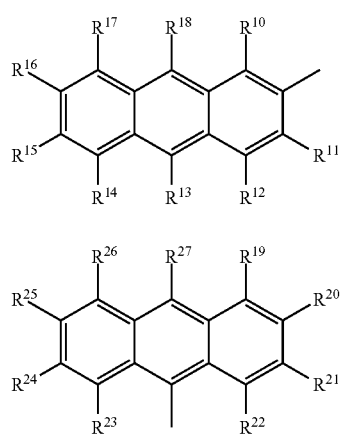

For the general formula (G2), $R^{10}$ to $R^{27}$ in the general formulae (An-1) and (An-2) represent any one of hydrogen, an alkyl group having 1 to 6 carbon atoms, and a substituted or unsubstituted aryl group having 6 to 13 carbon atoms. Further, when $R^{10}$ to $R^{27}$ have two or more substituents, the substituents may be bonded to each other to form a ring. In addition, when $R^{10}$ to $R^{27}$ have two or more substituents, one carbon atom may have two substituents, and in this case, the substituents may be bonded to each other to form a spiro ring.

($\alpha$-4)

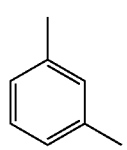

($\alpha$-5)

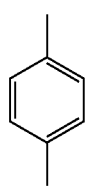

($\alpha$-6)

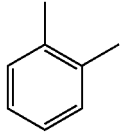

One embodiment of the present invention is the benzo[b]naphtho[1,2-d]furan compound represented by the general formula (G3).

(G3)

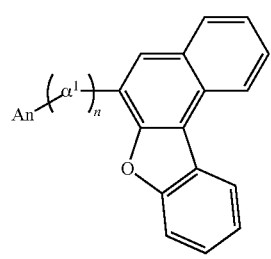

In the general formula (G3), An represents an anthryl group represented by the general formula (An-1) or (An-2) below, and $\alpha^1$ represents a phenylene group represented by the general formula ($\alpha$-4) or ($\alpha$-5) below. In addition, in the general formula (G3), n represents 0 or 1.

(An-1)

(An-2)

For the general formula (G3), $R^{10}$ to $R^{27}$ in the general formulae (An-1) and (An-2) represent any one of hydrogen, an alkyl group having 1 to 6 carbon atoms, and a substituted or unsubstituted aryl group having 6 to 13 carbon atoms. Further, when $R^{10}$ to $R^{27}$ have two or more substituents, the substituents may be bonded to each other to form a ring. In addition, when $R^{10}$ to $R^{27}$ have two or more substituents, one carbon atom may have two substituents, and in this case, the substituents may be bonded to each other to form a spiro ring.

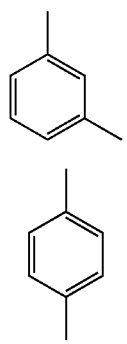
(α-4)

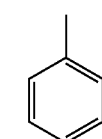
(α-5)

One embodiment of the present invention is the benzo[b]naphtho[1,2-d]furan compound represented by the general formula (G4).

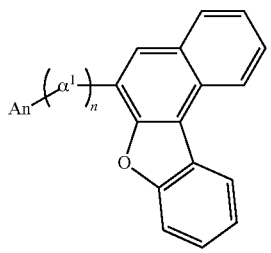
(G4)

In the general formula (G4), An represents an anthryl group represented by the general formula (An-3) or (An-4) below, and $\alpha^1$ represents a phenylene group represented by the general formula (α-4) or (α-5) below. In addition, in the general formula (G4), n represents 0 or 1.

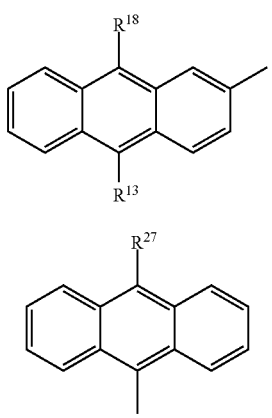
(An-3)

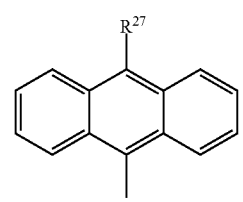
(An-4)

In the general formulae (An-3) and (An-4), $R^{13}$, $R^{18}$, and $R^{27}$ represent any one of hydrogen, an alkyl group having 1 to 6 carbon atoms, and a substituted or unsubstituted aryl group having 6 to 13 carbon atoms. Further, when $R^{13}$, $R^{18}$, and $R^{27}$ have two or more substituents, the substituents may be bonded to each other to form a ring. In addition, when $R^{13}$, $R^{18}$, and $R^{27}$ have two or more substituents, one carbon atom may have two substituents, and in this case, the substituents may be bonded to each other to form a spiro ring.

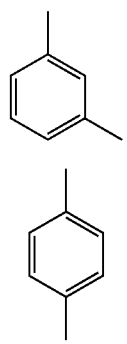

Examples of the specific structures of $R^1$ to $R^9$ and $R^{28}$ to $R^{39}$ are structural formulae (R-1) to (R-9) below and the like.

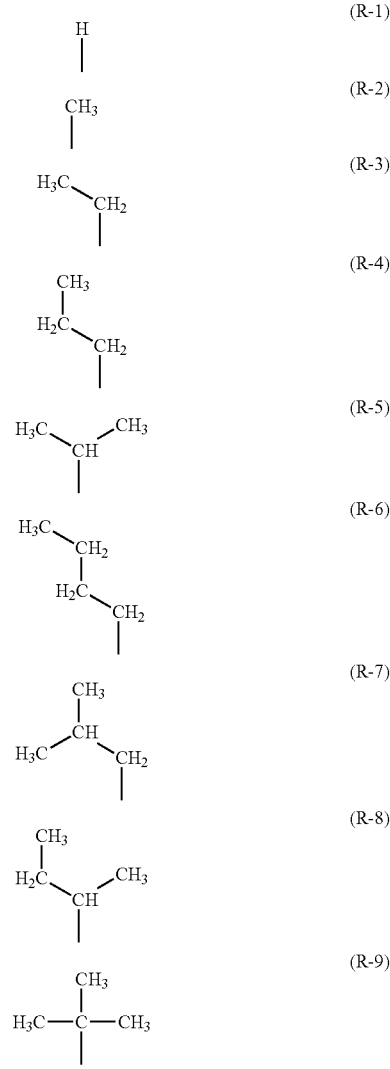

When any of $R^{10}$ to $R^{27}$ is an aryl group having 6 to 13 carbon atoms, the aryl group may further have a substituent. Note that the number of the carbon atoms of the aryl group described in this specification indicates the number of the carbon atoms in a ring of the main skeleton, not including the number of the carbon atoms in a substituent bonded to the main skeleton. In the case where any of $R^{10}$ to $R^{27}$ is an aryl group having 6 to 13 carbon atoms having a substituent, examples of the substituent are an alkyl group having 1 to 6 carbon atoms, a phenyl group, a naphthyl group, a fluorenyl group, and the like. Note that in the case where any of $R^{10}$ to $R^{27}$ is an aryl group having 6 to 13 carbon atoms and the aryl group further has substituents, the substituents may be bonded to each other to form a ring, and the ring structure may be a spiro ring.

Examples of the specific structures of $R^{10}$ to $R^{27}$ are structural formulae (R-1) to (R-24) below and the like. Note that the structural formulae (R-14) to (R-24) are the specific structures in the case where any of $R^{10}$ to $R^{27}$ is an aryl group having 6 to 13 carbon atoms and the aryl group further has substituents. Further, in the case where the substituents are bonded to each other to form a spiro ring structure, a specific example is the structural formula (R-21).

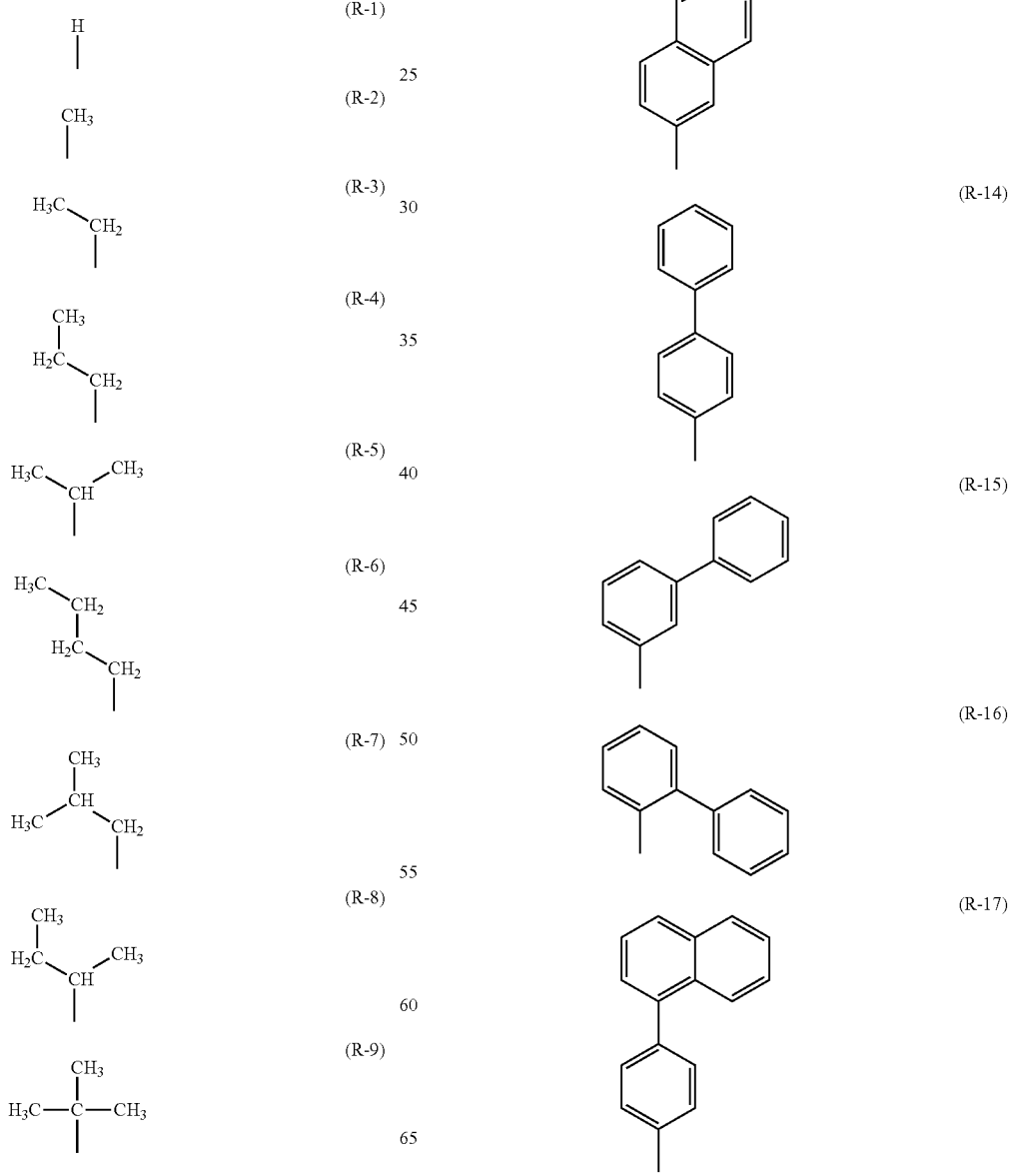

(R-18)
(R-19)
(R-20)
(R-21)
(R-22)
(R-23)

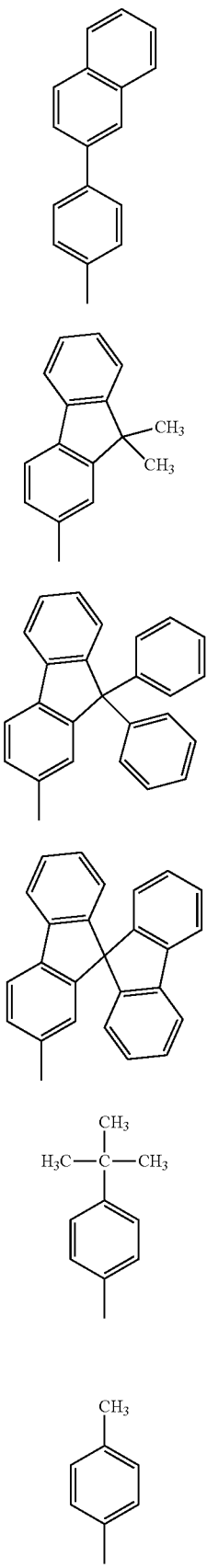

(R-24)

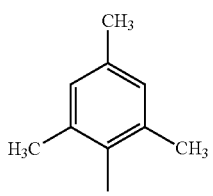

The benzo[b]naphtho[1,2-d]furan compounds according to one embodiment of the present invention, each of which has no other substituent than an alkyl group having 1 to 4 carbon atoms at the 5-position and has an anthryl group having a carrier-transport property the 6-position, have a large band gap and accordingly enable light emission at a relatively short wavelength; thus, the benzo[b]naphtho[1,2-d]furan compounds are the ones with which blue light emission with good color purity can be highly efficiently obtained. Further, the benzo[b]naphtho[1,2-d]furan compounds according to one embodiment of the present invention have high electrochemical stability.

The benzo[b]naphtho[1,2-d]furan compounds according to one embodiment of the present invention each have no other substituent than an alkyl group having 1 to 4 carbon atoms at the 5-position and have an anthryl group having a carrier-transport property at the 6-position. Since there is no bulky substituent having a π electron, such as an aryl group or a hetero aryl group, at the 5-position, even introduction of a bulkier aryl group such as an anthryl group than a phenyl group to the 6-position does not complicate the synthesis method; accordingly, a wide variety of structures can be easily obtained. Thus, they can be manufactured at high productivity and low cost, which enables higher purification, and high-quality benzo[b]naphtho[1,2-d]furan compounds can be provided inexpensively.

Specific examples of the benzo[b]naphtho[1,2-d]furan compounds represented by the general formulae (G1) to (G4) include, but are not limited to, the benzo[b]naphtho[1,2-d] furan compounds represented by the structural formulae (100) to (156).

(100)

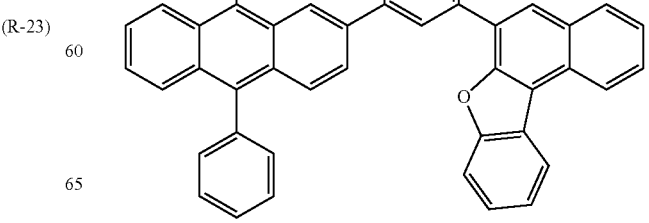

(101)
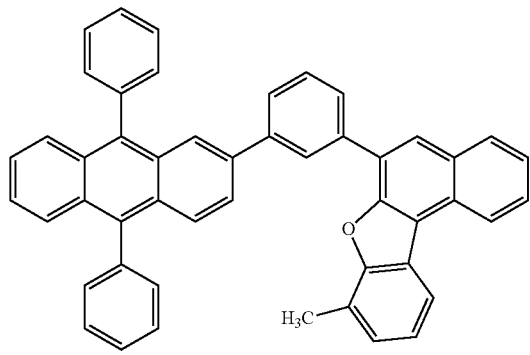
(102)
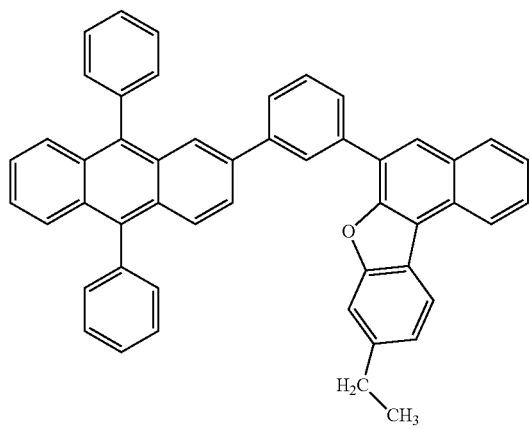
(103)
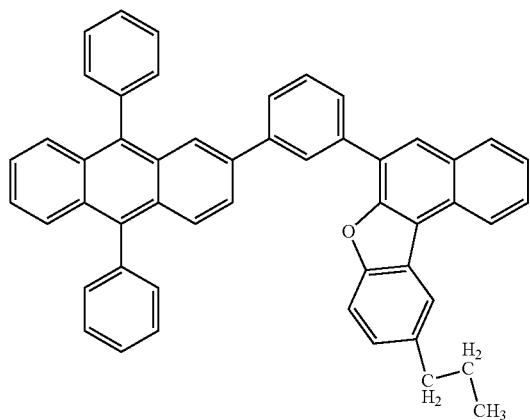
(104)
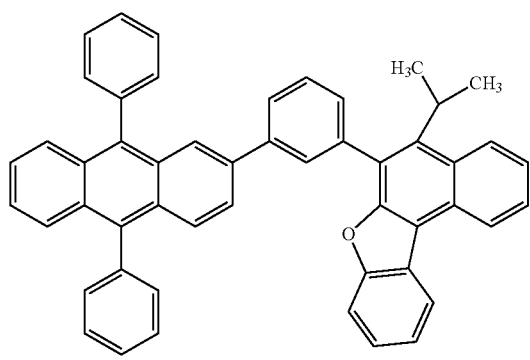
(105)
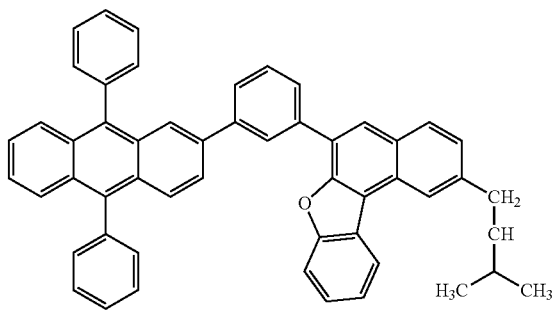
(106)
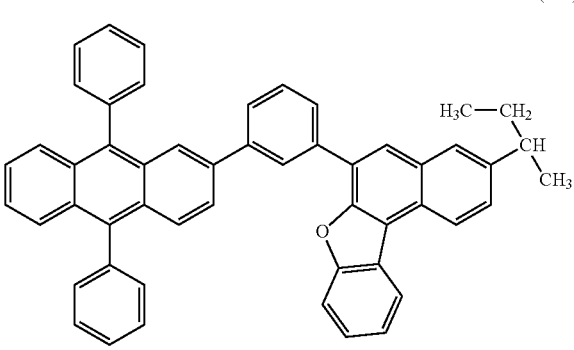
(107)
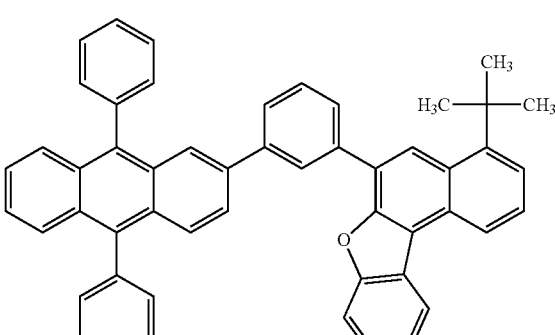
(108)
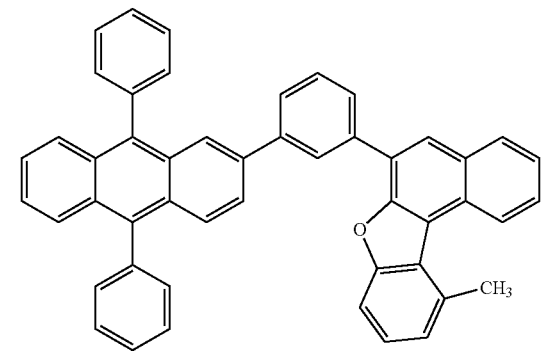

(109)
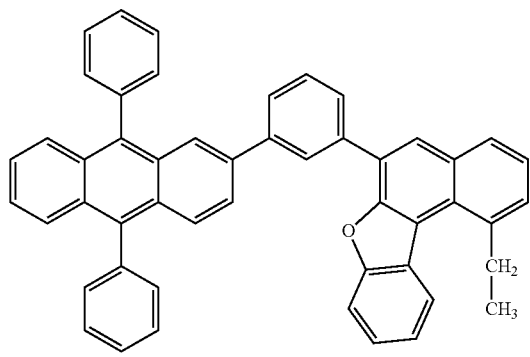
(110)
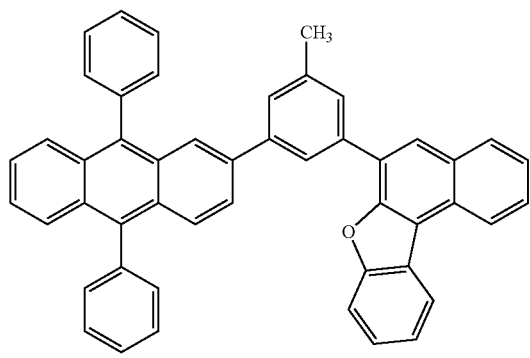
(111)
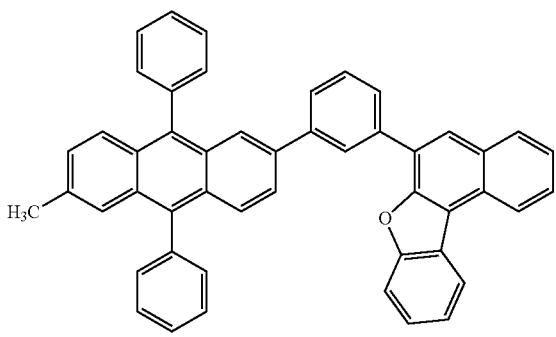
(112)
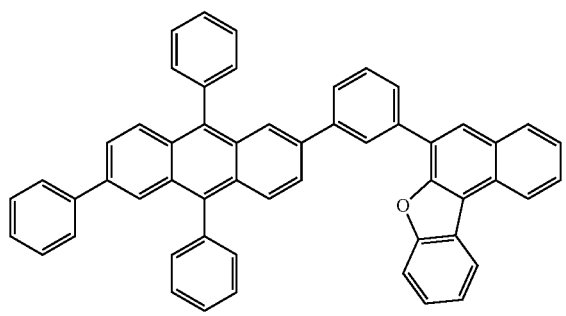
(113)
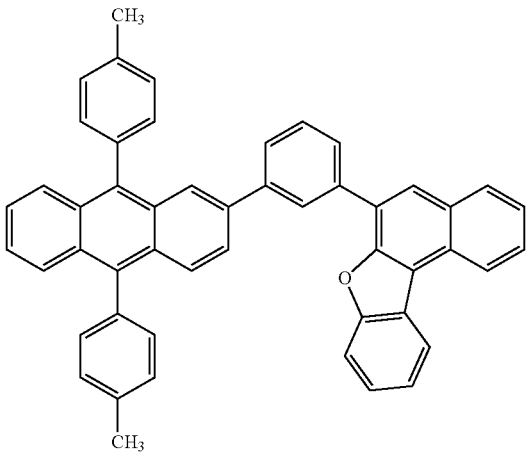
(114)
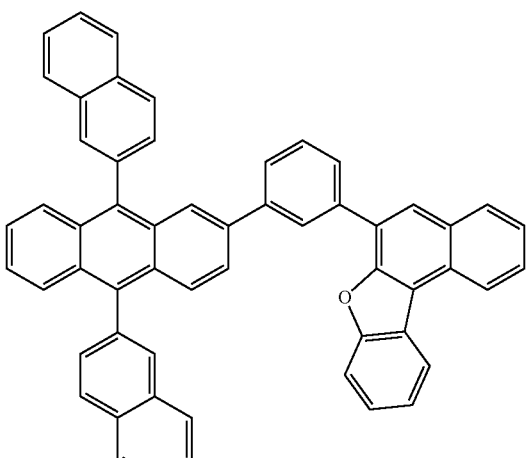
(115)
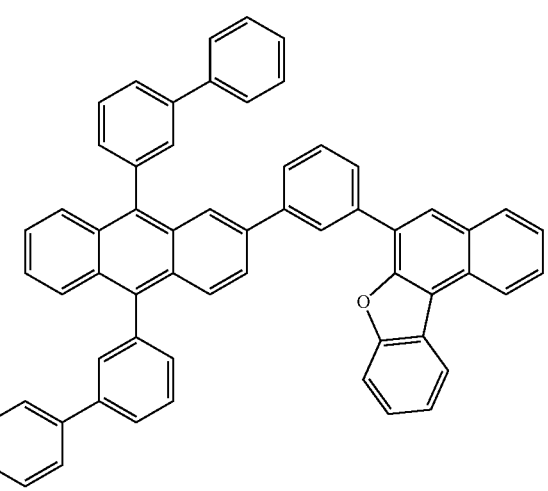

(116)
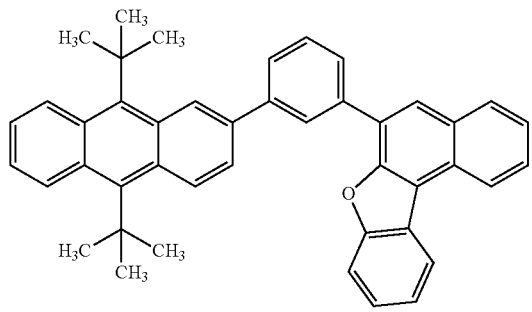
(117)
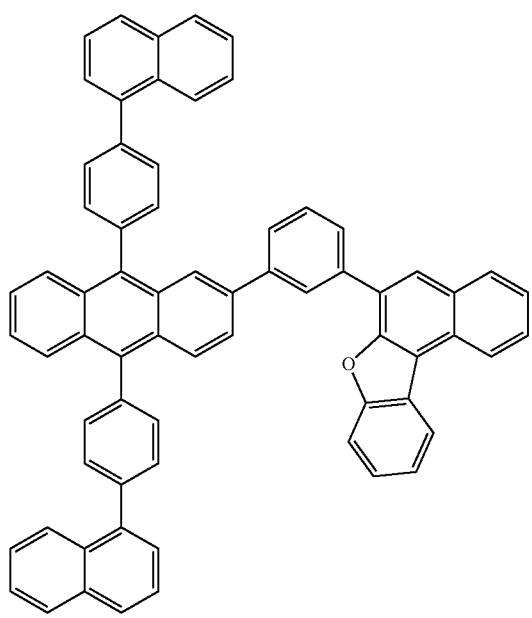
(118)
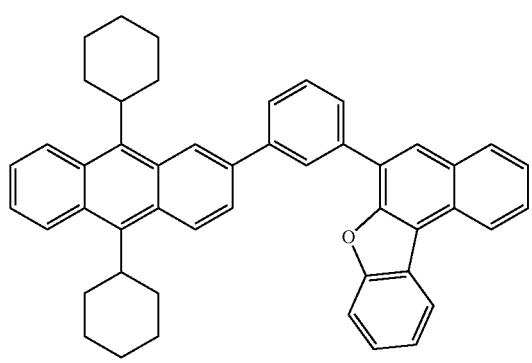
(119)
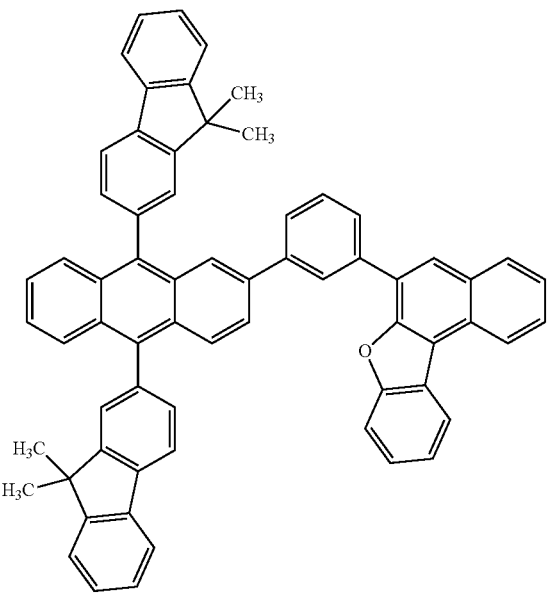
(120)
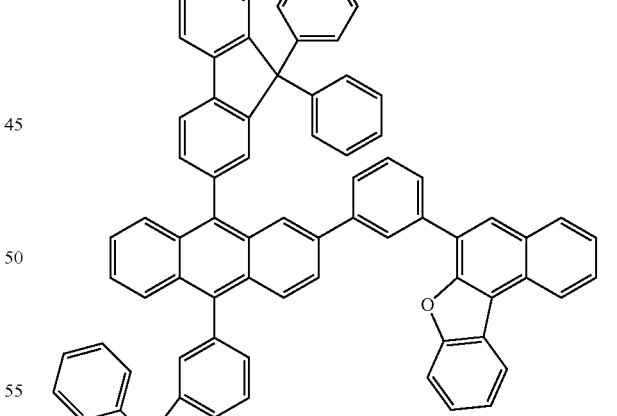

(121)
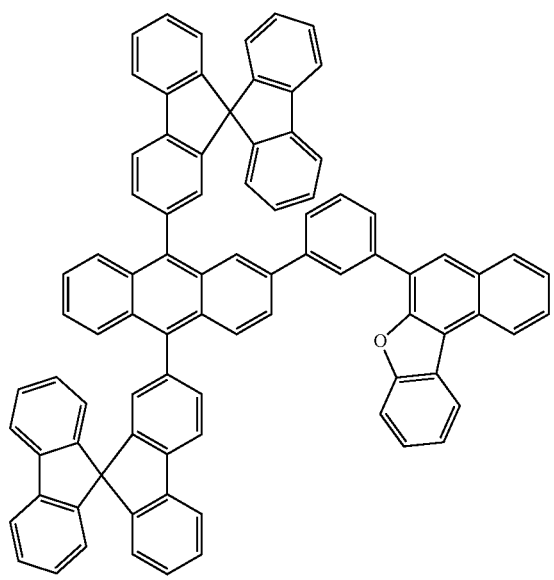
(122)
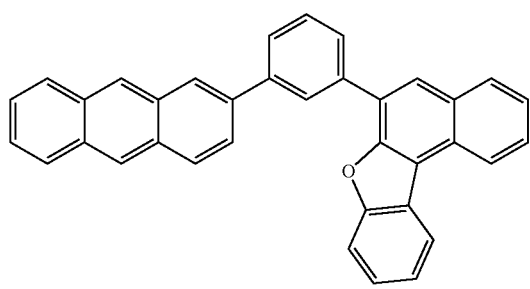
(123)
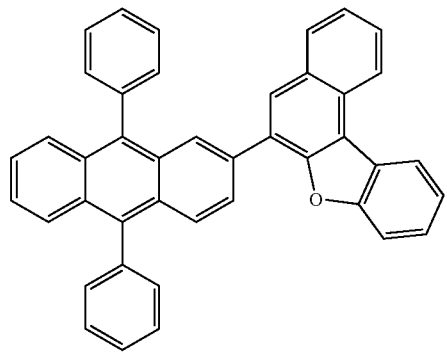
(124)
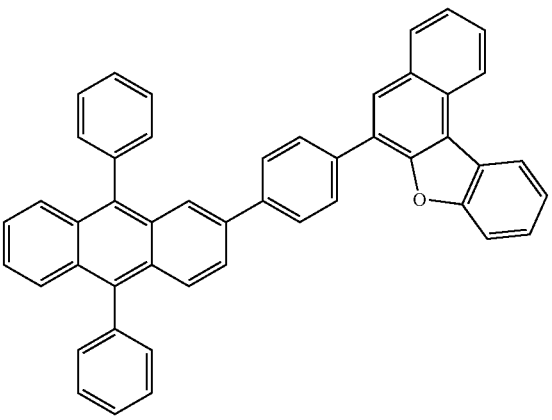
(125)
(126)
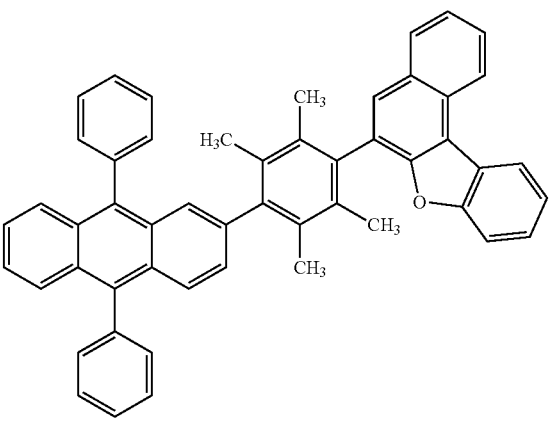

(127)
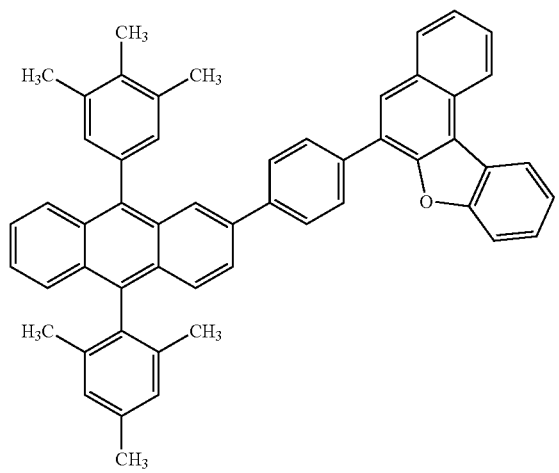
(128)
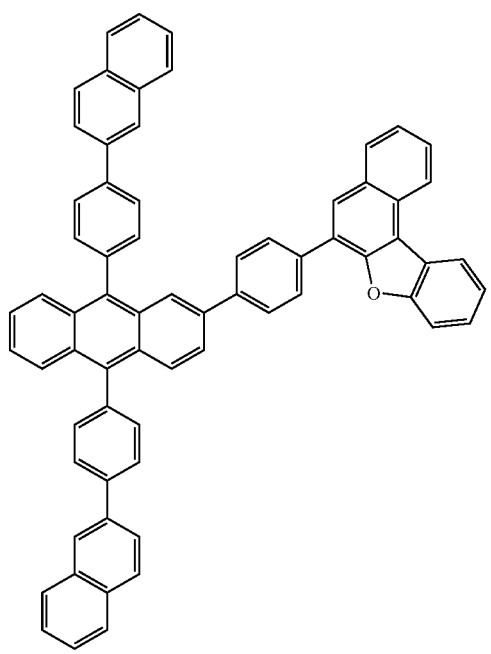
(129)
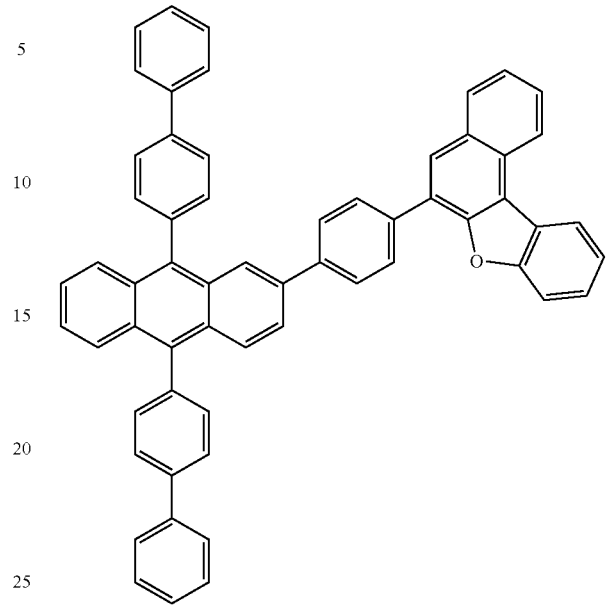
(130)
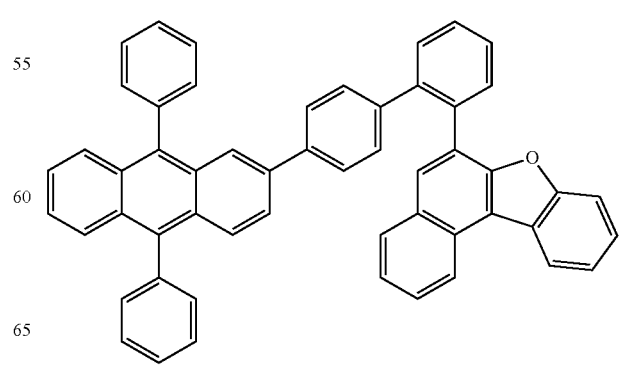
(131)

-continued
(132)
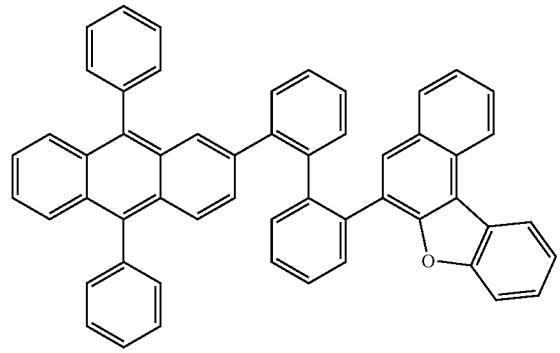
(133)
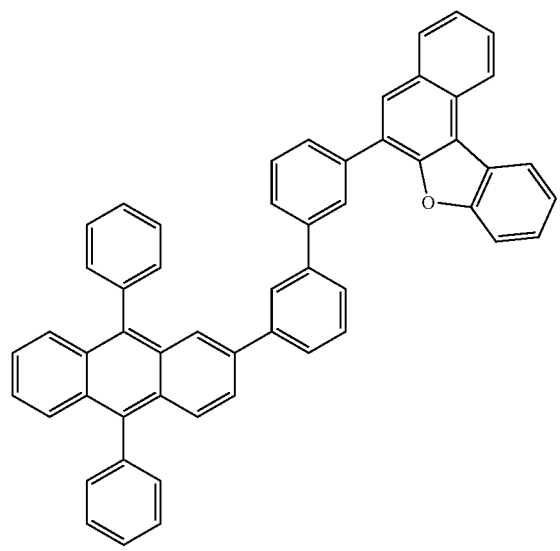
(134)
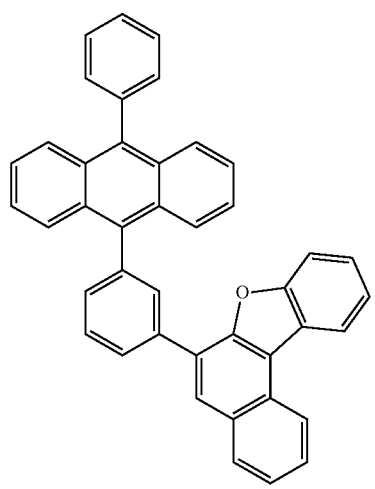
-continued
(135)
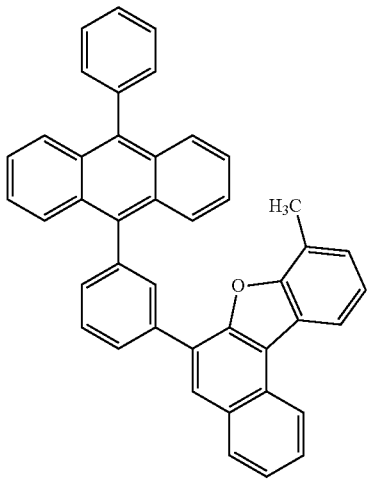
(136)
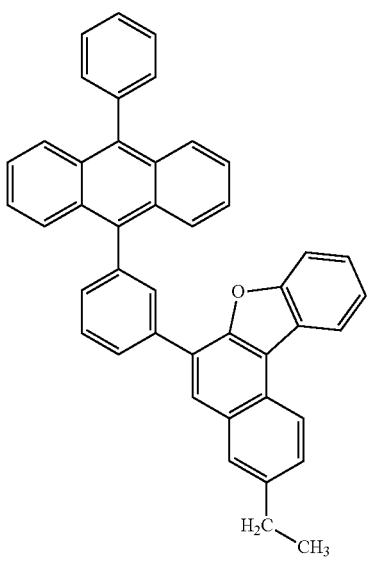
(137)
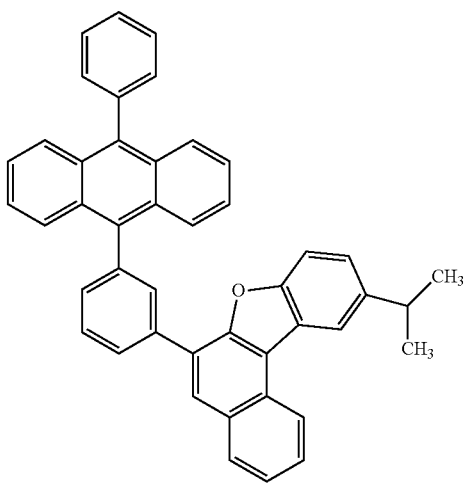

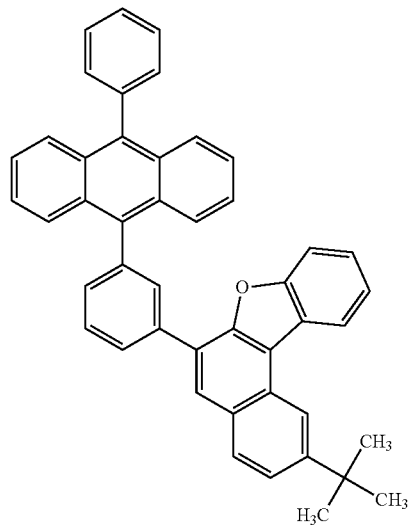
(138)
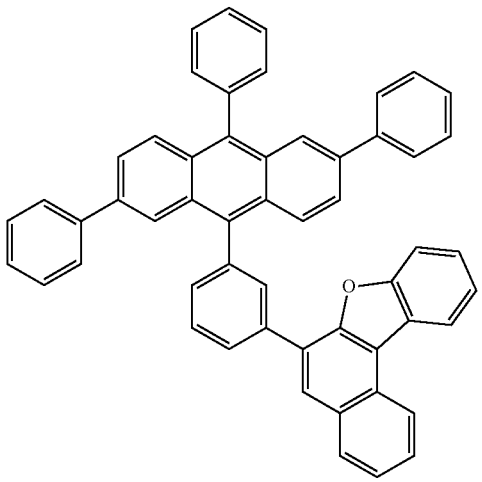
(141)
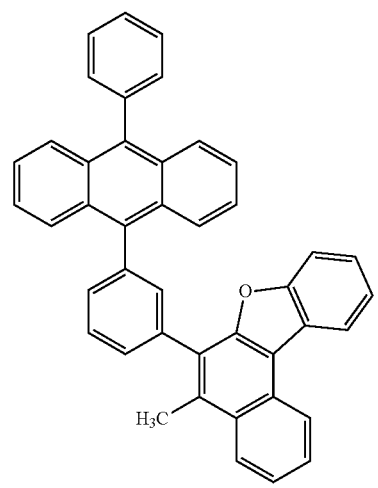
(139)
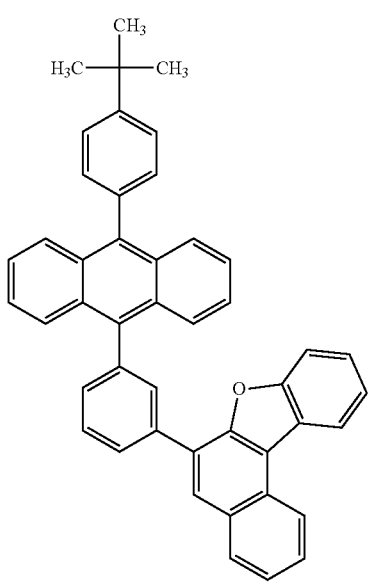
(142)
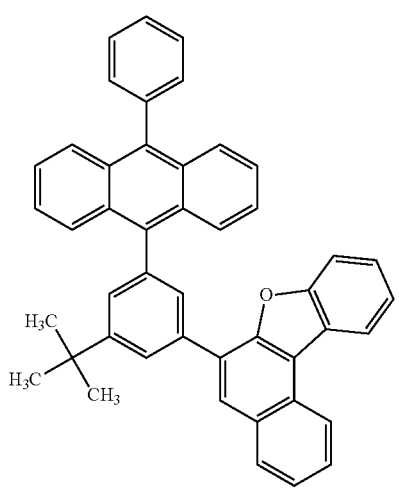
(140)
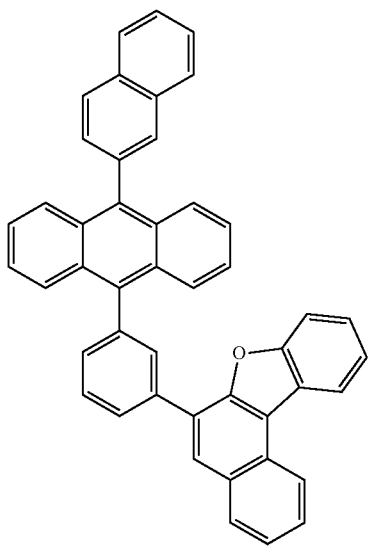
(143)

(144)
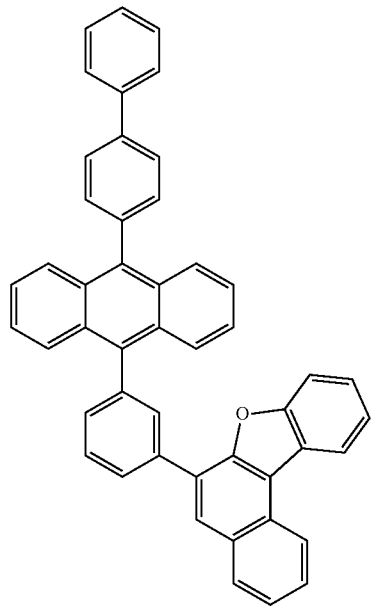
(145)
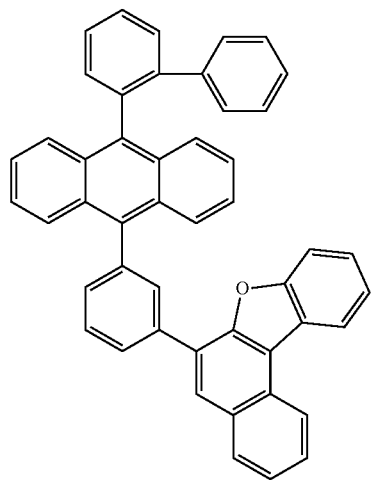
(146)
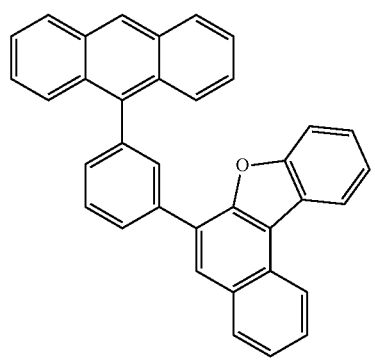
(147)
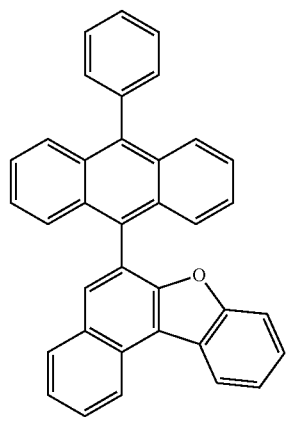
(149)
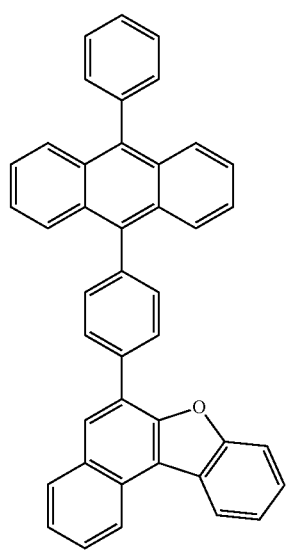
(150)
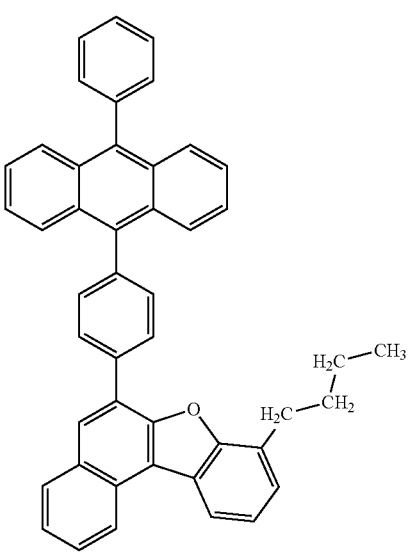

(151)
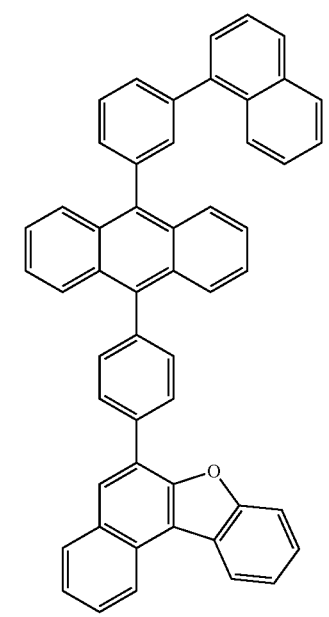
(152)
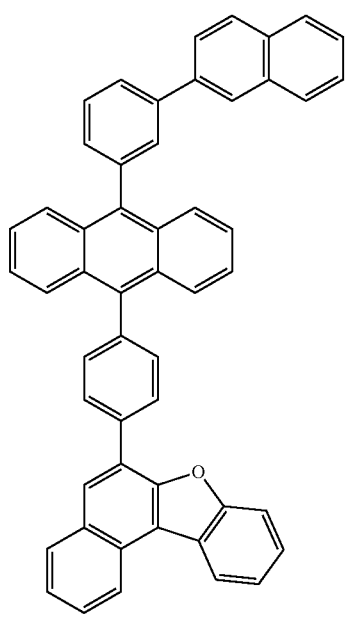
(153)
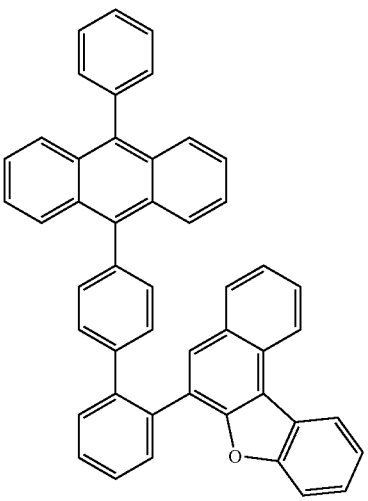
(154)
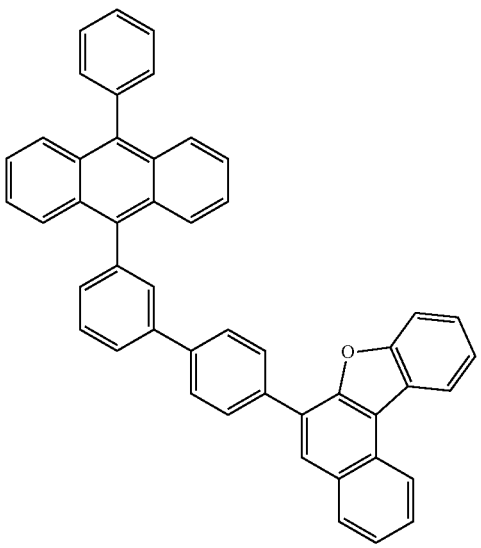
(155)
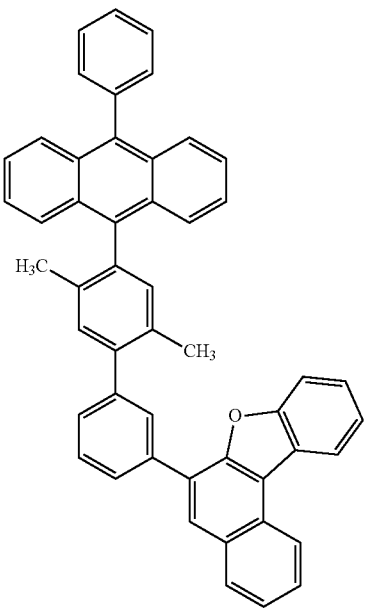

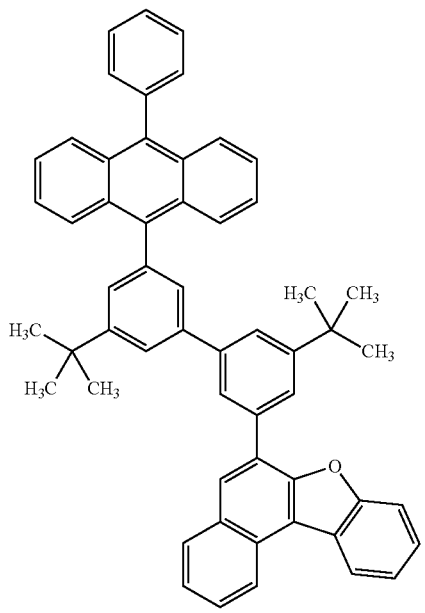

(156)

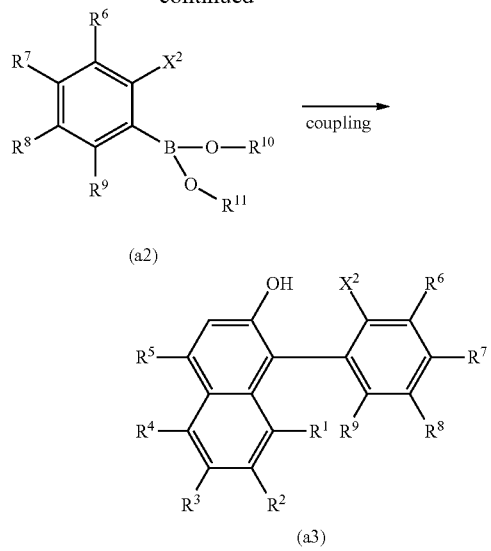

(a2)

(a3)

First, a β-naphthol derivative having a halogen group (a3) can be synthesized as in the synthesis scheme (A-1). Specifically, a halogen compound of a β-naphthol derivative or a compound of a β-naphthol derivative which has a triflate group (a1) undergoes coupling with an organoboron compound or boronic acid of an aryl derivative which has a halogen group (a2), using a Suzuki-Miyaura reaction with a palladium catalyst; thus, the β-naphthol derivative having a halogen group (a3) can be obtained.

In the synthesis scheme (A-1), $R^1$ to $R^9$ separately represent either hydrogen or an alkyl group having 1 to 4 carbon atoms. Further, $R^{10}$ and $R^{11}$ separately represent either hydrogen or an alkyl group having 1 to 6 carbon atoms, and may be the same or different and bonded to each other to form a ring. In addition, $X^1$ represents a halogen or a triflate group, and when $X^1$ is a halogen, bromine or iodine is particularly preferred. Further, $X^2$ represents a halogen, preferably fluorine, chlorine, iodine, or bromine, more preferably fluorine.

Examples of the palladium catalyst that can be used in the synthesis scheme (A-1) include palladium(II) acetate, tetrakis(triphenylphosphine)palladium(0), and the like. Examples of a ligand of the palladium catalyst which can be used in the synthesis scheme (A-1) include tri(ortho-tolyl)phosphine, triphenylphosphine, tricyclohexylphosphine, and the like. In addition, examples of the base that can be used include organic bases such as sodium tert-butoxide, inorganic bases such as potassium carbonate and sodium carbonate, and the like. Further, examples of the solvent that can be used are the following ones: toluene; xylene; an alcohol such as ethanol; a mixed solvent of toluene and an alcohol such as ethanol; a mixed solvent of xylene and an alcohol such as ethanol; a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane and water; and the like. Use of a mixed solvent of toluene and water or a mixed solvent of toluene, ethanol, and water is more preferred.

Alternatively, in this coupling, an organoboron compound or boronic acid of a β-naphthol derivative in which boron is bonded instead of $X^1$ may undergo coupling with a dihalogen Among the benzo[b]naphtho[1,2-d]furan compounds according to one embodiment of the present invention, the one having a structure in which an anthryl group is bonded to the 2-position is especially preferred because a light-emitting element using the material can have a longer lifetime.

A variety of reactions can be applied to the method of synthesizing benzo[b]naphtho[1,2-d]furan compounds according to one embodiment of the present invention. For example, synthesis reactions illustrated in synthesis schemes (A-1) to (A-5) below enable the synthesis of the benzo[b]naphtho[1,2-d]furan compounds represented by the general formulae (G1) and (G2) according to one embodiment of the present invention. Note that the methods of synthesizing the benzo[b]naphtho[1,2-d]furan compounds according to one embodiment of the present invention are not limited to the following ones.

Synthesis Method 1 of Benzo[b]naphtho[1,2-d]furan Compound Represented by General Formula (G1)

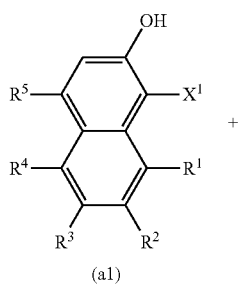

(A-1)

(a1)

compound of an aryl derivative in which carbon bonded to boron is halogenated, using a Suzuki-Miyaura reaction. Still alternatively, in this coupling, an organoboron compound or boronic acid of a β-naphthol derivative in which boron is bonded instead of $X^1$ may undergo coupling with a compound of an aryl derivative in which carbon bonded to boron has a triflate group, using a Suzuki-Miyaura reaction.

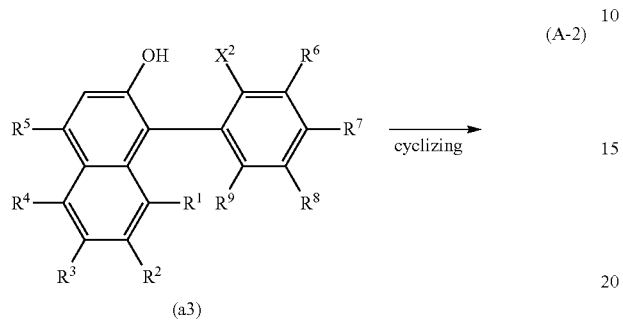

(A-2)

(a3)

(a4)

Next, a benzo[b]naphtho[1,2-d]furan compound (a4) can be synthesized as in the synthesis scheme (A-2). Specifically, according to a Williamson ether synthesis, the β-naphthol derivative (a3) is intramolecularly cyclized by formation of an ether bond to form a benzo[b]naphtho[1,2-d]furan ring, so that the benzo[b]naphtho[1,2-d]furan compound (a4) can be obtained.

Examples of the base that can be used in the synthesis scheme (A-2) are, but are not limited to, inorganic bases such as sodium hydride, potassium carbonate, potassium hydroxide, and the like. In addition, a salt such as sodium iodide may be added to the base. Examples of the solvent that can be used include, but are not limited to, aprotic polar solvents such as acetonitrile, N,N-dimethylformamide (DMF), dimethyl sulfoxide (DMSO), and N-methyl-pyrrolidone (NMP) and ketones such as cyclohexanone and 2-butanone, and, acetone.

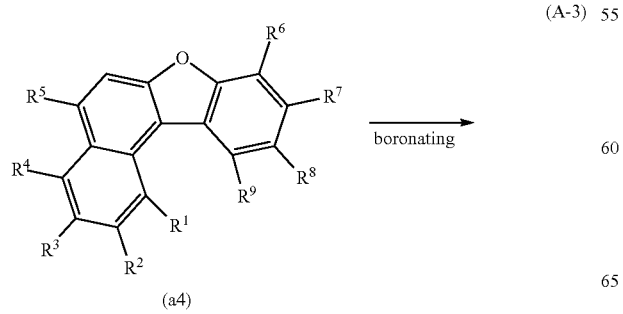

(A-3)

(a4)

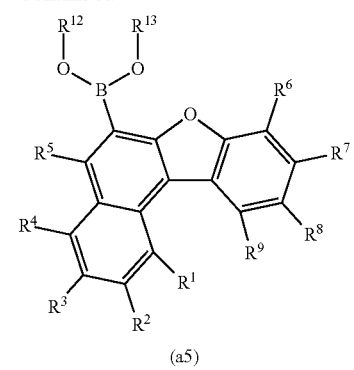

(a5)

Next, boronic acid or an organoboron compound of a benzo[b]naphtho[1,2-d]furan compound (a5) can be synthesized as in the synthesis scheme (A-3). Specifically, the benzo[b]naphtho[1,2-d]furan compound (a4) is converted into boronic acid or organoboron with use of an alkyllithium reagent and a boron reagent, so that the boronic acid of the benzo[b]naphtho[1,2-d]furan compound (a5) can be obtained. In the case where the compound (a5) is boronic acid, $R^{12}$ and $R^{13}$ each represent hydrogen. In addition, the boronic acid of the compound (a5) may be protected by ethylene glycol or the like, and in this case, $R^{12}$ and $R^{13}$ in the compound (a5) each represent an alkyl group having 1 to 6 carbon atoms. Alternatively, in the case where the compound (a5) is an organoboron compound, $R^{12}$ and $R^{13}$ may be the same or different and bonded to each other to form a ring.

In the synthesis scheme (A-3), an ether-based solvent such as diethyl ether, tetrahydrofuran (THF), or cyclopentyl methyl ether can be used. However, the solvent that can be used is not limited to these solvents. Further, the alkyllithium reagent may be, but not limited to, n-butyllithium, sec-butyl lithium, tert-butyl lithium, or the like. Furthermore, addition of a coordinating additive to such an alkyllithium reagent can enhance reactivity. The coordinating additive that can be used may be, but not limited to, tetramethylethylenediamine (TMEDA) or the like. In addition, the boron reagent may be, but not limited to, trimethyl borate, triisopropyl borate, or the like.

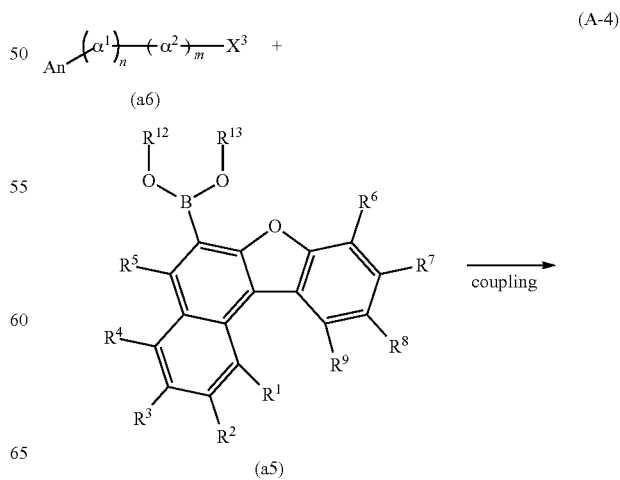

(A-4)

(a6)

(a5)

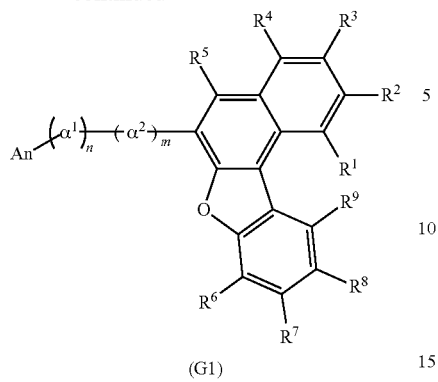

(G1)

Next, the benzo[b]naphtho[1,2-d]furan compound (G1) according to one embodiment of the present invention can be synthesized as in the synthesis scheme (A-4). Specifically, a halogen compound of an anthracene derivative or a compound of an anthracene derivative which has a triflate group (a6) undergoes coupling with boronic acid or an organoboron compound of the benzo[b]naphtho[1,2-d]furan compound (a5), using a Suzuki-Miyaura reaction with a palladium catalyst; thus, the benzo[b]naphtho[1,2-d]furan compound (G1) according to one embodiment of the present invention can be obtained.

In the synthesis scheme (A-4), An represents a substituted or unsubstituted anthracenyl group represented by the general formula (An-1) or (An-2) below. In addition, $R^{14}$ to $R^{31}$ separately represent any one of hydrogen, an alkyl group having 1 to 6 carbon atoms, and a substituted or unsubstituted aryl group having 6 to 13 carbon atoms.

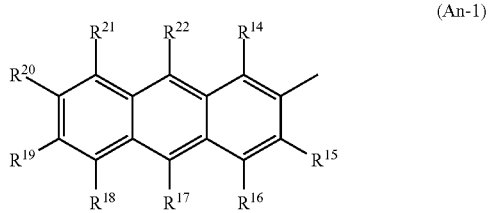

(An-1)

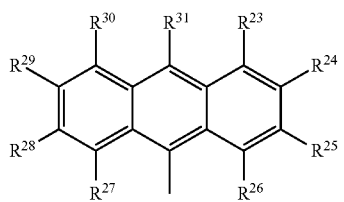

(An-2)

Furthermore, $X^3$ represents a halogen or a triflate group, and when $X^3$ is a halogen, chlorine, bromine, or iodine is especially preferred. In addition, $\alpha^1$ and $\alpha^2$ separately represent a substituted or unsubstituted phenylene group represented by any one of the general formulae (α-1) to (α-3) below. Further, $R^{32}$ to $R^{43}$ separately represent either hydrogen or an alkyl group having 1 to 4 carbon atoms. In addition, n and m separately represent 0 or 1.

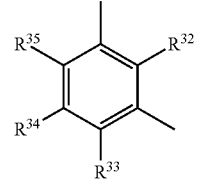

(α-1)

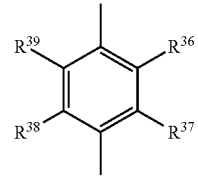

(α-2)

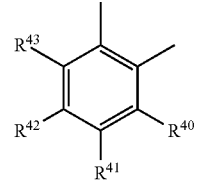

(α-3)

Examples of the palladium catalyst that can be used in the synthesis scheme (A-4) include palladium(II) acetate, tetrakis(triphenylphosphine)palladium(0), and the like. Examples of a ligand of the palladium catalyst which can be used in the synthesis scheme (A-4) include tri(ortho-tolyl)phosphine, triphenylphosphine, tricyclohexylphosphine, and the like. In addition, examples of the base that can be used include organic bases such as sodium tert-butoxide, inorganic bases such as potassium carbonate and sodium carbonate, and the like. Further, examples of the solvent that can be used are the following ones: toluene; xylene; an alcohol such as ethanol; a mixed solvent of toluene and an alcohol such as ethanol; a mixed solvent of xylene and an alcohol such as ethanol; a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane and water; and the like. Use of a mixed solvent of toluene and water or a mixed solvent of toluene, ethanol, and water is more preferred.

Alternatively, in this coupling, an organoboron compound or boronic acid of an anthracene compound in which boron is bonded instead of $X^3$ may undergo coupling with a halogen compound of a benzo[b]naphtho[1,2-d]furan compound in which carbon bonded to boron is halogenated, using a Suzuki-Miyaura reaction. Still alternatively, in this coupling, an organoboron compound or boronic acid of an anthracene compound in which boron is bonded instead of $X^3$ may undergo coupling with a compound of a benzo[b]naphtho[1, 2-d]furan compound in which carbon bonded to boron has a triflate group, using a Suzuki-Miyaura reaction.

Synthesis Method 2 of Benzo[b]naphtho[1,2-d]furan Compound Represented by General Formula (G1)

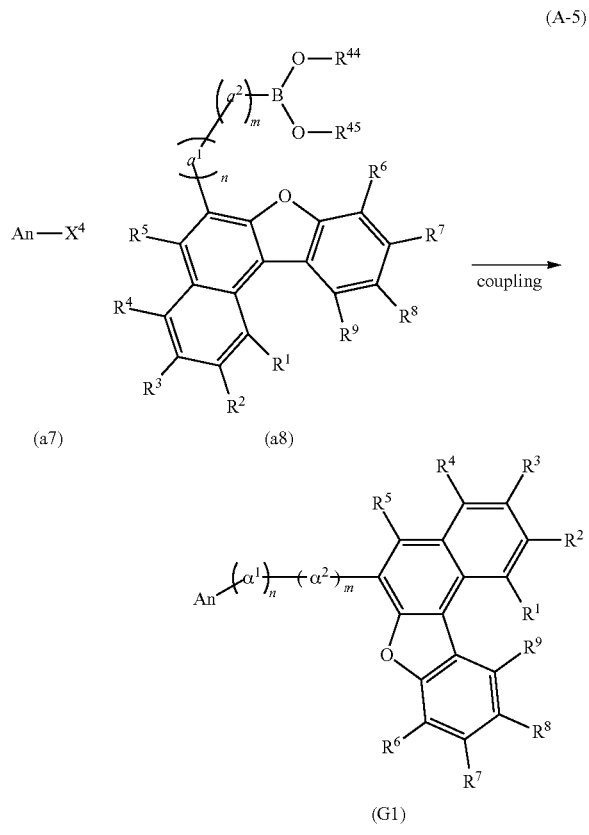

(G1)

The benzo[b]naphtho[1,2-d]furan compound (G1) according to one embodiment of the present invention can alternatively be synthesized as in the synthesis scheme (A-5). Specifically, a halogen compound of an anthracene derivative or a compound of an anthracene derivative which has a triflate group (a7) undergoes coupling with boronic acid or an organoboron compound of a benzo[b]naphtho[1,2-d]furan compound (a8), using a Suzuki-Miyaura reaction with a palladium catalyst; thus, the benzo[b]naphtho[1,2-d]furan compound (G1) according to one embodiment of the present invention can alternatively be obtained.

In the synthesis scheme (A-5), $R^{44}$ and $R^{45}$ separately represent either hydrogen or an alkyl group having 1 to 6 carbon atoms, and may be the same or different and bonded to each other to form a ring. In addition, $X^4$ represents a halogen or a triflate group, and when $X^4$ is a halogen, chlorine, bromine, or iodine is especially preferred.

Examples of the palladium catalyst that can be used in the synthesis scheme (A-5) include palladium(II) acetate, tetrakis(triphenylphosphine)palladium(0), and the like. Examples of a ligand of the palladium catalyst which can be used in the synthesis scheme (A-5) include tri(ortho-tolyl)phosphine, triphenylphosphine, tricyclohexylphosphine, and the like. In addition, examples of the base that can be used include organic bases such as sodium tert-butoxide, inorganic bases such as potassium carbonate and sodium carbonate, and the like. Further, examples of the solvent that can be used are the following ones: toluene; xylene; an alcohol such as ethanol; a mixed solvent of toluene and an alcohol such as ethanol; a mixed solvent of xylene and an alcohol such as ethanol; a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane and water; and the like. Use of a mixed solvent of toluene and water or a mixed solvent of toluene, ethanol, and water is more preferred.

Alternatively, in this coupling, an organoboron compound or boronic acid of an anthracene compound in which boron is bonded instead of $X^4$ may undergo coupling with a halogen compound of a benzo[b]naphtho[1,2-d]furan compound in which carbon bonded to boron is halogenated, using a Suzuki-Miyaura reaction. Still alternatively, in this coupling, an organoboron compound or boronic acid of an anthracene compound in which boron is bonded instead of $X^4$ may undergo coupling with a compound of a benzo[b]naphtho[1,2-d]furan compound in which carbon bonded to boron has a triflate group, using a Suzuki-Miyaura reaction.

Synthesis Method of β-Naphthol Compound Represented by General Formula (a11)

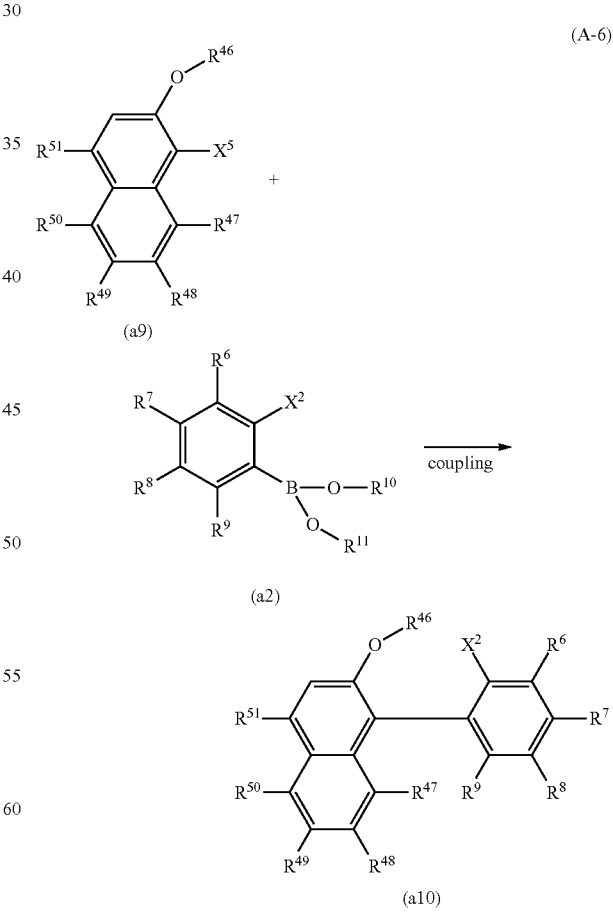

With use of a halogen compound of a naphthalene which has an alkoxide group or a compound of a naphthalene which has an alkoxide group which has a triflate group (a9), instead of the halogen compound of a β-naphthol derivative or the compound of a β-naphthol derivative which has a triflate group (a1) in the synthesis scheme (A-1), a hydroxyl group in (a1) can be protected, and a substituent can be more easily introduced into the halogen compound of a β-naphthol derivative or the compound of a β-naphthol derivative which has a triflate group (a3).

A halogen compound of a naphthalene derivative which has an alkoxide group or a compound of a naphthalene derivative which has an alkoxide group which has a triflate group (a10) can be synthesized as in a synthesis scheme (A-6). Specifically, the halogen compound of a naphthalene derivative which has an alkoxide group or the compound of a naphthalene which has an alkoxide group which has a triflate group (a9) undergoes coupling with the organoboron compound or boronic acid of an aryl derivative which has a halogen group (a2), using a Suzuki-Miyaura reaction with a palladium catalyst; thus, the alkoxide compound of a naphthalene derivative (a10) can be obtained.

In the synthesis scheme (A-6), $R^{46}$ represents an alkyl group having 1 to 6 carbon atoms. In addition, $R^{47}$ to $R^{51}$ separately represent either hydrogen or an alkyl group having 1 to 4 carbon atoms. In addition, $X^5$ represents a halogen or a triflate group, and when $X^5$ is a halogen, chlorine, bromine, or iodine is especially preferred.

Examples of the palladium catalyst that can be used in the synthesis scheme (A-6) include palladium(II) acetate, tetrakis(triphenylphosphine)palladium(0), and the like. Examples of a ligand of the palladium catalyst which can be used in the synthesis scheme (A-6) include tri(ortho-tolyl)phosphine, triphenylphosphine, tricyclohexylphosphine, and the like. In addition, examples of the base that can be used include organic bases such as sodium tert-butoxide, inorganic bases such as potassium carbonate and sodium carbonate, and the like. Further, examples of the solvent that can be used are the following ones: toluene; xylene; an alcohol such as ethanol; a mixed solvent of toluene and an alcohol such as ethanol; a mixed solvent of xylene and an alcohol such as ethanol; a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane and water; and the like. Use of a mixed solvent of toluene and water or a mixed solvent of toluene, ethanol, and water is more preferred.

Alternatively, in this coupling, an organoboron compound or boronic acid of an alkoxide compound of a naphthalene derivative in which boron is bonded instead of $X^5$ may undergo coupling with a halogen compound of an aryl derivative in which carbon bonded to boron is halogenated, using a Suzuki-Miyaura reaction. Still alternatively, in this coupling, an organoboron compound or boronic acid of an alkoxide compound of a naphthalene derivative in which boron is bonded instead of $X^5$ may undergo coupling with a compound of an aryl derivative in which carbon bonded to boron has a triflate group, using a Suzuki-Miyaura reaction.

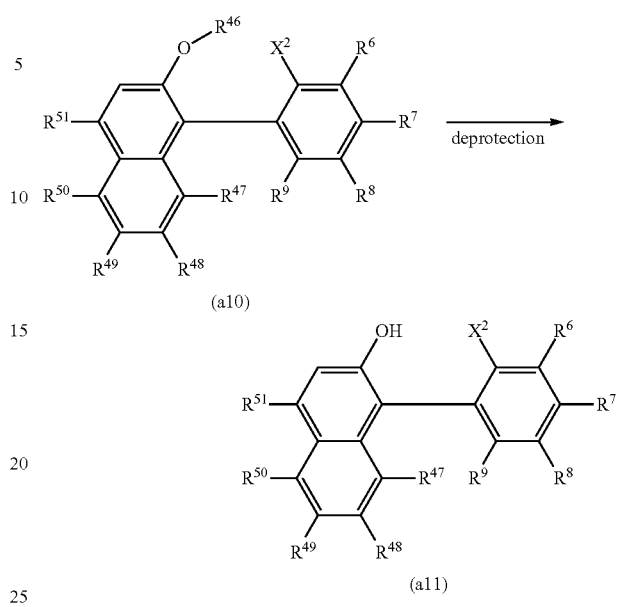

Next, deprotection of the naphthalene compound having an alkoxide group (a10) is described. A β-naphthol derivative having a halogen group (a11) can be synthesized as in a synthesis scheme (A-7). Specifically, the halogen compound of a naphthalene derivative which has an alkoxide group or the compound of a naphthalene derivative which has an alkoxide group which has a triflate group (a10) is deprotected with a Lewis acid; thus, the β-naphthol derivative having a halogen group (a11) can be obtained.

As the Lewis acid that can be used in the synthesis scheme (A-7), boron tribromide, trimethyliodosilane, or the like is preferred when $R^{46}$ is a methyl group. Alternatively, trifluoroacetic acid, a 4 mol/L hydrochloric acid.ethyl acetate solution or the like is preferred when $R^{46}$ is a tert-butyl group. Further, examples of the solvent that can be used include, but are not limited to, halogen-based solvents such as dichloromethane, chloroform, and carbon tetrachloride, and aromatic hydrocarbon-based solvents such as toluene and xylene.

As described above, the benzo[b]naphtho[1,2-d]furan compounds according to this embodiment can be synthesized.

The benzo[b]naphtho[1,2-d]furan compounds according to this embodiment have a very large band gap and accordingly enables blue light emission with good color purity. In addition, the benzo[b]naphtho[1,2-d]furan compounds according to this embodiment are bipolar materials having a hole-transport property and an electron-transport property. Further, the benzo[b]naphtho[1,2-d]furan compounds according to this embodiment are benzo[b]naphtho[1,2-d]furan compounds having high electrochemical stability and high thermal stability.

In addition to the capability of being used alone for an emission center material in a layer containing a light-emitting substance (light-emitting layer), the benzo[b]naphtho[1,2-d]furan compounds according to this embodiment can be used for a host material. With a structure in which a dopant material as a light-emitting substance is dispersed into any of the benzo[b]naphtho[1,2-d]furan compounds according to this embodiment, light emission from the dopant material as a light-emitting substance can be obtained. In the case where any of the benzo[b]naphtho[1,2-d]furan compounds according to one embodiment of the present invention is used for a host material, efficient light emission can be obtained from a dopant that has an emission maximum of about 450 nm to 700 nm. With the benzo[b]naphtho[1,2-d]furan compounds according to one embodiment of the present invention, even short-wavelength blue light emission with good color purity can be obtained.

Furthermore, as a layer containing a light-emitting substance, a layer in which any of the benzo[b]naphtho[1,2-d]furan compounds according to this embodiment is dispersed into a material (host) having a larger band gap than the benzo[b]naphtho[1,2-d]furan compound can be used, so that light emission form the benzo[b]naphtho[1,2-d]furan compound according to this embodiment can be obtained. That is, the benzo[b]naphtho[1,2-d]furan compounds according to this embodiment can also function as a dopant material. In this case, since the benzo[b]naphtho[1,2-d]furan compounds according to this embodiment have a very large band gap and show light emission at a short wavelength, it is possible to fabricate a light-emitting element with which blue light emission with good color purity can be obtained.

The benzo[b]naphtho[1,2-d]furan compounds according to this embodiment can be used for a carrier-transport material in a functional layer of a light-emitting element, for example, a hole-transport layer, a hole-injection layer, an electron-transport layer, or an electron-injection layer which are carrier-transport layers. Thus, the use of any of the benzo[b]naphtho[1,2-d]furan compounds according to this embodiment in a light-emitting element realizes the light-emitting element which has good carrier balance and low driving voltage.

Furthermore, a light-emitting element including any of the above benzo[b]naphtho[1,2-d]furan compounds according to this embodiment is a light-emitting element that does not easily deteriorate and has a long lifetime and high reliability.

This embodiment can be implemented in appropriate combination with any of the other embodiments.

[Embodiment 2]

In Embodiment 2, as one embodiment of the present invention, a light-emitting element including any of the benzo[b]naphtho[1,2-d]furan compounds described in Embodiment 1 is described with reference to FIGS. 1A and 1B.

In the light-emitting element of Embodiment 2, an EL layer including at least a light-emitting layer is interposed between a pair of electrodes. The EL layer may have a plurality of layers in addition to the light-emitting layer. The plurality of layers has a structure in which a layer containing a substance having a high carrier-injection property and a layer containing a substance having a high carrier-transport property are combined and stacked so that a light-emitting region is formed in a region away from the electrodes, that is, so that carriers recombine in a region away from the electrodes. The plurality of layers may include, for example, a hole-injection layer, an electron-injection layer, an electron-transport layer, and the like.

In the light-emitting element of Embodiment 2 which is illustrated in FIG. 1A, an EL layer 102 is provided between a pair of electrodes, a first electrode 101 and a second electrode 103. The EL layer 102 includes a hole-injection layer 111, a hole-transport layer 112, a light-emitting layer 113, an electron-transport layer 114, and an electron-injection layer 115. Note that, in the light-emitting element described in this embodiment, the first electrode 101 functions as an anode and the second electrode 103 functions as a cathode.

The substrate 100 is used as a support of the light-emitting element. For the substrate 100, for example, glass, quartz, plastic, or the like can be used. A flexible substrate may be used. The flexible substrate is a substrate that can be bent, such as a plastic substrate made of polycarbonate, polyarylate, or polyether sulfone, for example. A film made of polypropylene, polyester, polyvinyl fluoride, polyvinyl chloride, or the like, an inorganic film formed by evaporation, or the like can be used. Note that materials other than these can be used as far as they can function as a support of the light-emitting element.

For the first electrode 101, any of metals, alloys, electrically conductive compounds, mixtures thereof, and the like which has a high work function (specifically, a work function of 4.0 eV or more) is preferably used. Specific examples include indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide, and the like. Films of these electrically conductive metal oxides are usually formed by sputtering, but may be formed by application of a sol-gel method or the like. For example, a film of indium oxide-zinc oxide can be formed by a sputtering method using a target obtained by addition of 1 wt % to 20 wt % of zinc oxide to indium oxide. Further, a film of indium oxide containing tungsten oxide and zinc oxide can be formed by a sputtering method using a target obtained by addition of 0.5 wt % to 5 wt % of tungsten oxide and 0.1 wt % to 1 wt % of zinc oxide to indium oxide. Other examples are gold, platinum, nickel, tungsten, chromium, molybdenum, iron, cobalt, copper, palladium, nitrides of metal materials (e.g., titanium nitride), and the like.

When a layer included in the EL layer 102 and formed in contact with the first electrode 101 is formed using a later-described composite material in which an organic compound and an electron acceptor (acceptor) are mixed, as a substance used for the first electrode 101, any of a variety of metals, alloys, and electrically conductive compounds, a mixture thereof, and the like can be used regardless of the work function; for example, aluminum, silver, an alloy containing aluminum (e.g., Al—Si), or the like can also be used.

In the EL layer 102 formed over the first electrode 101, at least the light-emitting layer 113 includes any of the benzo[b]naphtho[1,2-d]furan compounds according to one embodiment of the present invention. Further, since the benzo[b]naphtho[1,2-d]furan compounds according to one embodiment of the present invention are materials having a bipolar property, they can each also be used for a material of a carrier-transport layer (e.g., the hole-transport layer or the electron-transport layer) in the EL layer 102. For part of the EL layer 102, a known substance can be used, and either a low molecular compound or a high molecular compound can be used. Note that substances included in the EL layer 102 may consist of organic compounds or may include an inorganic compound as a part.

The hole-injection layer 111 is a layer that includes a substance having a high hole-injection property. As the substance having a high hole-injection property, for example, any of metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide can be used. A phthalocyanine-based compound such as phthalocyanine (abbreviation: $H_2Pc$), or copper(II) phthalocyanine (abbreviation: CuPc) can also be used.

Further, examples of the substance that can be used are aromatic amine compounds which are low molecular organic compounds, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3N-[(1-naphthyl)-N-(9-phenylcarbazol-3-yl)amino]-9-phenylcarbazole (abbreviation: PCzPCN1).

Other examples of the substance that can be used are high molecular compounds (e.g., oligomers, dendrimers, and polymers), such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD), and high molecular compounds to which acid is added, such as poly(3,4-ethylenedioxythiophene)/poly(styrenesulfonic acid) (PEDOT/PSS) and polyaniline/poly(styrenesulfonic acid) (PAni/PSS).

For the hole-injection layer 111, the composite material in which an organic compound and an electron acceptor (acceptor) are mixed may be used. Such a composite material, in which the electron acceptor causes hole generation in the organic compound, has excellent hole-injection and hole-transport properties. The organic compound here is preferably a material excellent in transporting the generated holes (a substance having a high hole-transport property).

As the organic compound used for the composite material, any of a variety of compounds, such as aromatic amine compounds, carbazole derivatives, aromatic hydrocarbons, and high molecular compounds (e.g., oligomers, dendrimers, and polymers) can be used. Note that the organic compound used for the composite material is preferably an organic compound having a high hole-transport property. Specifically, a substance having a hole mobility of $10^{-6}$ cm$^2$/Vs or more is preferably used. Any of the benzo[b]naphtho[1,2-d]furan compounds described in Embodiment 1 can also be used. Other than these substances, a substance that has a property of transporting more holes than electrons may be used. Organic compounds that can be used for the composite material are specifically given below.

The benzo[b]naphtho[1,2-d]furan compounds according to one embodiment of the present invention are organic compounds having a high hole-transport property, and thus can be suitably used for the composite material. Other examples of the organic compound that can be used for the composite material are aromatic amine compounds, such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP), and carbazole derivatives, such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl]-2,3,5,6-tetraphenylbenzene.

Any of the following aromatic hydrocarbon compounds can be used: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Further, examples of the electron acceptor used for the composite material are organic compounds, such as 7,7,8,8-tetracyano-2,3,5,6-tetrafluoroquinodimethane (abbreviation: $F_4$-TCNQ) and chloranil, oxides of transition metals, and oxides of metals that belong to Groups 4 to 8 in the periodic table, and the like. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air, has a low hygroscopic property, and is easily treated.

The composite material may be formed using the above-described electron acceptor and the above-described high molecular compound such as PVK, PVTPA, PTPDMA, or Poly-TPD, so that the composite material may be used for the hole-injection layer 111.

The hole-transport layer 112 is a layer that includes a substance with a high hole-transport property. Examples of the substance having a high hole-transport property include aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), and the like. The substances mentioned here are mainly ones that have a hole mobility of $10^{-6}$ cm$^2$/V·s or more. Any of the benzo[b]naphtho[1,2-d]furan compounds described in Embodiment 1 can also be used. Other than these substances, a substance that has a property of transporting more holes than electrons may be used. Further, the layer containing a substance having a high hole-transport property is not limited to a single layer, and may be a stack of two or more layers containing any of the above substances.

A high molecular compound such as poly(N-vinylcarbazole) (abbreviation: PVK) or poly(4-vinyltriphenylamine) (abbreviation: PVTPA) can also be used for the hole-transport layer 112.

The light-emitting layer 113 is a layer that includes a light-emitting substance (the layer is also referred to as a light-emitting layer). In Embodiment 2, the light-emitting layer 113 is formed using any of the benzo[b]naphtho[1,2-d]furan compounds described in Embodiment 1. Since the benzo[b]naphtho[1,2-d]furan compounds described in Embodiment 1 emit blue light emission, they can be suitably used for a light-emitting substance in a light-emitting element.

Alternatively, the benzo[b]naphtho[1,2-d]furan compounds described in Embodiment 1 can also be used for a host. When the light-emitting layer 113 has a structure in which a dopant as a light-emitting substance is dispersed into any of the benzo[b]naphtho[1,2-d]furan compounds described in Embodiment 1, light emission from the dopant can be obtained. The benzo[b]naphtho[1,2-d]furan compounds described in Embodiment 1 enable a dopant having an emission maximum of about 450 nm to 700 nm to efficiently emit light. Since the benzo[b]naphtho[1,2-d]furan compounds described in Embodiment 1 have a large band gap, not light emission from the benzo[b]naphtho[1,2-d]furan compound but light emission from the dopant can be efficiently obtained even when the dopant that is used shows light emission at a relatively short wavelength. Specifically, even when a material having an emission maximum of about 450 nm to 470 nm, which is a light-emitting material showing excellent color purity of blue, is used for a dopant, a light-emitting element capable of blue light emission with good color purity can be obtained.

When any of the benzo[b]naphtho[1,2-d]furan compounds described in Embodiment 1 is used for a material into which another light-emitting substance is dispersed, it is possible to obtain the emission color due to the light-emitting substance. It is also possible to obtain an emission color that is a mixture of the emission color due to the benzo[b]naphtho[1,2-d]furan compound described in Embodiment 1 and the emission color due to the light-emitting substance dispersed into the benzo[b]naphtho[1,2-d]furan compound.

Alternatively, any of the benzo[b]naphtho[1,2-d]furan compounds described in Embodiment 1 is added in a layer containing a material (host) having a larger band gap than the benzo[b]naphtho[1,2-d]furan compound described in Embodiment 1 to fabricate a light-emitting element, so that light emission form the benzo[b]naphtho[1,2-d]furan compound described in Embodiment 1 can be obtained. That is, the benzo[b]naphtho[1,2-d]furan compounds described in Embodiment 1 can also function as a dopant. In this case, since the benzo[b]naphtho[1,2-d]furan compounds described in Embodiment 1 have a very large band gap and show light emission at a short wavelength, blue light emission with good color purity can be obtained with the fabricated light-emitting element.

A wide variety of materials can be used for the light-emitting substance dispersed into any of the benzo[b]naphtho[1,2-d]furan compounds described in Embodiment 1. Specifically, as a fluorescent compound, the following light-emitting materials can be given, for example: materials that emit blue light, such as N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl)triphenylamine (abbreviation: PCBAPA); materials that emit green light, such as N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), and N,N,9-triphenylanthracen-9-amine (abbreviation: DPhAPhA); materials that emit yellow light, such as rubrene and 5,12-bis(1,1'-biphenyl-4-yl)-6,11-diphenyltetracene (abbreviation: BPT); and materials that emit red light, such as N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-dia mine (abbreviation: p-mPhAFD).

As a phosphorescent compound for the light-emitting substance dispersed into any of the benzo[b]naphtho[1,2-d]furan compounds described in Embodiment 1, the following materials that emit red light can be given, for example: organometallic complexes such as bis[2-(2'-benzo[4,5-α]thienyl)pyridinato-N,$C^{3'}$)iridium(III)acetylacetonate (abbreviation: Ir(btp)$_2$(acac)), bis(1-phenylisoquinolinato-N,$C^{2'}$)iridium(III)acetylacetonate (abbreviation: Ir(piq)$_2$(acac), (acetylacetonato)bis[2,3-bis(4-fluorophenyl)quinoxalinato]iridium (III) (abbreviation: Ir(Fdpq)$_2$(acac)), acetylacetonatobis(2,3,5-triphenylpyrazinato)iridium(III) (abbreviation: Ir(tppr)$_2$(acac)), (dipivaloylmethanato)bis(2,3,5-niphenylpyrazinato)iridium(III) (abbreviation: Ir(tppr)$_2$(dpm)), and (2,3,7,8,12,13,17,18-octaethyl-21H,23H-porphine)platinum(II) (abbreviation: PtOEP). As the phosphorescent compound, any of the following rare-earth metal complexes can also be used: tris(acetylacetonato)(monophenanthroline)terbium (III) (abbreviation: [Tb(acac)$_3$(Phen)); tris(1,3-diphenyl-1,3-propanedionato)(monophenanthroline)europium(III) (abbreviation: Eu(DBM)$_3$(Phen)); and tris[1-(2-thenyl)-3,3,3-trifluoroacetonato](monophenanthroline)europium(III) (abbreviation: Eu(TTA)$_3$(Phen)), because their light emission is from a rare-earth metal ion (electronic transition between different multiplicities) in such a rare-earth metal complex.

As the light-emitting substance, a high molecular compound can also be used. Specifically, the following light-emitting materials can be given, for example: materials that emit blue light, such as poly(9,9-dioctylfluorene-2,7-diyl) (abbreviation: PFO), poly[(9,9-dioctylfluorene-2,7-diyl)-co-(2,5-dimethoxybenzene-1,4-diyl)] (abbreviation: PF-DMOP), and poly{(9,9-dioctylfluorene-2,7-diyl)-co-[N,N'-di-(p-butylphenyl)-1,4-diaminobenzene]} (abbreviation: TAB-PFH); materials that emit green light, such as poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), and poly[(9,9-dioctyl-2,7-divinylenefluorenylene)-alt-co-(2-methoxy-5-(2-ethylhexyloxy)-1,4-phenylene)]; and materials that emit orange to red light, such as poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-d]hexyl-2,7-bis(1-cyanovinylene)fluorenylene]-alt-co-[2,5-bis(N,N'-diphenylamino)-1,4-phenylene]}, and poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD).

In addition, more than one kind of substances can be used for the host material in the light-emitting layer 113. For example, besides the benzo[b]naphtho[1,2-d]furan compounds described in Embodiment 1, addition of a substance that suppresses crystallization, such as rubrene, is possible for suppression of crystallization. Addition of NPB, Alq, or the like is also possible for more efficient transfer of energy into a guest material.

With a structure in which the guest material is dispersed into the host material, crystallization of the light-emitting layer 113 can be suppressed. Further, concentration quenching due to high concentration of the guest material can be suppressed.

The light-emitting layer 113 may have a structure in which two or more layers are stacked; in this case, at least one of the layers include any of the benzo[b]naphtho[1,2-d]furan compounds according to one embodiment of the present invention. Note that in the case where the light-emitting layer 113 has a structure in which two or more layers are stacked, the emission colors of the layers may be the same or different. Further, it is possible to stack a layer including a fluorescent compound as a light-emitting substance and a layer including a phosphorescent compound as a light-emitting substance.

The electron-transport layer 114 is a layer that includes a substance having a high electron-transport property. As the substance having a high electron-transport property, any of the following substances can be used, for example: a metal complex having a quinoline skeleton or a benzoquinoline skeleton such as tris(8-quinolinolato)aluminum (abbreviation: Alq), tris(4-methyl-8-quinolinolato)aluminum (abbreviation: Almq$_3$), bis(10-hydroxybenzo[h]-quinolinato)beryllium (abbreviation: BeBq$_2$), or bis(2-methyl-8-quinolinolato)(4-phenylphenolato)aluminum (abbreviation: BAlq). Alternatively, it is possible to use a metal complex or the like including an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$) can be used. Besides the metal complexes, it is also possible to use 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like. The substances mentioned here are mainly ones that have an electron mobility of $10^{-6}$ cm$^2$/V·s or more. Any of the benzo[b]naphtho[1,2-d]furan compounds described in Embodiment 1 can also be used. Further, the electron-transport layer is not limited to a single layer, and may be a stack of two or more layers containing any of the above substances.

The electron-injection layer 115 is a layer that includes a substance having a high electron-injection property. For the electron-injection layer 115, an alkali metal, an alkaline-earth metal, or a compound thereof, such as lithium, cesium, calcium, lithium fluoride, cesium fluoride, calcium fluoride, or lithium oxide, can be used. A rare-earth metal compound such as erbium fluoride can also be used. The above-mentioned substances included in the electron-transport layer 114 can also be used.

Alternatively, a composite material in which an organic compound and an electron acceptor donor (donor) are mixed may be used for the electron-injection layer 115. Such a composite material, in which the electron donor causes electron generation in the organic compound, has excellent electron-injection and electron-transport properties. The organic compound here is preferably a material excellent in transporting the generated electrons, as which specifically any of the above substances (such as metal complexes and heteroaromatic compounds) included in the electron-transport layer 114 can be used. The electron donor is preferably a substance showing an electron-donating property with respect to the organic compound. Specifically, an alkali metal, an alkaline earth metal, and a rare earth metal are preferable, and lithium, cesium, magnesium, calcium, erbium, ytterbium, and the like can be given. Alkali metal oxides and alkaline-earth metal oxides are preferable, examples of which are lithium oxide, calcium oxide, barium oxide, and the like, and a Lewis base such as magnesium oxide or an organic compound such as tetrathiafulvalene (abbreviation: TTF) can be used.

The benzo[b]naphtho[1,2-d]furan compounds described in Embodiment 1 have a wide band gap and are bipolar materials having a high electron-transport property and a high hole-transport property. Therefore, the benzo[b]naphtho[1,2-d]furan compounds described in Embodiment 1 can be used for a carrier-transport layer to function as a hole-transport layer, a hole-injection layer, an electron-transport layer, or an electron-injection layer. Thus, a light-emitting element according to Embodiment 2 which uses any of the benzo[b]naphtho[1,2-d]furan compounds described in Embodiment 1 has good carrier balance and low driving voltage.

Further, the light-emitting element according to Embodiment 2 which includes any of the benzo[b]naphtho[1,2-d]furan compounds described in Embodiment 1 is a light-emitting element that does not easily deteriorate and has a long lifetime and high reliability.

Note that the hole-injection layer 111, the hole-transport layer 112, the light-emitting layer 113, the electron-transport layer 114, and the electron-injection layer 115 which are described above can each be formed by a method, such as an evaporation method (e.g., a vacuum evaporation method), an inkjet method, or a coating method.

When the second electrode 103 functions as a cathode, any of metals, alloys, electrically conductive compounds, mixtures thereof, and the like which has a low work function (specifically, a work function of 3.8 eV or less) is preferably used for the second electrode 103. Specific examples of the substance that can be used are elements that belong to Groups 1 and 2 in the periodic table, that is, alkali metals such as lithium and cesium, alkaline earth metals such as magnesium, calcium, and strontium, alloys thereof (e.g., Mg—Ag and Al—Li), rare earth-metals such as europium and ytterbium, alloys thereof, aluminum, silver, and the like.

When a layer included in the EL layer 102 and formed in contact with the second electrode 103 is formed using the above-described composite material in which the organic compound and the electron donor (donor) are mixed any of a variety of conductive materials, such as aluminum, silver, ITO, indium oxide-tin oxide containing silicon or silicon oxide, and graphene can be used regardless of the work function.

When the second electrode 103 is formed, a vacuum evaporation method or a sputtering method can be used. In the case where a silver paste or the like is used, a coating method, an inkjet method, or the like can be used.

In the above-described light-emitting element, a current flows due to a potential difference generated between the first electrode 101 and the second electrode 103 and holes and electrons recombine in the EL layer 102, so that light is emitted. Then, this light emission is extracted to the outside through one or both of the first electrode 101 and the second electrode 103. Therefore, one or both of the first electrode 101 and the second electrode 103 are electrodes having a property of transmitting visible light.

Further, the structure of the layers provided between the first electrode 101 and the second electrode 103 is not limited to the above-described structure. A structure other than the above may alternatively be employed as far as a light-emitting region in which holes and electrons recombine is provided in a portion away from the first electrode 101 and the second electrode 103 so as to prevent quenching due to proximity of the light-emitting region to metal.

In other words, there is no particular limitation on a stack structure of the layers, and the light-emitting layer may freely be combined with a layer including a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like.

Figure 1B:
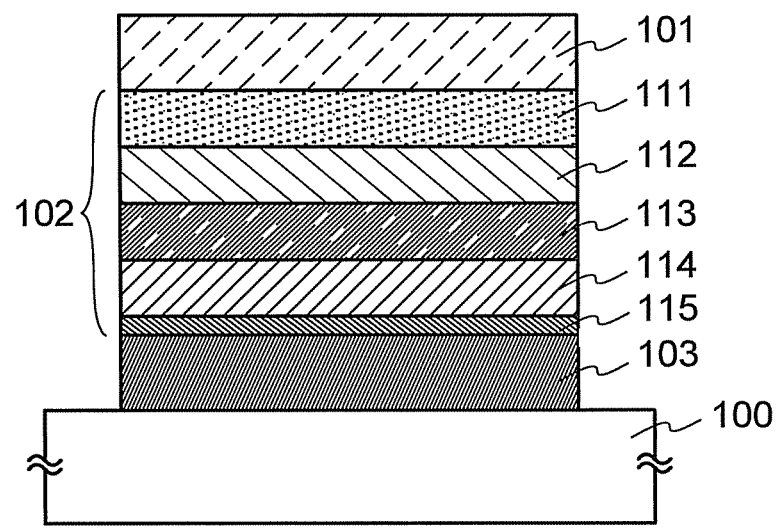

In the light-emitting element illustrated in FIG. 1B, the EL layer 102 is provided between a pair of electrodes, the first electrode 101 and the second electrode 103, over the substrate 100. The EL layer 102 includes the hole-injection layer 111, the hole-transport layer 112, the light-emitting layer 113, the electron-transport layer 114, and the electron-injection layer 115. The light-emitting element in FIG. 1B includes the second electrode 103 functioning as a cathode over the substrate 100, the electron-injection layer 115, the electron-transport layer 114, the light-emitting layer 113, the hole-transport layer 112, and the hole-injection layer 111, which are stacked over the second electrode 103 in this order, and the first electrode 101 provided thereover which functions as an anode.

A specific formation method of the light-emitting element is described below.

In the light-emitting element of Embodiment 2, the EL layer is interposed between the pair of electrodes. The electrodes (the first electrode and the second electrode) and the EL layer may be formed by any of wet processes such as a droplet discharging method (an inkjet method), a spin coating method, and a printing method, and by dry processes such as a vacuum evaporation method, a CVD method, and a sputtering method. Wet processes allow formation at atmospheric pressure with a simple device and a simple process, which gives the effects of simplifying the process and improving productivity. In contrast, dry processes do not need dissolution of a material and enable use of a material that has low solubility in a solution, which expands the range of material choices.

All the thin films included in the light-emitting element may be formed by a wet method. In this case, the light-emitting element can be manufactured with only facilities needed for a wet process. Alternatively, the following method may be employed: formation of the stacked layers up to formation of the light-emitting layer is performed using a wet process whereas a functional layer, the first electrode, and the like which are stacked over the light-emitting layer are formed using a dry process. Further alternatively, the following method may be employed: the second electrode and a functional layer are formed using a dry process before the formation of the light-emitting layer whereas the light-emitting layer, a functional layer stacked thereover, and the first electrode are formed using a wet process. Needless to say, this embodiment is not limited to these; appropriate selection and combination of wet processes and dry processes depending on a material to be used, necessary film thickness, and the interface state are possible so that the light-emitting element can be fabricated.

In the above manner, a light-emitting element can be fabricated using any of the above benzo[b]naphtho[1,2-d]furan compounds according to one embodiment of the present invention.

Note that a passive matrix light-emitting device or an active matrix light-emitting device in which a transistor controls driving of light-emitting elements can be fabricated using the light-emitting element described in Embodiment 2.

A light-emitting device including the light-emitting element described in Embodiment 2 is a light-emitting device with high color reproducibility or a light-emitting device with high display quality. The light-emitting device including the light-emitting element described, in Embodiment 2 is a light-emitting device with high reliability. The light-emitting device including the light-emitting element described in Embodiment 2 is a light-emitting device with low power consumption.

This embodiment can be implemented in appropriate combination with any of the other embodiments.

[Embodiment 3]

In this embodiment, a mode of a light-emitting element having a structure in which a plurality of light-emitting units is stacked (hereinafter, referred to as a stacked-type element) is described with reference to FIGS. 2A and 2B. This light-emitting element is a light-emitting element including a plurality of light-emitting units between a first electrode and a second electrode.

Figure 2A:
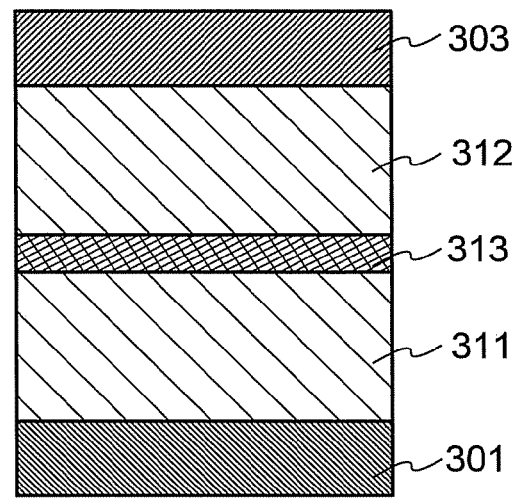
FIGS. 2A and 2B each illustrate a light-emitting element according to one embodiment of the present invention.

In FIG. 2A, a first light-emitting unit 311 and a second light-emitting unit 312 are stacked between a first electrode 301 and a second electrode 303. In this embodiment, the first electrode 301 functions as an anode and the second electrode 303 functions as a cathode. The first electrode 301 and the second electrode 303 can be the same as those in Embodiment 2. Further, the first light-emitting unit 311 and the second light-emitting unit 312 may have the same or different structures. The first light-emitting unit 311 and the second light-emitting unit 312 may have the same structure as the light-emitting layer 113 in Embodiment 2, or either of the units may differ in structure from the light-emitting layer 131 in Embodiment 2.

Further, a charge-generation layer 313 is provided between the first light-emitting unit 311 and the second light-emitting unit 312. The charge-generation layer 313 has a function of injecting electrons into one of the light-emitting units and injecting holes into the other of the light-emitting units when a voltage is applied between the first electrode 301 and the second electrode 303. In the case of this embodiment, when a voltage is applied so that the electric potential of the first electrode 301 is higher than that of the second electrode 303, the charge-generation layer 313 injects electrons into the first light-emitting unit 311 and injects holes into the second light-emitting unit 312.

Note that the charge-generation layer 313 preferably has a property of transmitting visible light in terms of light extraction efficiency. Further, the charge-generation layer 313 functions even if it has lower electric conductivity than the first electrode 301 or the second electrode 303.

The charge-generation layer 313 may have a structure in which it includes the organic compound having a high hole-transport property and the electron acceptor (acceptor) or a structure in which it includes an organic compound having a high electron-transport property and the electron donor (donor), or may be a stack of both of these structures. Note that the electron acceptor or the electron donor is at least capable of providing and receiving electrons with the assistance of an electric field.

In the case of a structure in which the electron acceptor is added to the organic compound having a high hole-transport property, any of the benzo[b]naphtho[1,2-d]furan compounds according to one embodiment of the present invention can be used as the organic compound having a high hole-transport property. Other examples are aromatic amine compounds, such as NPB, TPD, TDATA, MTDATA, and 4,4'-bis[N-(spiro-9,9'-bifluoren-2-yl)-N-phenylamino]biphenyl (abbreviation: BSPB), and the like.

Examples of the electron acceptor are 7,7,8,8-tetracyano-2,3,5,6-tetrafluoroquinodimethane (abbreviation: $F_4$-TCNQ), chloranil, oxides of transition metals, and oxides of metals that belong to Groups 4 to 8 in the periodic table, and the like. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air, has a low hygroscopic property, and is easily treated.

In the case of the structure in which the electron donor is added to the organic compound having a high electron-transport property, any of the following substances can be used as the organic compound having a high electron-transport property, for example: metal complexes having a quinoline skeleton or a benzoquinoline skeleton such as Alq, Ahmq$_3$, BeBq$_2$, and BAlq; metal complexes having an oxazole-based ligand or a thiazole-based ligand, such as Zn(BOX)$_2$ and Zn(BTZ)$_2$; and the like. Examples other than the metal complexes are PBD, OXD-7, TAZ, BPhen, BCP, and the like. Other examples that may be used are the benzo[b]naphtho[1,2-d]furan compounds according to one embodiment of the present invention.

As the electron donor, any of alkali metals, alkaline-earth metals, rare-earth metals, metals that belong to Group 13 in the periodic table and oxides or carbonates thereof can be used. Specifically, lithium, cesium, magnesium, calcium, ytterbium, indium, lithium oxide, cesium carbonate, or the like is preferably used. An organic compound, such as tetrathianaphthacene, may be used as the electron donor.

With the charge-generation layer 313 formed using any of the above materials, it is possible to suppress an increase in driving voltage caused when the EL layers are stacked.

Figure 2B:
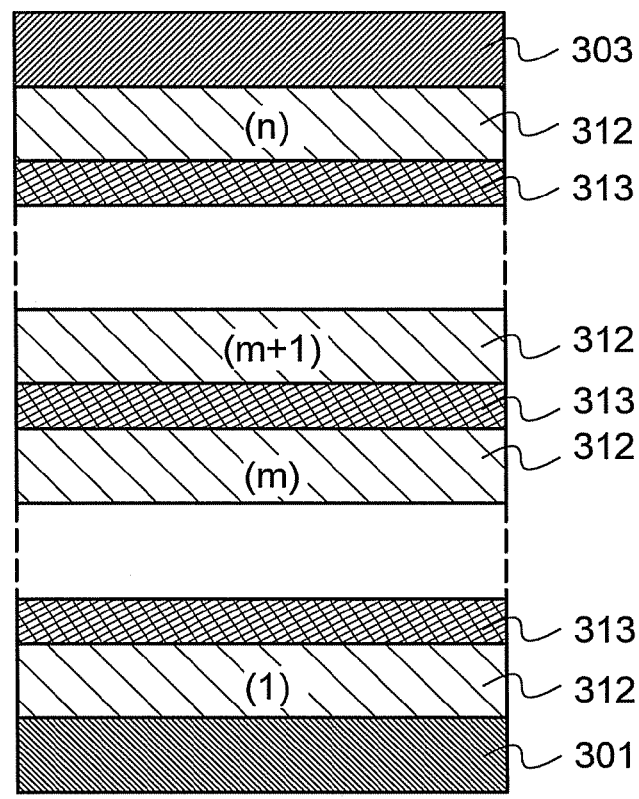

Although the light-emitting element having two light-emitting units is described in this embodiment, the embodiment can similarly be applied to a light-emitting element in which three or more light-emitting units are stacked as illustrated in FIG. 2B. With a plurality of light-emitting units partitioned by the charge-generation layer between a pair of electrodes, as in the light-emitting element according to this embodiment, light emission with high luminance can be realized while current density can be kept low; thus, a light-emitting element having a long lifetime can be realized.

Furthermore, different emission colors of the light-emitting units enable light emission having a desired color to be obtained from the light-emitting element as a whole. For example, the emission colors of first and second light-emitting units are complementary in a light-emitting element having the two light-emitting units, so that the light-emitting element can be made to emit white light as a whole. Note that the term "complementary" means color relationship in which an achromatic color is obtained when colors are mixed. Examples of complementary colors are blue and yellow, blue-green and red, and the like. In the case of a light-emitting element having three light-emitting units in which, for example, the emission color of the first light-emitting unit is red, the emission color of the second light-emitting unit is green, and the emission color of the third light-emitting unit is blue, white light emission can be obtained from the whole light-emitting element.

Note that this embodiment can be implemented in appropriate combination with any of the other embodiments.

[Embodiment 4]

Figure 3A:
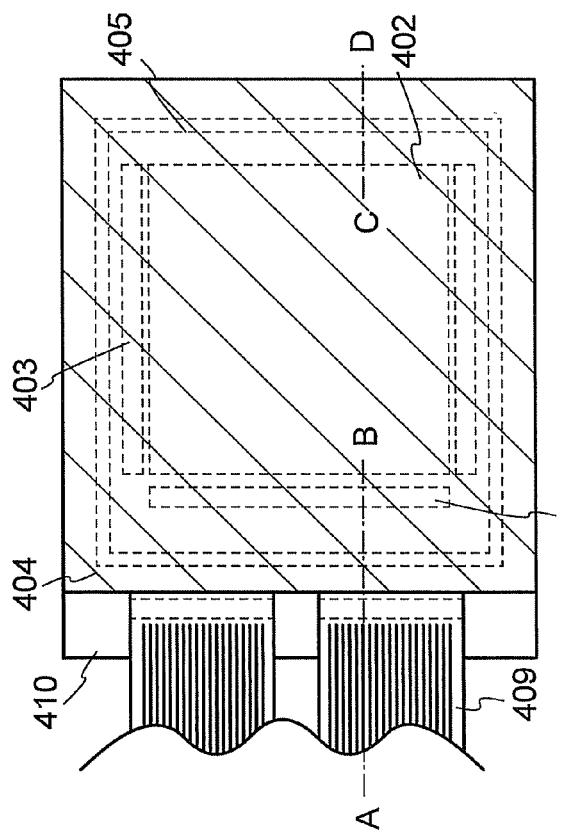
FIGS. 3A and 3B illustrate a light-emitting device according to one embodiment of the present invention.
Figure 3B:
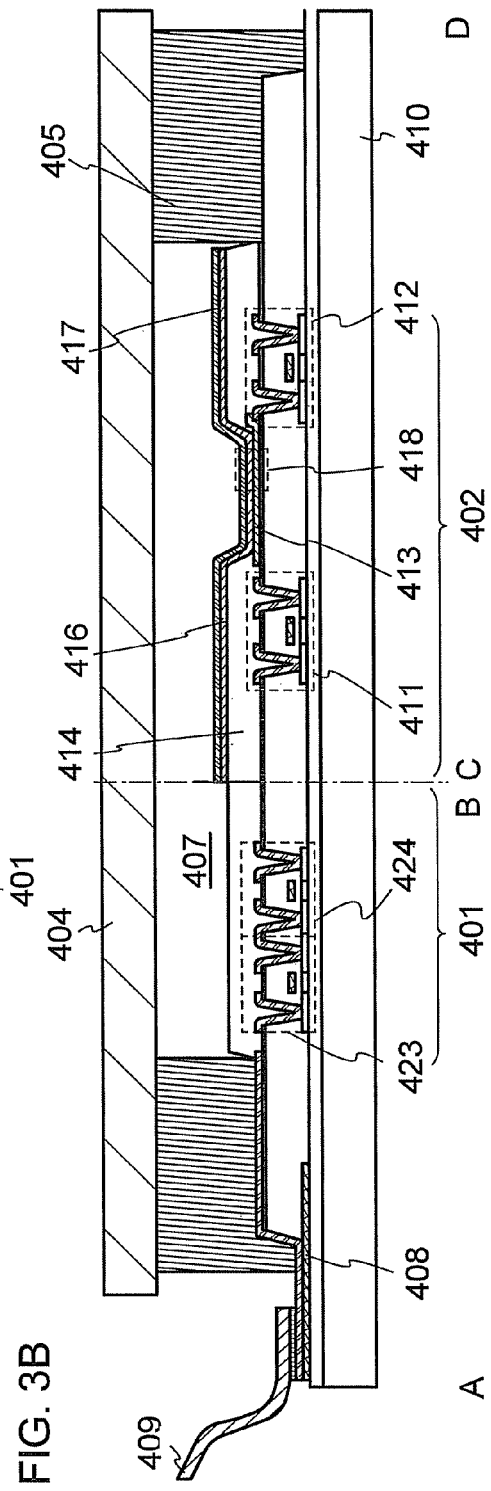

In Embodiment 4, a light-emitting device of one embodiment of the present invention is described with reference to FIGS. 3A and 3B, and FIG. 3A is a top view illustrating the light-emitting device while FIG. 3B is a cross-sectional view taken along lines A-B and C-D in FIG. 3A.

In FIG. 3A, reference numeral 401 denotes a driver circuit portion (source driver circuit), reference numeral 402 denotes a pixel portion, and reference numeral 403 denotes a driver circuit portion (gate driver circuit), which are each indicated by dotted lines. Reference numeral 404 denotes a sealing substrate, reference numeral 405 denotes a sealing material, and a portion enclosed by the sealing material 405 is a space.

Note that a lead wiring 408 is a wiring for transmitting signals that are to be input to the source driver circuit 401 and the gate driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to this FPC. The light-emitting device in this specification includes not only a light-emitting device itself but also a light-emitting device to which an FPC or a PWB is attached.

Next, a cross-sectional structure is described with reference to FIG. 3B. The driver circuit portion and the pixel portion are formed over an element substrate 410. Here, the source driver circuit 401 which is a driver circuit portion and one pixel in the pixel portion 402 are illustrated.

Note that as the source driver circuit 401, a CMOS circuit which includes an n-channel TFT 423 and a p-channel TFT 424 in combination is formed. Further, the driver circuit may be formed with any of a variety of circuits including TFTs, such as a CMOS circuit, a PMOS circuit, or an NMOS circuit. Although a driver-integrated type in which the driver circuit is formed over the substrate is described in this embodiment, the present invention is not limited to this type, and the driver circuit can be formed outside the substrate.

Further, the pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413. Here, the insulator 414 is formed using a positive type photosensitive acrylic resin film.

In order to improve coverage, the insulator 414 is formed such that either an upper end portion or a lower end portion of the insulator 414 has a curved surface with a curvature. For example, when positive photosensitive acrylic is used as a material for the insulator 414, it is preferable that only an upper end portion of the insulator 414 have a curved surface with a radius of curvature (0.2 μm to 3 μm). For the insulator 414, it is also possible to use either a negative type that is made insoluble in an etchant by light irradiation or a positive type that is made soluble in an etchant by light irradiation.

Over the first electrode 413, an EL layer 416 and a second electrode 417 are formed. For the first electrode 413, the EL layer 416, and the second electrode 417, the materials described in Embodiment 2 can be used. Note that the EL layer 416 includes at least a light-emitting layer and the light-emitting layer includes any of the benzo[b]naphtho[1,2-d]furan compounds described in Embodiment 1. In Embodiment 4, the first electrode 413 functions as an anode and the second electrode 417 functions as a cathode. Further, when the EL layer includes a carrier-transport layer, any of the benzo[b]naphtho[1,2-d]furan compounds described in Embodiment 1 can be used for the carrier-transport layer (e.g., a hole-transport layer, a hole-injection layer, an electron-transport layer, or an electron-injection layer).

Further, the sealing substrate 404 is attached to the element substrate 410 with the sealing material 405, so that a light-emitting element 418 is provided in a space 407 enclosed by the element substrate 410, the sealing substrate 404, and the sealing material 405. Note that the space 407 is filled with a filler, and may be filled with an inert gas (such as nitrogen or argon) or the sealing material 405.

Further, an epoxy-based resin is preferably used as the sealing material 405. Preferably, as little moisture and oxygen as possible penetrate such a material. As a material used for the sealing substrate 404, a plastic substrate formed of fiberglass-reinforced plastics (FRP), polyvinyl fluoride (PVF), polyester, acrylic, or the like can be used other than a glass substrate or a quartz substrate.

As described above, the active matrix light-emitting device including the light-emitting element according to one embodiment of the present invention can be obtained.

Figure 4A:
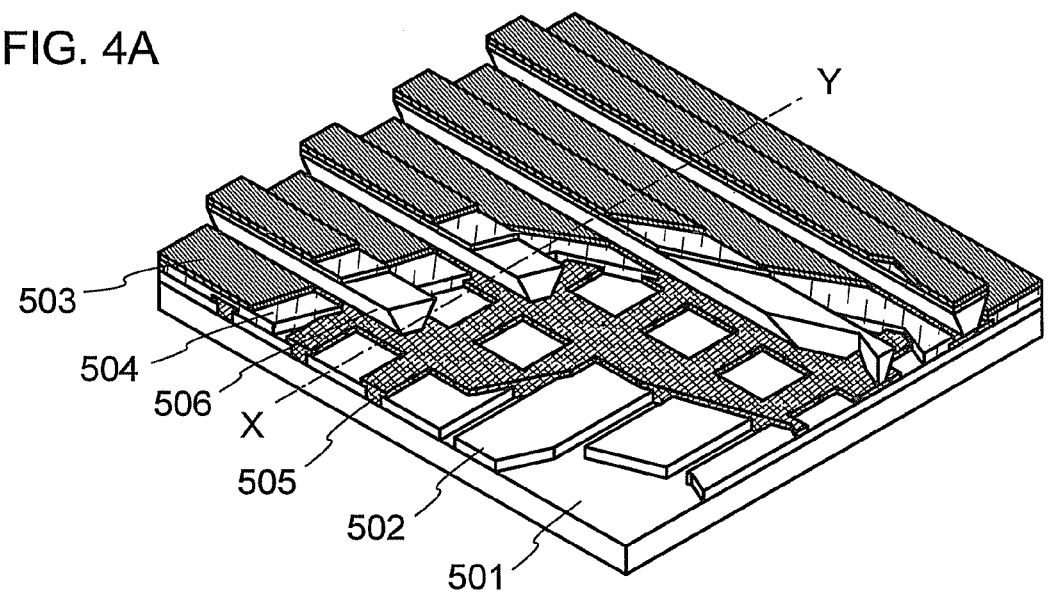
FIGS. 4A and 4B illustrate a light-emitting device according to one embodiment of the present invention.
Figure 4B:
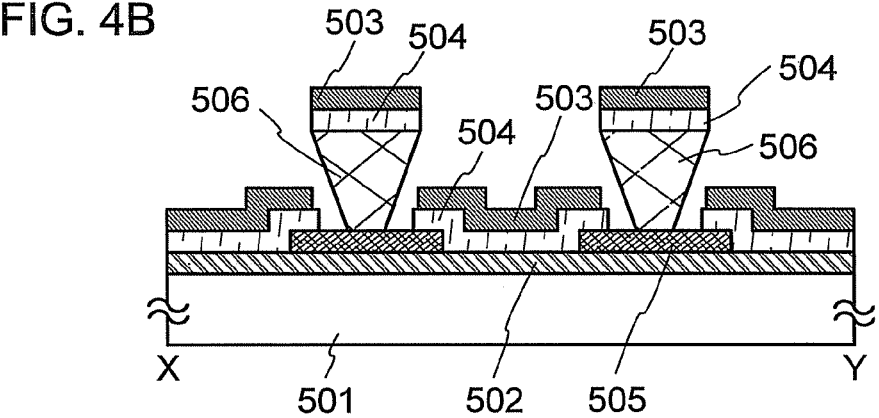

Further, a light-emitting element according to the present invention can be used for a passive matrix light-emitting device as well as the above active matrix light-emitting device. A perspective and cross-sectional views of a passive matrix light-emitting device including the light-emitting element according to one embodiment of the present invention are illustrated in FIGS. 4A and 4B. Note that FIG. 4A is the perspective view of the light-emitting device, and FIG. 4B is the cross-sectional view taken along line X-Y of FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that a distance between both the sidewalls is gradually narrowed toward the surface of the substrate. In other words, a cross section taken along the direction of the short side of the partition layer 506 is trapezoidal, and the base (a side which is in the same direction as a plane direction of the insulating layer 505 and in contact with the insulating layer 505) is shorter than the upper side (a side which is in the same direction as the plane direction of the insulating layer 505 and not in contact with the insulating layer 505). With the partition layer 506 provided in such a way, a defect of a light-emitting element due to crosstalk or the like can be prevented.

Thus, the passive matrix light-emitting device including the light-emitting element according to one embodiment of the present invention can be obtained.

The light-emitting devices described in this embodiment (the active matrix light-emitting device and the passive matrix light-emitting device) are both formed using the light-emitting element according to one embodiment of the present invention.

The light-emitting device described in this embodiment is a light-emitting device with high color reproducibility or a light-emitting device with high display quality. The light-emitting device described in this embodiment is a light-emitting device with high reliability. The light-emitting device described in this embodiment is a light-emitting device with low power consumption.

Note that this embodiment can be implemented in appropriate combination with any of the other embodiments.

[Embodiment 5]

In this embodiment, examples of a variety of electronic devices and a lighting device which are completed with use of a light-emitting device that is one embodiment of the present invention are described with reference to FIGS. 5A to 5E, FIG. 6, and FIG. 7.

Examples of the electronic devices to which the light-emitting device is applied are television devices (also referred to as TVs or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and a lighting device are illustrated in FIGS. 5A to 5E.

Figure 5A:
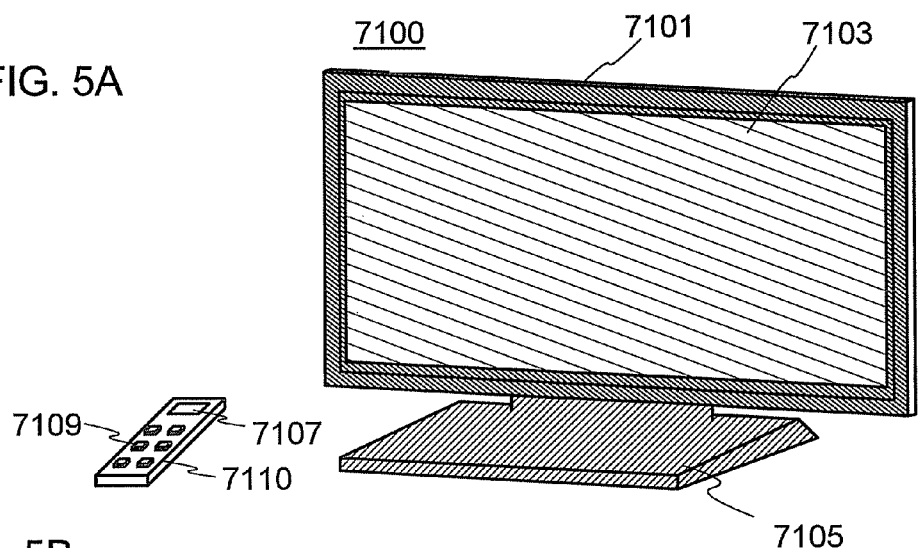
FIGS. 5A to 5E illustrate electronic devices and a lighting device according to one embodiment of the present invention.

An example of a television device is illustrate in FIG. 5A. In a television device 7100, a display portion 7103 is incorporated in a housing 7101. The display portion 7103 is capable of displaying images, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

The television device 7100 is provided with a receiver, a modem, and the like. With the receiver, a general television broadcast can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 5B:
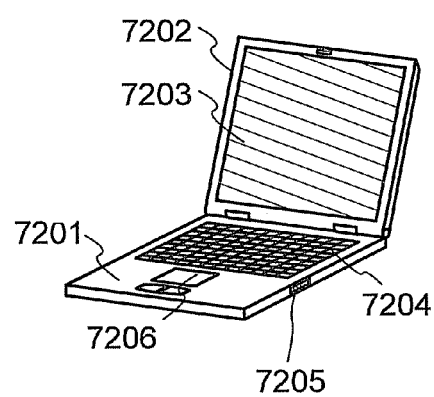

In FIG. 5B, a computer is illustrated which includes a main body 7201, a housing 7202, a display portion 7203, a keyboard 7204, an external connecting port 7205, a pointing device 7206, and the like. The computer is manufactured by using a light-emitting device for the display portion 7203.

Figure 5C:
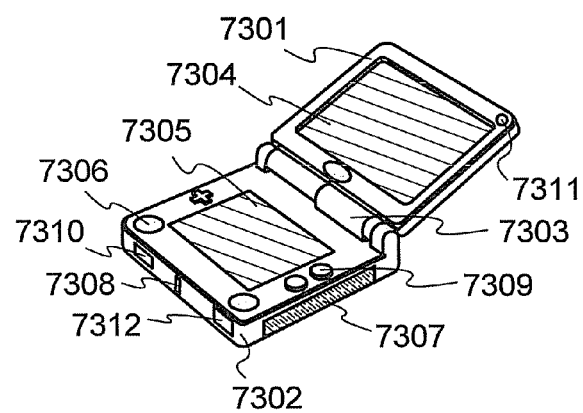

In FIG. 5C, a portable game machine is illustrated which includes two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. In addition, the portable game machine illustrated in FIG. 5C includes a speaker portion 7306, a recording medium insertion portion 7307, an LED lamp 7308, an input unit (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable game machine is not limited to the above as far as a light-emitting device is used for at least either the display portion 7304 or the display portion 7305, or both, and may include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above.

Figure 5D:
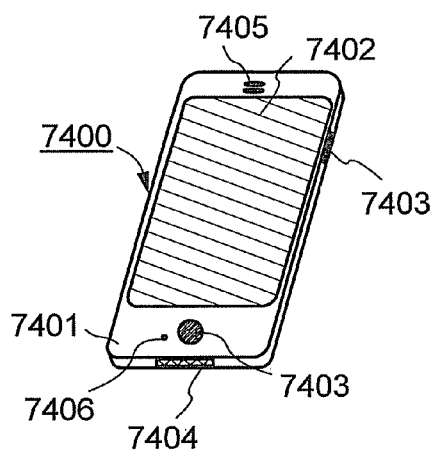

An example of a cellular phone is illustrated in FIG. 5D. The cellular phone 7400 is provided with operation buttons 7403, an external connection port 7404, a speaker 7405, a microphone 7406, and the like, in addition to a display portion 7402 incorporated in a housing 7401. Note that the cellular phone 7400 is manufactured using a light-emitting device for the display portion 7402.

When the display portion 7402 of the cellular phone 7400 illustrated in FIG. 5D is touched with a finger or the like, data can be input into the cellular phone 7400. Further, touch on the display portion 7402 with a finger or the like enables operations such as making a call and creating e-mail.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on a screen can be inputted. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or handling of the operation buttons 7403 of the housing 7401. Alternatively, the screen modes can be switched depending on the kinds of images displayed on the display portion 7402. For example, when a signal of an image displayed on the display portion is for moving image data, the screen mode is switched to the display mode. When the signal is for text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 can function as an image sensor. For example, an image of a palm print, a fingerprint, or the like is taken by touch on the display portion 7402 with the palm or the finger, so that personal authentication can be performed. Further, by use of a backlight or a sensing light source that emits near-infrared light in the display portion, an image of a finger vein, a palm vein, or the like can be taken.

Figure 5E:
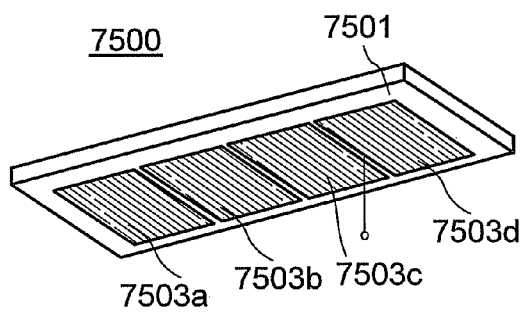

An example of a lighting device is illustrated in FIG. 5E. In a lighting device 7500, light-emitting devices 7503a to 7503d of one embodiment of the present invention are incorporated in a housing 7501 as light sources. The lighting device 7500 can be attached to a ceiling, a wall, or the like.

Since the light-emitting element is in the form of a thin film, the light-emitting device of one embodiment of the present invention can have a curved surface by being attached to a base having a curved surface. Further, with the light-emitting device put in a housing having a curved surface, an electronic device or a lighting device having a curved surface can be realized.

Figure 6:
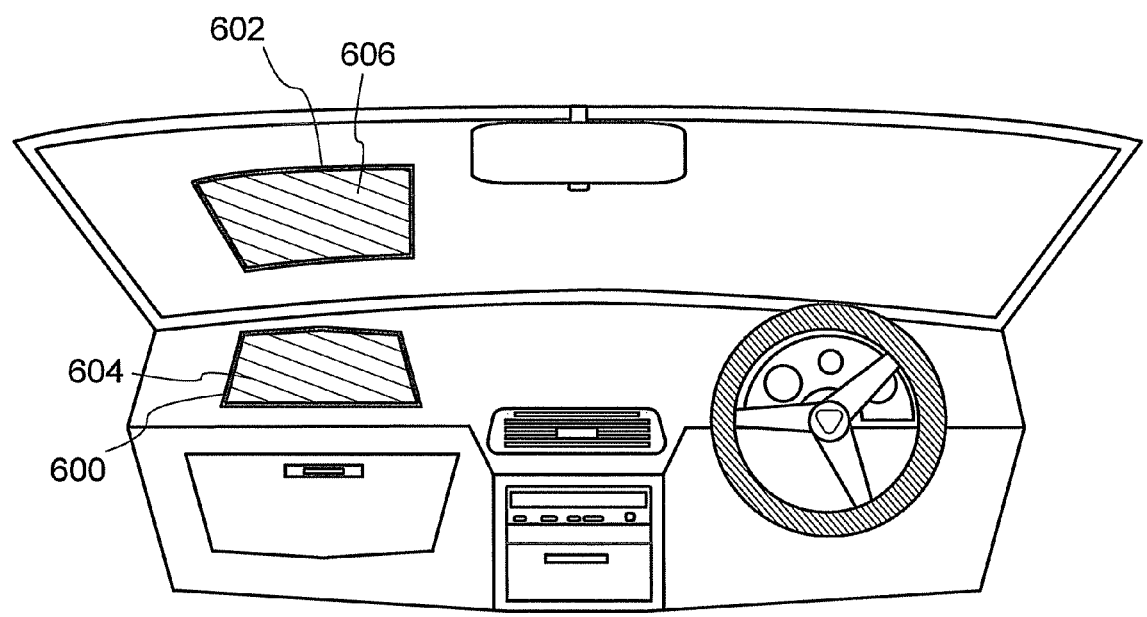
FIG. 6 illustrates an electronic device according to one embodiment of the present invention.

A driver seat and the periphery thereof inside a vehicle are illustrated in FIG. 6, showing an example in which a display device 600 is set on a dashboard and a display device 602 is set on a windshield. In the display device 600 illustrated in FIG. 6, a display portion 604 is incorporated in a housing with a curved surface and capable of displaying images. The light-emitting device of one embodiment of the present invention can be used for the display portion 604 in the display device 600.

In the display device 602 illustrated in FIG. 6, a display portion 606 is incorporated in a housing with a curved surface and the light-emitting device of one embodiment of the present invention can be used in the display portion 606. A pair of electrodes and a support of a light-emitting element which are included in the light-emitting device of one embodiment of the present invention are formed using a light-transmitting material, so that light can be extracted to the outside through both a top surface and a bottom surface of the light-emitting device. Thus, when this light-emitting device is used in the display portion 606, the outside can be seen through the display portion 606 on the windshield. Further, an image displayed on the display portion 606 can be seen from the outside through the windshield.

The display device 600 or the display device 602 illustrated in FIG. 6 can also be used as a lighting device.

Figure 7:
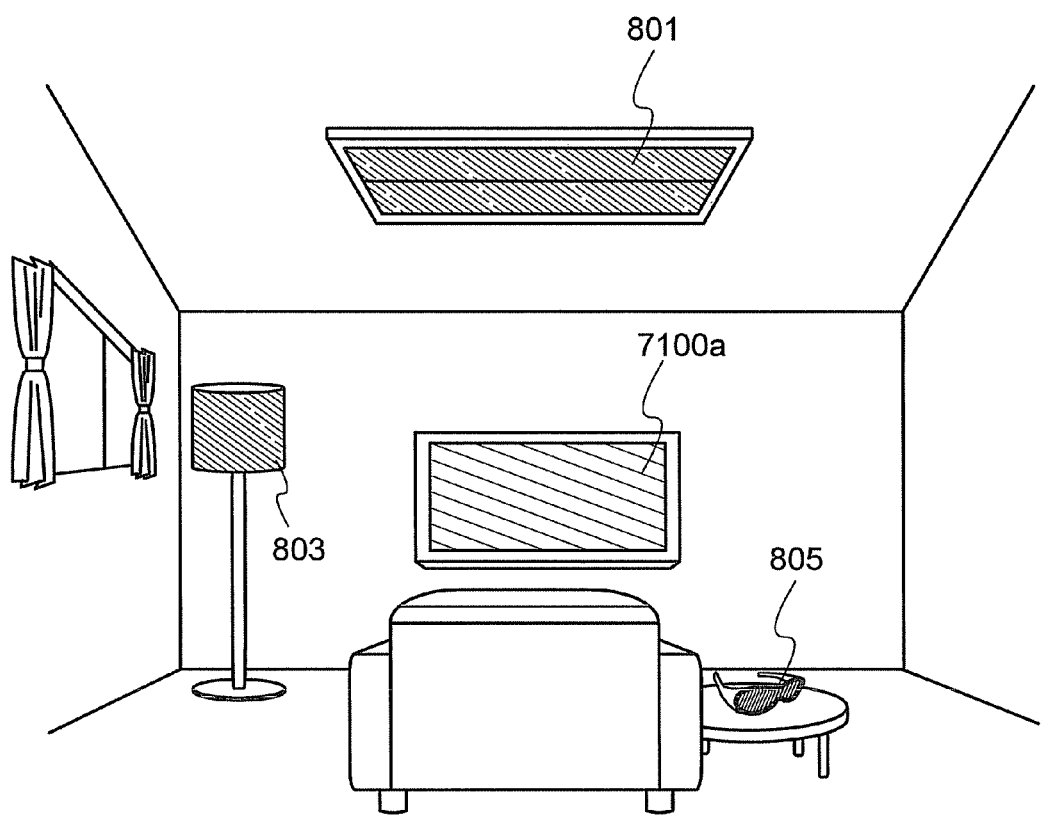
FIG. 7 illustrates electronic devices and lighting devices according to one embodiment of the present invention.

In FIG. 7, an example in which a light-emitting device is used for an interior lighting device 801 is illustrated. Since the light-emitting device can have a larger area, it can be used as a lighting device having a large area. In addition, a lighting device 803 in which a light-emitting region has a curved surface can also be obtained with the use of a housing with a curved surface. A light-emitting element included in the lighting device described in this embodiment is in a thin film form, so that the lighting device can be designed more freely. Accordingly, the lighting device can be elaborately designed in a variety of ways.

A television device 7100a like the one illustrated as an example in FIG. 5A can be set in a room provided with the lighting device to which one embodiment of the present invention is applied. The television device 7100a may have a three-dimensional display function as well as a normal two-dimensional display function. In FIG. 7, a three-dimensional image can be watched with glasses 805 for watching three-dimensional images.

As described above, electronic devices or lighting devices can be obtained by application of a light-emitting device. Application range of the light-emitting device is wide, so that the light-emitting device can be applied to electronic devices in a variety of fields.

Further, an electronic device to which one embodiment of the present invention is applied is an electronic device with high color reproducibility or an electronic device with high display quality. The electronic device to which one embodiment of the present invention is applied is an electronic device with high reliability. The electronic device to which one embodiment of the present invention is applied is an electronic device with low power consumption.

Note that the structure described in this embodiment can be combined with any of the structures described in Embodiments 1 to 4 as appropriate.

EXAMPLE 1

In Example 1, an example in which 6-[3-(9,10-diphenyl-2-anthryl)phenyl]-benzo[b]naphtho[1,2-d]furan (abbreviation: 2mBnfPPA) represented by the structural formula (100) in Embodiment 1 is described.

[Step 1] Synthesis of Benzo[b]naphtho[1,2-d]furan-6-boronic acid

SYNTHESIS EXAMPLE 1

Synthesis Example 1 of benzo[b]naphtho[1,2-d]furan-6-boronic acid is described.

[Step 1-1-1] Synthesis of 1-(2-Fluorophenyl)-2-naphthol

Into a 200 mL three-neck flask were placed 1.4 g (10 mmol) of 2-fluorophenylboronic acid, 2.2 g (10 mmol) of 1-bromo-2-naphthol, 153 mg (0.50 mmol) of tri(ortho-tolyl)phosphine, 25 mL of toluene, 25 mL of ethanol, and 5.0 mL of a 2M aqueous solution of potassium carbonate. This mixture was degassed under reduced pressure, and the air in the system was replaced with nitrogen. This mixture was stirred at 80° C., 23 mg (0.10 mmol) of palladium(II) acetate was added thereto, and the mixture was refluxed at about 100° C. for 6.5 hours. After the reflux, this mixture was washed with water, and the aqueous layer was subjected to extraction with ethyl acetate. The obtained solution of the extract and the organic layer were combined and washed with saturated brine. The obtained organic layer was dried over magnesium sulfate. This mixture was gravity-filtered, and the obtained filtrate was concentrated to give a brown oily substance. This oily substance was purified by silica gel column chromatography (developing solvent: toluene), so that 1.6 g of a brown oily substance of the object of the synthesis was obtained in 69% yield. The above-described synthesis, scheme is illustrated in the following scheme (B-1).

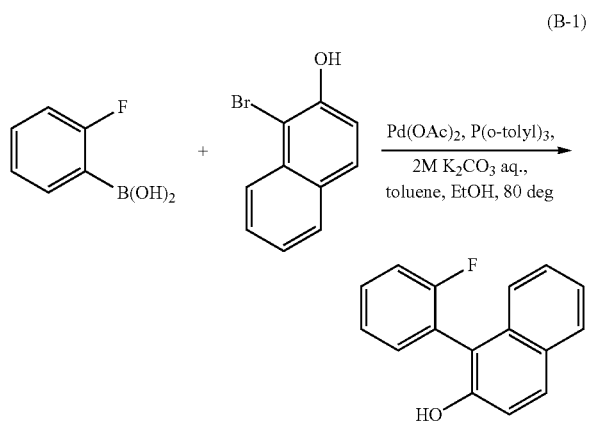

(B-1)

[Step 1-1-2] Synthesis of Benzo[b]naphtho[1,2-d]furan

Into a 1 L three-neck flask were placed 15 g (63 mmol) of 1-(2-fluorophenyl)-2-naphthol, 300 mL of N-methyl-2-pyrrolidone (NMP), and 18 g (130 mmol) of potassium carbonate. The mixture in this flask was stirred at 150° C. for 6 hours under a nitrogen stream. After that, this mixture was cooled down to room temperature and added to about 500 mL of water. The aqueous layer of this mixture was subjected to extraction with ethyl acetate, and the obtained solution of the extract and the organic layer were combined and washed with water and saturated brine. The organic layer was dried over magnesium sulfate, and after that, this mixture was gravity-filtered. The obtained filtrate was concentrated to give an oily substance. The obtained oily substance was purified by silica gel column chromatography (developing solvent: hexane) to give an oily substance. The obtained oily substance was dried under reduced pressure, so that 11.8 g of a colorless transparent oily substance of the object of the synthesis was obtained in 86% yield. The above-described synthesis scheme is illustrated in the following scheme (B-2).

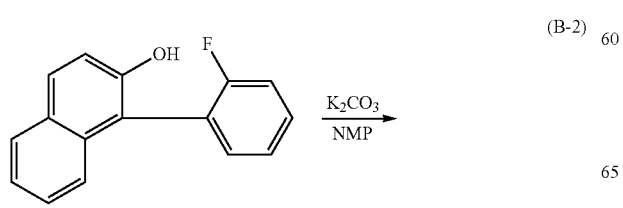

(B-2)

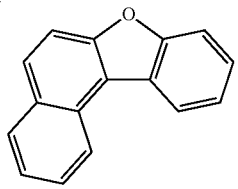

[Step 1-1-3] Synthesis of Benzo[b]naphtho[1,2-d]furan-6-boronic acid

After the air in a 500 mL three-neck flask was replaced with nitrogen, 5.8 g (50 mmol) of tetramethylethylenediamine (TMEDA) and 180 mL of tetrahydrofuran (THF) were placed into the flask, and this solution was cooled to –80° C. Then, 50 mL (50 mmol) of sec-butyl lithium (a 1.0 mol/L solution of cyclohexane and n-hexane) was dripped into this solution with a syringe. After that, this solution was stirred at the same temperature for 30 minutes. Then, 10 g (45 mmol) of benzo[b]naphtho[1,2-d]furan dissolved in 70 mL of THF was added dropwise to this solution with a dropping funnel. After that, this solution was stirred at the same temperature for 2 hours. Then, 11 mL (100 mmol) of trimethyl borate was added to this solution, and the mixture was stirred for 2 days while its temperature was returned to room temperature. After that, the aqueous layer of this mixture was subjected to extraction with ethyl acetate, and the obtained solution of the extract and the organic layer were combined and washed with a saturated aqueous solution of sodium hydrogen carbonate and saturated brine. The organic layer was dried over magnesium sulfate, and after that, this mixture was gravity-filtered. The obtained filtrate was concentrated to give a white solid. Toluene/hexane was added to the obtained solid, the mixture was irradiated with ultrasonic waves, and a solid was collected by suction filtration, so that 9.2 g of a white powder of the object of the synthesis was obtained in 78% yield. The above-described synthesis scheme is illustrated in the following scheme (B-3).

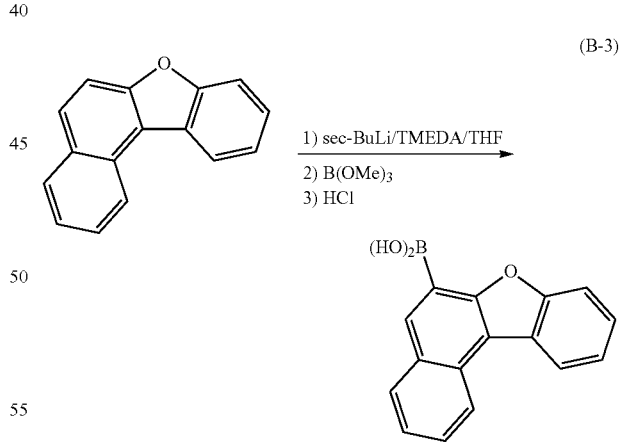

(B-3)

SYNTHESIS EXAMPLE 2

Synthesis Example 2 of the benzo[b]naphtho[1,2-d]furan-6-boronic acid is described.

[Step 1-2-1] Synthesis of 1-(2-Fluorophenyl)-2-methoxynaphthalene

Into a 500 mL three-neck flask were placed 8.7 g (35 mmol) of 1-bromo-2-methoxynaphthalene, and 5.0 g (35 mmol) of 2-fluorophenylboronic acid. The air in the flask was replaced with nitrogen. To this mixture were added 120 mL of toluene, 60 mL of ethanol, and 40 mL of an aqueous solution of sodium carbonate (2.0 mol/L). While the pressure was reduced; this mixture was stirred to be degassed. To this mixture was added 2.0 g (1.7 mmol) of tetrakis(triphenylphosphine)palladium(0), and the mixture was stirred at 80° C. for 8 hours under a nitrogen stream. The aqueous layer of the obtained mixture was subjected to extraction with toluene, and the obtained solution of the extract and the organic layer were combined and washed with saturated brine. The organic layer was dried over magnesium sulfate, and this mixture was gravity-filtered. An oily substance obtained by concentration of the obtained filtrate was dissolved in about 30 mL of toluene. This solution was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). An oily substance obtained by concentration of the obtained filtrate was dried under reduced pressure, so that 5.3 g of a pale yellow oily substance of the object of the synthesis was obtained in 60% yield. The above-described synthesis scheme is illustrated in the following scheme (C-1).

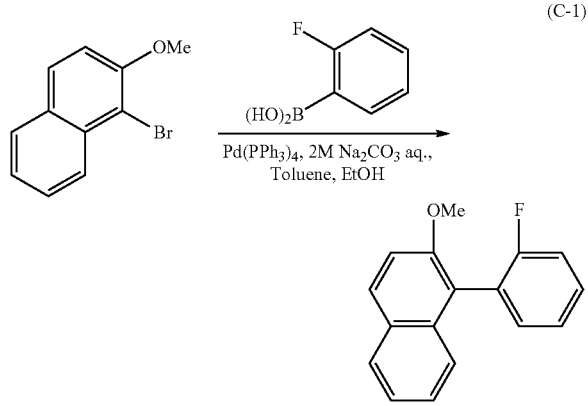

[Step 1-2-2] Synthesis of 1-(2-Fluorophenyl)-2-naphthol

Into a 500 mL three-neck flask were placed 5.3 g (21 mmol) of 1-(2-fluorophenyl)-2-methoxynaphthalene and 150 mL of dichloromethane. At 0° C. under a nitrogen stream, 45 mL (45 mmol) of boron tribromide (a 1M dichloromethane solution) was added dropwise to this solution with a dropping funnel. After that, the mixture was stirred at the same temperature for 6 hours. Then, this solution was stirred at room temperature for 2 days. After that, about 100 mL of water was added to this solution, and the solution was stirred for 1 hour. Then, addition of about 100 mL of a saturated aqueous solution of sodium hydrogen carbonate was followed by one-hour stirring. Then, the aqueous layer of this mixture was subjected to extraction with dichloromethane, and the obtained solution of the extract and the organic layer were combined and washed with water and a saturated aqueous solution of sodium hydrogen carbonate. The organic layer was dried over magnesium sulfate. Then, this mixture was gravity-filtered. The obtained filtrate was concentrated to give an oily substance. The obtained oily substance was dried under reduced pressure, so that 4.8 g of a brown solid of the object of the synthesis was obtained in 97% yield. The above-described synthesis scheme is illustrated in the following scheme (C-2).

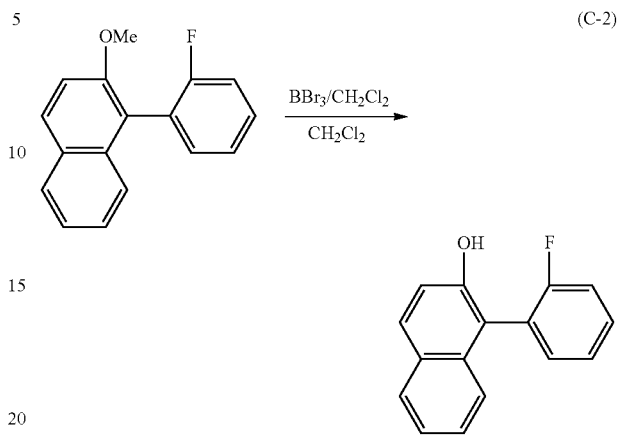

The subsequent steps in Synthesis Example 2 are performed in the same manner as in Steps 1-1-2 and 1-1-3 in Synthesis Example 1 above, and therefore not detailed.

In order to specify which position of benzo[b]naphtho[1,2-d]furan is converted into boronic acid with use of a compound obtained through a reaction in which benzo[b]naphtho[1,2-d]furan is converted into a boronic acid compound, a compound obtained through the following synthesis scheme (D-1) is subjected to X-ray structure analysis.

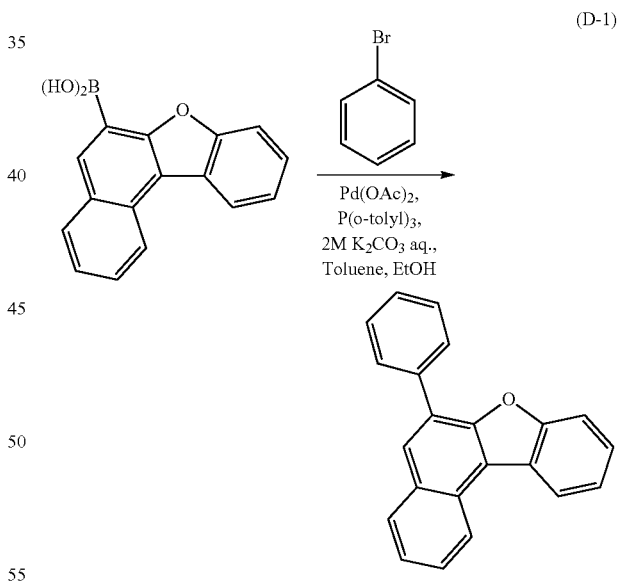

Into a 200 mL three-neck flask were placed 0.90 g (5.7 mmol) of bromobenzene and 1.5 g (5.7 mol) of benzo[b]naphtho[1,2-d]furan-6-boronic acid, and the air in the flask was replaced with nitrogen. To this mixture were added 20 mL of toluene, 10 mL of ethanol, and 6.0 mL of an aqueous solution of sodium carbonate (2.0 mol/L). While the pressure was reduced, this mixture was stirred to be degassed. To this mixture was added 0.33 g (0.28 mmol) of tetrakis(triphenylphosphine)palladium(0), and the mixture was stirred at 80° C. for 2 hours under a nitrogen stream. After that, the aqueous layer of this mixture was subjected to extraction with toluene, and the obtained solution of the extract and the organic layer were combined and washed with saturated brine. The organic layer was dried over magnesium sulfate, and this mixture was gravity-filtered. An oily substance obtained by concentration of the obtained filtrate was purified by silica gel column chromatography (a developing solvent in which the ratio of hexane to toluene was 19:1) to give a white solid. The obtained solid was recrystallized from toluene/hexane, so that 0.95 g of white needle-like crystals of the object of the synthesis were obtained in 56% yield.

Figure 61:
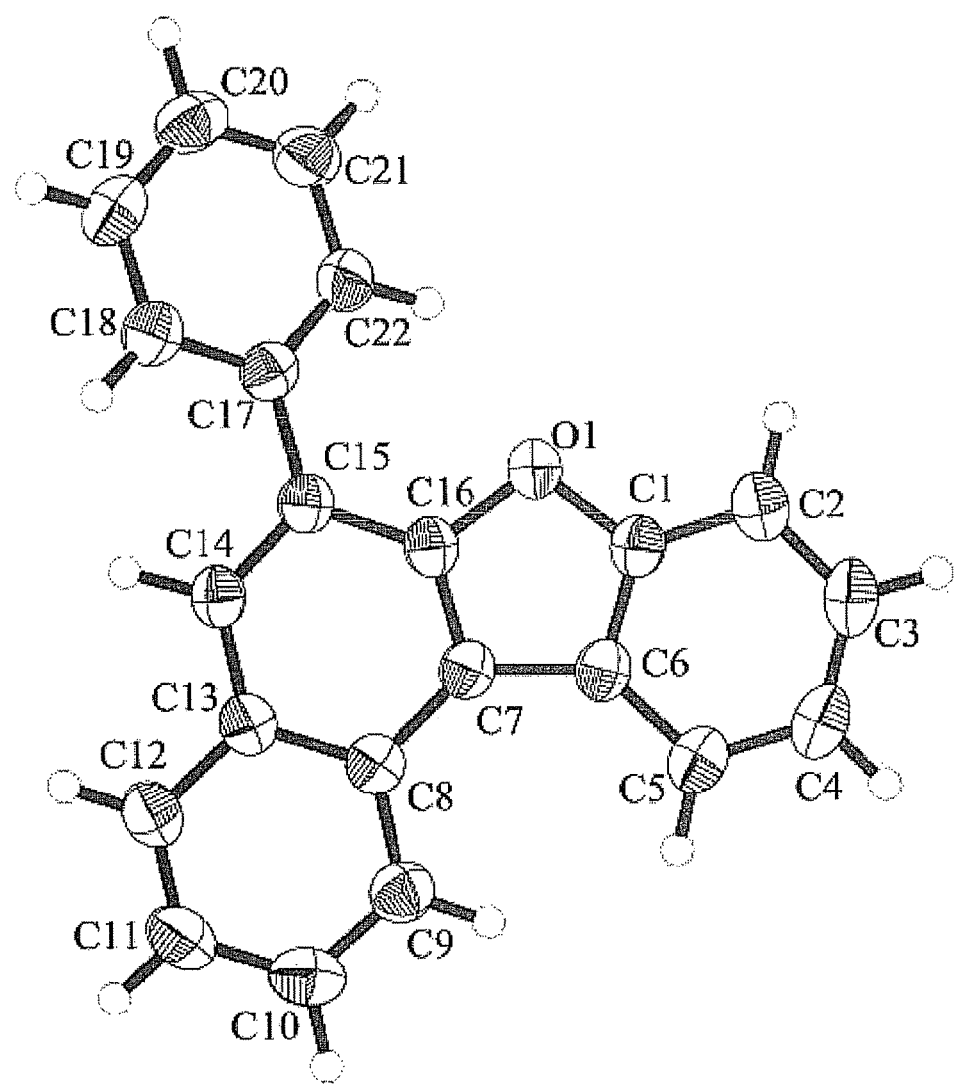
FIG. 61 is an ORTEP drawing from X-ray crystallography.

A result of the X-ray crystallography of the obtained white needle-like crystals is shown in FIG. 61, which is an ORTEP (oak ridge thermal ellipsoid plot) drawing. It is confirmed from FIG. 61 that the 6-position of benzo[b]naphtho[1,2-d]furan is converted into boronic acid by the synthesis scheme (B-3).

[Step 2] Synthesis of 6-[3-(9,10-Diphenyl-2-anthryl)phenyl]-benzo[b]naphtho[1,2-d]furan (abbreviation: 2mBnfPPA)

Into a 50 mL three-neck flask were placed 1.1 g (2.4 mmol) of 2-(3-bromophenyl)-9,10-diphenylanthracene and 0.63 g (2.4 mmol) of benzo[b]naphtho[1,2-d]furan-6-boronic acid, and the air in the flask was replaced with nitrogen. To this mixture were added 10 mL of toluene, 4.0 mL of ethanol, and 3.0 mL of an aqueous solution of sodium carbonate (2.0 mol/L). While the pressure was reduced, this mixture was stirred to be degassed. To this mixture was added 0.14 g (0.12 mmol) of tetrakis(triphenylphosphine)palladium(0), and the mixture was stirred at 80° C. for 3 hours under a nitrogen stream. After that, the aqueous layer of this mixture was subjected to extraction with toluene, and the obtained solution of the extract and the organic layer were combined and washed with saturated brine. The organic layer was dried over magnesium sulfate, and this mixture was gravity-filtered. An oily substance obtained by concentration of the obtained filtrate was purified by silica gel column chromatography (a developing solvent in which the ratio of hexane to toluene was 5:1) to give an oily substance. The obtained oily substance was recrystallized from toluene/hexane, so that 1.0 g of a pale yellow powder of the object of the synthesis was obtained in 66% yield.

By a train sublimation method, 1.0 g of the obtained pale yellow powdery solid was purified. In the sublimation purification, the pale yellow powdery solid was heated at 290° C. under a pressure of 2.2 Pa with a flow rate of argon at 5.0 mL/min. After the sublimation purification, 0.91 g of a pale yellow solid of 2mBnfPPA was recovered in 91% yield. The above-described synthesis scheme is illustrated in the following scheme (E-1).

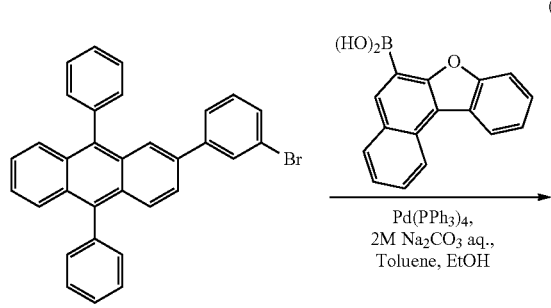

(E-1)

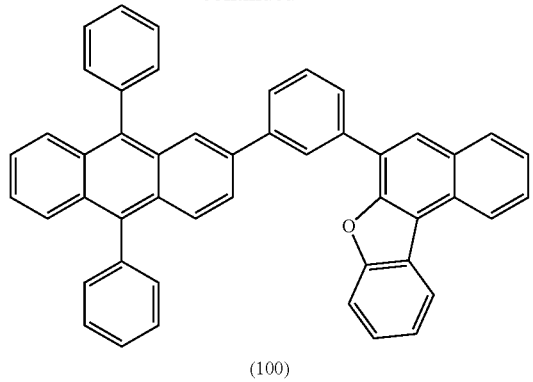

(100)

Nuclear magnetic resonance (NMR) spectroscopy identified this compound as 6-[3-(9,10-diphenyl-2-anthryl)phenyl]-benzo[b]naphtho[1,2-d]furan (abbreviation: 2mBnfPPA), which was the object of the synthesis.

$^1$H-NMR measurement data of the obtained compound are as follows: $^1$H-NMR (CDCl$_3$, 300 MHz): δ=7.33 (d, J=3.0 Hz, 1H), 7.35 (d, J$_7$ 3.0 Hz, 1H), 7.49-7.75 (m, 20H), 7.83 (d, J=9.3 Hz, 1H), 7.94 (d, J=7.5 Hz, 1H), 8.01-8.07 (m, 3H), 8.14 (s, 1H), 8.43-8.47 (m, 1H), 8.66 (d, J$_1$=8.4 Hz, 1H)

Figure 9A:
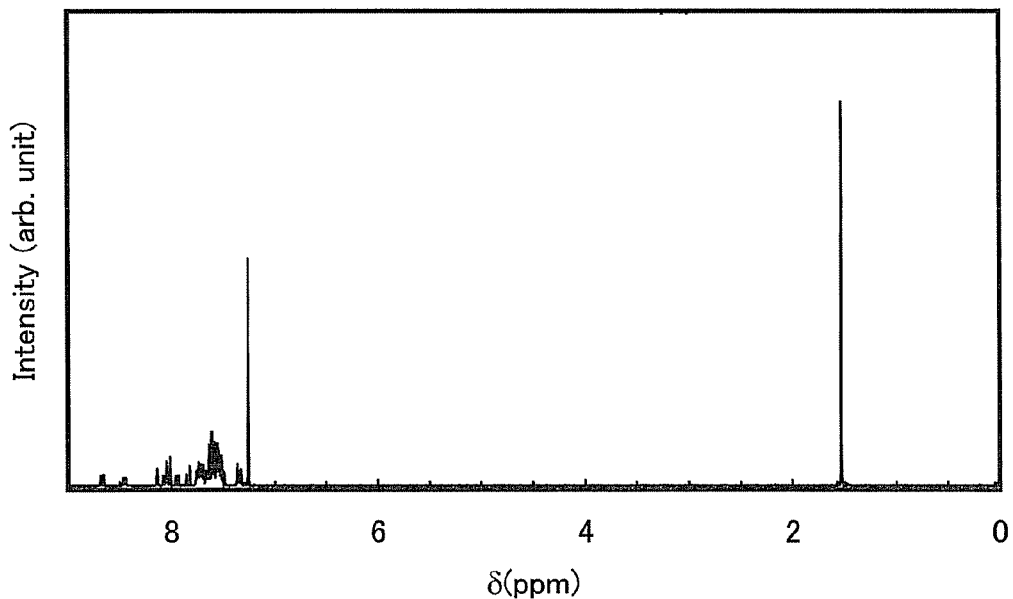
FIGS. 9A and 9B show NMR charts of 2mBnfPPA.
Figure 9B:
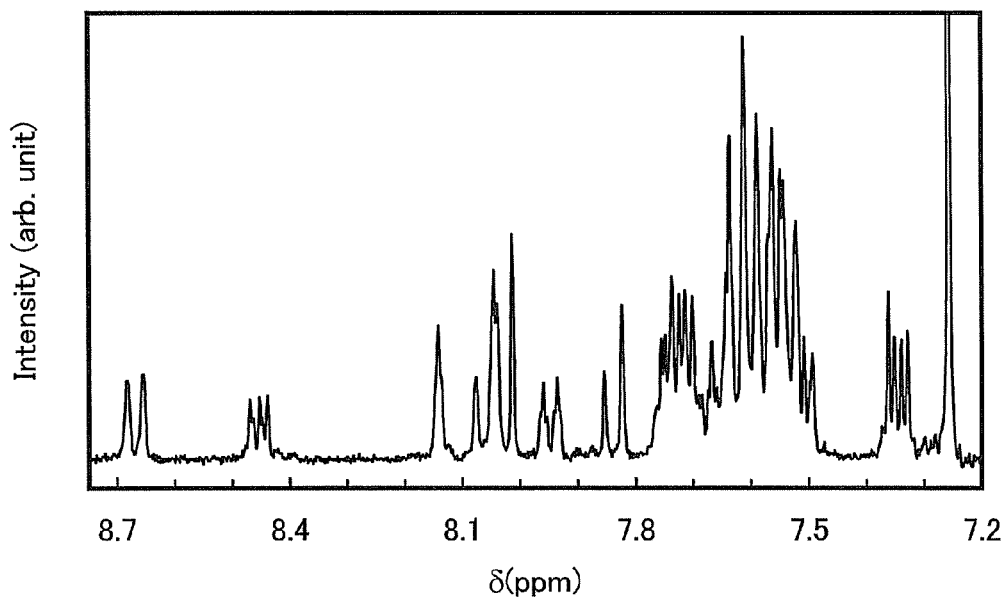

Further, $^1$H-NMR charts are shown in FIGS. 9A and 9B. Note that FIG. 9B is a chart where the range of from 7.2 ppm to 8.75 ppm in FIG. 9A is enlarged.

Furthermore, 2mBnfPPA, which was obtained, was subjected to thermogravimetry-differential thermal analysis (TG-DTA). The temperature at which the weight becomes 95% of that at the start of the measurement under atmospheric pressure (hereinafter, this temperature is referred to as "5% weight loss temperature") was found to be 429° C. by the measurement with a thermogravimetry/differential thermal analysis apparatus (TG/DTA-320, manufactured by Seiko Instruments Inc.). This result indicates that 2mBnfPPA is a material having high heat resistance.

Figure 10A:
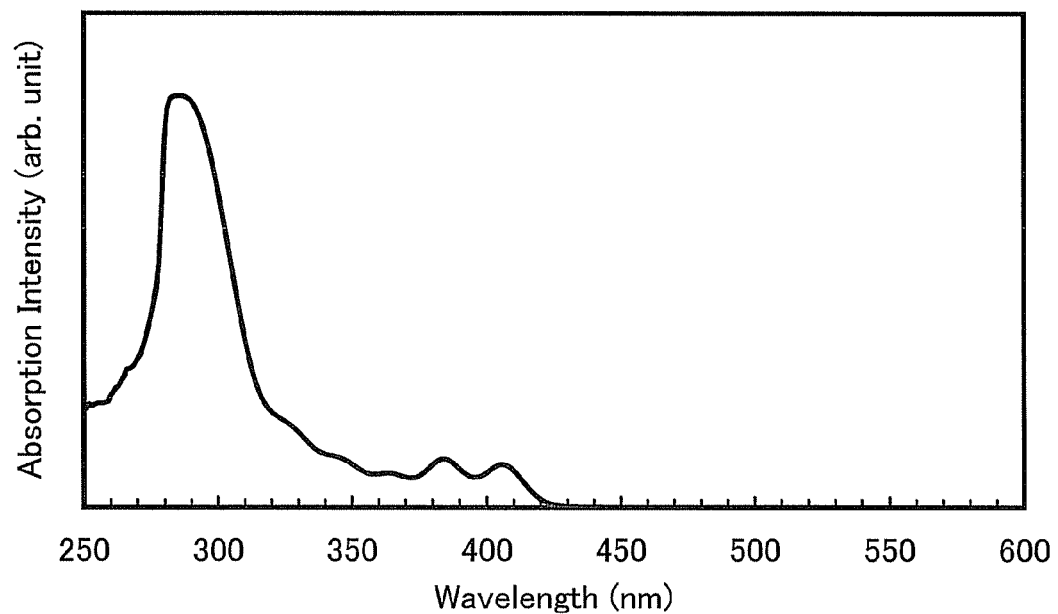
FIGS. 10A and 10B show an absorption spectrum and an emission spectrum of 2mBnfPPA in a toluene solution of 2mBnfPPA.
Figure 10B:
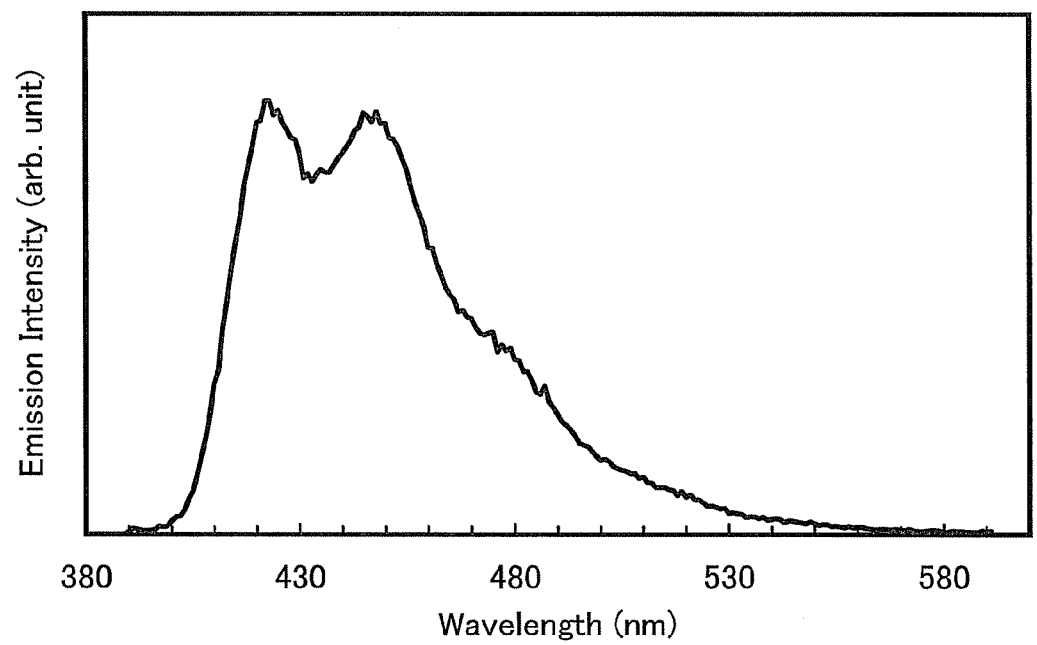
Figure 11A:
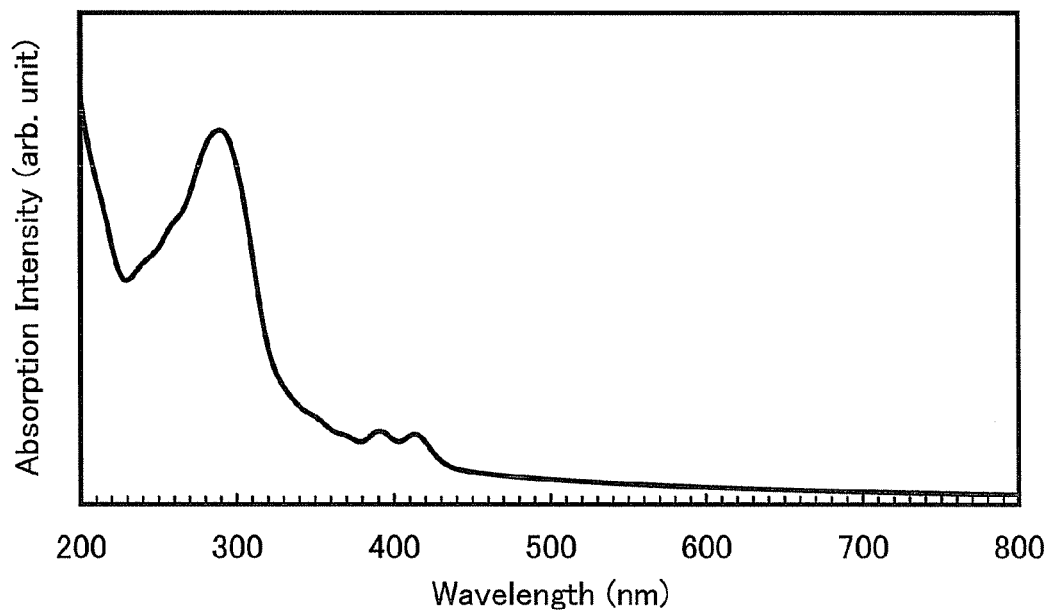
FIGS. 11A and 11B show an absorption spectrum and an emission spectrum of a thin film of 2mBnfPPA.
Figure 11B:
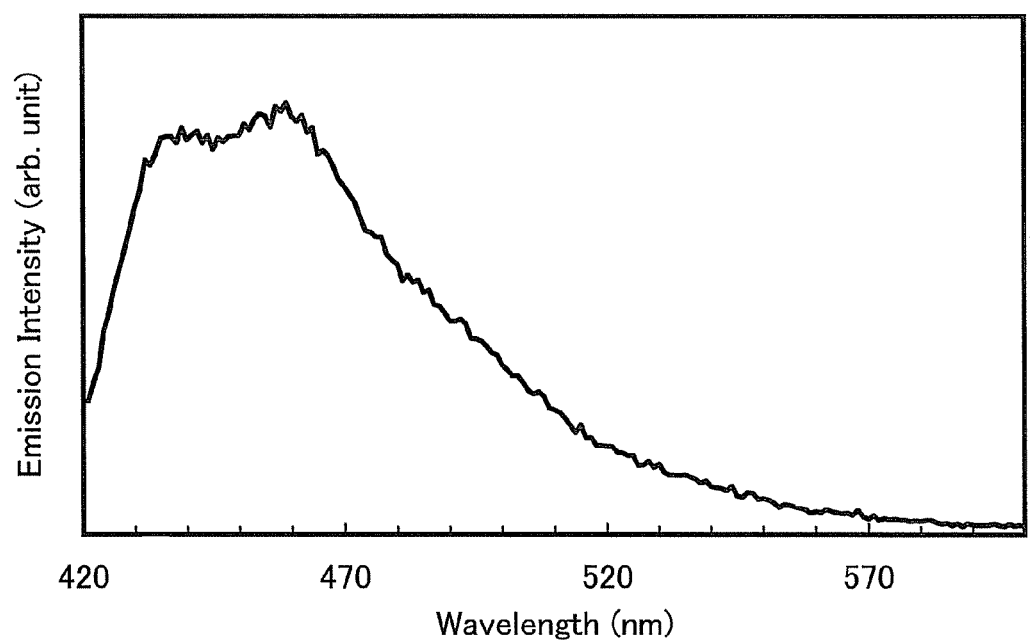

Further, FIG. 10A shows an absorption spectrum of 2mBnfPPA in a toluene solution of 2mBnfPPA, and FIG. 10B shows an emission spectrum thereof. Furthermore, FIG. 11A shows an absorption spectrum of a thin film of 2mBnfPPA, and FIG. 11B shows an emission spectrum thereof. An ultraviolet-visible spectrophotometer (V-550, manufactured by JASCO Corporation) was used for the measurements of the absorption spectra. The measurements were performed with samples prepared in such a way that the solution was put in a quartz cell while the thin film was obtained by evaporation onto a quartz substrate. The figures show the absorption spectrum of the solution which was obtained by subtraction of the absorption spectra of quartz and toluene from those of quartz and the solution, and the absorption spectrum of the thin film which was obtained by subtraction of the absorption spectrum of a quartz substrate from those of the quartz substrate and the thin film. In FIG. 10A and FIG. 11A, the horizontal axis represents wavelength (nm) and the vertical axis represents absorption intensity (arbitrary unit). Similarly, in FIG. 10B and FIG. 11B, the horizontal axis represents wavelength (nm) and the vertical axis represents emission intensity (arbitrary unit). In the case of the toluene solution, absorption peaks were observed at around 285 nm, 364 nm, 384 nm, and 406 nm, and emission wavelength peaks were at 423 nm and 446 nm (at an excitation wavelength of 385 nm). Further, in the case of the thin film, absorption peaks were observed at around 244 nm, 263 nm, 290 nm, 347 nm, 366 nm, 391 nm, and 413 nm, and emission wavelength peaks were at 440 nm and 458 nm (at an excitation wavelength of 414 nm).

Further, the HOMO level and LUMO level of 2mBnfPPA in the thin film state were measured. The value of the HOMO level was obtained by conversion of the value of the ionization potential measured with a photoelectron spectrometer (AC-2, manufactured by Riken Keiki Co., Ltd.) in the air into a negative value. The value of the LUMO level was obtained in such a way that the absorption edge was found from a Tauc plot with an assumption of direct transition using the data of the absorption spectrum of the thin film of 2mBnfPPA which is shown in FIG. 11A and the absorption edge was added, as an optical energy gap, to the value of the HOMO level. As a result, the HOMO level, energy gap, and LUMO level of 2mBnfPPA were −5.73 eV, 2.85 eV, and −2.88 eV, respectively.

EXAMPLE 2

In Example 2, an example in which 6-[3-(10-phenyl-9-anthryl)phenyl]-benzo[b]naphtho[1,2-d]furan (abbreviation: mBnfPA) represented by the structural formula (124) in Embodiment 1 is described.

Synthesis of 6-[3-(10-Phenyl-9-anthryl)phenyl] benzo[b]naphtho[1,2-d]furan (mBnfPA)

Into a 50 mL three-neck flask were placed 1.5 g (3.8 mmol) of 9-(3-bromophenyl)-10-phenylanthracene, 1.0 g (3.8 mmol) of benzo[b]naphtho[1,2-d]furan-6-boronic acid synthesized in Step 1 of Example 1, and 0.29 g (0.95 mmol) of tri(ortho-tolyl)phosphine, and the air in the flask was replaced with nitrogen. To this mixture were added 15 mL of toluene, 5.0 mL of ethanol, and 4.0 mL of an aqueous solution of potassium carbonate (2.0 mol/L). While the pressure was reduced, this mixture was stirred to be degassed. To this mixture was added 43 mg (0.19 mmol) of palladium(II) acetate, and the mixture was stirred at 80° C. for 4 hours under a nitrogen stream. After that, the aqueous layer of this mixture was subjected to extraction with toluene, and the obtained solution of the extract and the organic layer were combined and washed with saturated brine. The organic layer was dried over magnesium sulfate, and this mixture was gravity-filtered. An oily substance obtained by concentration of the obtained filtrate was purified by silica gel column chromatography (a developing solvent in which the ratio of hexane to toluene was 5:1) to give an oily substance. The obtained oily substance was recrystallized from toluene/hexane, so that 1.4 g of a white powder of the object of the synthesis was obtained in 67% yield.

By a train sublimation method, 1.1 g of the obtained white powdery solid was purified. In the sublimation purification, mBnfPA was heated at 270° C. under a pressure of 2.2 Pa with a flow rate of argon at 5.0 mL/min. After the sublimation purification, 1.0 g of a pale yellow solid of mBnfPA was recovered in 90% yield. The above-described synthesis scheme is illustrated in the following scheme (F-1).

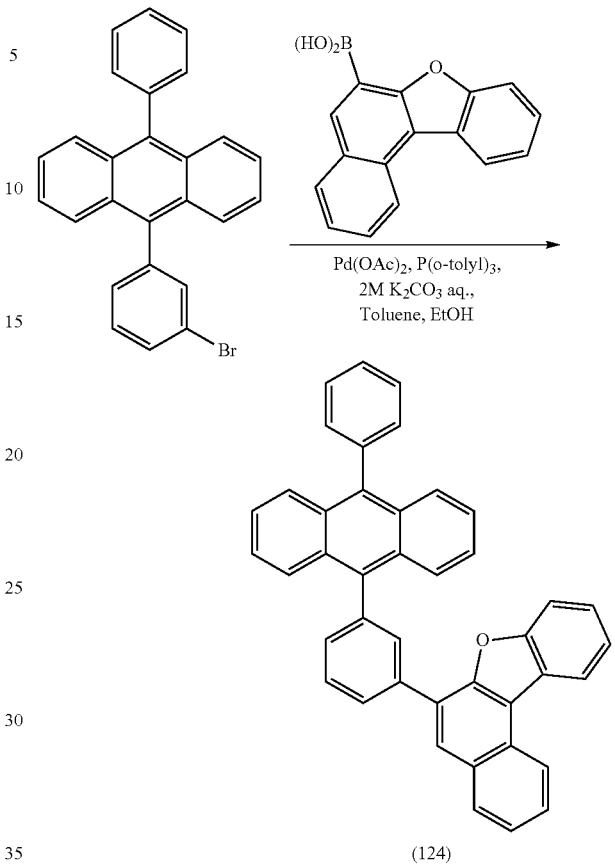

(F-1)

Nuclear magnetic resonance (NMR) spectroscopy identified this compound as 6-[3-(10-phenyl-9-anthryl)phenyl]-benzo[b]naphtho[1,2-d]furan (mBnfPA), which was the object of the synthesis.

$^1$H-NMR measurement data of the obtained compound are as follows: $^1$H-NMR (CDCl$_3$, 300 MHz): δ=7.34-7.44 (m, 4H), 7.48-7.63 (m, 9H), 7.69-7.74 (m, 4H), 7.83 (t, J=7.5 Hz, 1H), 7.96 (dd, J$_1$=1.8 Hz, J$_2$=7.8 Hz, 2H), 8.04 (d, J=7.8 Hz, 1H), 8.13 (s, 1H), 8.15 (t, J=1.5 Hz, 1H), 8.26 (d, J=7.8 Hz, 1H), 8.43-8.46 (m, 1H), 8.66 (d, J=7.8 Hz, 1H)

Figure 12A:
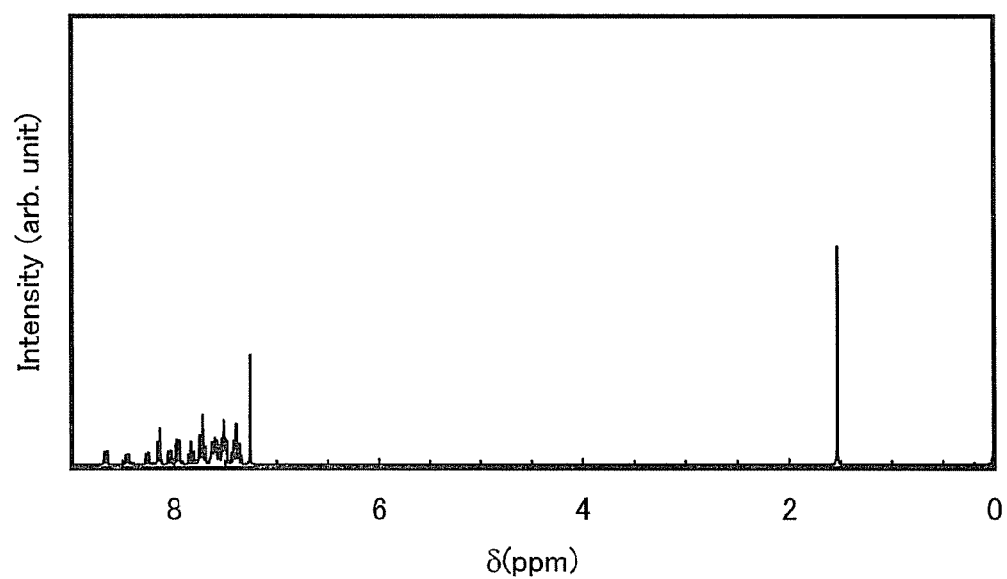
FIGS. 12A and 12B show NMR charts of mBnfPA.
Figure 12B:
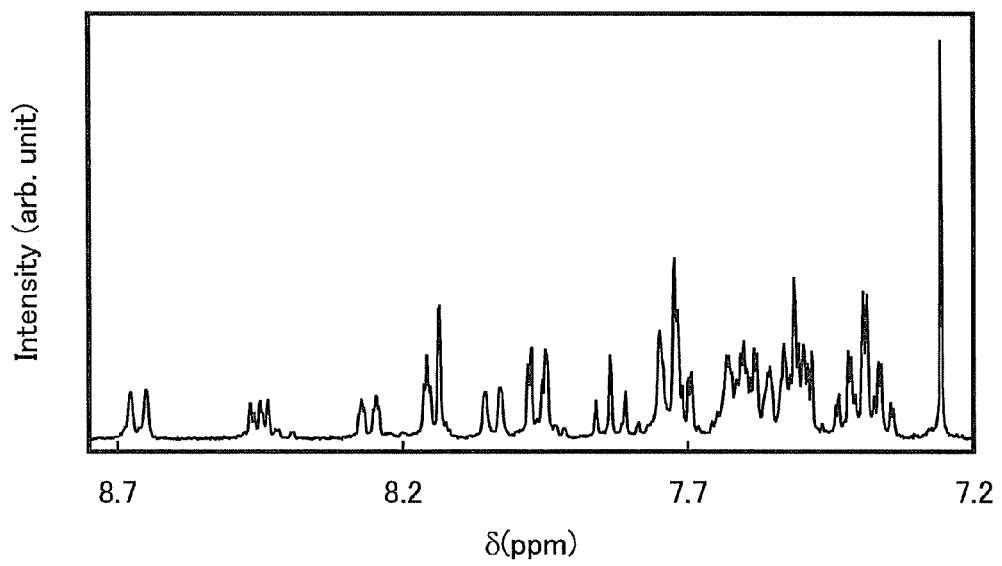

Further, $^1$H-NMR charts are shown in FIGS. 12A and 12B. Note that FIG. 12B is a chart where the range of from 7.2 ppm to 8.75 ppm in FIG. 12A is enlarged.

Furthermore, mBnfPA, which was obtained, was subjected to thermogravimetry-differential thermal analysis (TG-DTA). The temperature at which the weight becomes 95% of that at the start of the measurement under atmospheric pressure (hereinafter, this temperature is referred to as "5% weight loss temperature") was found to be 403° C. by the measurement with a thermogravimetry/differential thermal analysis apparatus (TG/DTA-320, manufactured by Seiko Instruments Inc.). This result indicates that mBnfPA is a material having high heat resistance.

Figure 13A:
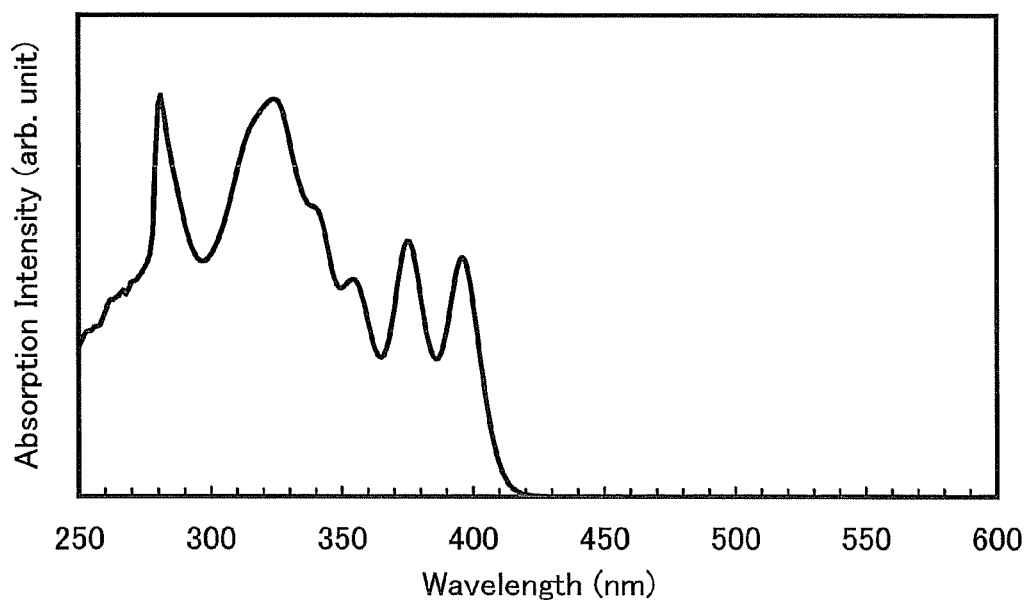
FIGS. 13A and 13B show an absorption spectrum and an emission spectrum of mBnfPA in a toluene solution of mBnfPA.
Figure 13B:
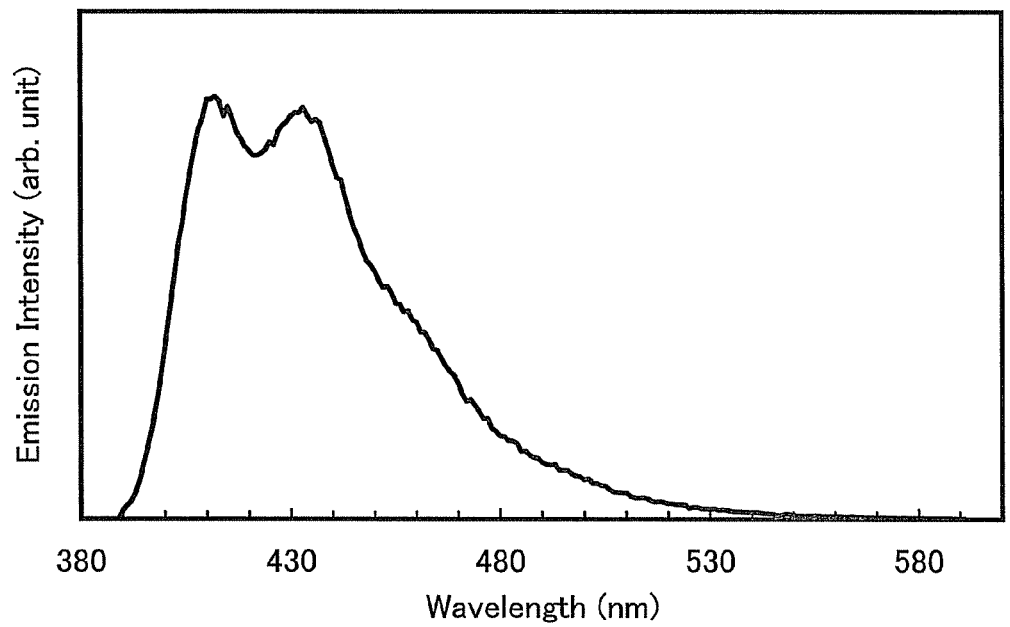
Figure 14A:
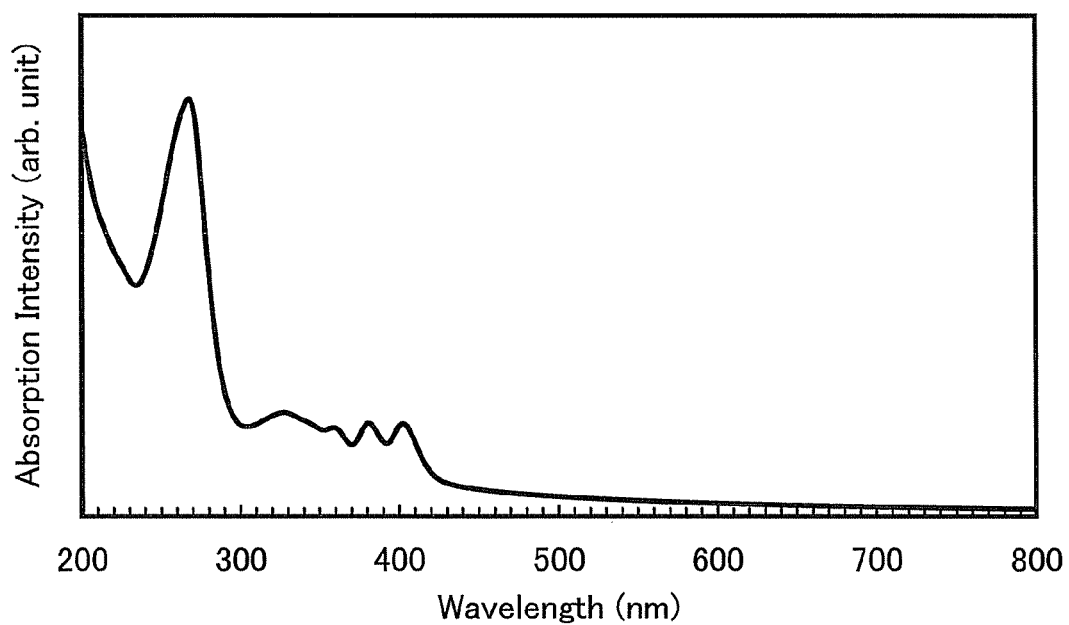
FIGS. 14A and 14B show an absorption spectrum and an emission spectrum of a thin film of mBnfPA.
Figure 14B:
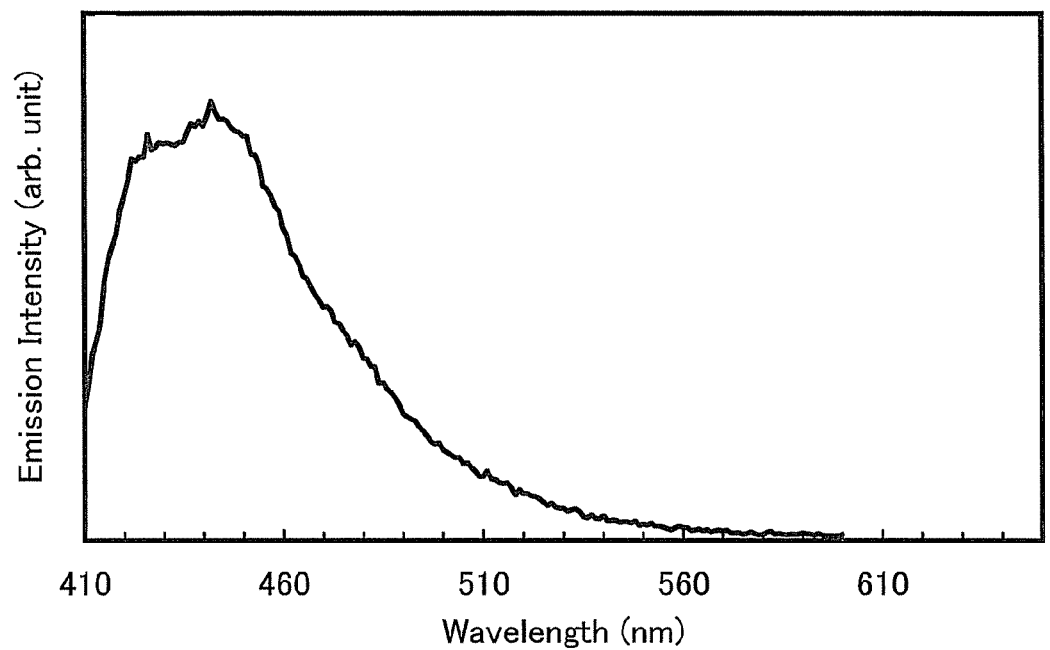

Further, FIG. 13A shows an absorption spectrum of mBnfPA in a toluene solution of mBnfPA, and FIG. 13B shows an emission spectrum thereof. Furthermore, FIG. 14A shows an absorption spectrum of a thin film of mBnfPA, and FIG. 14B shows an emission spectrum thereof. An ultraviolet-visible spectrophotometer (V-550, manufactured by JASCO Corporation) was used for the measurements of the absorption spectra. The measurements were performed with samples prepared in such a way that the solution was put in a quartz cell while the thin film was obtained by evaporation onto a quartz substrate. The figures show the absorption spectrum of the solution which was obtained by subtraction of the absorption spectra of quartz and toluene from those of quartz and the solution, and the absorption spectrum of the thin film which was obtained by subtraction of the absorption spectrum of a quartz substrate from those of the quartz substrate and the thin film. In FIG. 13A and FIG. 14A, the horizontal axis represents wavelength (nm) and the vertical axis represents absorption intensity (arbitrary unit). Similarly, in FIG. 13B and FIG. 14B, the horizontal axis represents wavelength (nm) and the vertical axis represents emission intensity (arbitrary unit). In the case of the toluene solution, absorption peaks were observed at around 267 nm, 281 nm, 324 nm, 354 nm, 375 nm, and 396 nm, and emission wavelength peaks were at 411 nm and 434 nm (at an excitation wavelength of 376 nm). Further, in the case of the thin film, absorption peaks were observed at around 268 nm, 328 nm, 359 nm, 381 nm, and 402 nm, and emission wavelength peaks were at 430 nm and 442 nm (at an excitation wavelength of 402 nm).

Further, the HOMO level and LUMO level of mBnfPA in the thin film state were measured. The value of the HOMO level was obtained by conversion of the value of the ionization potential measured with a photoelectron spectrometer (AC-2, manufactured by Riken Keiki Co., Ltd.) in the air into a negative value. The value of the LUMO level was obtained in such a way that the absorption edge was found from a Tauc plot with an assumption of direct transition using the data of the absorption spectrum of the thin film of mBnfPA which is shown in FIG. 14A and the absorption edge was added as an optical energy gap to the value of the HOMO level. As a result, the HOMO level, energy gap, and LUMO level of mBnfPA were −5.79 eV, 2.96 eV, and −2.83 eV, respectively.

EXAMPLE 3

In Example 3, an example in which 6-[4-(9,10-diphenyl-2-anthryl)phenyl]-benzo[b]naphtho[1,2-d]furan (abbreviation: 2BnfPPA) represented by the structural formula (116) in Embodiment 1 is described.

Synthesis of 6-[4-(9,10-diphenyl-2-anthryl)phenyl]-benzo[b]naphtho[1,2-d]furan (abbreviation: 2Bnf-PPA)

Into a 50 mL three-neck flask were placed 1.8 g (3.8 mmol) of 2-(4-bromophenyl)-9,10-diphenylanthracene and 1.0 g (3.8 mmol) of benzo[b]naphtho[1,2-d]furan-6-boronic acid synthesized in Step 1 of Example 1, and the air in the flask was replaced with nitrogen. To this mixture were added 15 mL of toluene, 5.0 mL of ethanol, and 4.0 mL of an aqueous solution of sodium carbonate. While the pressure was reduced, this mixture was stirred to be degassed. To this mixture was added 0.22 g (0.19 mmol) of tetrakis(triphenylphosphine)palladium (0), and the mixture was stirred at 80° C. for 3 hours under a nitrogen stream, so that a solid was precipitated. After the mixture was cooled to room temperature, the precipitated solid was collected by suction filtration. The collected solid was purified by silica gel column chromatography (a developing solvent in which the ratio of hexane to toluene was 5:1) to give a solid. The obtained solid was recrystallized from toluene/hexane, so that 1.4 g of a yellow powder of the object of the synthesis was obtained in 62% yield.

By a train sublimation method, 1.0 g of the obtained yellow powdery solid was purified. In the sublimation purification, 2BnfPPA was heated at 295° C. under a pressure of 2.7 Pa with a flow rate of argon at 5.0 mL/min. After the sublimation purification, 0.85 g of a yellow solid of 2BnfPPA was recovered in 85% yield. The above-described synthesis scheme is illustrated in the following scheme (G-1).

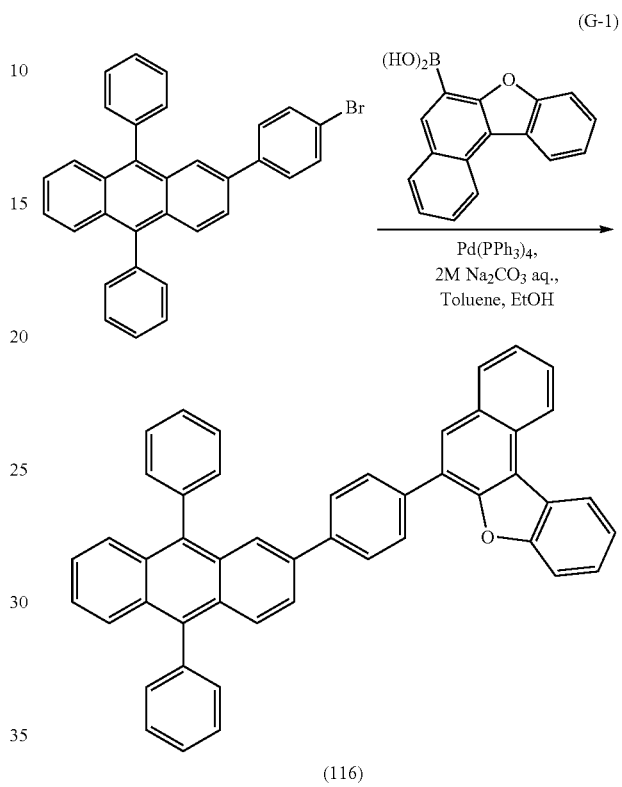

Nuclear magnetic resonance (NMR) spectroscopy identified this compound as 6-[4-(9,10-diphenyl-2-anthryl)phenyl]-benzo[b]naphtho[1,2-d]furan (abbreviation: 2BnfPPA), which was the object of the synthesis.

$^1$H-NMR measurement data of the obtained compound are as follows: $^1$H-NMR (CDCl$_3$, 300 MHz): δ=7.34 (d, J=3.3 Hz, 1H), 7.36 (d, J=3.3 Hz, 1H), 7.49-7.85 (m, 21H), 8.03-8.08 (m, 5H), 8.44-8.47 (m, 1H), 8.66 (d, J$_1$=7.8 Hz, 1H)

Figure 15A:
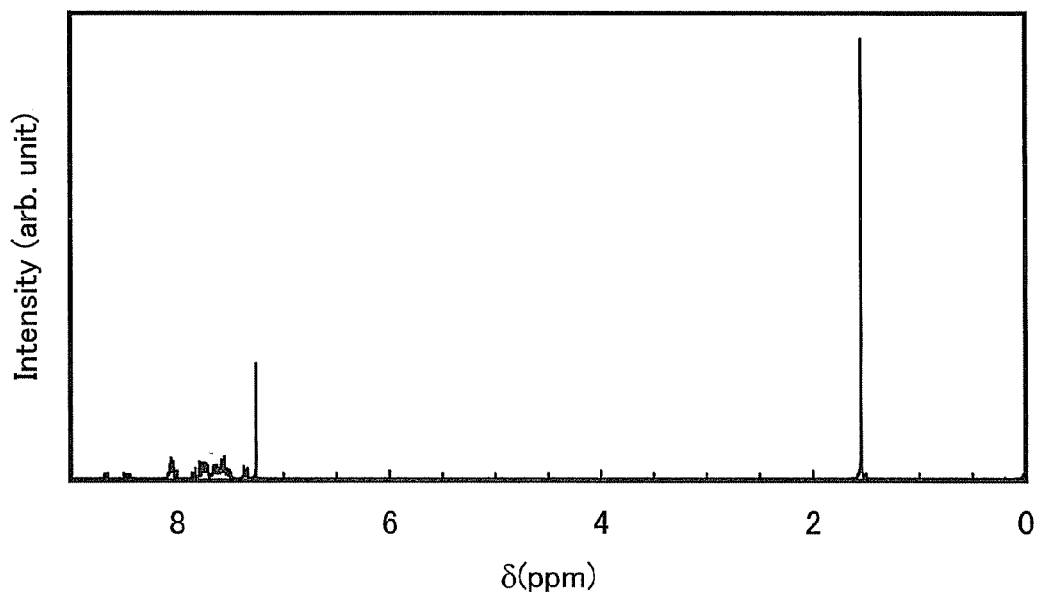
FIGS. 15A and 15B show NMR charts of 2BnfPPA.
Figure 15B:
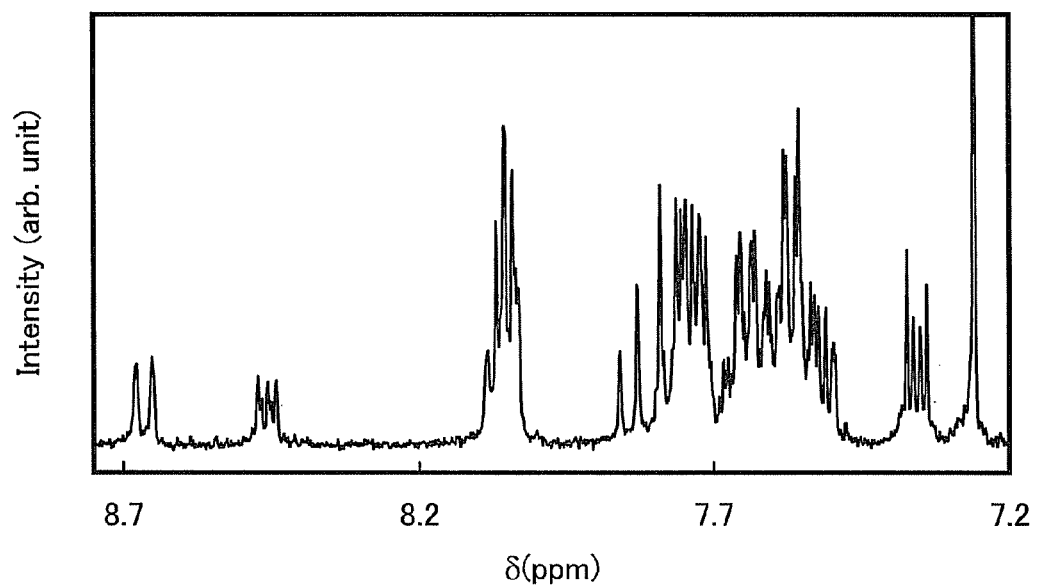

Further, $^1$H-NMR charts are shown in FIGS. 15A and 15B. Note that FIG. 15B is a chart where the range of from 7.2 ppm to 8.75 ppm in FIG. 15A is enlarged.

Furthermore, 2BnfPPA, which was obtained, was subjected to thermogravimetry-differential thermal analysis (TG-DTA). The temperature at which the weight becomes 95% of that at the start of the measurement under atmospheric pressure (hereinafter, this temperature is referred to as "5% weight loss temperature") was found to be 435° C. by the measurement with a thermogravimetry/differential thermal analysis apparatus (TG/DTA-320, manufactured by Seiko Instruments Inc.). This result indicates that 2BnfPPA is a material having high heat resistance.

Figure 16A:
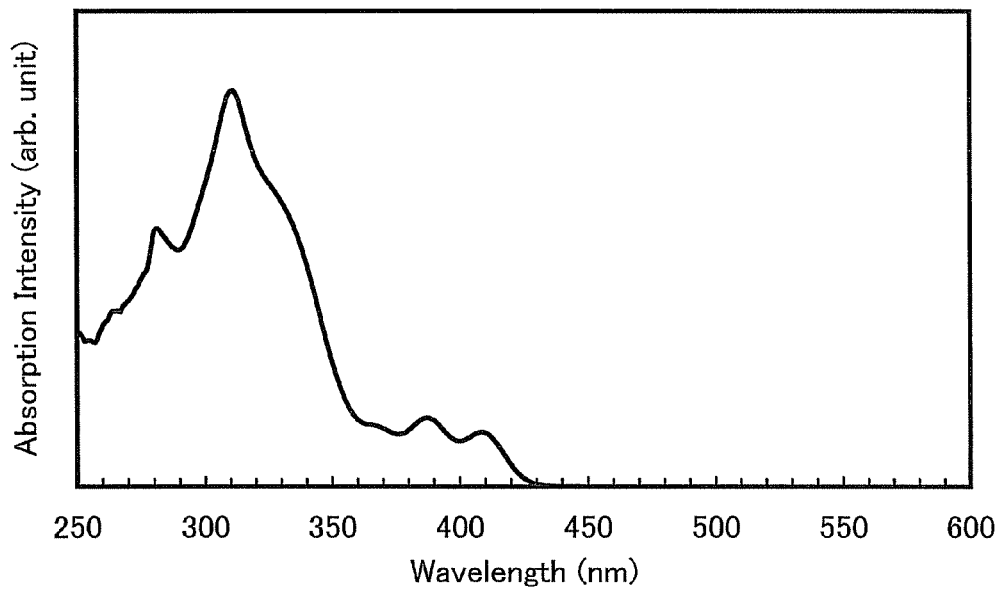
FIGS. 16A and 16B show an absorption spectrum and an emission spectrum of 2BnfPPA in a toluene solution of 2BnfPPA.
Figure 16B:
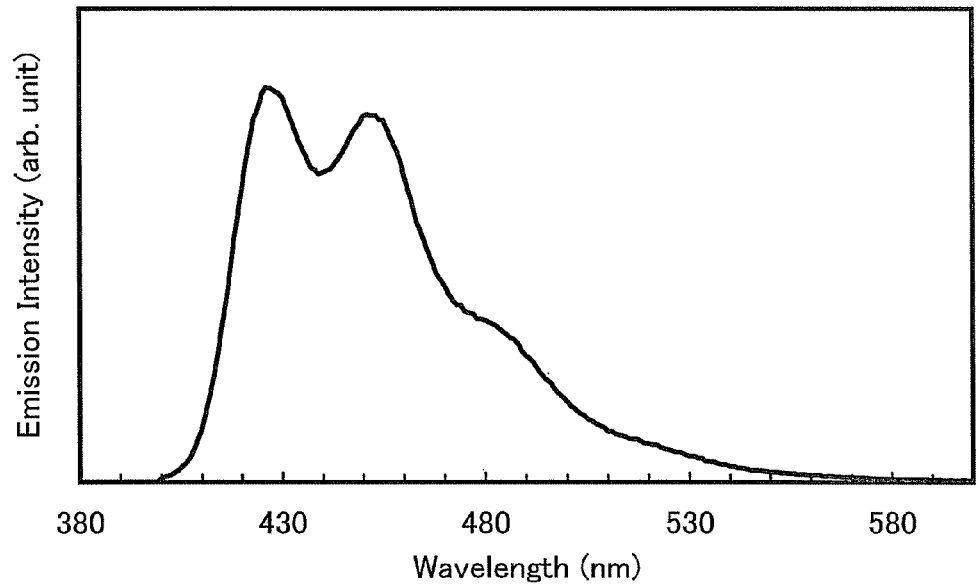
Figure 17A:
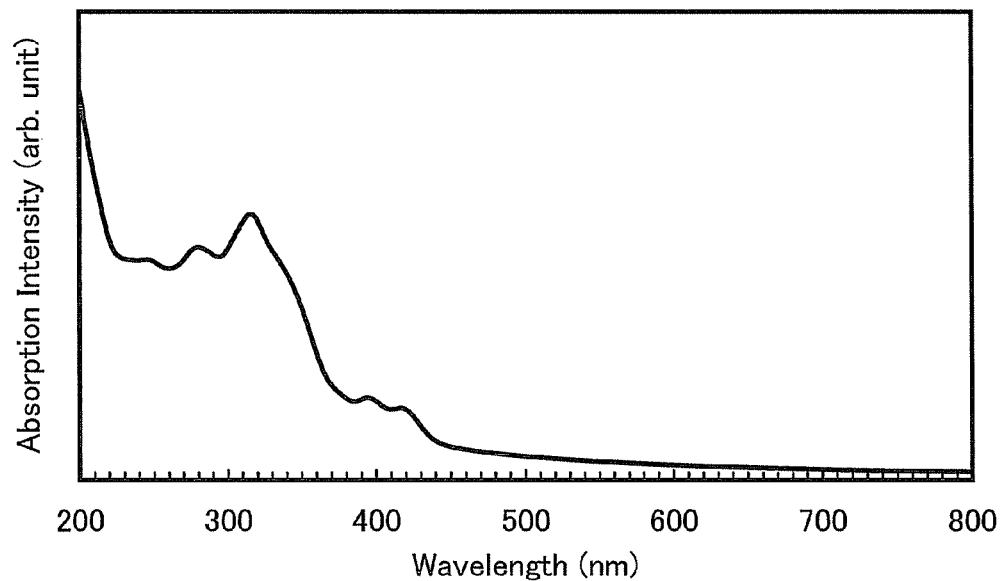
FIGS. 17A and 17B show an absorption spectrum and an emission spectrum of a thin film of 2BnfPPA.
Figure 17B:
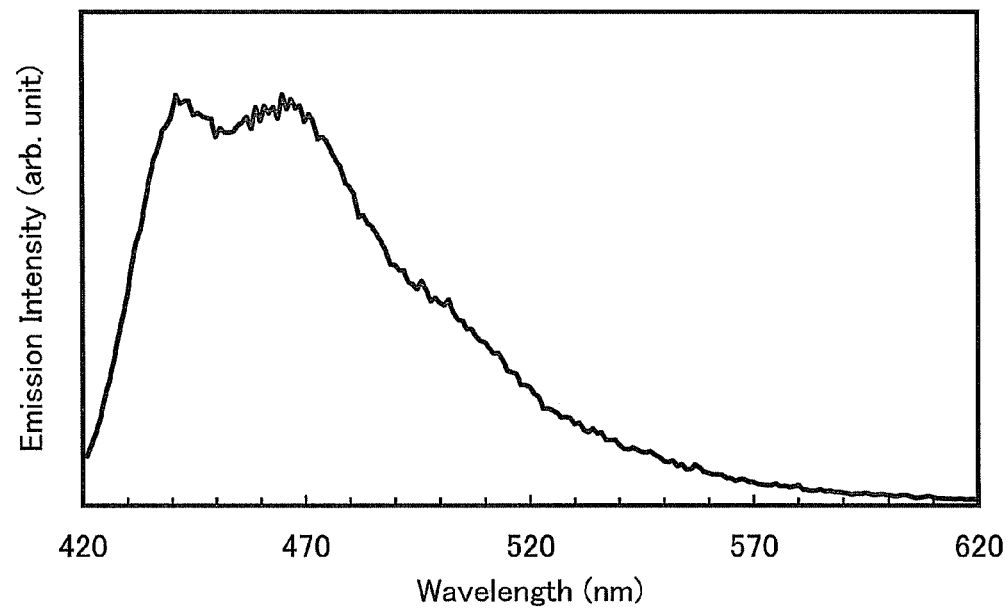

Further, FIG. 16A shows an absorption spectrum of 2BnfPPA in a toluene solution of 2BnfPPA, and FIG. 16B shows an emission spectrum thereof. Furthermore, FIG. 17A shows an absorption spectrum of a thin film of 2BnfPPA, and FIG. 17B shows an emission spectrum thereof. An ultraviolet-visible spectrophotometer (V-550, manufactured by JASCO Corporation) was used for the measurements of the absorption spectra. The measurements were performed with samples prepared in such a way that the solution was put in a quartz cell while the thin film was obtained by evaporation onto a quartz substrate. The figures show the absorption spectrum of the solution which was obtained by subtraction of the absorption spectra of quartz and toluene from those of quartz and the solution, and the absorption spectrum of the thin film which was obtained by subtraction of the absorption spectrum of a quartz substrate from those of the quartz substrate and the thin film. In FIG. 16A and FIG. 17A, the horizontal axis represents wavelength (nm) and the vertical axis represents absorption intensity (arbitrary unit). Similarly, in FIG. 16B and FIG. 17B, the horizontal axis represents wavelength (nm) and the vertical axis represents emission intensity (arbitrary unit). In the case of the toluene solution, absorption peaks were observed at around 281 nm, 311 nm, 387 nm, and 409 nm, and emission wavelength peaks were at 427 nm and 452 nm (at an excitation wavelength of 388 nm). Further, in the case of the thin film, absorption peaks were observed at around 245 nm, 280 nm, 316 nm, 333 nm, 394 nm, and 416 nm, and emission wavelength peaks were at 442 nm and 466 nm (at an excitation wavelength of 418 nm).

Further, the HOMO level and LUMO level of 2BnfPPA in the thin film state were measured. The value of the HOMO level was obtained by conversion of the value of the ionization potential measured with a photoelectron spectrometer (AC-2, manufactured by Riken Keiki Co., Ltd.) in the air into a negative value. The value of the LUMO level was obtained in such a way that the absorption edge was found from a Tauc plot with an assumption of direct transition using the data of the absorption spectrum of the thin film of 2BnfPPA which is shown in FIG. 17A and the absorption edge was added as an optical energy gap to the value of the HOMO level. As a result, the HOMO level, energy gap, and LUMO level of 2BnfPPA were −5.75 eV, 2.81 eV, and −2.94 eV, respectively.

EXAMPLE 4

In Example 4, an example in which 6-[4-(10-phenyl-9-anthryl)phenyl]-benzo[b]naphtho[1,2-d]furan (abbreviation: BnfPA) represented by the structural formula (134) in Embodiment 1 is described.

Synthesis of 6-[4-(10-phenyl-9-anthryl)phenyl]-benzo[b]naphtho[1,2-d]furan (abbreviation: BnfPA)

Into a 100 mL three-neck flask were placed 1.8 g (4.5 mmol) of 9-(4-bromophenyl)-10-phenylanthracene and 1.2 g (4.5 mmol) of benzo[b]naphtho[1,2-d]furan-6-boronic acid synthesized in Step 1 of Example 1, and the air in the flask was replaced with nitrogen. To this mixture were added 15 mL of toluene, 7.0 mL of ethanol, and 5.0 mL of an aqueous solution of sodium carbonate (2.0 mol/L). While the pressure was reduced, this mixture was stirred to be degassed. To this mixture was added 0.26 g (0.22 mmol) of tetrakis(triphenylphosphine)palladium(0), and the mixture was stirred at 80° C. for 6 hours under a nitrogen stream, so that a solid was precipitated. This flask was cooled to room temperature, and this mixture was suction-filtered. The obtained solid was dissolved in about 500 mL of hot toluene, and this solution was suction-filtered through Celite (produced by Wako Pure Chemical Industries, Ltd., Catalog No. 531-16855), alumina, silica gel, and Florisil (produced by Wako Pure Chemical Industries, Ltd., Catalog No. 540-00135). A solid obtained by concentration of the obtained filtrate was recrystallized from toluene, so that 0.77 g of a white powder of the object of the synthesis was obtained in 31% yield.

By a train sublimation method, 0.77 g of the obtained white powdery solid was purified. In the sublimation purification, BnfPA was heated at 275° C. under a pressure of 2.7 Pa with a flow rate of argon at 5.0 mL/min. After the sublimation purification, 0.70 g of a pale yellow solid of BnfPA was recovered in 90% yield. The above-described synthesis scheme is illustrated in the following scheme (H-1).

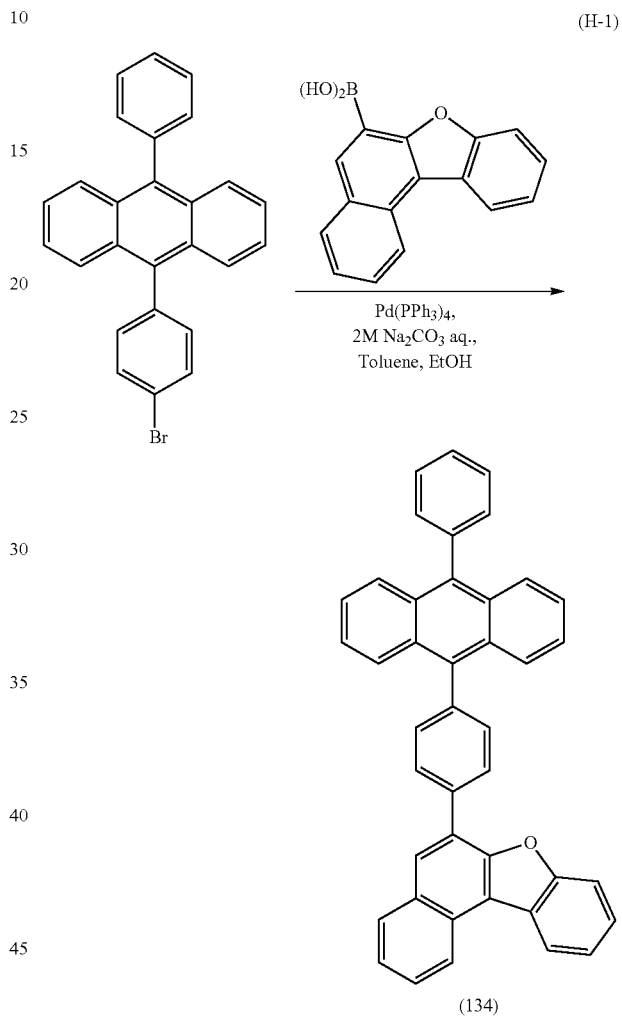

Nuclear magnetic resonance (NMR) spectroscopy identified this compound as 6-[4-(10-phenyl-9-anthryl)phenyl]-benzo[b]naphtho[1,2-d]furan (abbreviation: BnfPA), which was the object of the synthesis.

$^1$H-NMR measurement data of the obtained compound are as follows: $^1$H-NMR (CDCl$_3$, 300 MHz): δ=7.34-7.43 (m, 4H), 7.50-7.66 (m, 8H), 7.70-7.77 (m, 5H), 7.80-7.84 (m, 1H), 7.88-7.91 (m, 2H), 8.15 (d, J=7.8 Hz, 1H), 8.27 (t, J=7.8 Hz, 3H), 8.49-8.52 (m, 1H), 8.72 (d, J=8.4 Hz, 1H)

Figure 18A:
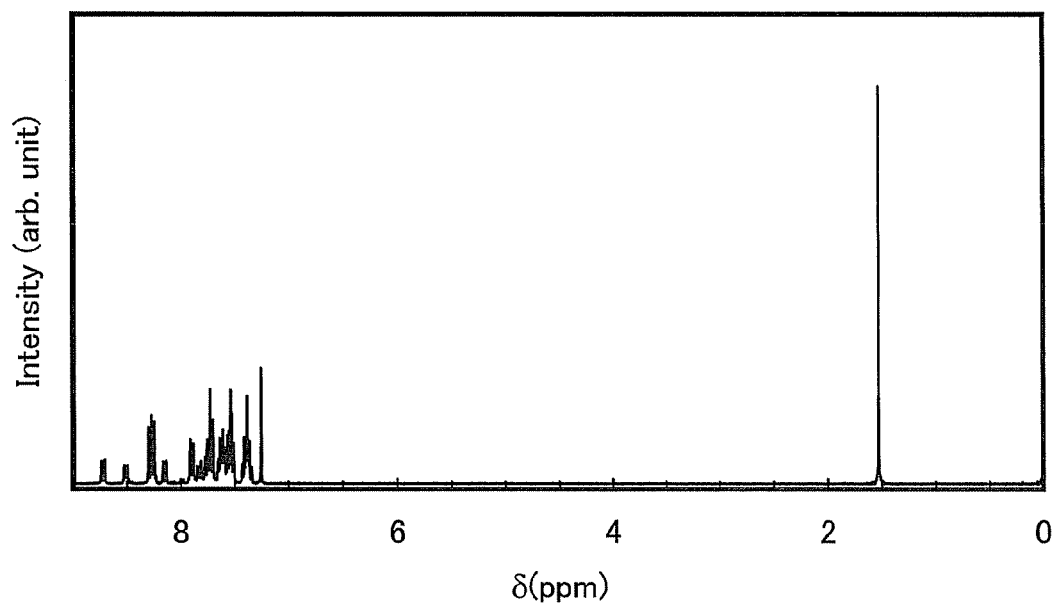
FIGS. 18A and 18B show NMR charts of BnfPA.
Figure 18B:
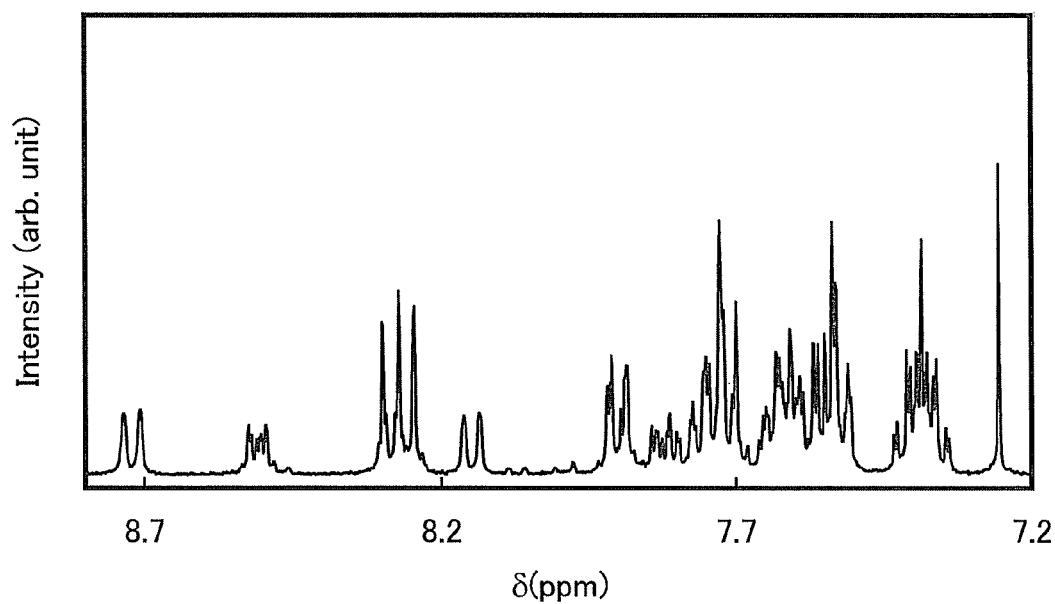

Further, $^1$H-NMR charts are shown in FIGS. 18A and 18B. Note that FIG. 18B is a chart where the range of from 7.2 ppm to 8.8 ppm in FIG. 18A is enlarged.

Furthermore, BnfPA, which was obtained, was subjected to thermogravimetry-differential thermal analysis (TG-DTA). The temperature at which the weight becomes 95% of that at the start of the measurement under atmospheric pressure (hereinafter, this temperature is referred to as "5% weight loss temperature") was found to be 420° C. by the measurement with a thermogravimetry/differential thermal analysis apparatus (TG/DTA-320, manufactured by Seiko Instruments Inc.). This result indicates that BnfPA is a material having high heat resistance.

Figure 19A:
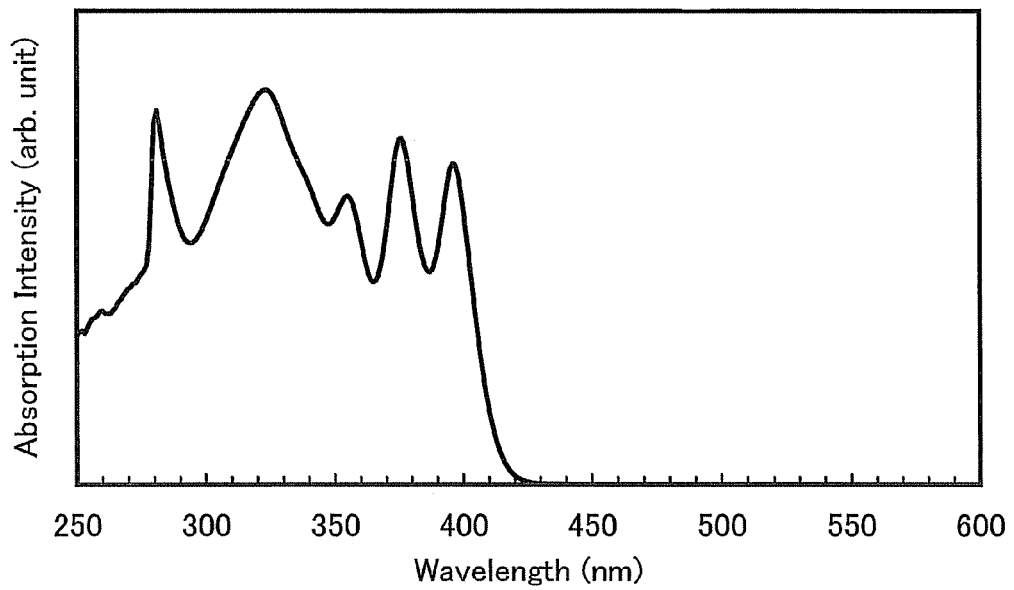
FIGS. 19A and 19B show an absorption spectrum and an emission spectrum of BnfPA in a toluene solution of BnfPA.
Figure 19B:
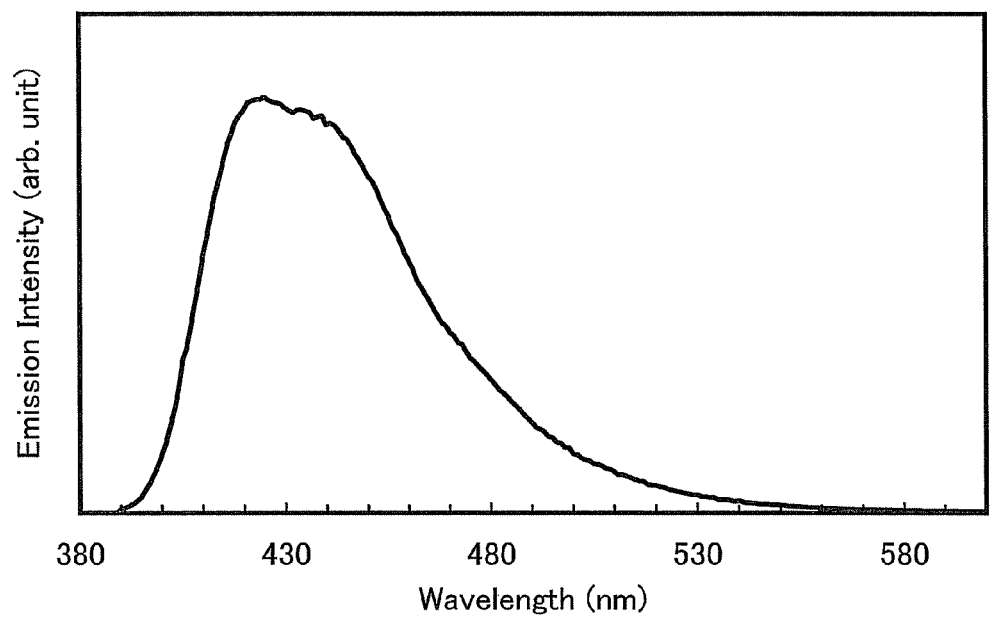
Figure 20A:
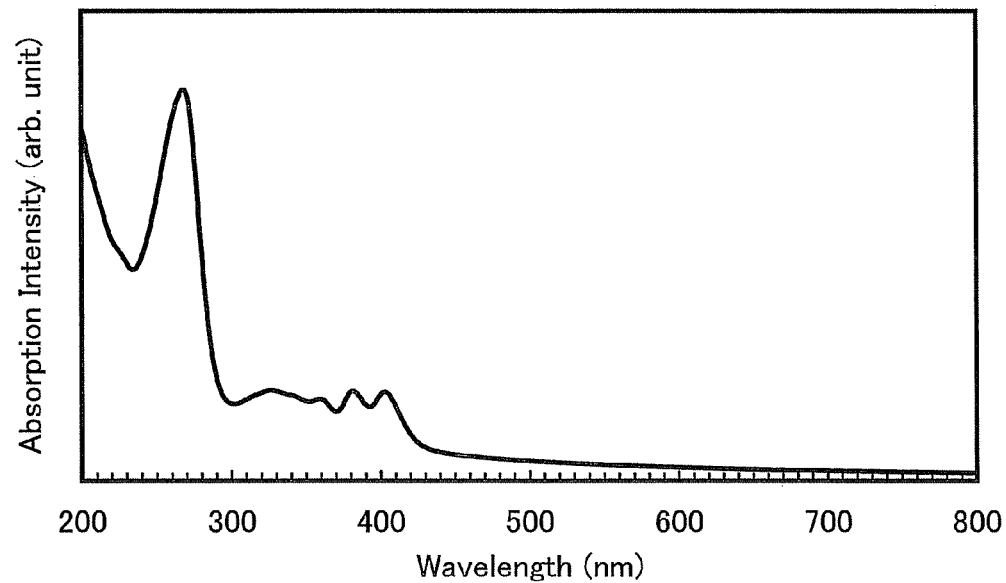
FIGS. 20A and 20B show an absorption spectrum and an emission spectrum of a thin film of BnfPA.
Figure 20B:
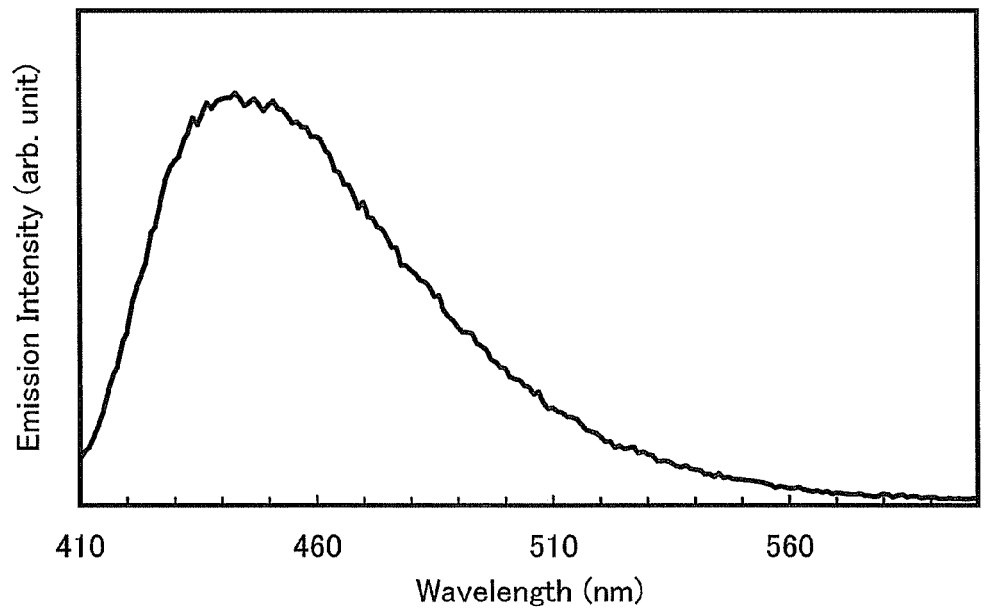

Further, FIG. 19A shows an absorption spectrum of BnfPA in a toluene solution of BnfPA, and FIG. 19B shows an emission spectrum thereof. Furthermore, FIG. 20A shows an absorption spectrum of a thin film of BnfPA, and FIG. 20B shows an emission spectrum thereof. An ultraviolet-visible spectrophotometer (V-550, manufactured by JASCO Corporation) was used for the measurements of the absorption spectra. The measurements were performed with samples prepared in such a way that the solution was put in a quartz cell while the thin film was obtained by evaporation onto a quartz substrate. The figures show the absorption spectrum of the solution which was obtained by subtraction of the absorption spectra of quartz and toluene from those of quartz and the solution, and the absorption spectrum of the thin film which was obtained by subtraction of the absorption spectrum of a quartz substrate from those of the quartz substrate and the thin film. In FIG. 19A and FIG. 20A, the horizontal axis represents wavelength (nm) and the vertical axis represents absorption intensity (arbitrary unit). Similarly, in FIG. 19B and FIG. 20B, the horizontal axis represents wavelength (nm) and the vertical axis represents emission intensity (arbitrary unit). In the case of the toluene solution, absorption peaks were observed at around 281 nm, 323 nm, 355 nm, 376 nm, and 396 nm, and emission wavelength peaks were at 423 nm and 446 nm (at an excitation wavelength of 376 nm). Further, in the case of the thin film, absorption peaks were observed at around 208 nm, 223 nm, 268 nm, 327 nm, 359 nm, 381 nm, and 403 nm, and an emission wavelength peak was at 443 nm (at an excitation wavelength of 403 nm).

Further, the HOMO level and LUMO level of BnfPA in the thin film state were measured. The value of the HOMO level was obtained by conversion of the value of the ionization potential measured with a photoelectron spectrometer (AC-2, manufactured by Riken Keiki Co., Ltd.) in the air into a negative value. The value of the LUMO level was obtained in such a way that the absorption edge was found from a Tauc plot with an assumption of direct transition using the data of the absorption spectrum of the thin film of BnfPA which is shown in FIG. 20A and the absorption edge was added as an optical energy gap to the value of the HOMO level. As a result, the HOMO level, energy gap, and LUMO level of BnfPA were −5.81 eV, 2.94 eV, and −2.87 eV, respectively.

EXAMPLE 5

In this example, a fabrication method of the light-emitting element according to one embodiment of the present invention and measurement results of element characteristics of the light-emitting element are described with reference to drawings.

Figure 8:
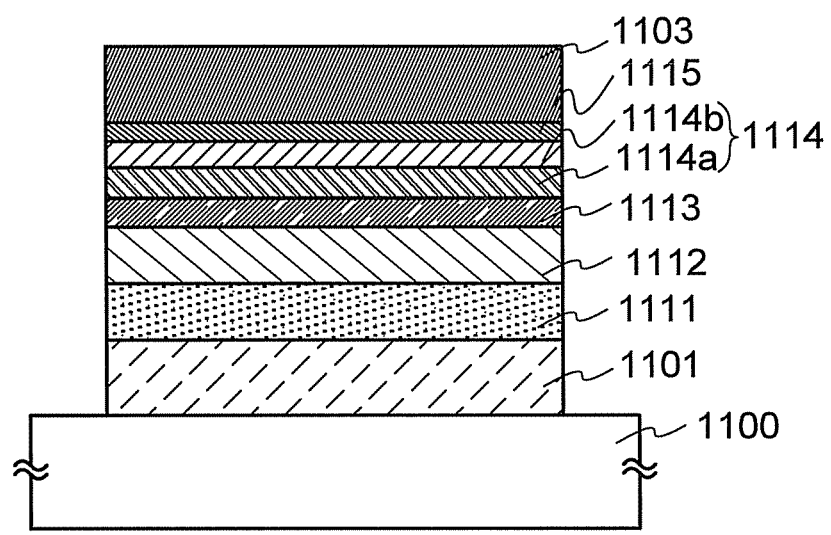
FIG. 8 illustrates a light-emitting element of Examples.

A method of fabricating light-emitting elements 1-1 to 1-3, 2, 3-1, 3-2, 4-1, 4-2, and 5 of this example is described with reference to FIG. 8. Structural formulae of the following organic compounds used in this example are illustrated below: Alq; BPhen; 9-phenyl-3-[4-(10-phenyl-9-anthryl)phenyl]-9H-carbazole (abbreviation: PCzPA); 9-[4-(N-carbazolyl)]phenyl-10-phenylanthracene (abbreviation: CzPA); N,N'-bis[4-(9-phenyl-9H-fluoren-9-yl)phenyl]-N,N'-diphenyl-pyrene-1,6-diamine (abbreviation: 1,6FLPAPrn); and N'-bis(3-methylphenyl)-N,N'-bis[3-(9-phenyl-9H-fluoren-9-yl)phenyl]-pyrene-1,6-diamine (abbreviation: 1,6mMemFLPAPrn).

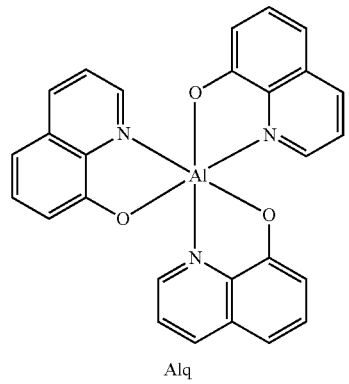

Alq

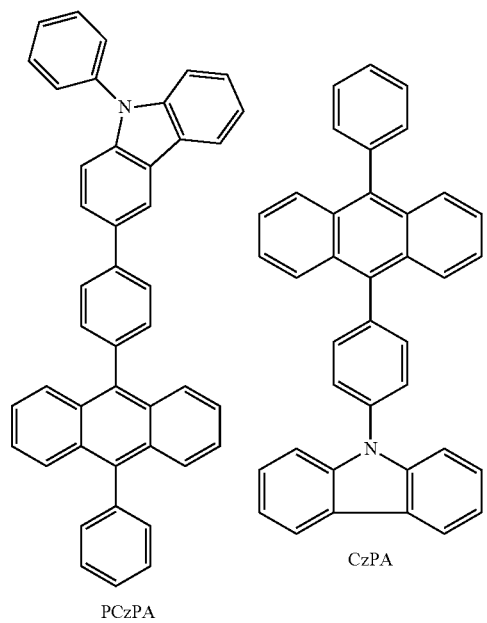

PCzPA        CzPA

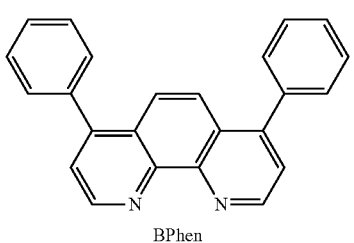

BPhen

-continued

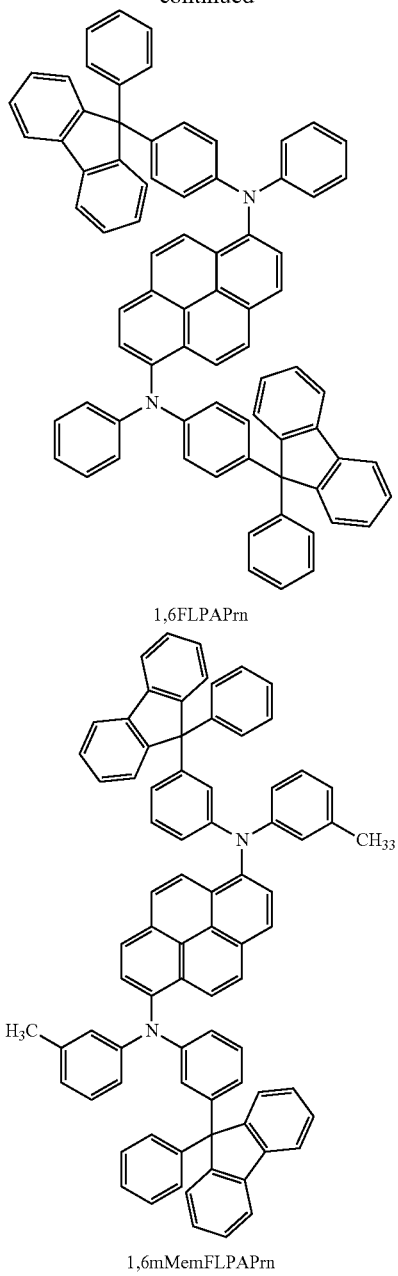

1,6FLPAPrn 1,6mMemFLPAPrn

For each of the light-emitting elements 1-1 to 1-3, 2, 3-1, 3-2, 4-1, 4-2, and 5, over a substrate 1100 which was a glass substrate, a film of indium tin oxide containing silicon oxide (ITSO) was formed using a sputtering method, so that a first electrode 1101 was formed. The thickness of the first electrode 1101 was set to 110 nm and the electrode area was set to 2 mm×2 mm. In this example, the first electrode 1101 was used as an anode.

Next, the substrate 1100 provided with the first electrode 1101 was fixed to a substrate holder in the vacuum evaporation apparatus so that a surface over which the first electrode 1101 was provided faced downward. The pressure in the vacuum evaporation apparatus was reduced to about $10^{-4}$ Pa. Then, over the first electrode 1101, PCzPA and molybdenum (VI) oxide were co-evaporated to form a hole-injection layer 1111. The weight ratio of PCzPA to molybdenum oxide was adjusted to 4:2. The thickness of the hole-injection layer 1111 was set to 50 nm for each of the light-emitting elements 1-1, 2, 3-1, 3-2, 4-1, 4-2, and 5, and 70 nm for each of the light-emitting elements 1-2 and 1-3. Note that the co-evaporation method refers to an evaporation method in which evaporation is carried out from a plurality of evaporation sources at the same time in one treatment chamber.

Next, over the hole-injection layer 1111, a PCzPA film was formed to form a hole-transport layer 1112. The thickness of the hole-transport layer 1112 was set to 10 nm for each of the light-emitting elements 1-1, 2, 3-1, 3-2, 4-1, 4-2, and 5, and 30 nm for each of the light-emitting elements 1-2 and 1-3.

For the light-emitting element 1-1, over the hole-transport layer 1112, 2mBnfPPA synthesized in Example 1 and 1,6FLPAPrn were co-evaporated so that the weight ratio of 2mBnfPPA to 1,6FLPAPrn was 1:0.05; thus, a light-emitting layer 1113 was formed. The thickness of the light-emitting layer 1113 was set to 30 nm.

For each of the light-emitting elements 1-2 and 1-3, over the hole-transport layer 1112, 2mBnfPPA synthesized in Example 1 and 1,6mMemFLPAPrn were co-evaporated so that the weight ratio of 2mBnfPPA to 1,6mMemFLPAPrn was 1:0.03; thus, the light-emitting layer 1113 was formed. The thickness thereof was set to 25 nm.

For the light-emitting element 2, over the hole-transport layer 1112, mBnfPA synthesized in Example 2 and 1,6FLPAPrn were co-evaporated so that the weight ratio of mBnfPA to 1,6FLPAPrn was 1:0.05; thus, the light-emitting layer 1113 was formed. The thickness thereof was set to 30 nm.

For the light-emitting element 3-1, over the hole-transport layer 1112, 2BnfPPA synthesized in Example 3 and 1,6FLPAPrn were co-evaporated so that the weight ratio of 2BnfPPA to 1,6FLPAPrn was 1:0.05; thus, the light-emitting layer 1113 was formed. The thickness thereof was set to 30 nm.

For the light-emitting element 3-2, over the hole-transport layer 1112, 2BnfPPA synthesized in Example 3 and 1,6FLPAPrn were co-evaporated so that the weight ratio of 2BnfPPA to 1,6FLPAPrn was 1:0.03; thus, the light-emitting layer 1113 was formed. The thickness thereof was set to 30 nm.

For each of the light-emitting elements 4-1 and 4-2, over the hole-transport layer 1112, BnfPA synthesized in Example 3 and 1,6FLPAPrn were co-evaporated so that the weight ratio of BnfPA to 1,6FLPAPrn was 1:0.05; thus, the light-emitting layer 1113 was formed. The thickness thereof was set to 30 nm.

For the light-emitting element 5, over the hole-transport layer 1112, 2mBnfPA synthesized in Example 6 and 1,6FLPAPrn were co-evaporated so that the weight ratio of 2 mBnfPA to 1,6FLPAPrn was 1:0.05; thus, the light-emitting layer 1113 was formed. The thickness thereof was set to 30 nm.

For each of the light-emitting elements 1-1, 2, 3-1, 4-1, and 5, over the light-emitting layer 1113, an Alq film was formed to a thickness of 10 nm, so that a first electron-transport layer 1114*a* was formed.

For each of the light-emitting elements 1-3, 3-2, and 4-2, over the light-emitting layer 1113, a CzPA film was formed to a thickness of 10 nm, so that the first electron-transport layer 1114*a* was formed.

For each of the light-emitting elements 1-1, 1-3, 2, 3-1, 3-2, 4-1, 4-2, and 5, over the first electron-transport layer 1114*a*, a film of bathophenanthroline (abbreviation: BPhen) was formed to a thickness of 15 nm, so that a second electron-transport layer 1114*b* was formed.

For the light-emitting element 1-2, a single layer is used as an electron-transport layer; over the light-emitting layer 1113, a BPhen film was formed to a thickness of 15 nm, so that an electron-transport layer 1114 was formed.

For each of the light-emitting elements 1-1 to 1-3, 2, 3-1, 3-2, 4-1, 4-2, and 5, over the electron-transport layer 1114 or the second electron-transport layer 1114b, a lithium fluoride (LiF) film was formed to a thickness of 1 nm by evaporation, so that an electron-injection layer 1115 was formed.

For each of the light-emitting elements 1-1 to 1-3, 2, 3-1, 3-2, 4-1, 4-2, and 5, an aluminum film was formed by evaporation to a thickness of 200 nm as a second electrode 1103 functioning as a cathode. Thus, the light-emitting elements 1-1 to 1-3, 2, 3-1, 3-2, 4-1, 4-2, and 5 of this example were fabricated.

Note that, in the above evaporation processes, evaporation was all performed using a resistance heating method.

Table 1 shows element structures of the light-emitting elements 1-1 to 1-3, 2, 3-1, 3-2, 4-1, 4-2, and 5 obtained as described above.

TABLE 1

| Elements | 1101 | 1111 | 1112 | 1113 | 11114 1114a | 1114b | 1115 | 1103 |
|---|---|---|---|---|---|---|---|---|
| 1-1 | ITSO 110 nm | PCzPA:MoOx (=4:2) 50 nm | PCzPA 10 nm | 2mBnfPPA:1,6FLPAPrn (=1:0.05) 30 nm | Alq 10 nm | BPhen 15 nm | LiF 1 nm | Al 200 nm |
| 1-2 | ITSO 110 nm | PCzPA:MoOx (=4:2) 70 nm | PCzPA 30 nm | 2mBnfPPA:1,6mMemFLPAPrn (=1:0.03) 25 nm | BPhen 15 nm | | LiF 1 nm | Al 200 nm |
| 1-3 | ITSO 110 nm | PCzPA:MoOx (=4:2) 70 nm | PCzPA 30 nm | 2mBnfPPA:1,6mMemFLPAPrn (=1:0:03) 25 nm | CzPA 10 nm | BPhen 15 nm | LiF 1 nm | Al 200 nm |
| 2 | ITSO 110 nm | PCzPA:MoOx (=4:2) 50 nm | PCzPA 10 nm | mBnfPA:1,6FLPAPrn (=1:0.05) 30 nm | Alq 10 nm | BPhen 15 nm | LiF 1 nm | Al 200 nm |
| 3-1 | ITSO 110 nm | PCzPA:MoOx (=4:2) 50 nm | PCzPA 10 nm | 2BnfPPA:1,6FLPAPrn (=1:0.05) 30 nm | Alq 10 nm | BPhen 15 nm | LiF 1 nm | Al 200 nm |
| 3-2 | ITSO 110 nm | PCzPA:MoOx (=4:2) 50 nm | PCzPA 10 nm | 2BnfPPA:1,6FLPAPrn (=1:0.03) 30 nm | CzPA 10 nm | BPhen 15 nm | LiF 1 nm | Al 200 nm |
| 4-1 | ITSO 110 nm | PCzPA:MoOx (=4:2) 50 nm | PCzPA 10 nm | BnfPA:1,6FLPAPrn (=1:0.05) 30 nm | Alq 10 nm | BPhen 15 nm | LiF 1 nm | Al 200 nm |
| 4-2 | ITSO 110 nm | PCzPA:MoOx (=4:2) 50 nm | PCzPA 10 nm | BnfPA:1,6FLPAPrn (=1:0.05) 30 nm | CzPA 10 nm | BPhen 15 nm | LiF 1 nm | Al 200 nm |
| 5 | ITSO 110 nm | PCzPA:MoOx (=4:2) 50 nm | PCzPA 10 nm | 2BnfPA:1,6FLPAPrn (=1:0.05) 30 nm | Alq 10 nm | BPhen 15 nm | LiF 1 nm | Al 200 nm |

*All mixture ratios are weight ratios.

The light-emitting elements 1-1 to 1-3, 2, 3-1, 3-2, 4-1, 4-2, and 5 were sealed in a glove box under a nitrogen atmosphere so as not to be exposed to air. After that, the operation characteristics of the elements were measured. Note that the measurement was carried out at room temperature (in an atmosphere kept at 25° C.).

Figure 21:
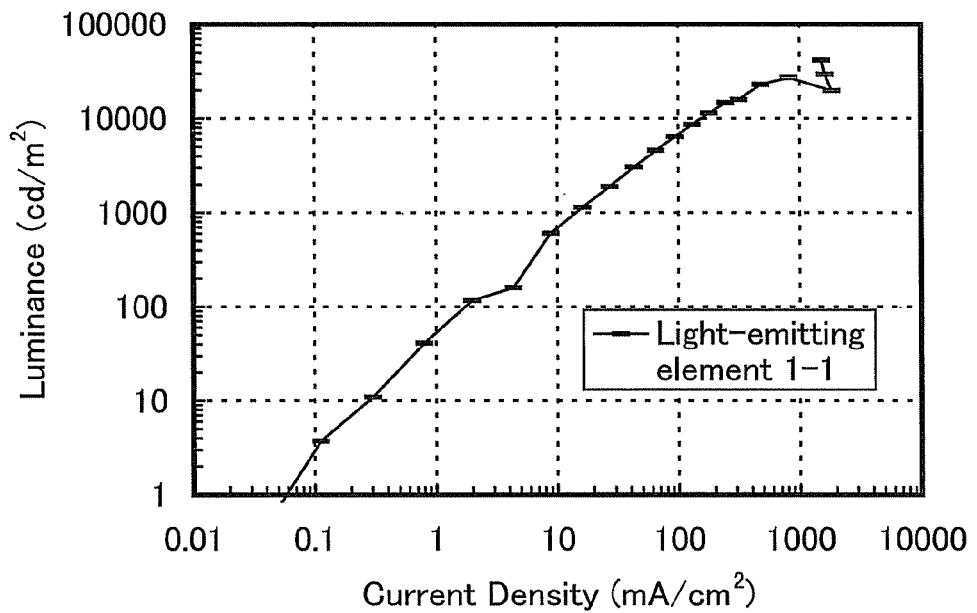
FIG. 21 shows luminance versus current density characteristics of a light-emitting element 1-1 (2mBnfPPA)
Figure 22:
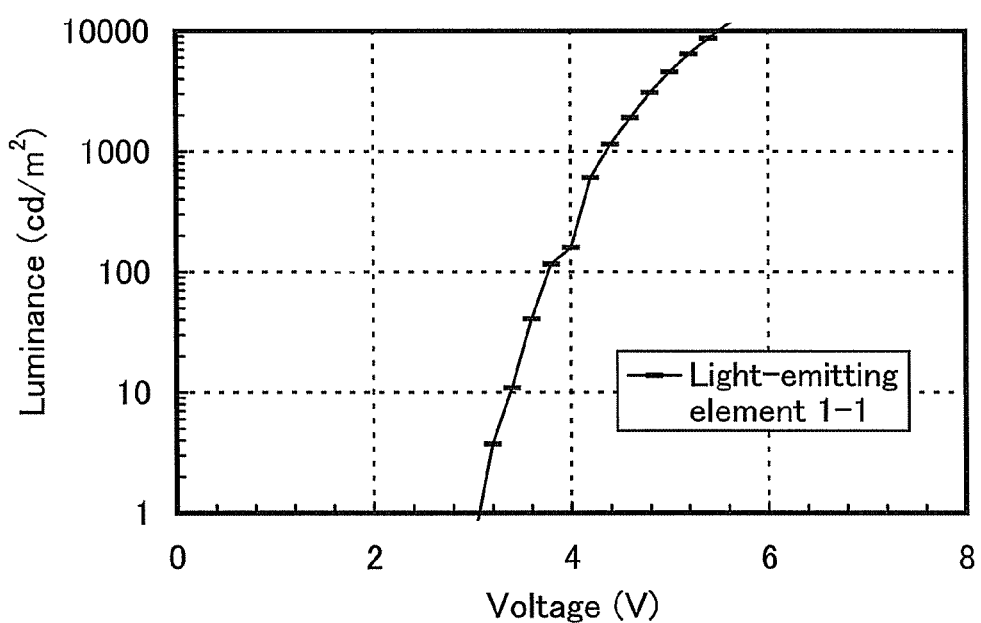
FIG. 22 shows luminance versus voltage characteristics of the light-emitting element 1-1 (2mBnfPPA)
Figure 23:
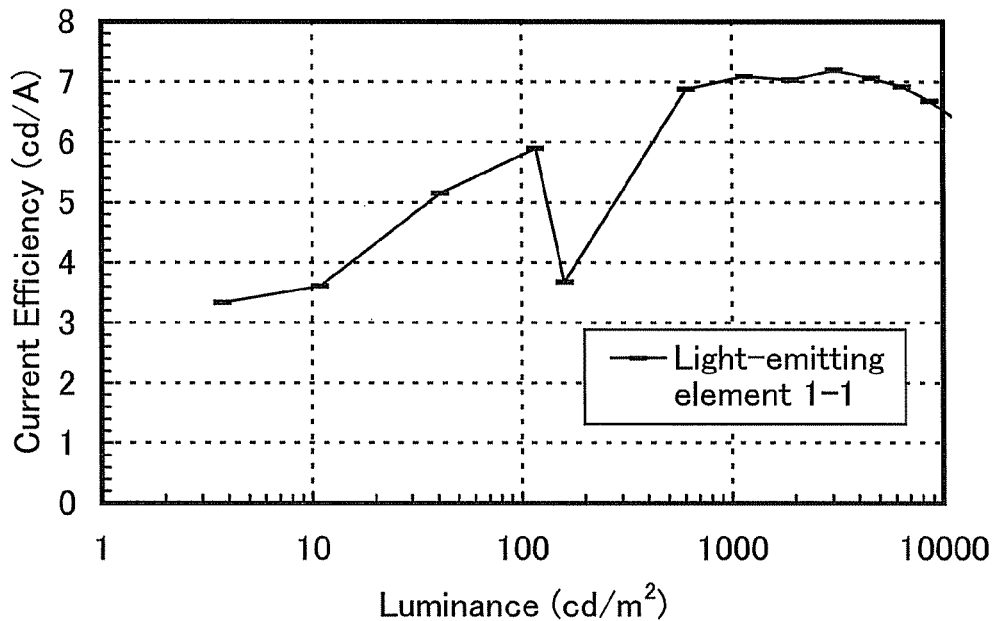
FIG. 23 shows current efficiency versus luminance characteristics of the light-emitting element 1-1 (2mBnfPPA)
Figure 24:
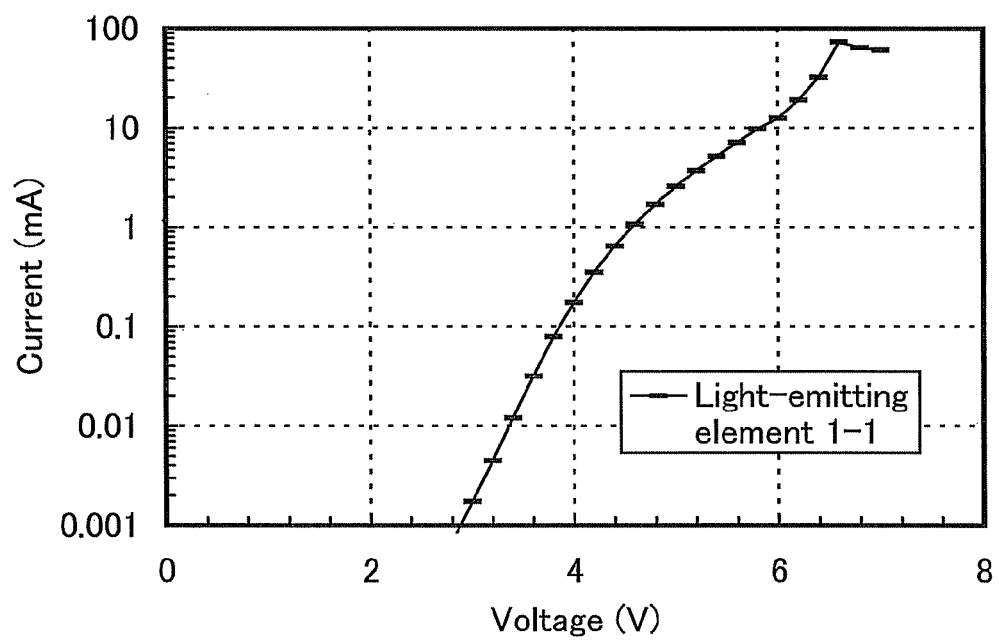
FIG. 24 shows current versus voltage characteristics of the light-emitting element 1-1 (2mBnfPPA)
Figure 27:
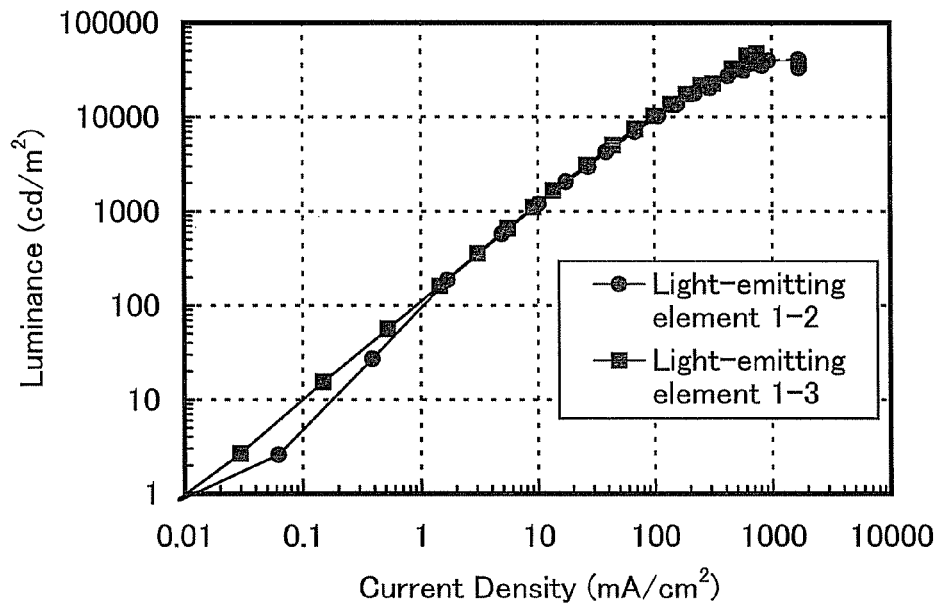
FIG. 27 shows luminance versus current density characteristics of light-emitting elements 1-2 and 1-3 (2mBnfPPA)
Figure 28:
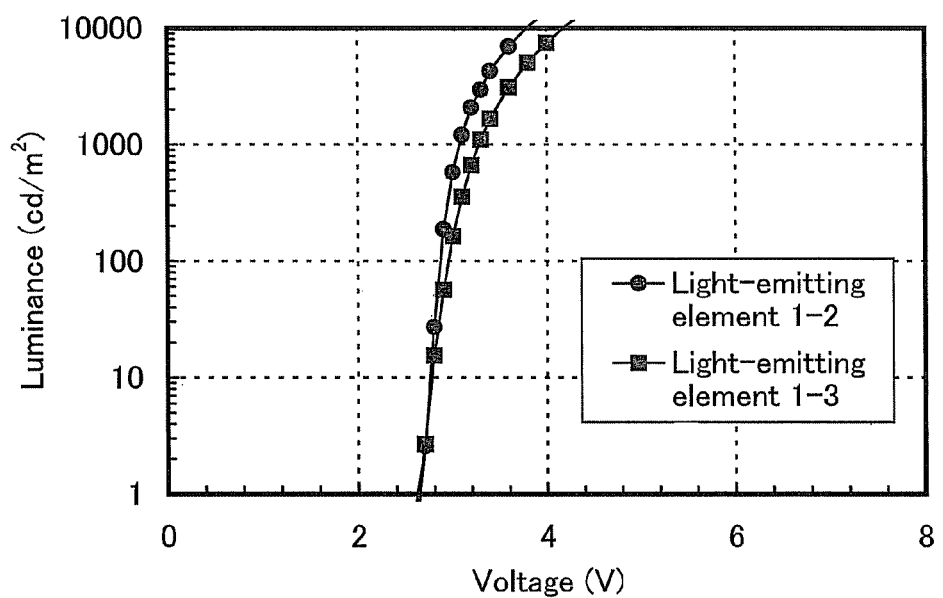
FIG. 28 shows luminance versus voltage characteristics of the light-emitting elements 1-2 and 1-3 (2mBnfPPA)
Figure 29:
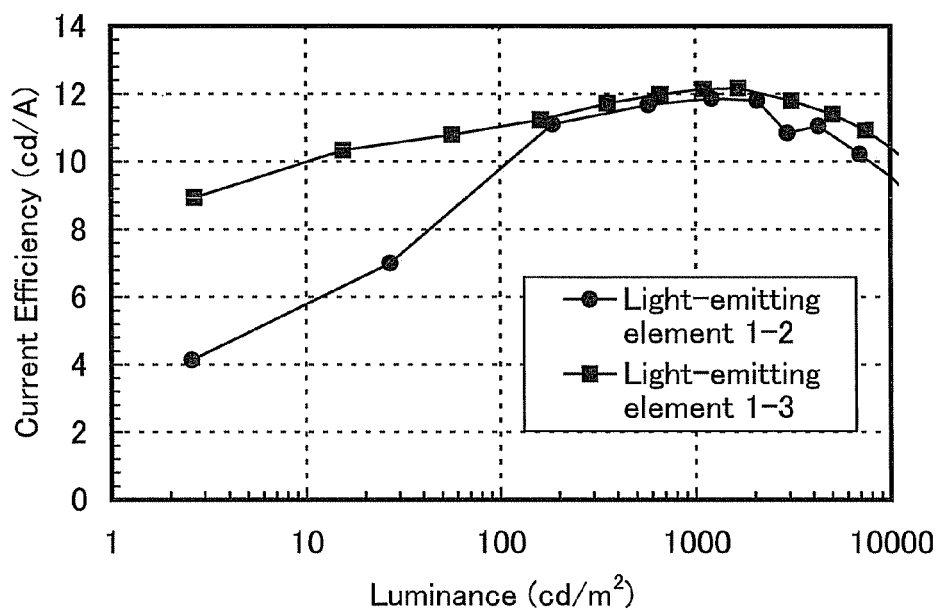
FIG. 29 shows current efficiency versus luminance characteristics of the light-emitting elements 1-2 and 1-3 (2mBnfPPA)
Figure 30:
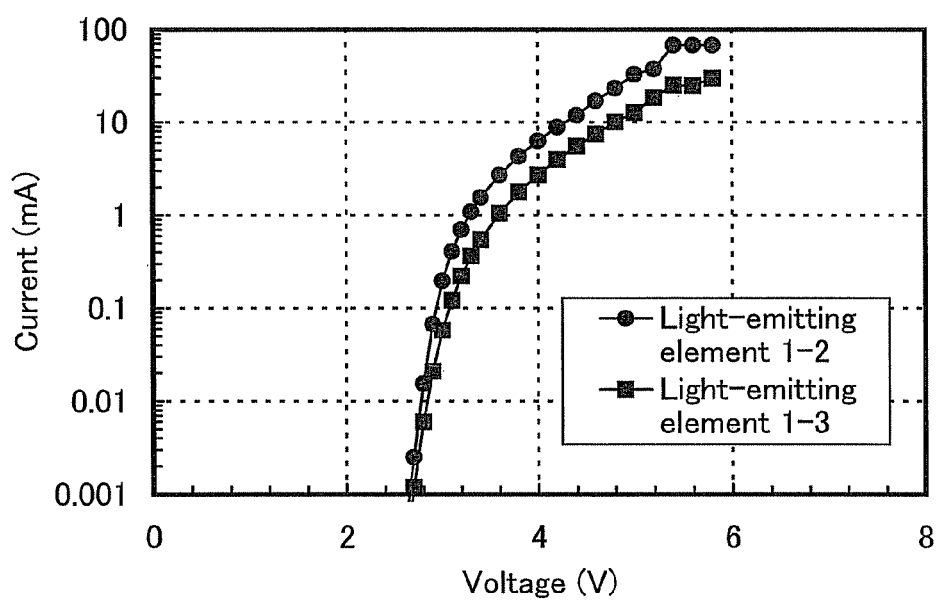
FIG. 30 shows current versus voltage characteristics of the light-emitting elements 1-2 and 1-3 (2mBnfPPA)
Figure 31:
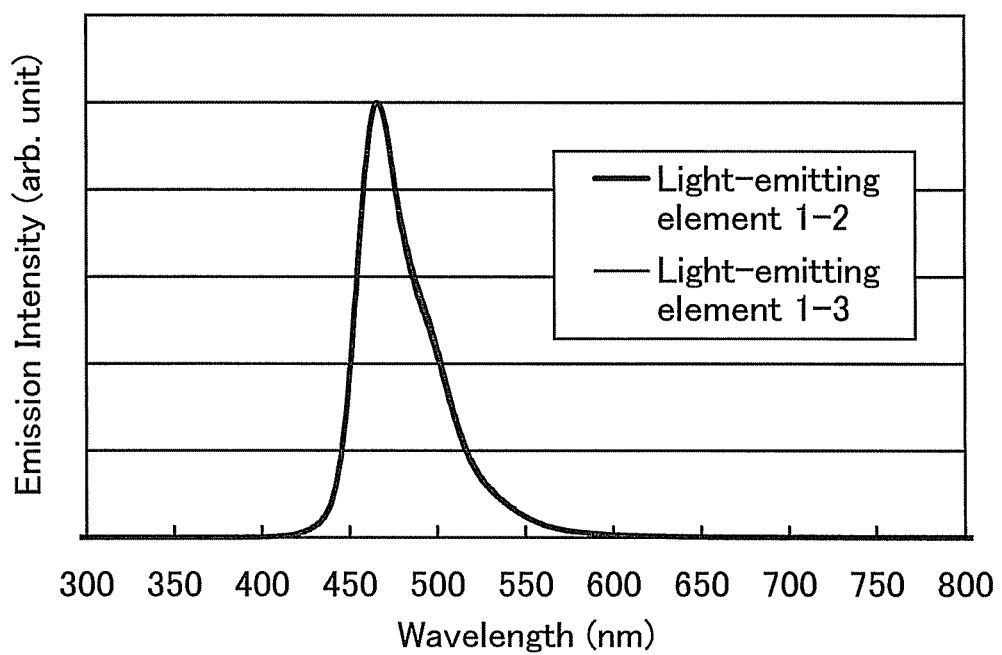
FIG. 31 shows emission spectra of the light-emitting elements 1-2 and 1-3 (2mBnfPPA)
Figure 33:
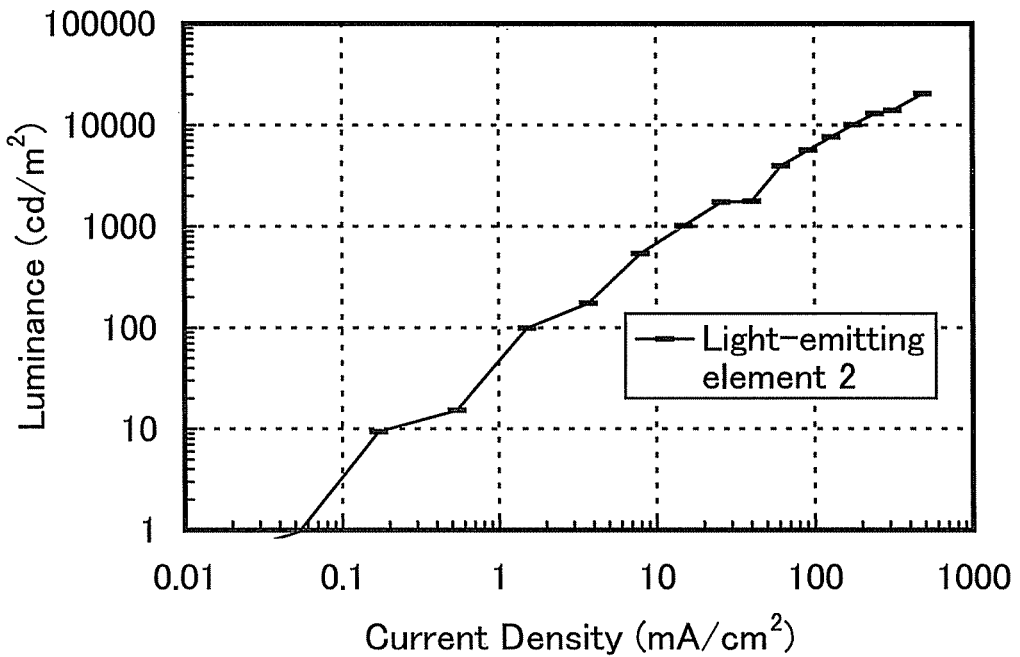
FIG. 33 shows luminance versus current density characteristics of a light-emitting element 2 (mBnfPA)
Figure 34:
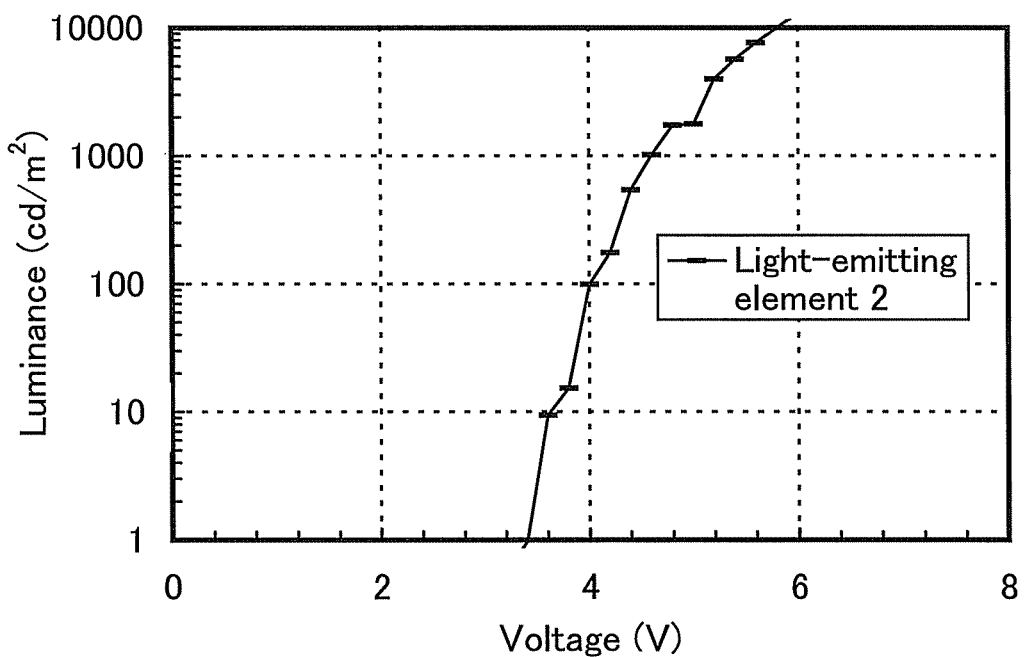
FIG. 34 shows luminance versus voltage characteristics of the light-emitting element 2 (mBnfPA)
Figure 35:
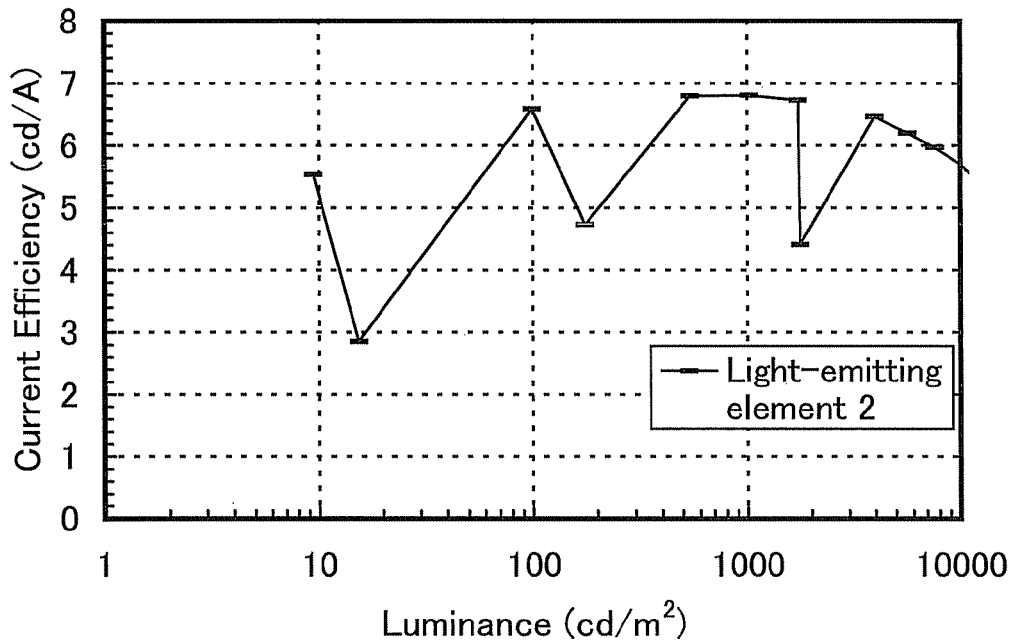
FIG. 35 shows current efficiency versus luminance characteristics of the light-emitting element 2 (mBnfPA)
Figure 36:
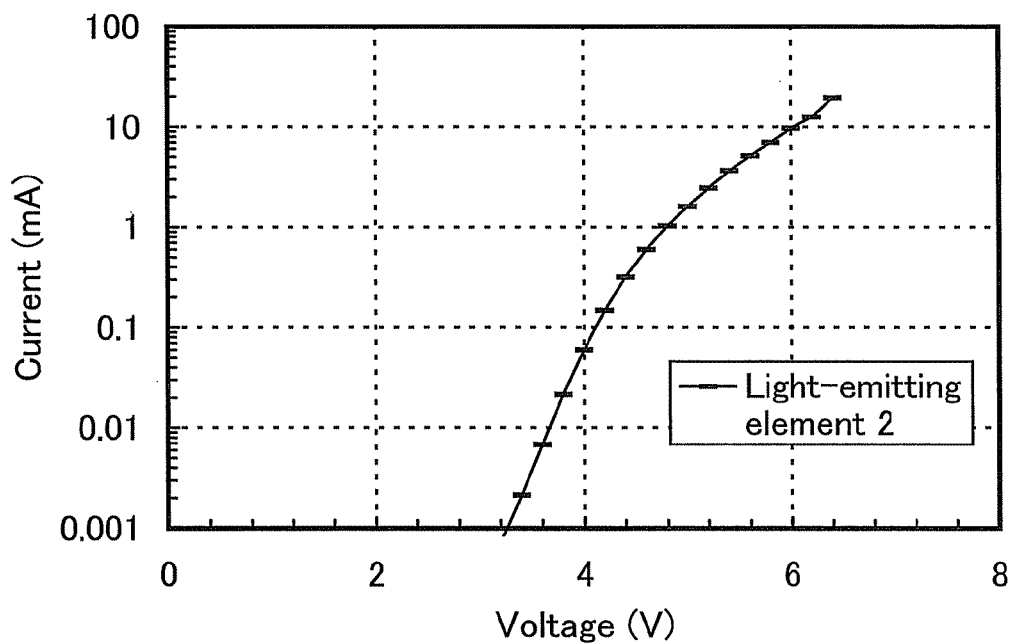
FIG. 36 shows current versus voltage characteristics of the light-emitting element 2 (mBnfPA)
Figure 37:
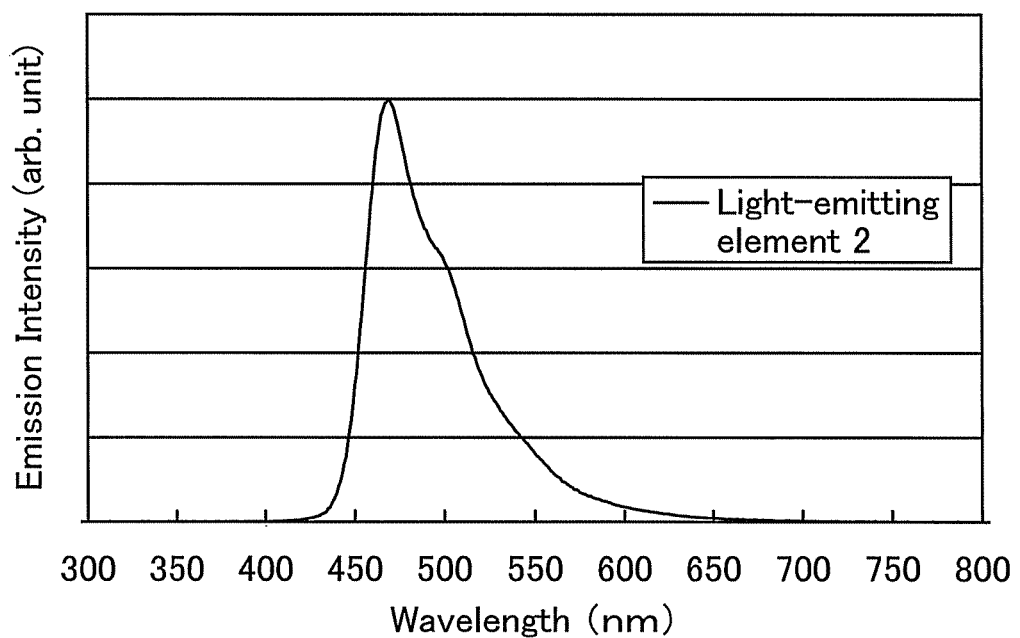
FIG. 37 shows an emission spectrum of the light-emitting element 2 (mBnfPA)
Figure 39:
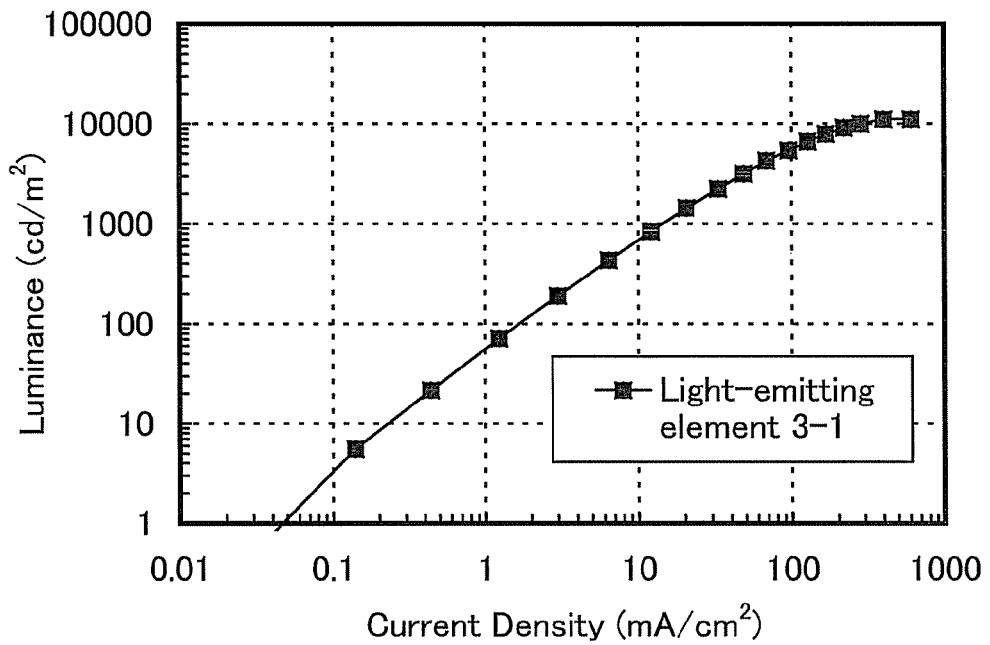
FIG. 39 shows luminance versus current density characteristics of a light-emitting element 3-1 (2BnfPPA)
Figure 40:
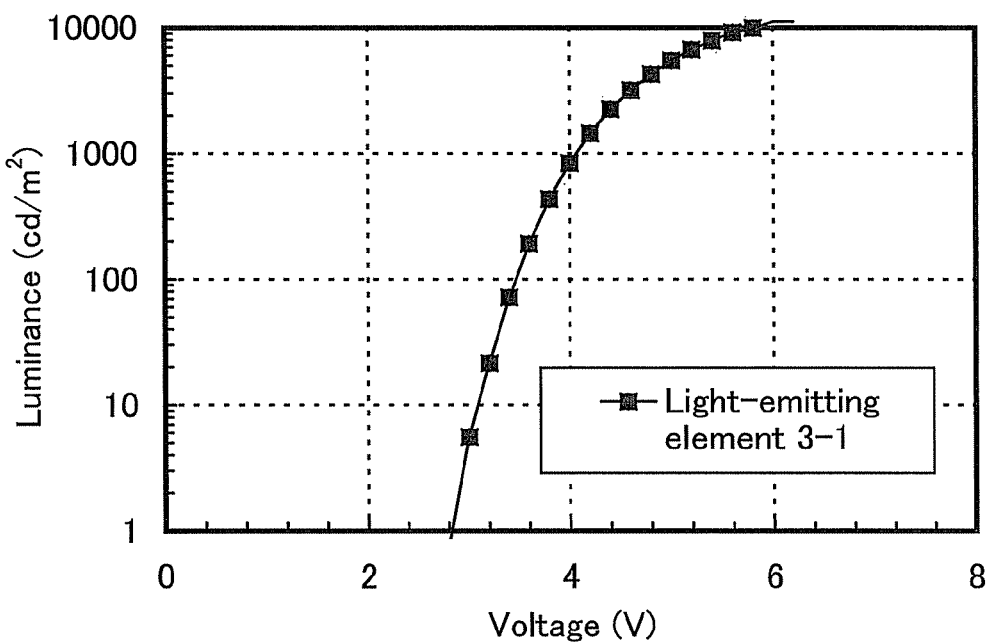
FIG. 40 shows luminance versus voltage characteristics of the light-emitting element 3-1 (2BnfPPA)
Figure 41:
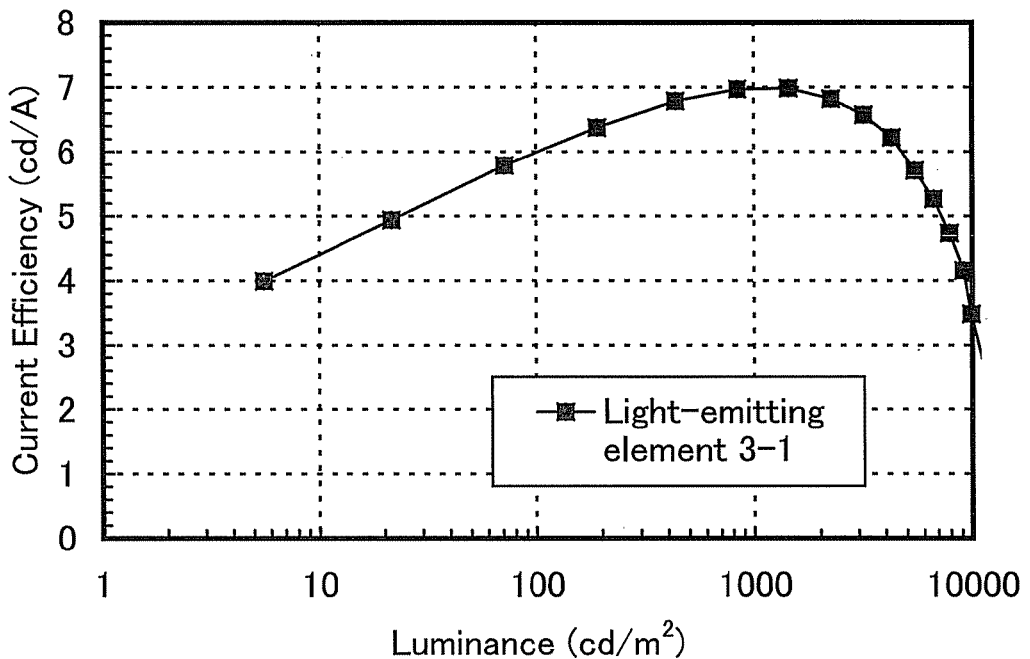
FIG. 41 shows current efficiency versus luminance characteristics of the light-emitting element 3-1 (2BnfPPA)
Figure 42:
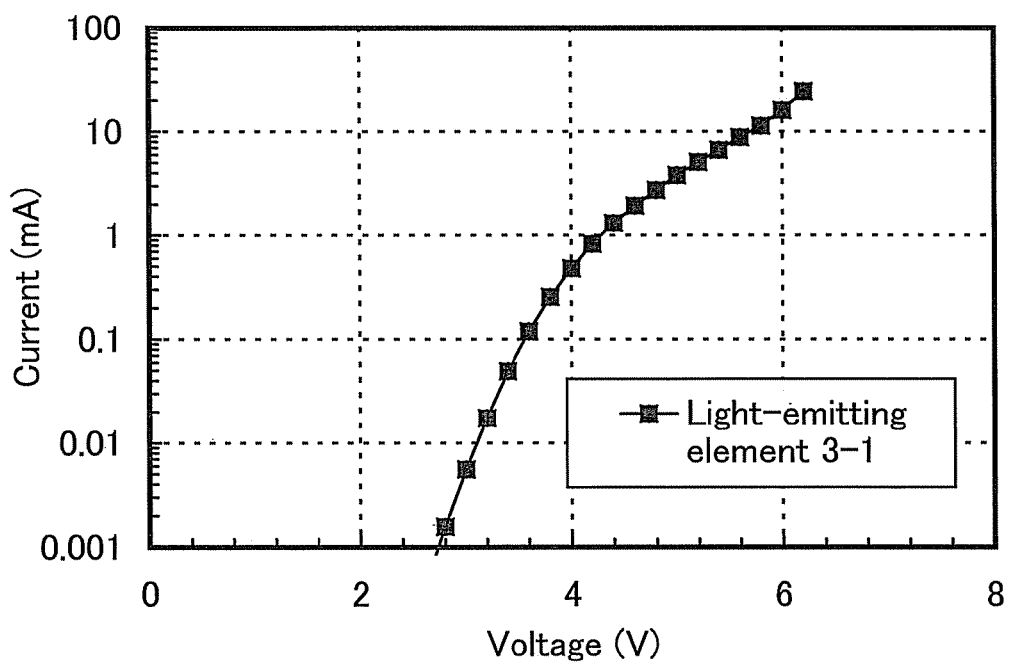
FIG. 42 shows current versus voltage characteristics of the light-emitting element 3-1 (2BnfPPA)
Figure 43:
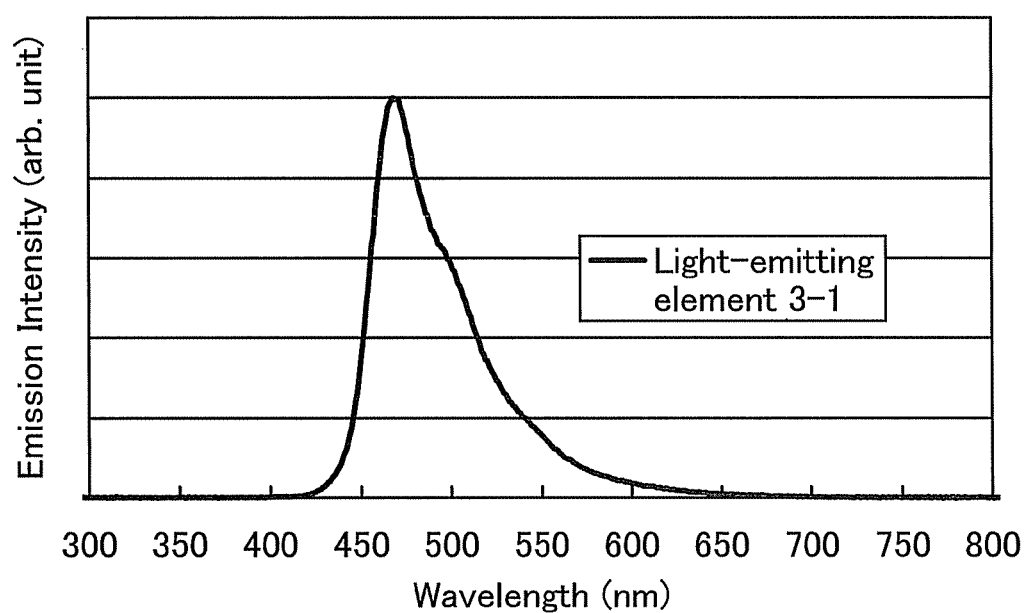
FIG. 43 shows an emission spectrum of the light-emitting element 3-1 (2BnfPPA)
Figure 45:
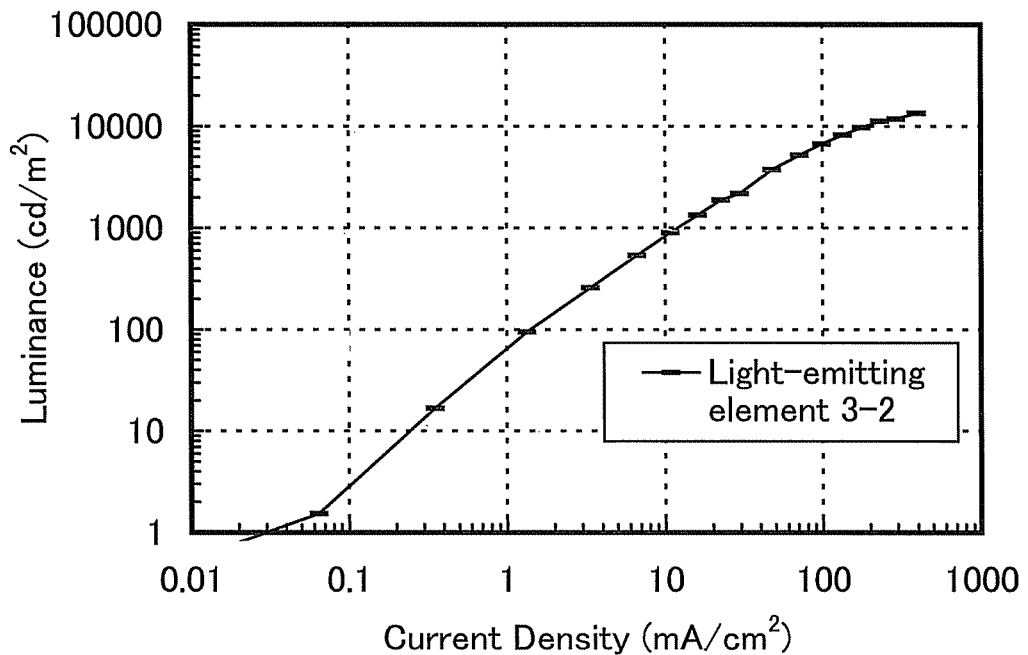
FIG. 45 shows luminance versus current density characteristics of a light-emitting element 3-2 (2BnfPPA)
Figure 46:
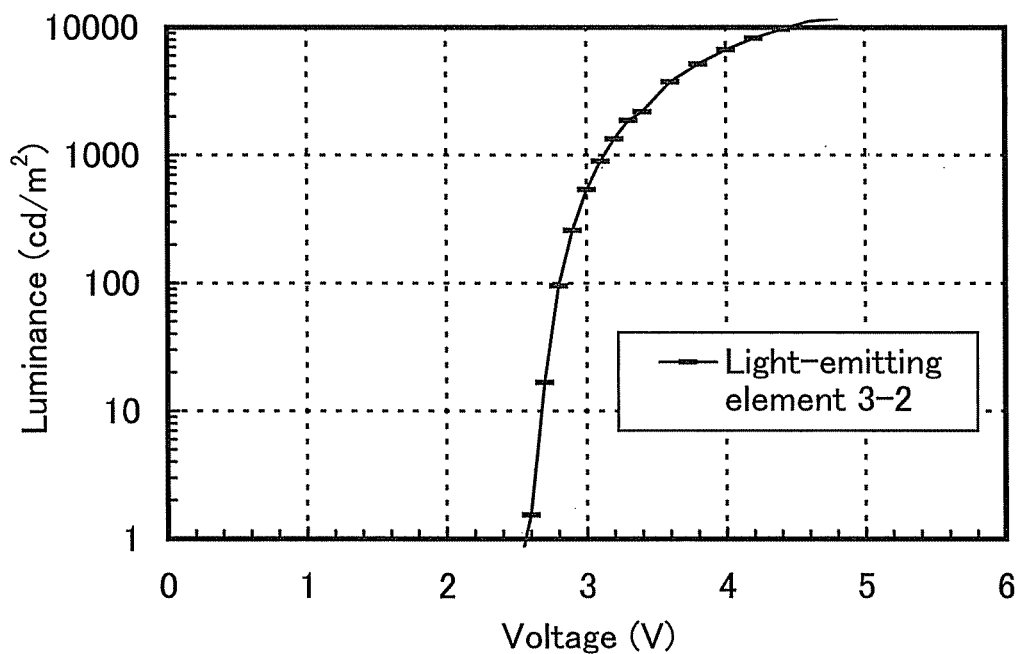
FIG. 46 shows luminance versus voltage characteristics of the light-emitting element 3-2 (2BnfPPA)
Figure 47:
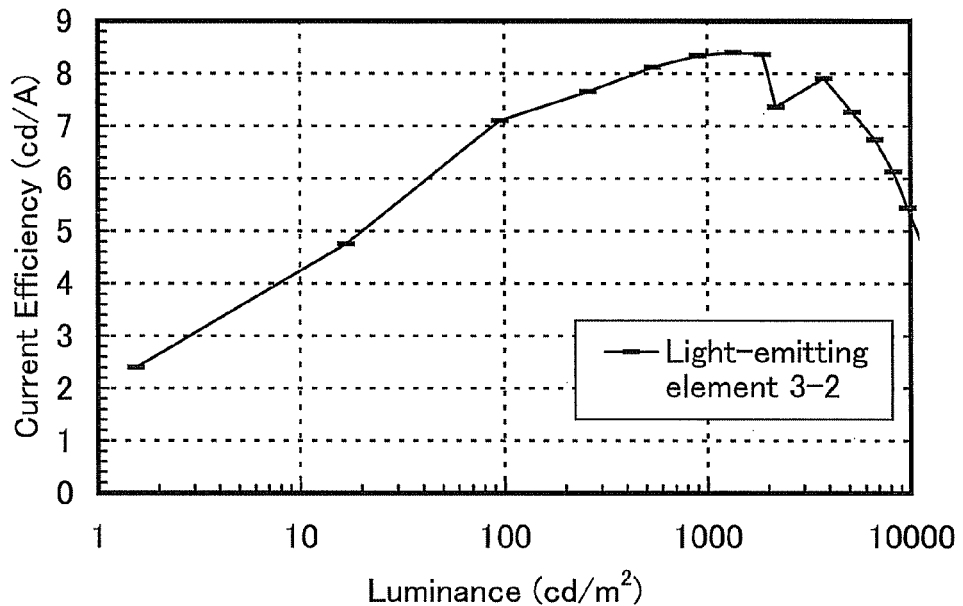
FIG. 47 shows current efficiency versus luminance characteristics of the light-emitting element 3-2 (2BnfPPA)
Figure 48:
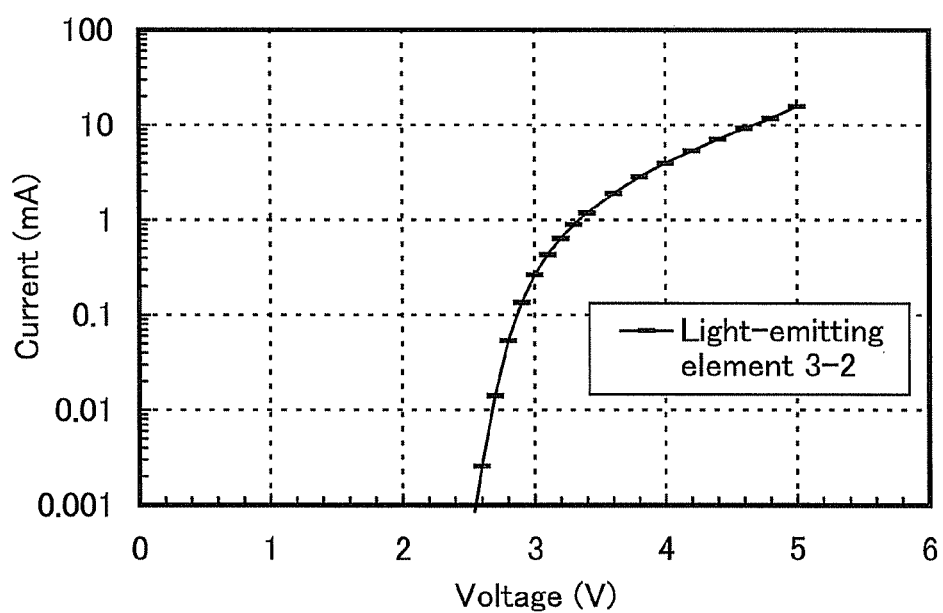
FIG. 48 shows current versus voltage characteristics of the light-emitting element 3-2 (2BnfPPA)
Figure 49:
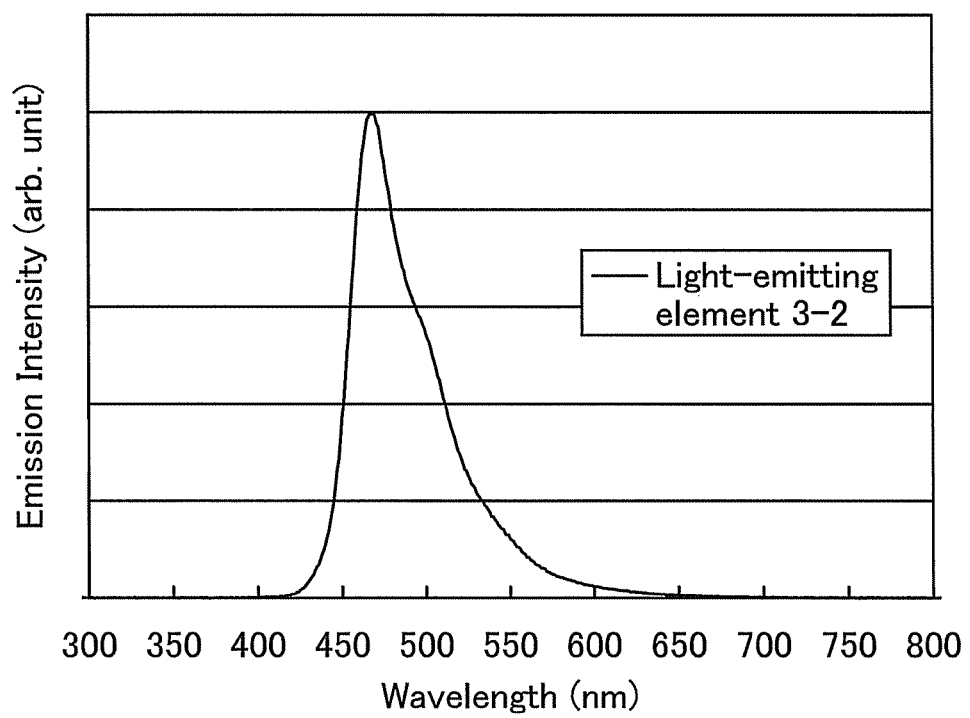
FIG. 49 shows an emission spectrum of the light-emitting element 3-2 (2BnfPPA)
Figure 50:
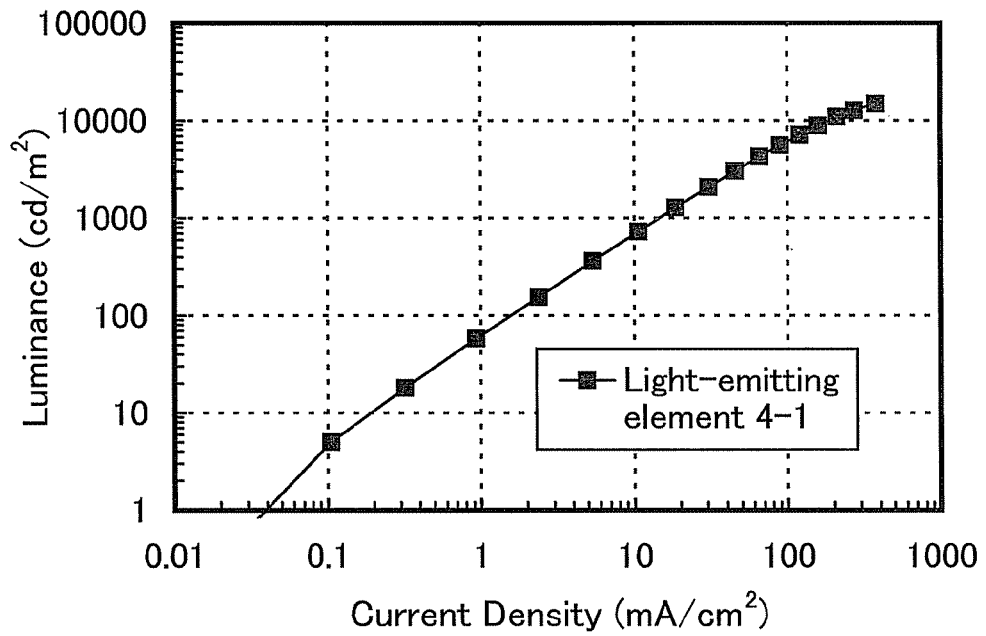
FIG. 50 shows luminance versus current density characteristics of a light-emitting element 4-1 (BnfPA)
Figure 51:
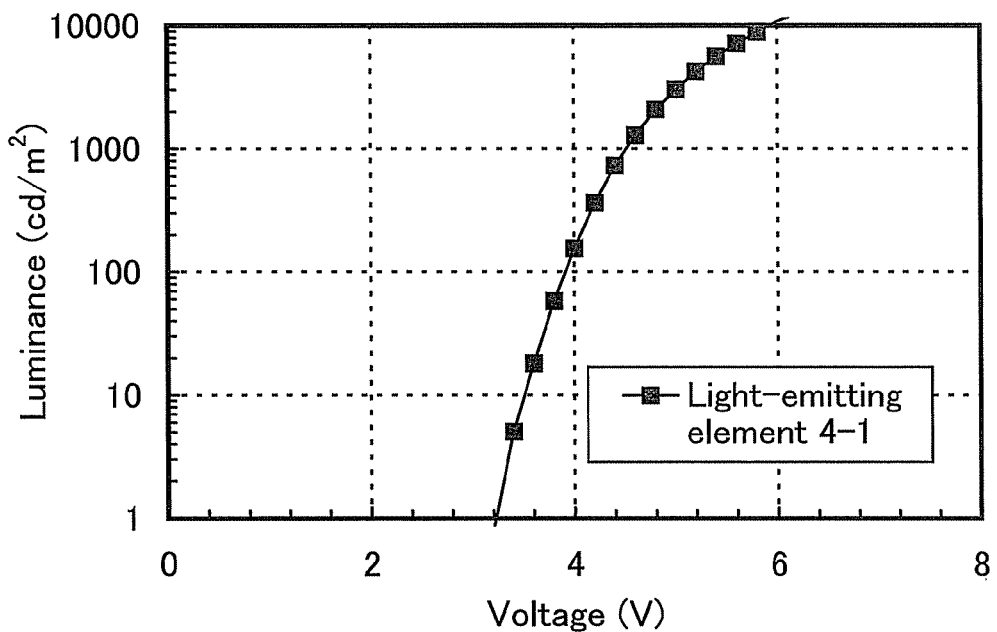
FIG. 51 shows luminance versus voltage characteristics of the light-emitting element 4-1 (BnfPA)
Figure 52:
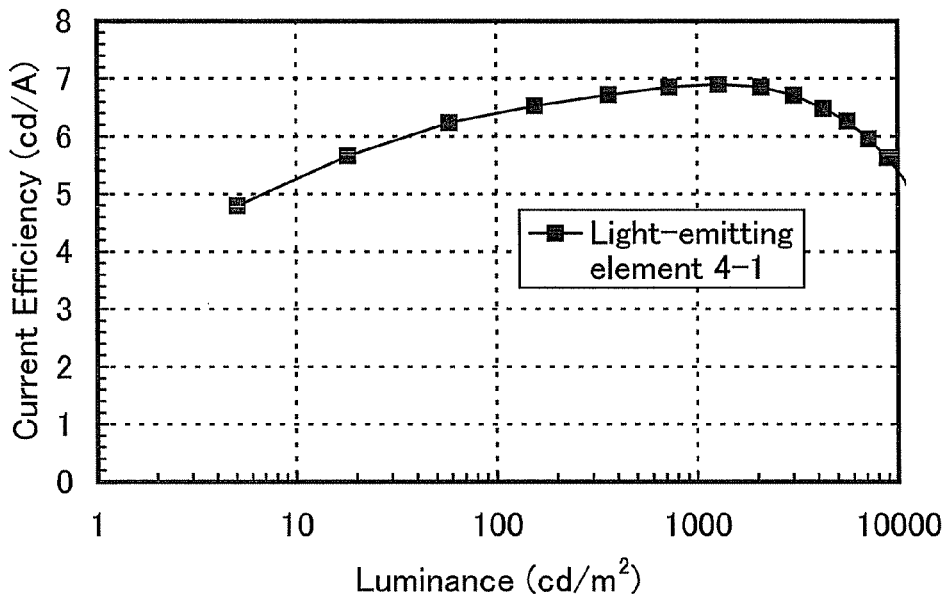
FIG. 52 shows current efficiency versus luminance characteristics of the light-emitting element 4-1 (BnfPA)
Figure 53:
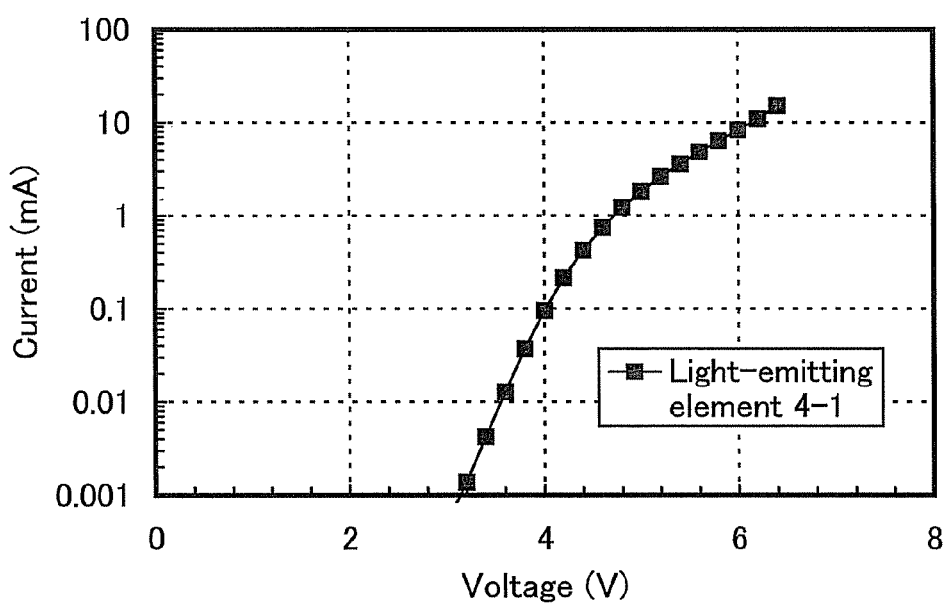
FIG. 53 shows current versus voltage characteristics of the light-emitting element 4-1 (BnfPA)
Figure 54:
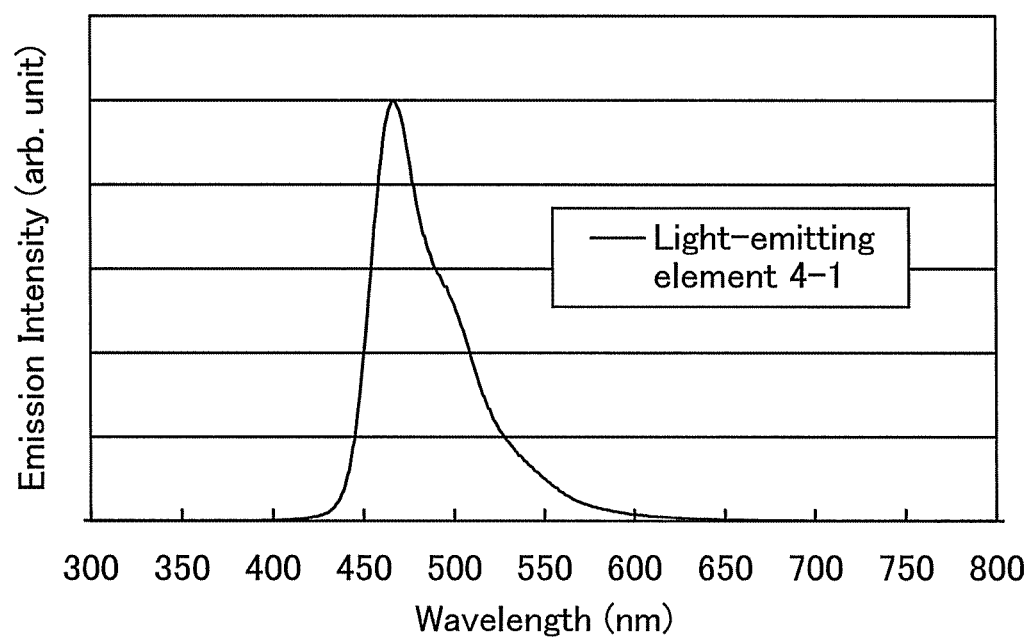
FIG. 54 shows an emission spectrum of the light-emitting element 4-1 (BnfPA)
Figure 56:
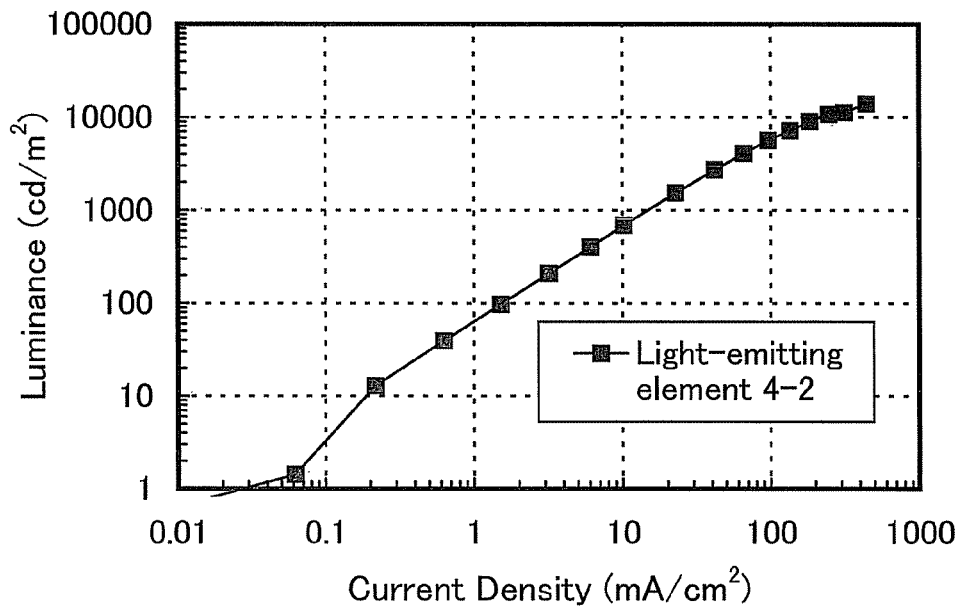
FIG. 56 shows luminance versus current density characteristics of a light-emitting element 4-2 (BnfPA)
Figure 57:
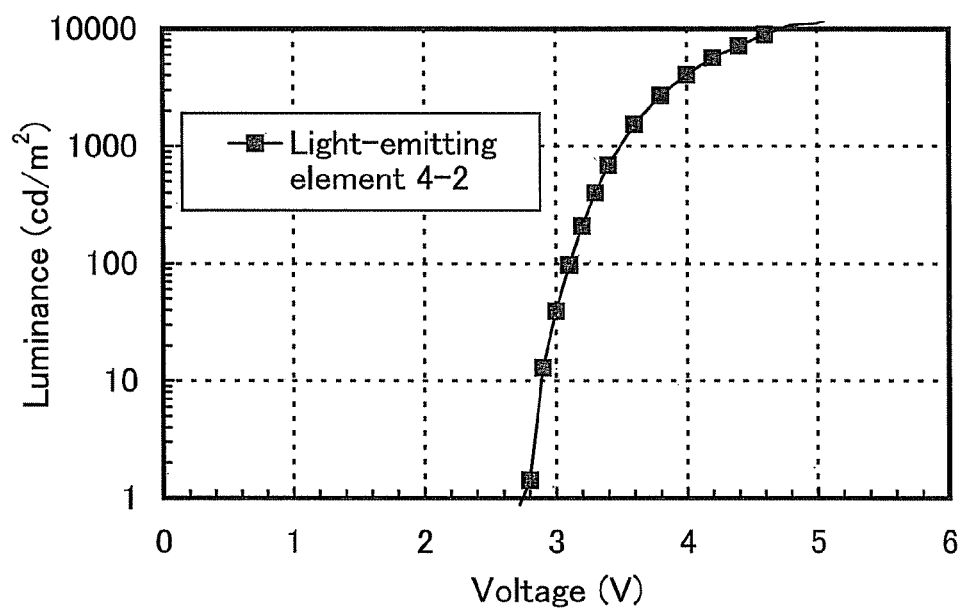
FIG. 57 shows luminance versus voltage characteristics of the light-emitting element 4-2 (BnfPA)
Figure 58:
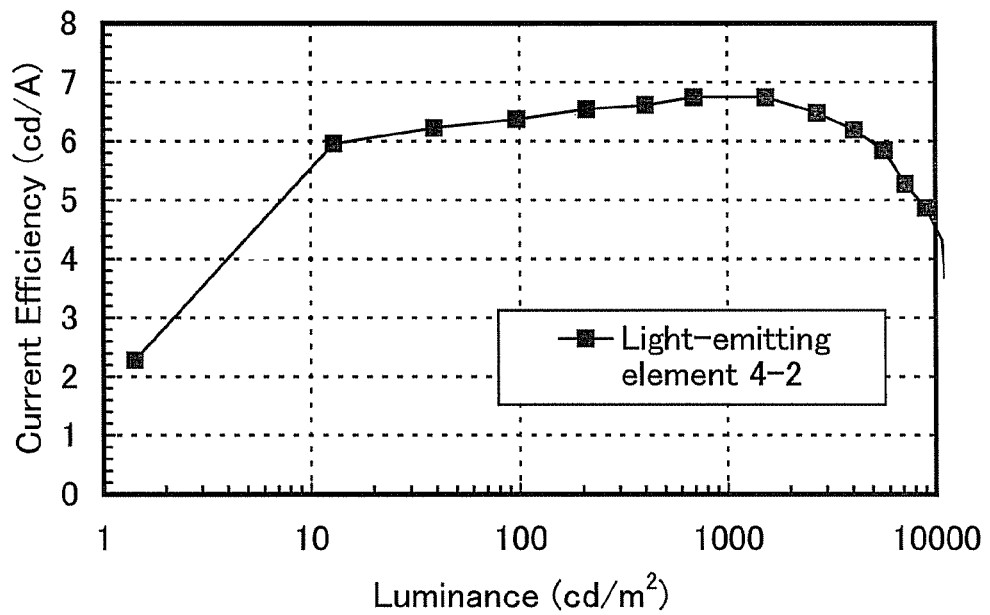
FIG. 58 shows current efficiency versus luminance characteristics of the light-emitting element 4-2 (BnfPA)
Figure 59:
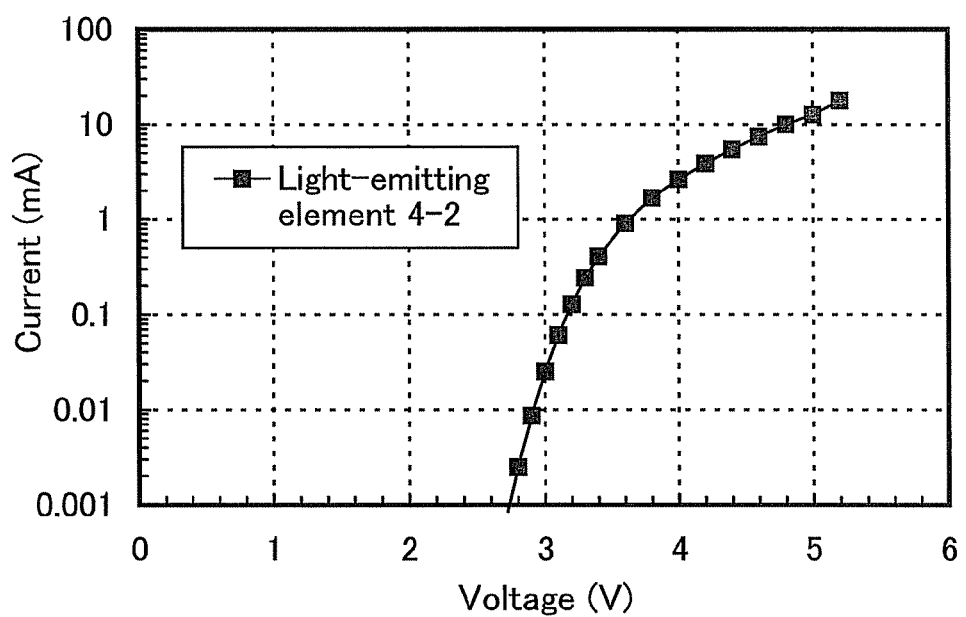
FIG. 59 shows current versus voltage characteristics of the light-emitting element 4-2 (BnfPA)
Figure 60:
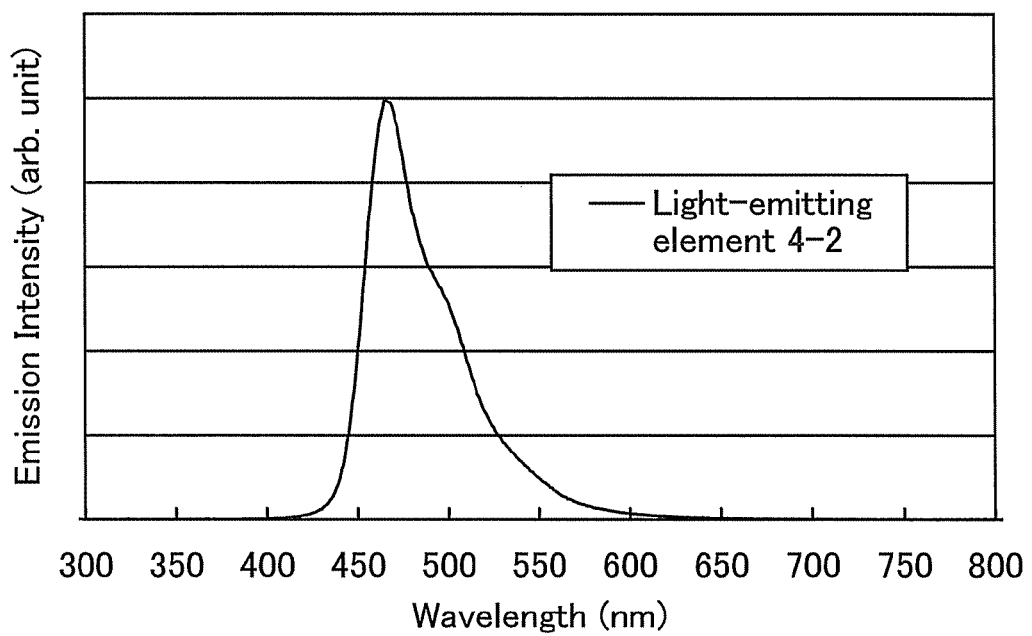
FIG. 60 shows an emission spectrum of the light-emitting element 4-2 (BnfPA)
Figure 65:
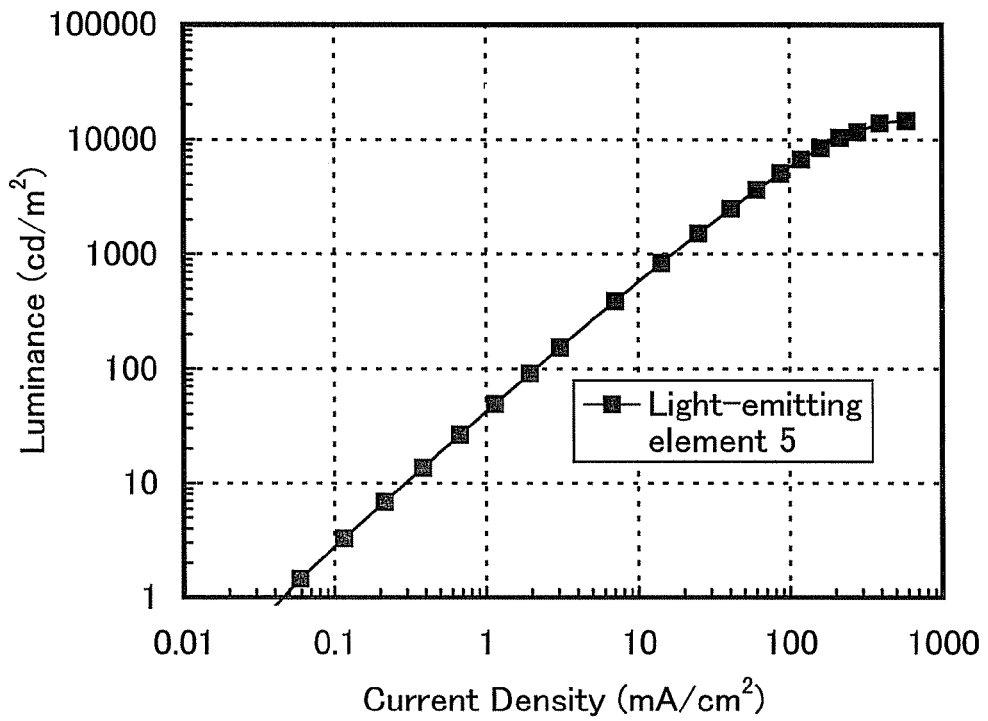
FIG. 65 shows luminance versus current density characteristics of a light-emitting element 5 (2BnfPA)
Figure 66:
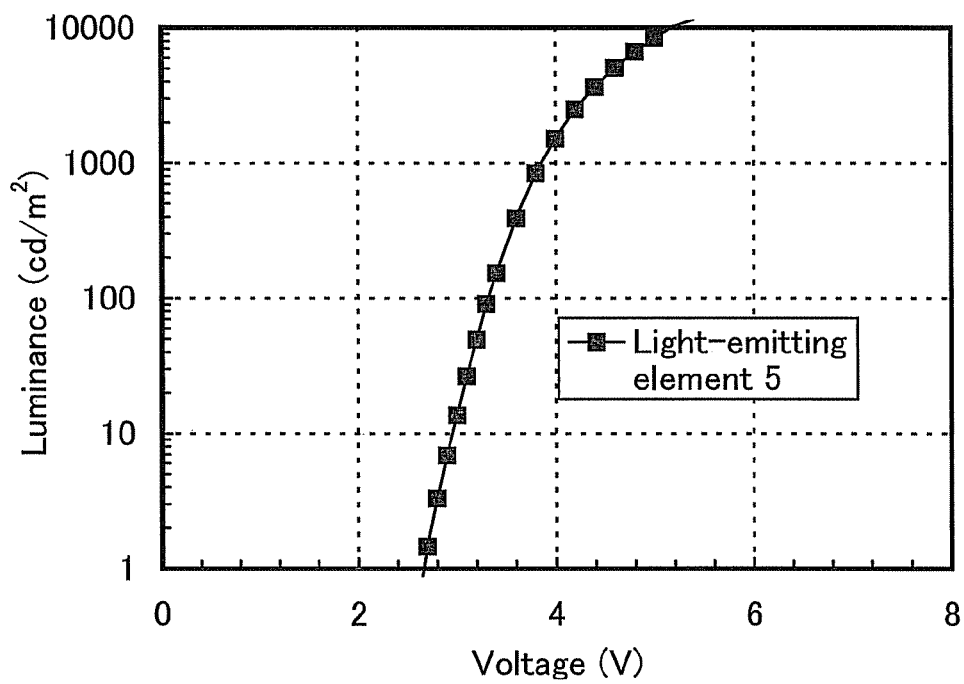
FIG. 66 shows luminance versus voltage characteristics of the light-emitting element 5 (2BnfPA)
Figure 67:
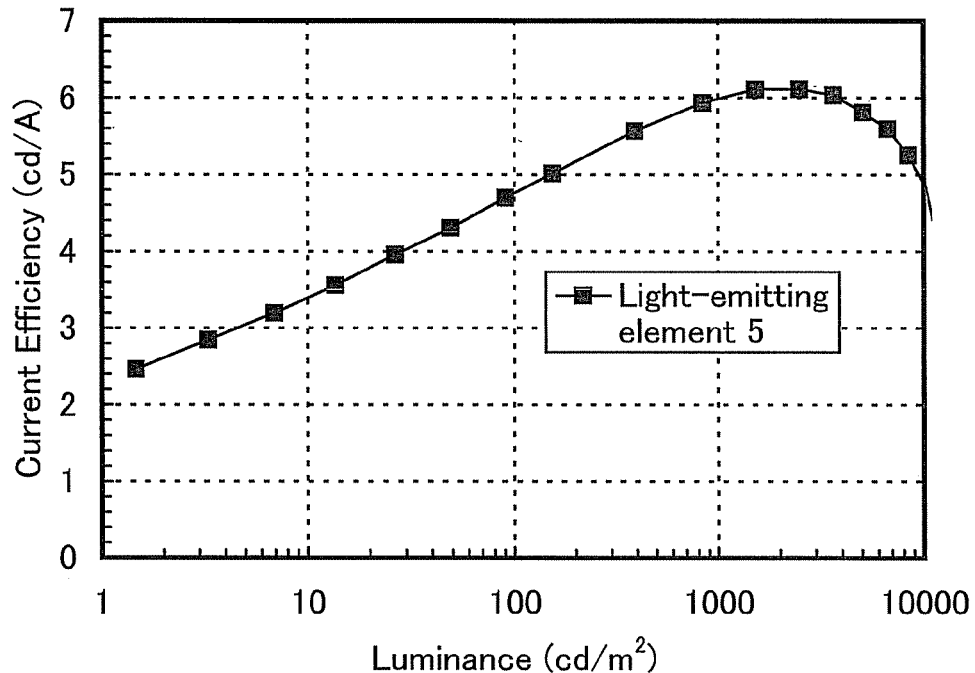
FIG. 67 shows current efficiency versus luminance characteristics of the light-emitting element 5 (2BnfPA)
Figure 68:
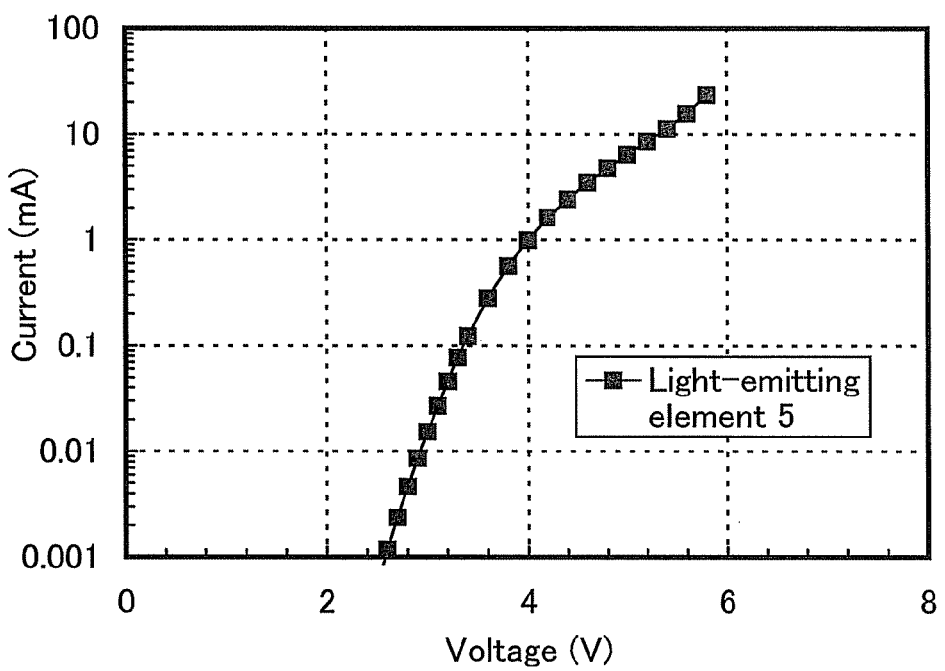
FIG. 68 shows current versus voltage characteristics of the light-emitting element 5 (2BnfPA)
Figure 69:
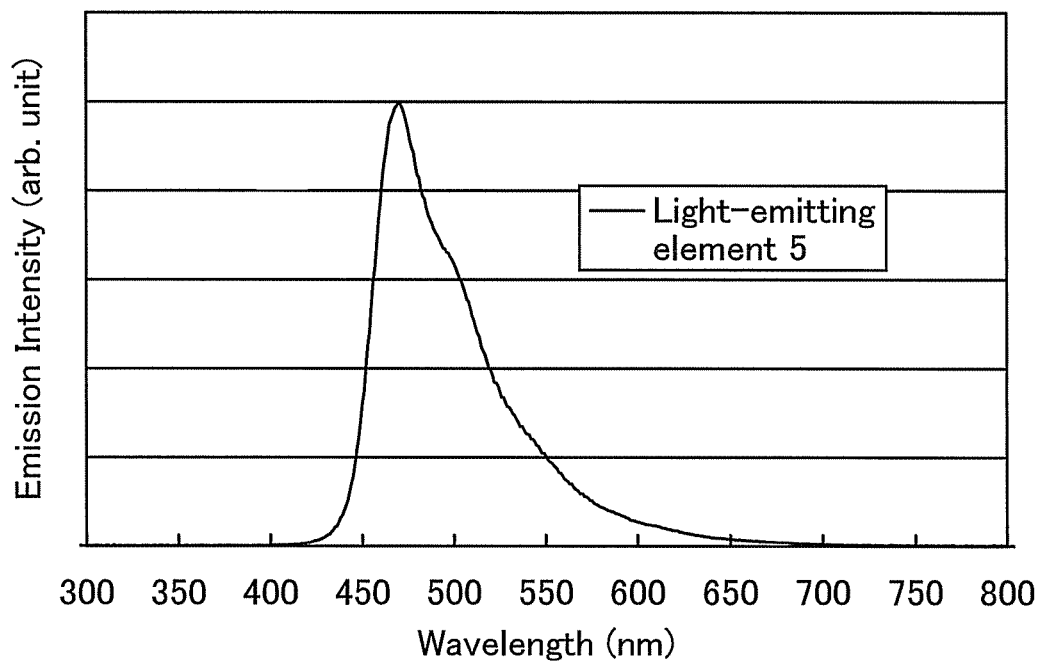
FIG. 69 shows an emission spectrum of the light-emitting element 5 (2BnfPA).

Luminance versus current density characteristics of the light-emitting elements are shown in FIG. 21 (light-emitting element 1-1), FIG. 27 (light-emitting elements 1-2 and 1-3), FIG. 33 (light-emitting element 2), FIG. 39 (light-emitting element 3-1), FIG. 45 (light-emitting element 3-2), FIG. 50 (light-emitting element 4-1), FIG. 56 (light-emitting element 4-2), and FIG. 65 (light-emitting element 5). Luminance versus voltage characteristics of the light-emitting elements are shown in FIG. 22 (light-emitting element 1-1), FIG. 28 (light-emitting elements 1-2 and 1-3), FIG. 34 (light-emitting element 2), FIG. 40 (light-emitting element 3-1), FIG. 46 (light-emitting element 3-2), FIG. 51 (light-emitting element 4-1), FIG. 57 (light-emitting element 4-2), and FIG. 66 (light-emitting element 5). Current efficiency versus luminance characteristics of the light-emitting elements are shown in FIG. 23 (light-emitting element 1-1), FIG. 29 (light-emitting elements 1-2 and 1-3), FIG. 35 (light-emitting element 2), FIG. 41 (light-emitting element 3-1), FIG. 47 (light-emitting element 3-2), FIG. 52 (light-emitting element 4-1), FIG. 58 (light-emitting element 4-2), and FIG. 67 (light-emitting element 5). Current versus voltage characteristics of the light-emitting elements are shown in FIG. 24 (light-emitting element 1-1), FIG. 30 (light-emitting elements 1-2 and 1-3), FIG. 36 (light-emitting element 2), FIG. 42 (light-emitting element 3-1), FIG. 48 (light-emitting element 3-2), FIG. 53 (light-emitting element 4-1), FIG. 59 (light-emitting element 4-2), and FIG. 68 (light-emitting element 5).

Figure 25:
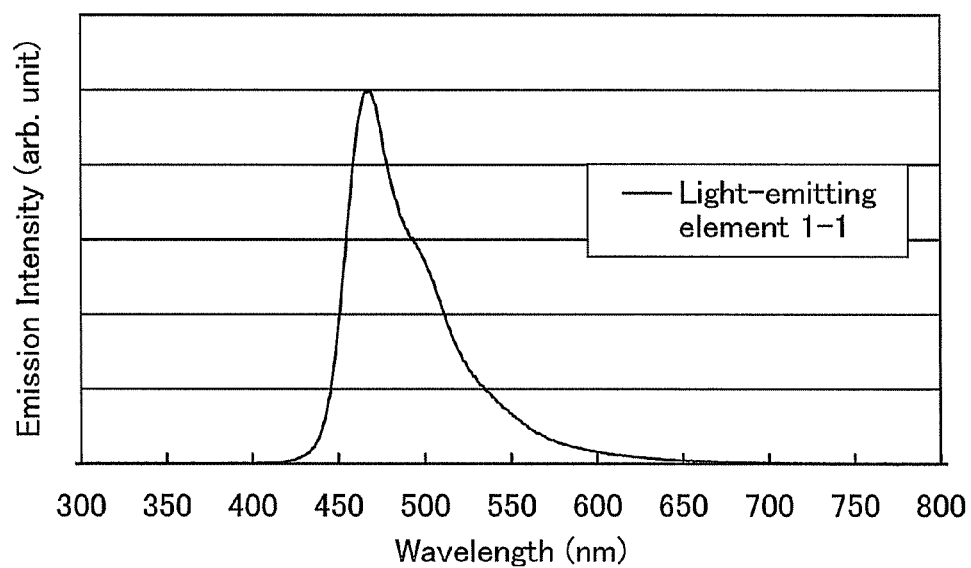
FIG. 25 shows an emission spectrum of the light-emitting element 1-1 (2mBnfPPA)

In FIG. 21, FIG. 27, FIG. 33, FIG. 39, FIG. 45, FIG. 50, and FIG. 56, the horizontal axis represents current density (mA/cm$^2$) and the vertical axis represents luminance (cd/m$^2$). In FIG. 22, FIG. 28, FIG. 34, FIG. 40, FIG. 46, FIG. 51, and FIG. 57, the horizontal axis represents voltage (V) and the vertical axis represents luminance (cd/m$^2$). In addition, in FIG. 23, FIG. 29, FIG. 35, FIG. 41, FIG. 47, FIG. 52, and FIG. 58, the horizontal axis represents luminance (cd/m$^2$) and the vertical axis represents current efficiency (cd/A). In FIG. 24, FIG. 30, FIG. 36, FIG. 42, FIG. 48, FIG. 53, and FIG. 59, the horizontal axis represents voltage (V) and the vertical axis represents current (mA). Further, the emission spectrum/spectra of the light-emitting elements are shown in FIG. 25 (light-emitting element 1-1), FIG. 31 (light-emitting elements 1-2 and 1-3), FIG. 37 (light-emitting element 2), FIG. 43 (light-emitting element 3-1), FIG. 49 (light-emitting element 3-2), FIG. 54 (light-emitting element 4-1), FIG. 60 (light-emitting element 4-2), and FIG. 69 (light-emitting element 5). In FIG. 25, FIG. 31, FIG. 37, FIG. 43, FIG. 49, FIG. 54, FIG. 60, and FIG. 69, the horizontal axis represents wavelength (nm) and the vertical axis represents emission intensity (arbitrary unit).

It was found that, with the light-emitting element 1-1, favorable blue light emission from 1,6FLPAPrn, which has a peak at around 470 nm, was obtained. At a luminance of 1145 cd/m$^2$, the CIE chromaticity coordinates of the light-emitting element 1-1 were (x=0.16, y=0.23), which indicates favorable blue light emission. Further, the current efficiency, external quantum efficiency, voltage, current density, and power efficiency at a luminance of 1145 cd/m$^2$ were 7.1 cd/A, 4.6%, 4.4 V, 16.1 mA/cm$^2$, and 5.1 lm/W, respectively.

It was found that, with the light-emitting element 1-2, favorable blue light emission from 1,6mMemFLPAPrn, which has a peak at around 469 nm, was obtained. At a luminance of 1211 cd/m$^2$; the CIE chromaticity coordinates of the light-emitting element 1-2 were (x=0.14, y=0.17), which indicates favorable blue light emission. Further, the current efficiency, external quantum efficiency, voltage, current density, and power efficiency at a luminance of 1211 cd/m$^2$ were 11.9 cd/A, 10.2%, 3.1 V, 10.2 mA/cm$^2$, and 12.0 lm/W, respectively.

It was found that, with the light-emitting element 1-3, favorable blue light emission from 1,6mMemFLPAPrn, which has a peak at around 470 nm, was obtained. At a luminance of 1106 cd/m$^2$, the CIE chromaticity coordinates of the light-emitting element 1-3 were (x=0.14, y=0.17), which indicates favorable blue light emission. Further, the current efficiency, external quantum efficiency, voltage, current density, and power efficiency at a luminance of 1106 cd/m$^2$ were 12.1 cd/A, 10.2%, 3.3 V, 9.1 mA/cm$^2$, and 11.6 lm/W, respectively.

It was found that, with the light-emitting element 2, favorable blue light emission from 1,6FLPAPrn, which has a peak at around 472 nm, was obtained. At a luminance of 1018 cd/m$^2$, the CIE chromaticity coordinates of the light-emitting element 2 were (x=0.16, y=0.25), which indicates favorable blue light emission. Further, the current efficiency, external quantum efficiency, voltage, current density, and power efficiency at a luminance of 1018 cd/m$^2$ were 6.8 cd/A, 4.1%, 4.6 V, 15.0 mA/cm$^2$, and 4.7 lm/W, respectively.

It was found that, with the light-emitting element 3-1, favorable blue light emission from 1,6FLPAPrn, which has a peak at around 470 nm, was obtained. At a luminance of 840 cd/m$^2$, the CIE chromaticity coordinates of the light-emitting element 3-1 were (x=0.16, y=0.25), which indicates favorable blue light emission. Further, the current efficiency, external quantum efficiency, voltage, current density, and power efficiency at a luminance of 840 cd/m$^2$ were 7.0 cd/A, 4.3%, 4.0 V, 12.0 mA/cm$^2$, and 5.5 lm/W, respectively.

It was found that, with the light-emitting element 3-2, favorable blue light emission from 1,6FLPAPrn, which has a peak at around 470 nm, was obtained. At a luminance of 900 cd/m$^2$, the CIE chromaticity coordinates of the light-emitting element 3-2 were (x=0.15, y=0.22), which indicates favorable blue light emission. Further, the current efficiency, external quantum efficiency, voltage, current density, and power efficiency at a luminance of 900 cd/m$^2$ were 8.3 cd/A, 5.5%, 3.1 V, 10.8 mA/cm$^2$, and 8.5 lm/W, respectively.

It was found that, with the light-emitting element 4-1, favorable blue light emission from 1,6FLPAPrn, which has a peak at around 470 nm, was obtained. At a luminance of 728 cd/m$^2$, the CIE chromaticity coordinates of the light-emitting element 4-1 were (x=0.15, y=0.21), which indicates favorable blue light emission. Further, the current efficiency, external quantum efficiency, voltage, current density, and power efficiency at a luminance of 728 cd/m$^2$ were 6.9 cd/A, 4.8%, 4.4 V, 10.6 mA/cm$^2$, and 4.9 lm/W, respectively.

It was found that, with the light-emitting element 4-2, favorable blue light emission from 1,6FLPAPrn, which has a peak at around 470 nm, was obtained. At a luminance of 689 cd/m$^2$, the CIE chromaticity coordinates of the light-emitting element 4-2 were (x=0.15, y=0.21), which indicates favorable blue light emission. Further, the current efficiency, external quantum efficiency, voltage, current density, and power efficiency at a luminance of 689 cd/m$^2$ were 6.7 cd/A, 4.8%, 3.4 V, 10.2 mA/cm$^2$, and 6.2 lm/W, respectively.

It was found that, with the light-emitting element 5, favorable blue light emission from 1,6FLPAPrn, which has a peak at around 470 nm, was obtained. At a luminance of 839 cd/m$^2$, the CIE chromaticity coordinates of the light-emitting element 5 were (x=0.17, y=0.27), which indicates favorable blue light emission. Further, the current efficiency, external quantum efficiency, voltage, current density, and power efficiency at a luminance of 839 cd/m$^2$ were 5.9 cd/A, 3.4%, 3.8 V, 14.1 mA/cm$^2$, and 4.9 lm/W, respectively.

Further, the fabricated light-emitting elements 1-1 to 1-3, 2, 3-1, 3-2, and 4-1 were subjected to reliability tests. The reliability tests were performed as follows. For each of the light-emitting elements 1-1, 2, 3-1, 3-2, and 4-1, the luminance was measured after every certain period of time passes, with a continuous flow of the same amount of current as the current that flows through the element during its light emission at a luminance of 1000 cd/m$^2$ in the initial state. For each of the light-emitting elements 1-2 and 1-3, the luminance was measured after every certain period of time passes, with a continuous flow of the same amount of current as the current that flows through the element during its light emission at a luminance of 5000 cd/m$^2$ in the initial state.

Figure 26:
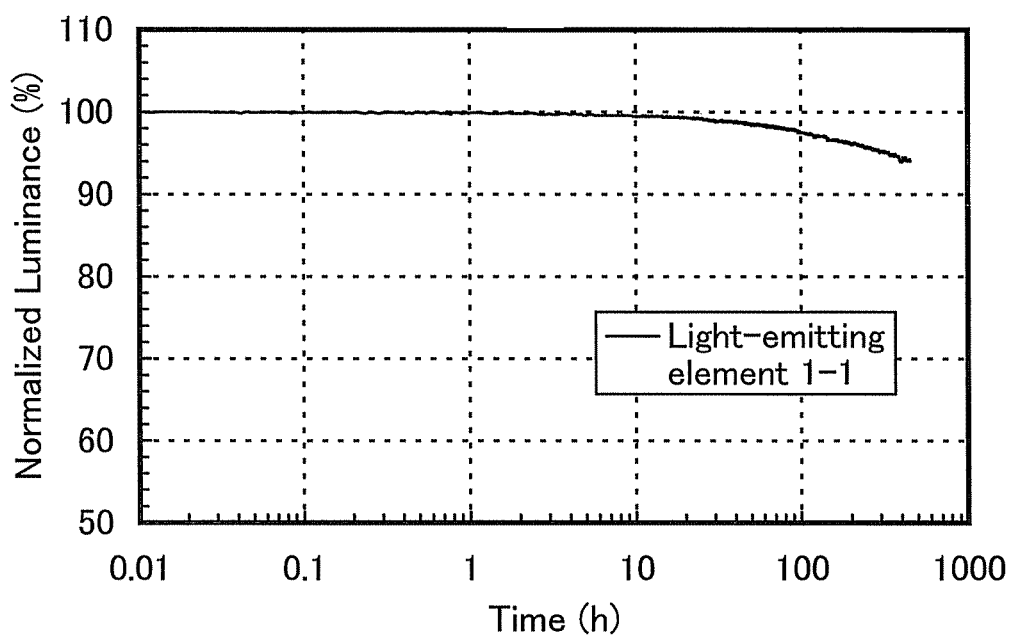
FIG. 26 shows results of reliability tests of the light-emitting element 1-1 (2mBnfPPA)
Figure 32:
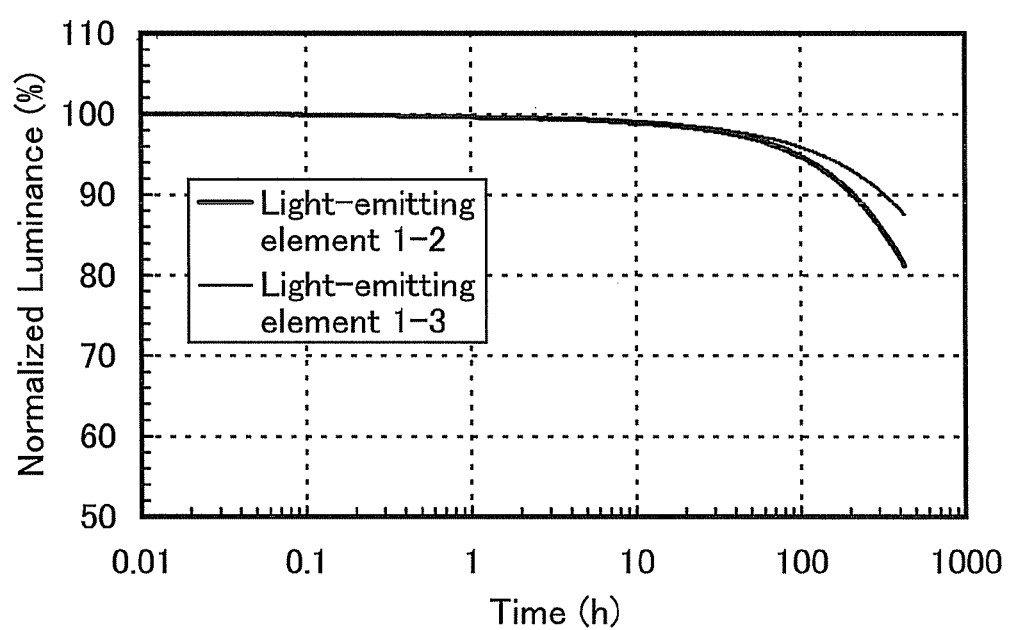
FIG. 32 shows results of reliability tests of the light-emitting elements 1-2 and 1-3 (2mBnfPPA)
Figure 38:
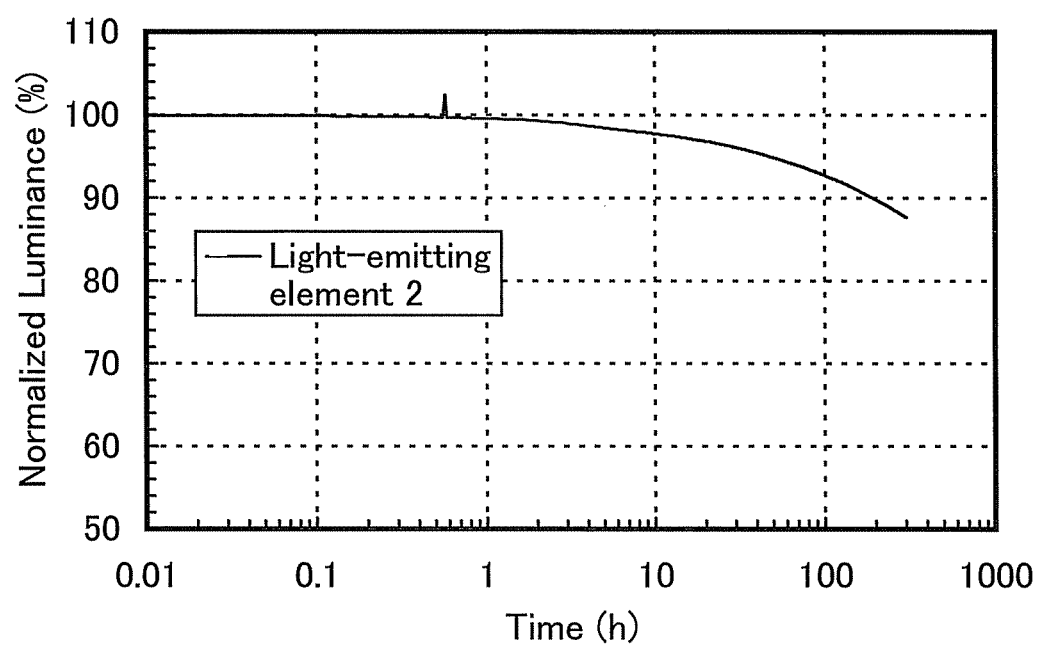
FIG. 38 shows results of reliability tests of the light-emitting element 2 (mBnfPA)
Figure 44:
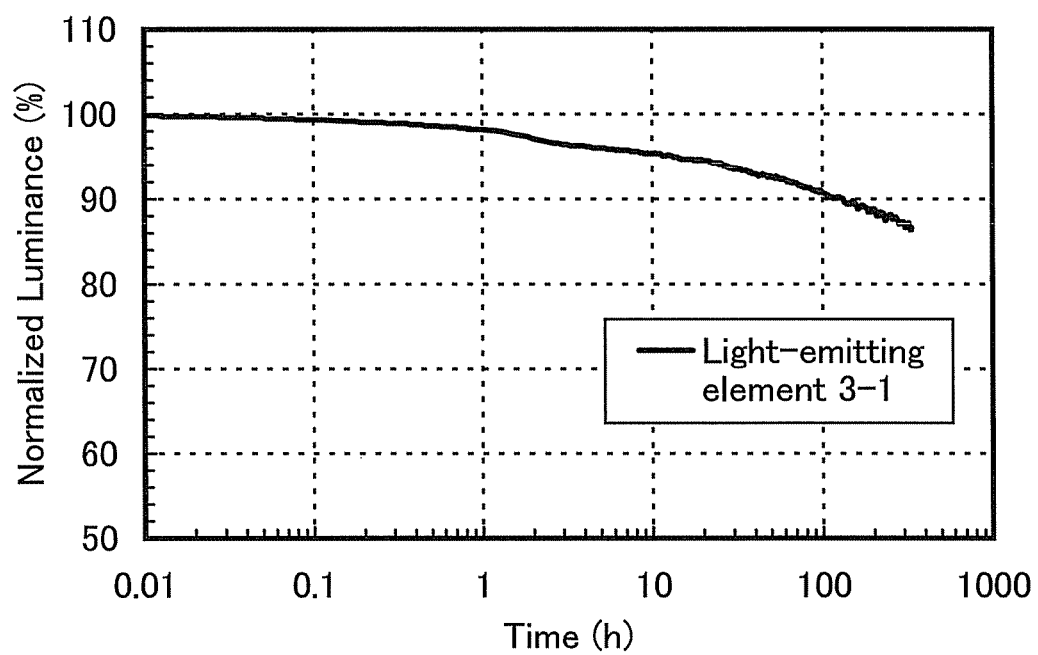
FIG. 44 shows results of reliability tests of the light-emitting element 3-1 (2BnfPPA)
Figure 55:
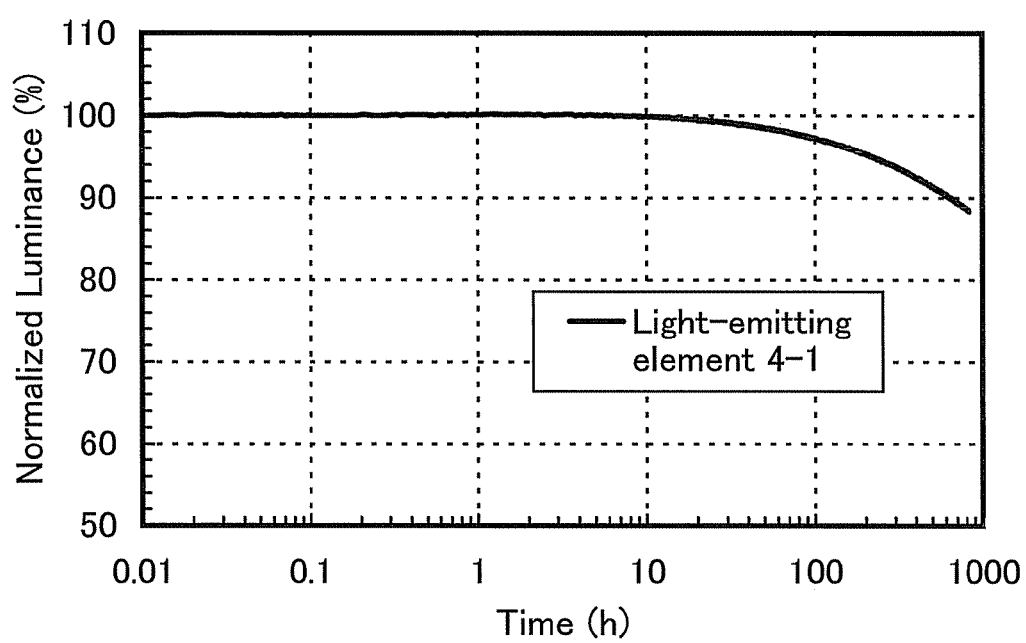
FIG. 55 shows results of reliability tests of the light-emitting element 4-1 (BnfPA)

Results of the reliability tests of the light-emitting elements 1-1 to 1-3, 2, 3-1, and 4-1 are shown in FIG. 26 (light-emitting element 1-1), FIG. 32 (light-emitting elements 1-2 and 1-3), FIG. 38 (light-emitting element 2), FIG. 44 (light-emitting element 3-1), and FIG. 55 (light-emitting element 4-1). A change over time in luminance is shown in each of FIG. 26, FIG. 32, FIG. 38, FIG. 44, and FIG. 55. Note that in FIG. 26, FIG. 32, FIG. 38, FIG. 44, and FIG. 55, the horizontal axis represents current flow time (hour) and the vertical axis represents the proportion of luminance with respect to the initial luminance at each time, that is, normalized luminance (%).

The reliability tests revealed achievements of the longer lifetime of the light-emitting elements 1-1 to 1-3 using 2mBnfPPA and of the light-emitting element 3-1 using 2BnfPPA, in each of which an anthryl group is bonded to the 2-position, and high reliability of the elements can be confirmed.

Through this example, it was confirmed that the light-emitting elements according to the present invention had sufficient characteristics to function as a light-emitting element with which light emission with good color purity can be highly efficiently obtained. Further, the results of the reliability tests demonstrated the high reliability of the obtained light-emitting elements in that even continuous emission did not lead to a short circuit due to defects of the film or the like.

REFERENCE EXAMPLE

Materials used in the light-emitting elements of Example 5 are described in Reference Example.

Synthesis Example of 1,6FLPAPrn

An example in which N,N'-bis[4-(9-phenyl-9H-fluoren-9-yl)phenyl]-N,N'-diphenyl-pyrene-1,6-diamine (abbreviation: 1,6FLPAPrn), which was used for a material in the light-emitting elements 1-1, 2, 3-1, 3-2, 4-1, and 4-2, is described.

Step 1: Synthesis Method of 9-(4-Bromophenyl)-9-phenylfluorene

In a 100 mL three-neck flask, 1.2 g (50 mmol) of magnesium was heated and stirred for 30 minutes under reduced pressure to be activated. This was cooled to room temperature, and the flask was made to contain a nitrogen atmosphere. Then, several drops of dibromoethane were added, so that foam formation and heat generation were confirmed. To this, 12 g (50 mmol) of 2-bromobiphenyl dissolved in 10 mL of diethyl ether was slowly added dropwise, and then the mixture was heated and stirred under reflux for 2.5 hours, so that a Grignard reagent was prepared.

Into a 500 mL three-neck flask were placed 10 g (40 mmol) of 4-bromobenzophenone and 100 mL of diethyl ether. To this mixture, the Grignard reagent which was synthesized in advance was slowly added dropwise, and then the mixture was heated and stirred under reflux for 9 hours After reaction, this mixture solution was filtered to give a residue. The obtained residue was dissolved in 150 mL of ethyl acetate, and 1M hydrochloric acid was added to the mixture, and the mixture was stirred for 2 hours. The organic layer portion of this liquid was washed with water, and magnesium sulfate was added so as to adsorb moisture. This suspension was filtered, and the obtained filtrate was concentrated to give an oily substance.

Into a 500 mL recovery flask were placed the obtained oily substance, 50 mL of glacial acetic acid, and 1.0 mL of hydrochloric acid. The mixture was stirred and heated at 130° C. for 1.5 hours under a nitrogen atmosphere to be reacted.

After the reaction, this reaction mixture solution was filtered to give a residue. The obtained residue was washed with water, an aqueous solution of sodium hydroxide, water, and methanol in this order. Then, the mixture was dried, so that 11 g of a white powder of the object of the synthesis was obtained in 69% yield. The synthesis scheme of Step 1 above is illustrated in the following scheme (I-1).

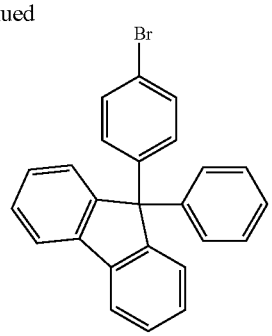

Step 2: Method of Synthesizing N,N'-Bis[4-(9-phenyl-9H-fluoren-9-yl)phenyl]-N,N'-diphenyl-pyrene-1,6-diamine (abbreviation: 1,6FLPAPrn)

Into a 50 mL three-neck flask were placed 0.4 g (1.2 mmol) of 1,6-dibromopyrene, 1.0 g (2.4 mmol) of 4-(9-phenyl-9H-fluoren-9-yl)diphenylamine (abbreviation: FLPA), and 0.3 g (3.6 mmol) of sodium tert-butoxide. The air in the flask was replaced with nitrogen. To this mixture were added 11.5 mL of toluene and 0.2 mL of a 10% hexane solution of tri(tert-butyl)phosphine. The temperature of this mixture was set to 70° C., 31.1 mg (0.05 mmol) of bis(dibenzylideneacetone)palladium(0) was added to the mixture, and the mixture was stirred for 4.0 hours. After that, the mixture was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. The obtained filtrate was concentrated. A solid obtained by concentration of the obtained filtrate was purified by silica gel column chromatography (developing solvent: chloroform). The obtained fraction was concentrated to give a yellow solid. The obtained solid was washed with a mixed solvent of toluene and hexane, and then the mixture was suction-filtered to give a yellow solid. The obtained yellow solid was washed with a mixed solvent of chloroform and hexane, so that 0.8 g of a pale yellow powdery solid of the object of the synthesis was obtained in 68% yield.

By a train sublimation method, 0.8 g of the obtained yellow solid was purified. Under a pressure of 2.7 Pa with a flow rate of argon at 5 mL/min, the sublimation purification was carried out at 360° C. After the sublimation purification, 0.4 g of the object of the synthesis was obtained in 56% yield. The synthesis scheme of the above step is illustrated in the following scheme (I-2).

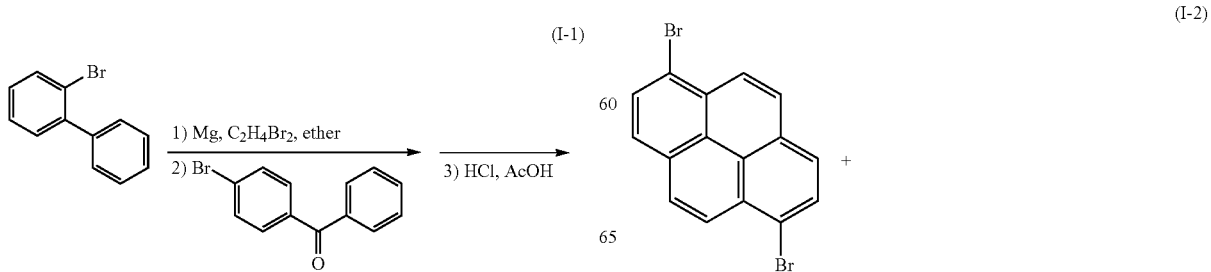

-continued

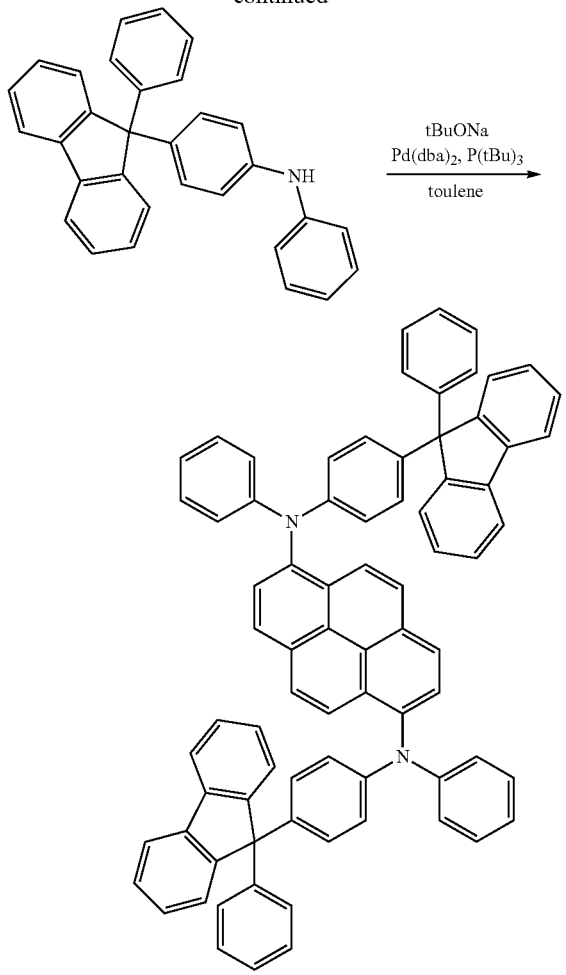

Nuclear magnetic resonance (NMR) spectroscopy and a mass spectrometry identified this compound as N,N'-bis[4-(9-phenyl-9H-fluoren-9-yl)phenyl]-N,N'-diphenyl-pyrene-1,6-diamine (abbreviation: 1,6FLPAPrn), which was the object of the synthesis.

$^1$H NMR measurement data of the obtained compound are as follows: $^1$H NMR (CDCl$_3$, 300 MHz): δ=6.88-6.91 (m, 6H), 7.00-7.03 (m, 8H), 7.13-7.40 (m, 26H), 7.73-7.80 (m, 6H), 7.87 (d, J=9.0 Hz, 2H), 8.06-8.09 (m, 4H)

Synthesis Example of 1,6mMemFLPAPrn

An example in which N'-bis(3-methylphenyl)-N,N'-bis[3-(9-phenyl-9H-fluoren-9-yl)phenyl]-pyrene-1,6-diamine (abbreviation: 1,6mMemFLPAPrn), which was used for a material of the light-emitting elements 1-2 and 1-3, is synthesized is described.

Step 1: Synthesis Method of 3-Methylphenyl-3-(9-phenyl-9H-fluoren-9-yl)phenylamine (abbreviation: mMemFLPA)

Into a 200 mL three-neck flask were placed 3.2 g (8.1 mmol) of 9-(3-bromophenyl)-9-phenylfluorene and 2.3 g (24.1 mmol) of sodium tert-butoxide. The air in the flask was replaced with nitrogen. To this mixture were added 40.0 mL of toluene, 0.9 mL (8.3 mmol) of m-toluidine, and 0.2 mL of a 10% hexane solution of tri(tert-butyl)phosphine. The temperature of this mixture was set to 60° C., and 44.5 mg (0.1 mmol) of bis(dibenzylideneacetone)palladium(0) was added to the mixture. The temperature of this mixture was raised to 80° C., and the mixture was stirred for 2.0 hours. After that, the mixture was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. A solid obtained by concentration of the obtained filtrate was purified by silica gel column chromatography (a developing solvent in which the ratio of hexane to toluene was 1:1) and recrystallized from a mixed solvent of toluene and hexane. Accordingly, 2.8 g of a white solid of the object of the synthesis was obtained in 82% yield. The synthesis scheme of Step 1 above is illustrated in the following scheme (J-1).

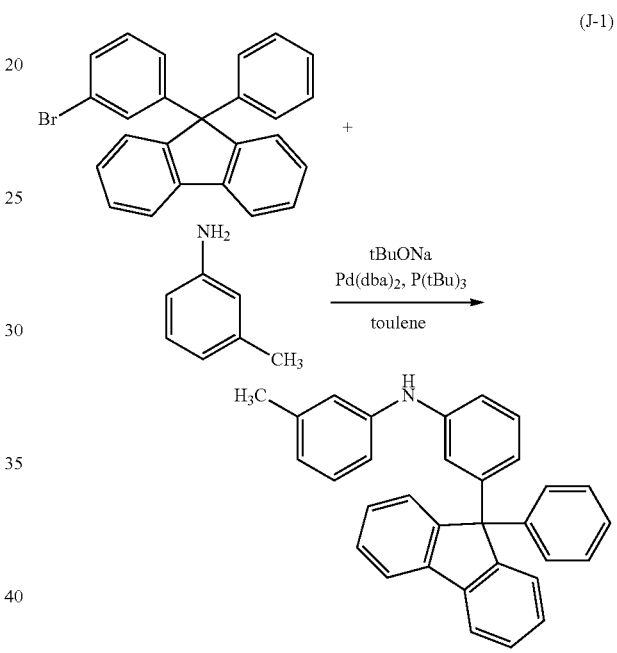

(J-1)

Step 2: Synthesis Method of N,N'-Bis(3-methylphenyl)-N,N'-bis[3-(9-phenyl-9H-fluoren-9-yl)phenyl]-pyrene-1,6-diami ne (abbreviation: 1,6mMemFLPAPrn)

Into a 100 mL three-neck flask were placed 0.6 g (1.7 mmol) of 1,6-dibromopyrene, 1.4 g (3.4 mmol) of 3-methylphenyl-3-(9-phenyl-9H-fluoren-9-yl)phenylamine, and 0.5 g (5.1 mmol) of sodium tert-butoxide. The air in the flask was replaced with nitrogen. To this mixture were added 21.0 mL of toluene and 0.2 mL of a 10% hexane solution of tri(tert-butyl)phosphine. The temperature of this mixture was set to 60° C., and 34.9 mg (0.1 mmol) of bis(dibenzylideneacetone) palladium(0) was added to the mixture. The temperature of this mixture was raised to 80° C., and the mixture was stirred for 3.0 hours. After that, 400 mL of toluene was added to the mixture, and the mixture was heated. While the mixture was kept hot, it was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. The filtrate was concentrated to give a solid, which was then purified by silica gel column chromatography (a developing solvent in which the ratio of hexane to toluene was 3:2) to give a yellow solid. Recrystallization of the obtained yellow solid from a mixed solvent of toluene and hexane gave 1.2 g of a yellow solid of the object of the synthesis in 67% yield.

By a train sublimation method, 1.0 g of the obtained yellow solid was purified. In the sublimation purification, the yellow solid was heated at 317° C. under a pressure of 2.2 Pa with a flow rate of argon gas of 5.0 mL/min. After the sublimation purification, 1.0 g of a yellow solid of the object of the synthesis was obtained in a yield of 93%. The synthesis scheme of Step 2 above is shown in the following scheme (J-2).

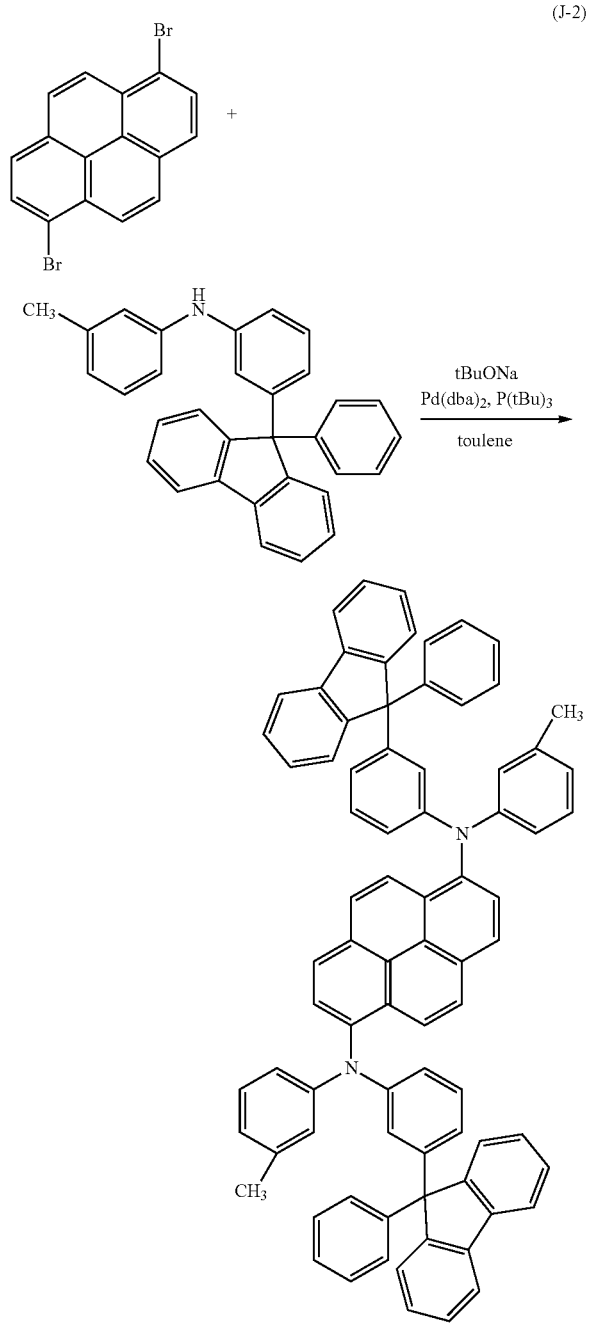

A nuclear magnetic resonance (NMR) method identified this compound as N,N'-bis(3-methylphenyl)-N,N'-bis[3-(9-phenyl-9H-fluoren-9-yl)phenyl]-pyrene-1,6-diami ne (abbreviation: 1,6mMemFLPAPrn), which was the object of the synthesis.

$^1$H NMR measurement data of the obtained compound are as follows: $^1$H NMR (CDCl$_3$, 300 MHz): δ=2.21 (s, 6H), 6.67 (d, J=7.2 Hz, 2H), 6.74 (d, J=7.2 Hz, 2H), 7.17-7.23 (m, 34H), 7.62 (d, J=7.8 Hz, 4H), 7.74 (d, J=7.8 Hz, 2H), 7.86 (d, J=9.0 Hz, 2H), 8.04 (d, J=8.7 Hz, 4H)

EXAMPLE 6

In Example 6, an example in which 6-(9,10-diphenyl-2-anthryl)-benzo[b]naphtho[1,2-d]furan (abbreviation: 2BnfPA) represented by the structural formula (123) in Embodiment 1 is described.

Into a 50 mL three-neck flask were placed 1.5 g (3.2 mmol) of 2-iodo-9,10-diphenylanthracene and 0.86 g (3.2 mmol) of benzo[b]naphtho[1,2-d]furan-6-boronic acid, and the air in the flask was replaced with nitrogen. To this mixture were added 10 mL of toluene, 5.0 mL of ethanol, and 4.0 mL of an aqueous solution of sodium carbonate (2.0 mol/L). While the pressure was reduced, this mixture was stirred to be degassed. To this mixture was added 0.18 g (0.16 mmol) of tetrakis(triphenylphosphine)palladium(0), and the mixture was stirred at 80° C. for 6 hours under a nitrogen stream, so that a solid was precipitated. This mixture was cooled to room temperature, and the precipitated solid was collected by suction filtration. The collected solid dissolved in about 30 mL of hot toluene, and this solution was suction-filtered through Celite, alumina, and Florisil. This obtained filtrate was concentrated to give a solid. The obtained solid was recrystallized from toluene/hexane, so that 1.0 g of a pale yellow powder of the object of the synthesis was obtained in 58% yield.

By a train sublimation method, 1.0 g of the obtained pale yellow powdery solid was purified. In the sublimation purification, 2mBnfPPA was heated at 290° C. under a pressure of 10 Pa with a flow rate of argon at 5.0 mL/min. After the sublimation purification, 0.91 g of a pale yellow solid of 2mBnfPPA was recovered in 91% yield. The above-described synthesis scheme is illustrated in the following scheme (K-1).

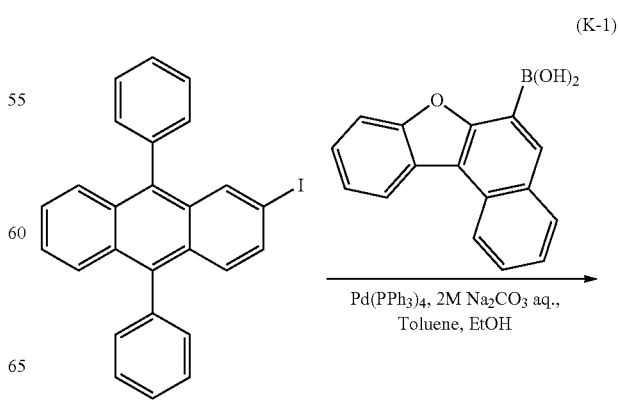

-continued

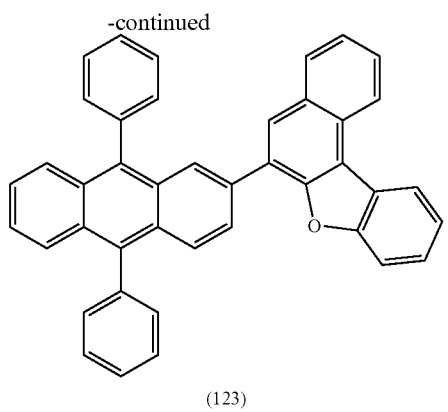

(123)

Nuclear magnetic resonance (NMR) spectroscopy identified this compound as 6-(9,10-diphenyl-2-anthryl)-benzo[b]naphtho[1,2-d]furan (abbreviation: 2BnfPA), which was the object of the synthesis.

$^1$H-NMR measurement data of the obtained compound are as follows: $^1$H-NMR (CDCl$_3$, 300 MHz): δ=7.37 (dd, J=3.6 Hz, 3.3 Hz, 2H), 7.45-7.79 (m, 17H), 7.89 (d, j=8.7 Hz, 1H), 98 (dd, J=9.0 Hz, 1.8 Hz, 1H), 8.04 (t, J=4.5 Hz, 2H), 8.42 (dd, J=6.0 Hz, 2.1 Hz, 1H), 8.50 (d, J=1.5 Hz, 1H), 8.62 (d, J=9.0 Hz, 1H).

Figure 62A:
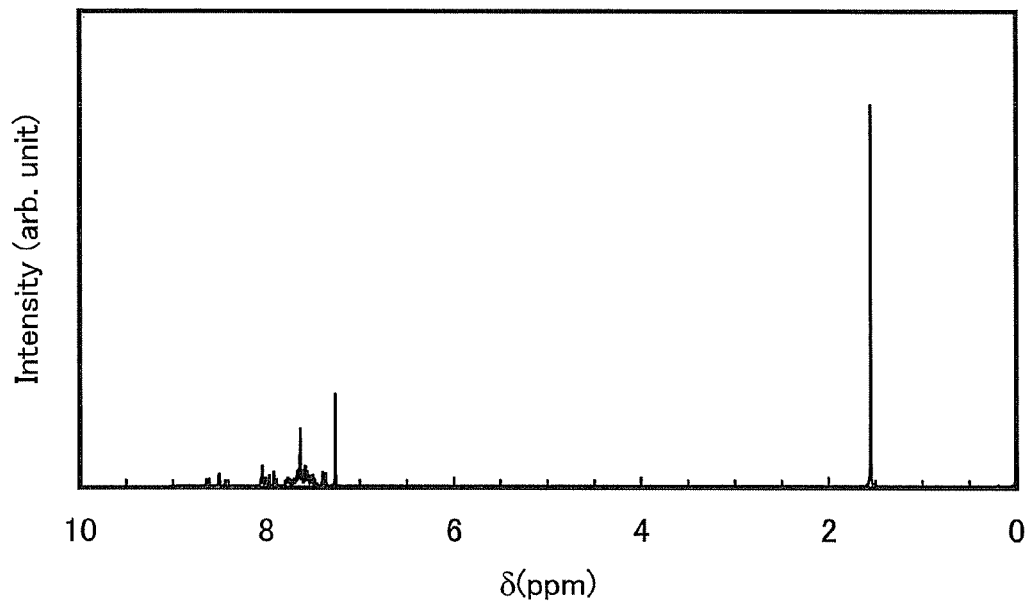
FIGS. 62A and 62B show NMR charts of 2BnfPA.
Figure 62B:
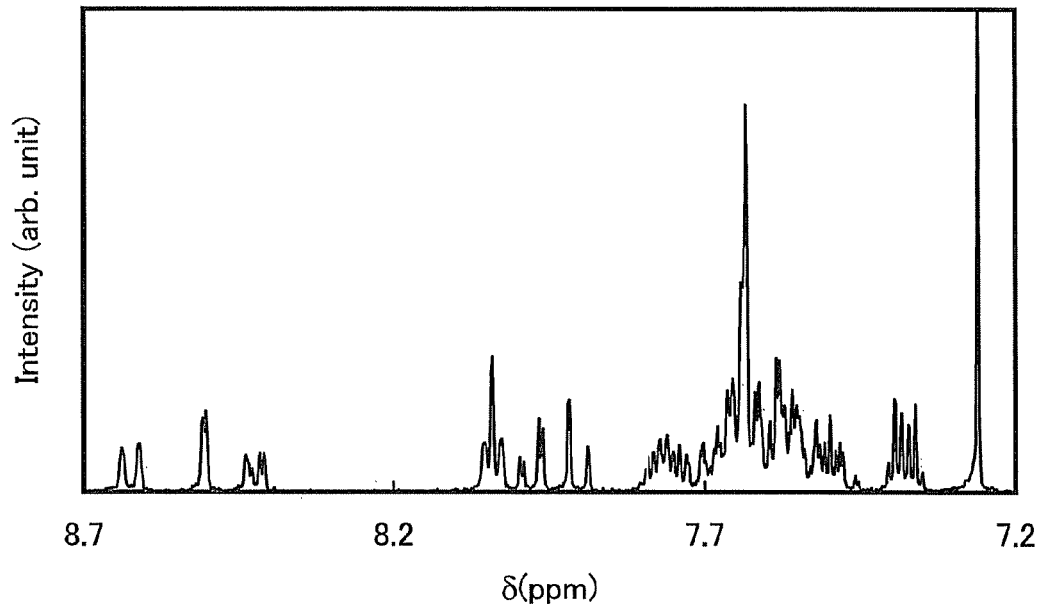

Further, $^1$H-NMR charts are shown in FIGS. 62A and 62B. Note that FIG. 62B is a chart where the range of from 7.2 ppm to 8.7 ppm in FIG. 62A is enlarged.

Figure 63A:
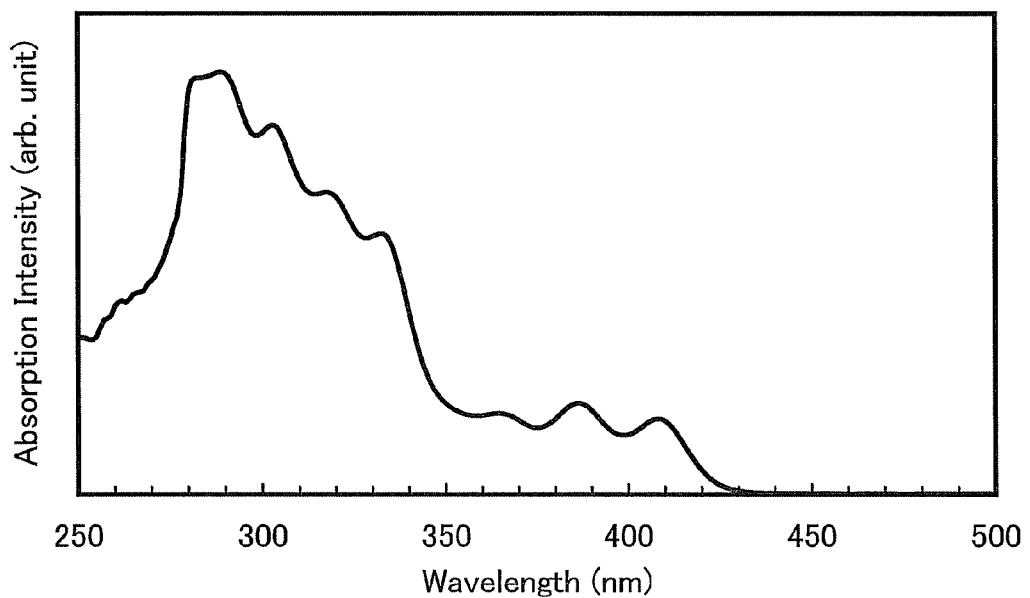
FIGS. 63A and 63B show an absorption spectrum and an emission spectrum of 2BnfPA in a toluene solution of 2BnfPA.
Figure 63B:
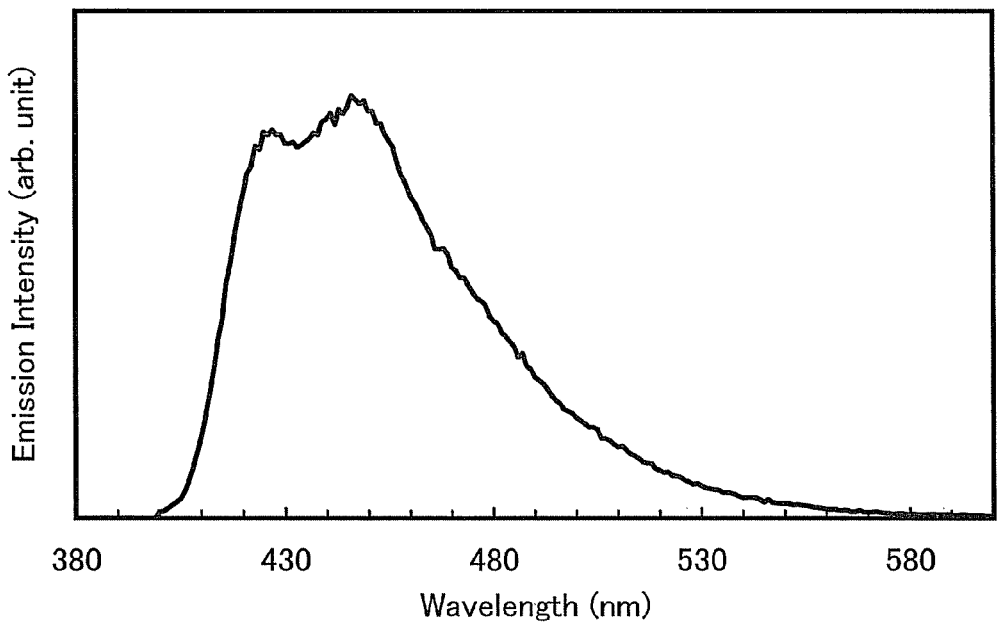
Figure 64A:
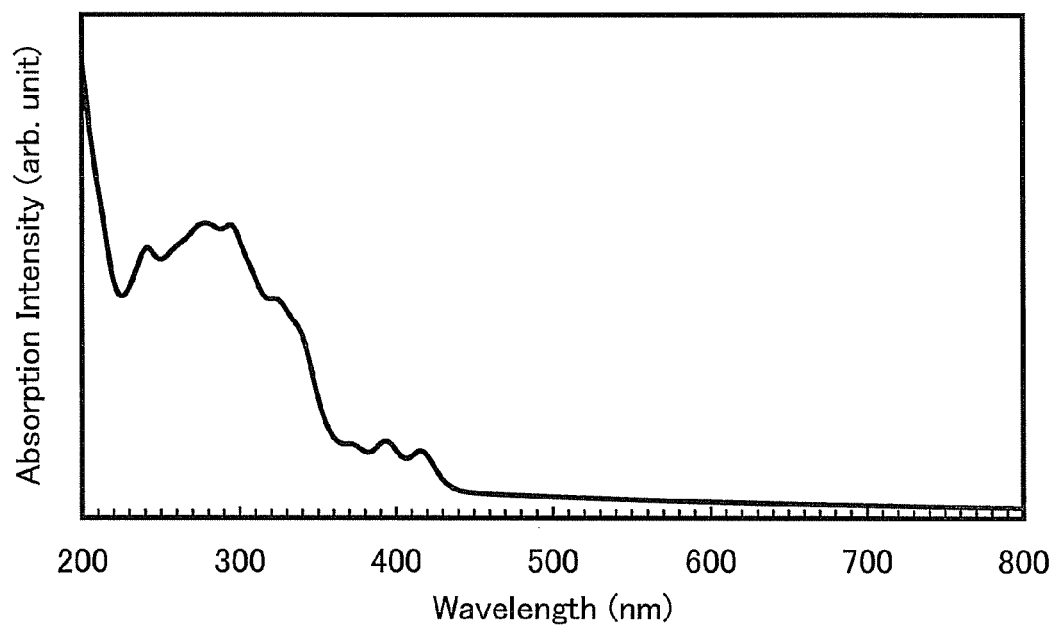
FIGS. 64A and 64B show an absorption spectrum and an emission spectrum of a thin film of 2BnfPA.
Figure 64B:
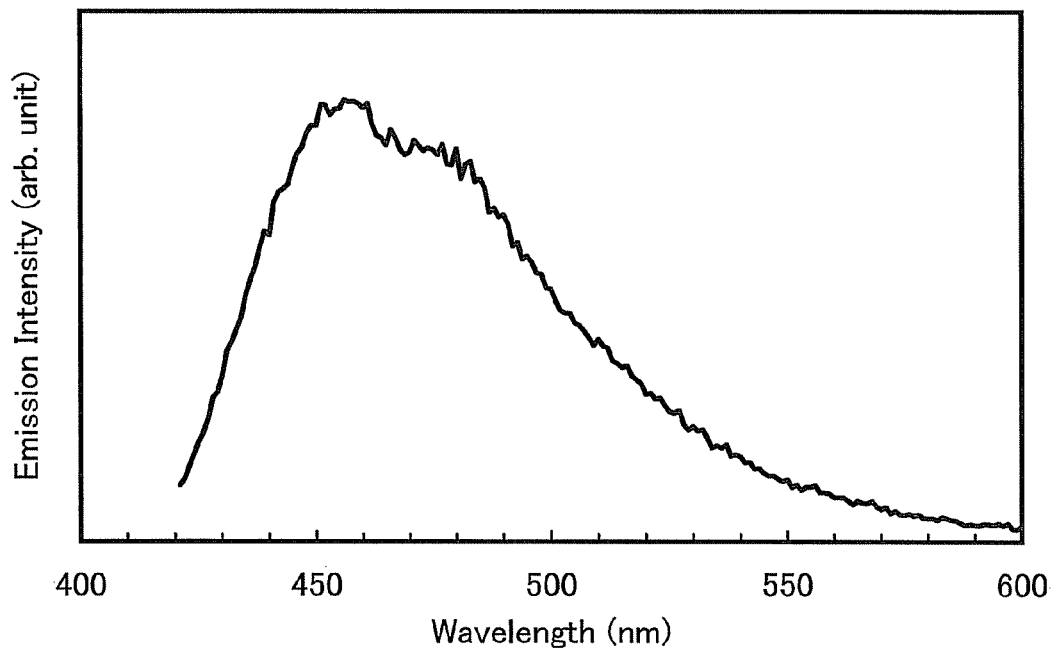

Further, FIG. 63A shows an absorption spectrum of 2BnfPA in a toluene solution of 2BnfPA, and FIG. 63B shows an emission spectrum thereof. Furthermore, FIG. 64A shows an absorption spectrum of a thin film of 2BnfPA, and FIG. 64B shows an emission spectrum thereof. An ultraviolet-visible spectrophotometer (V-550, manufactured by JASCO Corporation) was used for the measurements of the absorption spectra. The measurements were performed with samples prepared in such a way that the solution was put in a quartz cell while the thin film was obtained by evaporation onto a quartz substrate. The figures show the absorption spectrum of the solution which was obtained by subtraction of the absorption spectra of quartz and toluene from those of quartz and the solution, and the absorption spectrum of the thin film which was obtained by subtraction of the absorption spectrum of a quartz substrate from those of the quartz substrate and the thin film. In FIG. 63A and FIG. 64A, the horizontal axis represents wavelength (nm) and the vertical axis represents absorption intensity (arbitrary unit). Similarly, in FIG. 63B and FIG. 64B, the horizontal axis represents wavelength (nm) and the vertical axis represents emission intensity (arbitrary unit). In the case of the toluene solution, absorption peaks were observed at around 289 nm, 303 nm, 318 nm, 332 nm, 365 nm, 386 nm, and 408 nm, and emission wavelength peaks were at 427 nm and 447 nm (at an excitation wavelength of 387 nm). Further, in the case of the thin film, absorption peaks were observed at around 241 nm, 262 nm, 278 nm, 294 nm, 323 nm, 336 nm, 371 nm, 393 nm, and 416 nm, and emission wavelength peaks were at 363 nm, 457 nm, 474 nm, and 457 nm (at an excitation wavelength of 415 nm).

Further, the HOMO level and LUMO level of 2BnfPA in the thin film state were measured. The value of the HOMO level was obtained by conversion of the value of the ionization potential measured with a photoelectron spectrometer (AC-2, manufactured by Riken Keiki Co., Ltd.) in the air into a negative value. The value of the LUMO level was obtained in such a way that the absorption edge was found from a Tauc plot with an assumption of direct transition using the data of the absorption spectrum of the thin film of 2BnfPA which is shown in FIG. 64A and the absorption edge was added as an optical energy gap to the value of the HOMO level. As a result, the HOMO level, energy gap, and LUMO level of 2BnfPA were −5.66 eV, 2.86 eV, and −2.80 eV, respectively.

Explanation of References

100: substrate, 101: first electrode, 102: EL layer, 103: second electrode, 111: hole-injection layer, 112: hole-transport layer, 113: light-emitting layer, 114: electron-transport layer, 115: electron-injection layer, 301: first electrode, 303: second electrode, 311: first light-emitting unit, 312: second light-emitting unit, 313: charge generation layer, 401: source driver circuit, 402: pixel portion, 403: gate driver circuit 404: sealing substrate, 405: sealant, 407: space, 408: wiring, 410: element substrate, 411: switching TFT, 412: current control TFT, 413: first electrode, 414: insulator, 416: EL layer, 417: second electrode, 418: light-emitting element, 423: n-channel TFT, 424: p-channel TFT, 501: substrate, 502: first electrode, 503: second electrode, 504: EL layer, 505: insulating layer, 506: partition layer, 600: display device, 602: display device, 604: display portion, 606: display portion, 801: lighting device, 803: lighting device, 805: glasses, 1100: substrate, 1101: first electrode, 1103: second electrode, 1111: hole-injection layer, 1112: hole-transport layer, 1113: light-emitting layer, 1114: electron-transport layer, 1114a: electron-transport layer, 1114b: electron-transport layer, 1115: electron-injection layer, 7100: television device, 7100a: television device, 7101: housing, 7103: display portion, 7105: stand, 7107: display portion, 7109: operation key, 7110: remote control, 7201: main body, 7202: housing, 7203: display portion, 7204: keyboard, 7205: external connection port, 7206: pointing device, 7301: housing, 7302: housing, 7303: joint portion, 7304: display portion, 7305: display portion, 7306: speaker portion, 7307: storage medium insertion portion, 7308: LED lamp, 7309: operation key, 7310: connection terminal, 7311: sensor, 7312: microphone, 7400: cellular phone, 7401: housing, 7402: display portion, 7403: operation button, 7404: external connection port, 7405: speaker, 7406: microphone, 7500: lighting device, 7501: housing, 7503a: light-emitting device, 7503b: light-emitting device, 7503c: light-emitting device, 7503d: light-emitting device.

This application is based on Japanese Patent Application Serial No. 2010-292638 filed with the Japan Patent Office on Dec. 28, 2010, the entire contents of which are hereby incorporated by reference.

The invention claimed is:

1. A benzo[b]naphtho[1,2-d]furan compound represented by a formula (G1):

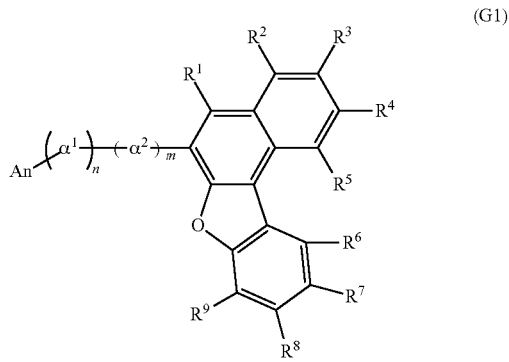

(G1)

wherein, in the formula (G1), the An represents an anthryl group represented by a formula (An-1) or a formula (An-2), the $\alpha^1$ and $\alpha^2$ separately represent a substituted or unsubstituted phenylene group represented by any one of formula ($\alpha$-1) to ($\alpha$-3), the $R^1$ to $R^9$ separately represent either hydrogen or an alkyl group having 1 to 4 carbon atoms, and at least one of the n and m represents 1,

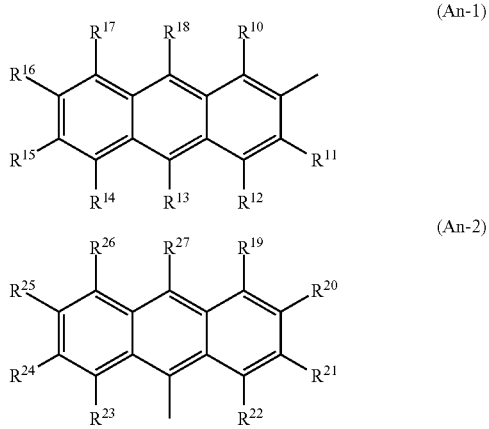

wherein, in the formulae (An-1) and (An-2), the $R^{10}$ to $R^{27}$ separately represent any one of hydrogen, an alkyl group having 1 to 6 carbon atoms, and a substituted or unsubstituted aryl group having 6 to 13 carbon atoms,

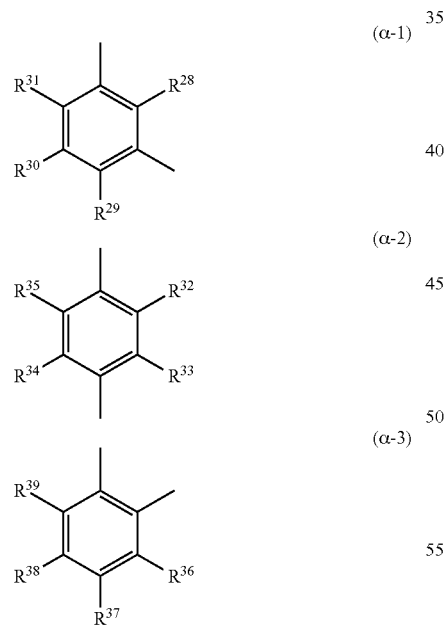

wherein, in the formulae ($\alpha$-1) to ($\alpha$-3), the $R^{28}$ to $R^{39}$ separately represent either hydrogen or an alkyl group having 1 to 4 carbon atoms.

2. The benzo[b]naphtho[1,2-d]furan compound according to claim 1, wherein the $R^{10}$ to $R^{27}$ have two or more substituents bonded to each other to form a ring including a spiro ring.

3. A light-emitting element material comprising the benzo[b]naphtho [1,2-d]furan compound according to claim 1.

4. A light-emitting element comprising the benzo[b]naphtho[1,2-d]furan compound according to claim 1, in a light-emitting layer.

5. A light-emitting element comprising the benzo[b]naphtho[1,2-d]furan compound according to claim 1, for a host material in a light-emitting layer.

6. A light-emitting element comprising the benzo[b]naphtho[1,2-d]furan compound according to claim 1, for an emission center material.

7. A benzo[b]naphtho[1,2-d]furan compound represented by a formula (G2):

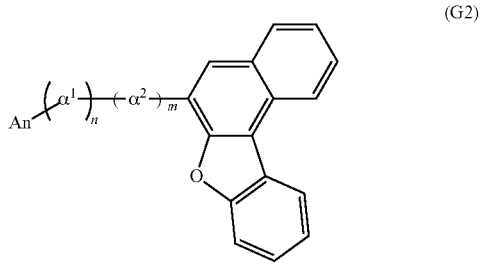

wherein, in the formula (G2), the An represents an anthryl group represented by a formula (An-1) or a formula (An-2), the $\alpha^1$ and $\alpha^2$ separately represent a phenylene group represented by any one of formulae ($\alpha$-4) to ($\alpha$-6), at least one of the n and m represents 1, and

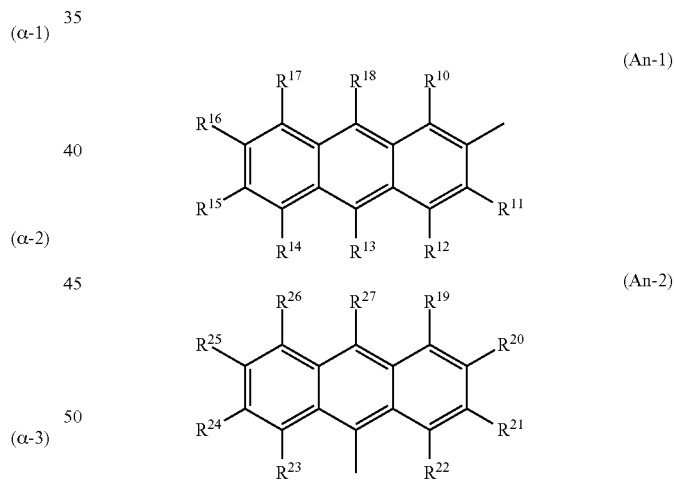

wherein, in the formulae (An-1) and (An-2), the $R^{10}$ to $R^{27}$ separately represent any one of hydrogen, an alkyl group having 1 to 6 carbon atoms, and a substituted or unsubstituted aryl group having 6 to 13 carbon atoms,

(α-5)

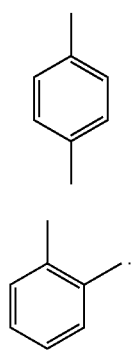

(α-6)

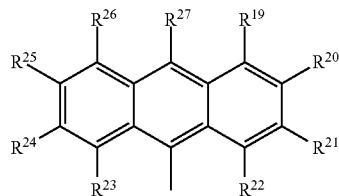

(An-2)

wherein, in the formulae (An-1) and (An-2), the $R^{10}$ to $R^{27}$ separately represent any one of hydrogen, an alkyl group having 1 to 6 carbon atoms, and a substituted or unsubstituted aryl group having 6 to 13 carbon atoms, 8. The benzo[b]naphtho[1,2-d]furan compound according to claim 7, wherein the $R^{10}$ to $R^{27}$ have two or more substituents bonded to each other to form a ring including a spiro ring.

9. A light-emitting element material comprising the benzo[b]naphtho [1,2-d]furan compound according to claim 7.

10. A light-emitting element comprising the benzo[b]naphtho[1,2-d]furan compound according to claim 7, in a light-emitting layer.

11. A light-emitting element comprising the benzo[b]naphtho [1,2-d]furan compound according to claim 7, for a host material in a light-emitting layer.

12. A light-emitting element comprising the benzo[b]naphtho[1,2-d]furan compound according to claim 7, for an emission center material.

13. A benzo[b]naphtho[1,2-d]furan compound represented by a formula (G3):

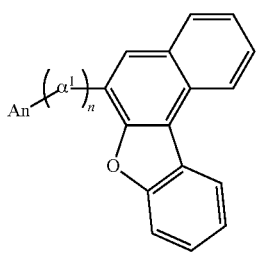

(G3)

wherein, in the formula (G3), the An represents an anthryl group represented by a formula (An-1) or a formula (An-2), the $\alpha^1$ represents a phenylene group represented by a formula (a-4) or a formula (α-5), and the n represents 1, and

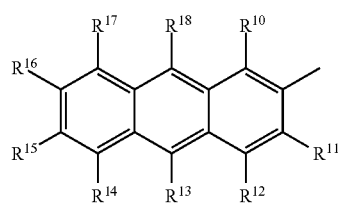

(An-1)

(α-4)

(α-5)

14. The benzo[b]naphtho[1,2-d]furan compound according to claim 13, wherein the $R^{10}$ to $R^{27}$ have two or more substituents bonded to each other to form a ring including a spiro ring.

15. A light-emitting element material comprising the benzo[b]naphtho[1,2-d]furan compound according to claim 13.

16. A light-emitting element comprising the benzo[b]naphtho[1,2-d]furan compound according to claim 13, in a light-emitting layer.

17. A light-emitting element comprising the benzo[b]naphtho [1,2-d]furan compound according to claim 13, for a host material in a light-emitting layer.

18. A light-emitting element comprising the benzo[b]naphtho[1,2-d]furan compound according to claim 13, for an emission center material.

19. A benzo[b]naphtho[1,2-d]furan compound represented by a formula (G4):

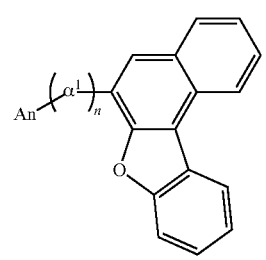

(G4)

wherein, in the formula (G4), the An represents an anthryl group represented by a formula (An-3) or a formula (An-4), the $\alpha^1$ represents a phenylene group represented by a formula ($\alpha$-4) or a formula ($\alpha$-5), and
the n represents 1, and (An-3)

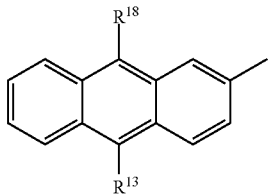

(An-4)

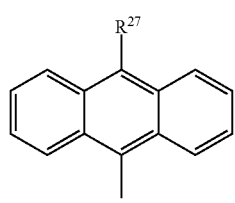

wherein, in the formulae (An-3) and (An-4), the $R^{13}$, $R^{18}$, and $R^{27}$ separately represent any one of hydrogen, an alkyl group having 1 to 6 carbon atoms, and a substituted or unsubstituted aryl group having 6 to 13 carbon atoms, and ($\alpha$-4)

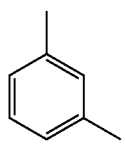

($\alpha$-5)

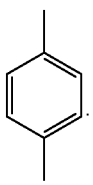

20. The benzo[b]naphtho[1,2-d]furan compound according to claim 19, wherein the $R^{13}$, $R^{18}$ and $R^{27}$ have two or more substituents bonded to each other to form a ring including a spiro ring.

21. A light-emitting element material comprising the benzo [b]naphtho [1,2-d]furan compound according to claim 19.

22. A light-emitting element comprising the benzo[b]naphtho[1,2-d]furan compound according to claim 19, in a light-emitting layer.

23. A light-emitting element comprising the benzo[b]naphtho[1,2-d]furan compound according to claim 19, for a host material in a light-emitting layer.

24. A light-emitting element comprising the benzo[b]naphtho[1,2-d]furan compound according to claim 19, for an emission center material.

* * * * *